United States Patent
Sohn et al.

(10) Patent No.: US 11,590,096 B2
(45) Date of Patent: *Feb. 28, 2023

(54) COMPOSITIONS FOR PREVENTION OR TREATMENT OF ACUTE RADIATION SYNDROME AND OTHER RADIATION EXPOSURE

(71) Applicant: Enzychem Lifesciences Corporation, Englewood Cliffs, NJ (US)

(72) Inventors: Ki Young Sohn, Seoul (KR); Sun Young Yoon, Daejeon (KR)

(73) Assignee: Enzychem Lifesciences Corporation, Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/114,473

(22) Filed: Dec. 7, 2020

(65) Prior Publication Data

US 2021/0100767 A1     Apr. 8, 2021

Related U.S. Application Data

(63) Continuation of application No. 16/888,716, filed on May 30, 2020, which is a continuation-in-part of application No. PCT/IB2018/059538, filed on Nov. 30, 2018.

(60) Provisional application No. 62/691,604, filed on Jun. 28, 2018.

(51) Int. Cl.
  *A61K 31/231*  (2006.01)
  *A61P 43/00*   (2006.01)
  *A61K 45/06*   (2006.01)
  *A61K 38/19*   (2006.01)
  *A61P 39/00*   (2006.01)

(52) U.S. Cl.
  CPC .......... *A61K 31/231* (2013.01); *A61K 38/193* (2013.01); *A61K 45/06* (2013.01); *A61P 39/00* (2018.01); *A61P 43/00* (2018.01)

(58) Field of Classification Search
  CPC .... A61K 31/231; A61K 38/193; A61K 45/06; A61K 9/0053; A61K 2300/00; A61P 43/00; A61P 39/00; A23L 33/115; A23L 33/10; A23V 2002/00; A23V 2250/182
  See application file for complete search history.

(56) References Cited

U.S. PATENT DOCUMENTS

| | | |
|---|---|---|
| 7,662,853 B2 | 2/2010 | Kim |
| 9,895,337 B2 | 2/2018 | Kim et al. |
| 2016/0128966 A1* | 5/2016 | Han .................. A61K 31/7048 424/85.1 |
| 2017/0128404 A1 | 5/2017 | Sohn |
| 2017/0183287 A1 | 6/2017 | Lee et al. |
| 2019/0008820 A1 | 1/2019 | Oh et al. |
| 2020/0397737 A1 | 12/2020 | Sohn et al. |

FOREIGN PATENT DOCUMENTS

| | | |
|---|---|---|
| WO | 2015-176012 A1 | 11/2015 |
| WO | 2016-019313 A1 | 2/2016 |
| WO | 2016109002 A2 | 7/2016 |

OTHER PUBLICATIONS

Jeong, J. et al., "PLAG (1-Palmitoyl-2-Linoleoyl-3-Acetyl-rac-Glycerol) Modulates Eosinophil Chemotaxis by Regulating CCL26 Expression from Epithelial Cells", PLOS One, Mar. 24, 2016, vol. 11, Iss. 3, e0151758, Internal pp. 1-14.
Yoon, S. Y. et al., "1-palmitoyl-2-linoleoyl-3-acetyl-rac-glycerol (EC-18) modulates Th2 immunity through attenuation of IL-4 expression", Immune Network, Apr. 2015, vol. 15, No. 2, pp. 100-109.
Written Opinion of PCT/IB18/59538 dated Mar. 22, 2019.
International Search Report of PCT/IB18/59538 dated Mar. 22, 2019.
Yang, H.O. et al., "Stimulatory Effects of Monoacetyldiglycerides on Hematopoiesis", Biol. Pharm. Bull. 27(7) 1121-1125 (2004).
Extended European Search Report for European Patent Application No. 18882935, dated Jul. 5, 2021, 6 pages.
Andrea L. DiCarlo et al.: :Medical Countermeasures for Platelet Regeneration after Radiation Exposure, Radiation Research, 2011, vol. 176, pp. e0001-e0015.
Lars Heslet et al.: "Acute radiation syndrome (ARS)—treatment of the reduced host defense", International Journal of General Medicine, 2012, vol. 5, pp. 105-115.
Russian Search Report dated May 12, 2022 in RU 2020121489/04.

* cited by examiner

*Primary Examiner* — Kortney L. Klinkel
*Assistant Examiner* — Jason Deck
(74) *Attorney, Agent, or Firm* — Fox Rothschild LLP

(57) ABSTRACT

In one aspect, use of 1-palmitoyl-2-linoleoyl-3-acetylglycerol (PLAG) for treating or preventing acute radiation syndrome is provided.

15 Claims, 88 Drawing Sheets

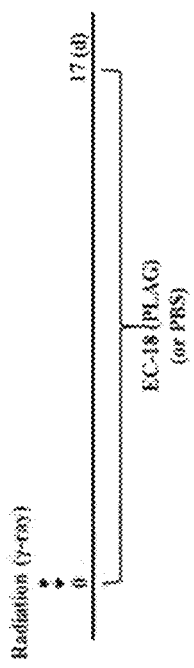
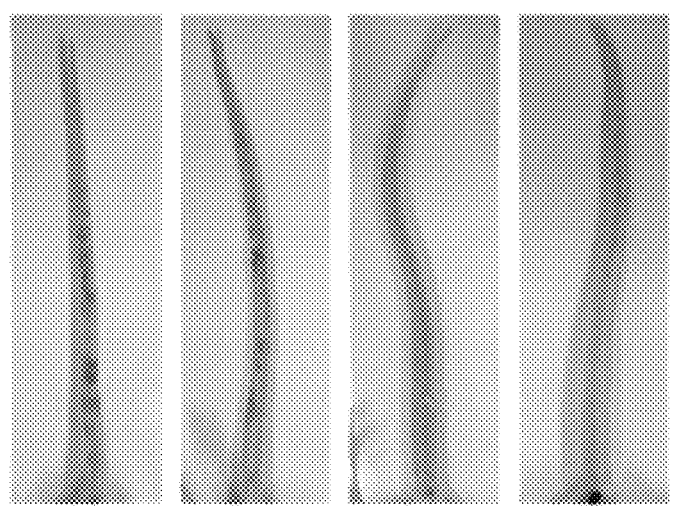
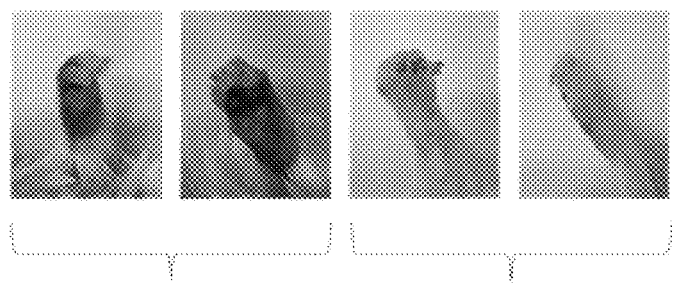
FIG. 13A
FIG. 13B

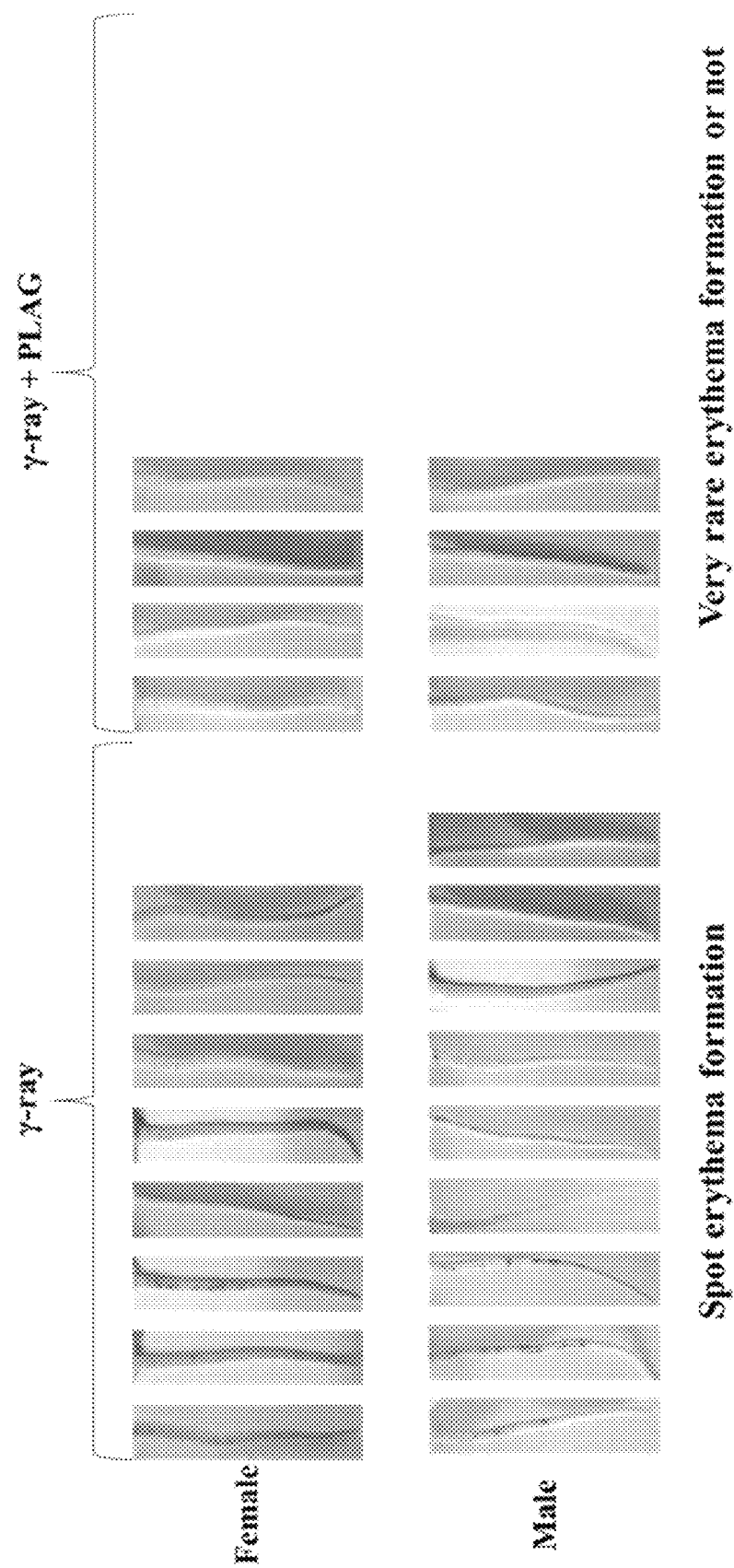

EC-18 promotes the removal of DAMP in a short period of time, thus inhibiting the continuous release of neutrophils from blood vessel.

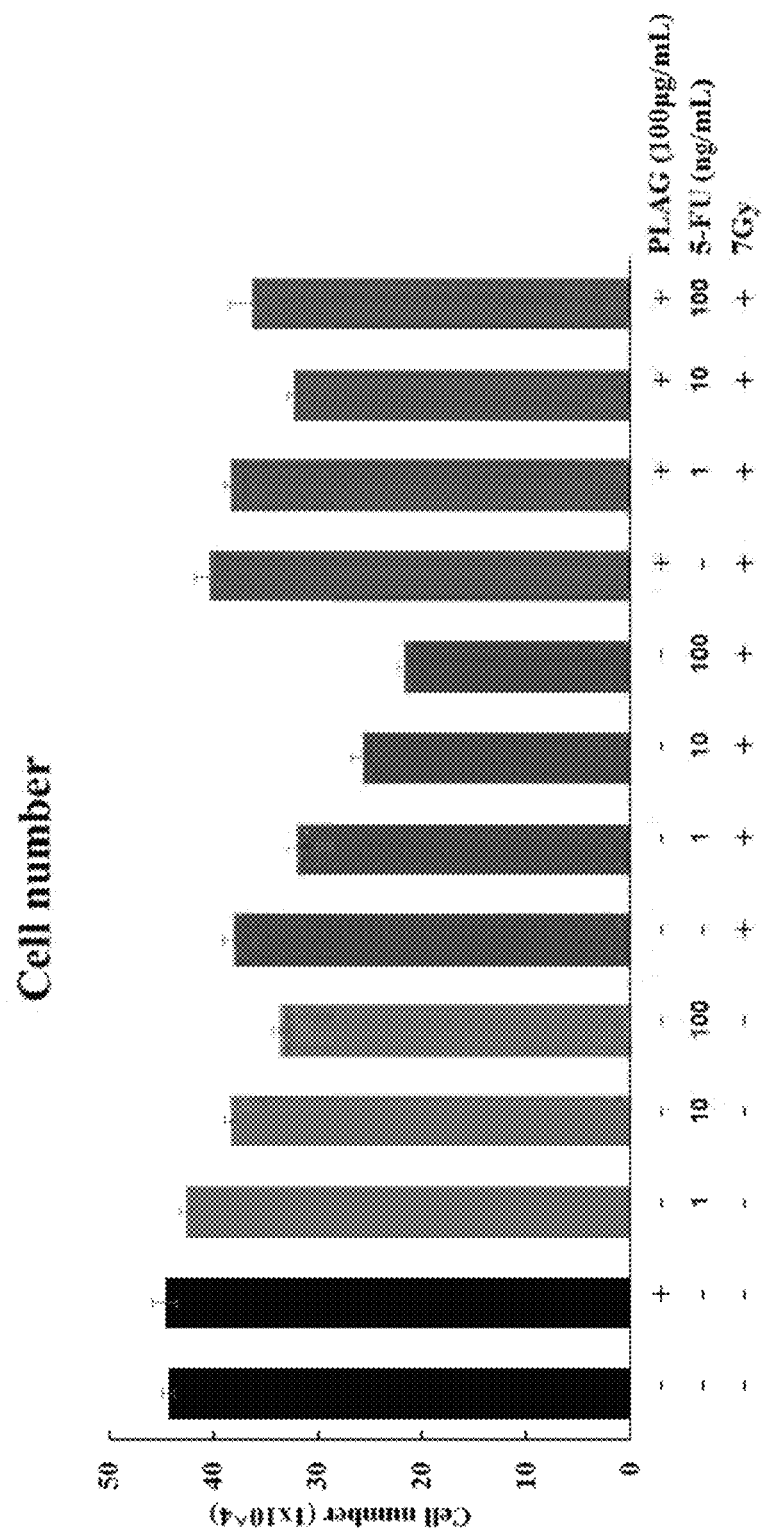

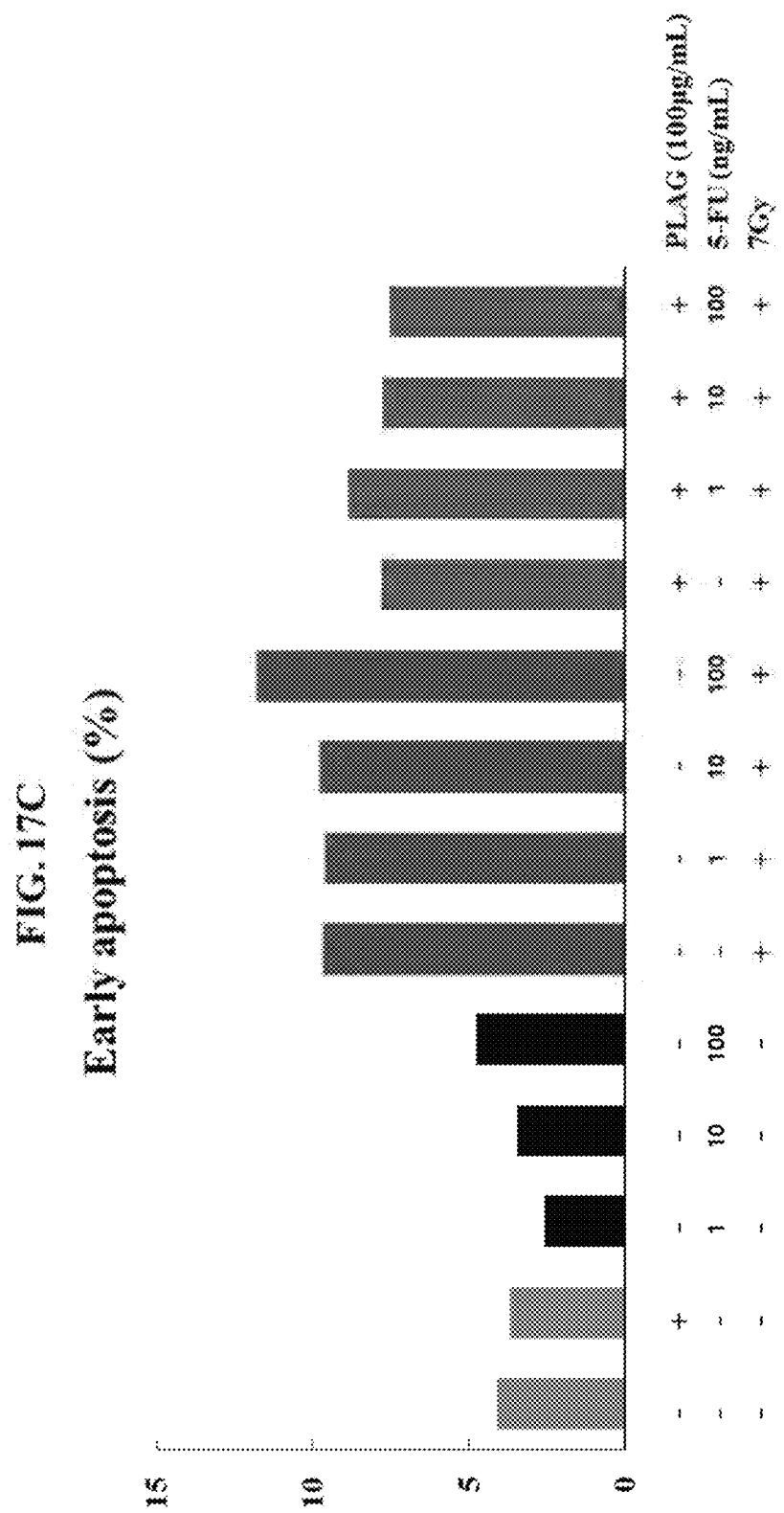

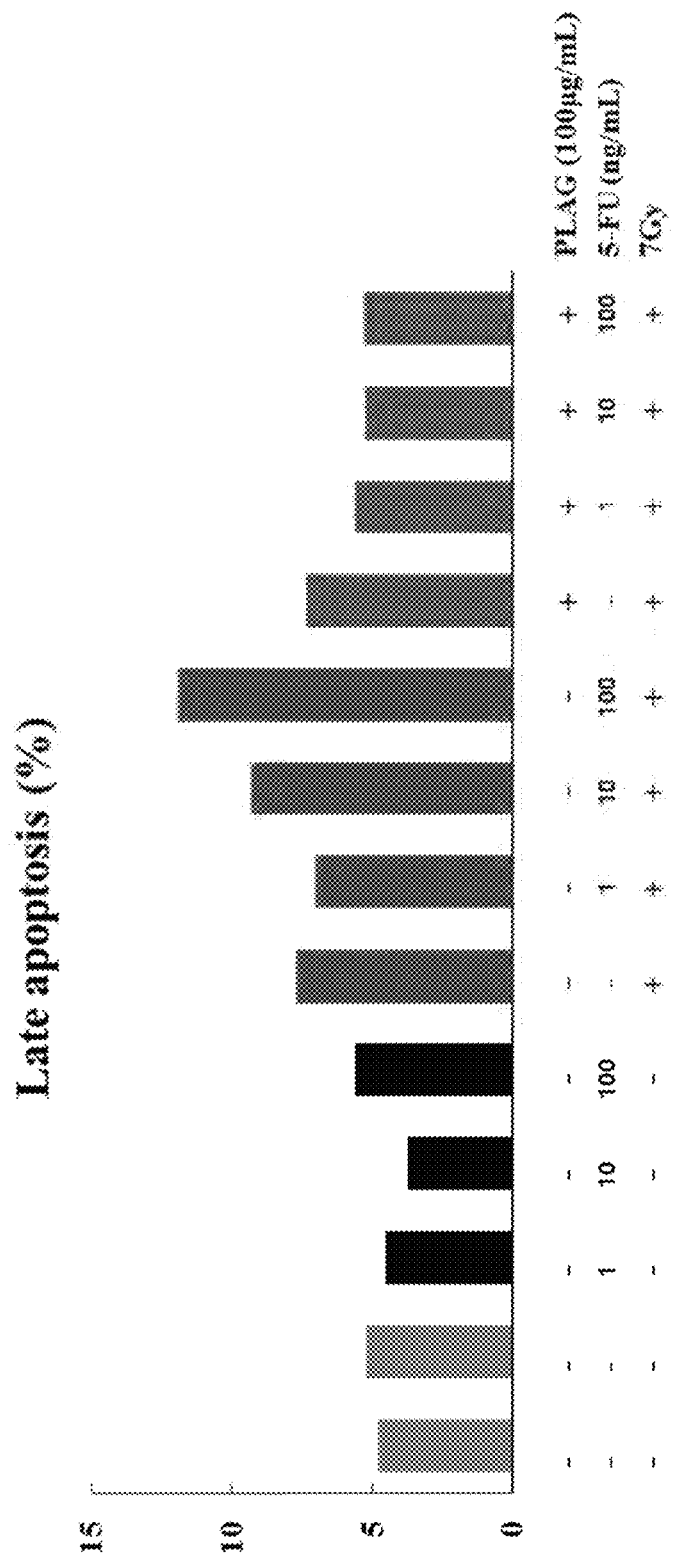

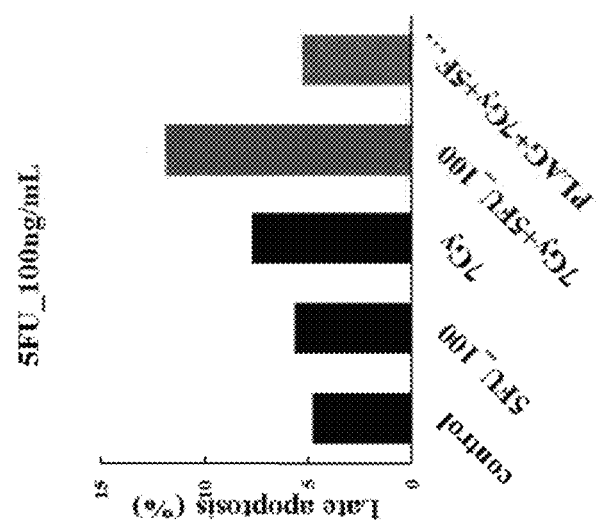
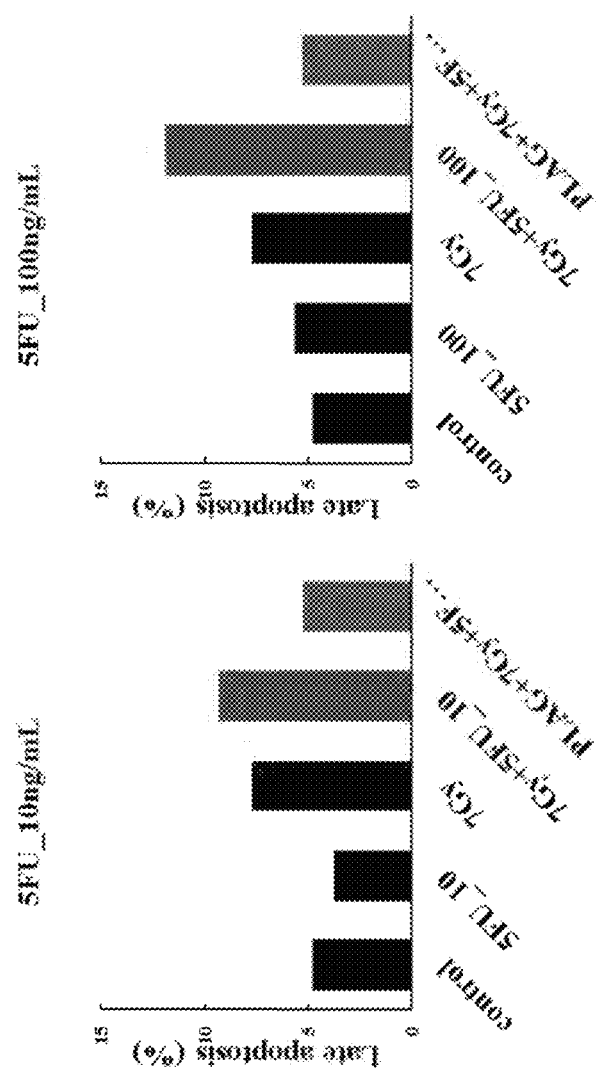
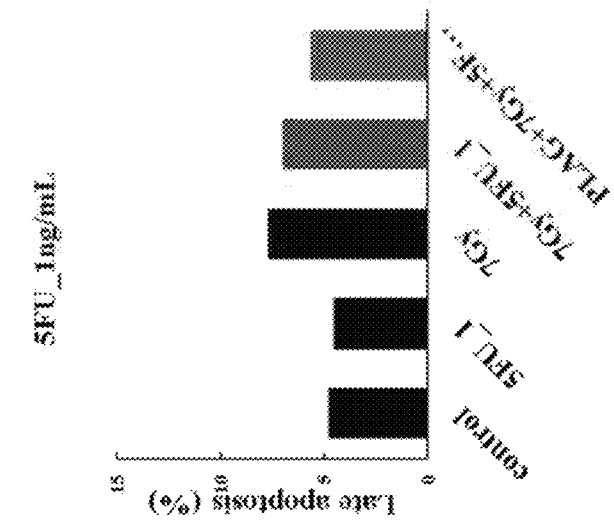

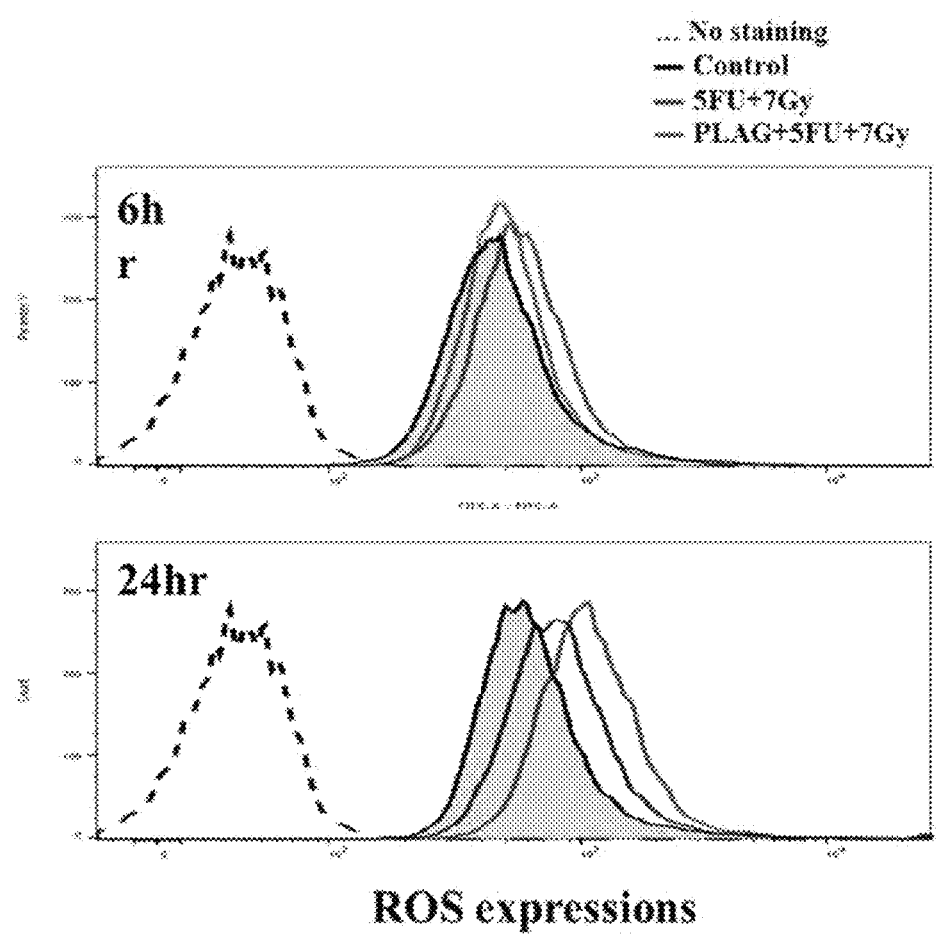

FIG. 26

| | G-CSF | EC-18 |
|---|---|---|
| Administration Route | Parenteral (biologics) | Oral (small molecule) |
| Manufacturing cost | High | Low |
| Use in CCRT* | Contraindicated | Can be used |
| Use in leukemia | Not recommended for AML* or MDS* | Can be used |
| Neutrophils | Increase | Increase |
| Thrombocytes (Platelets) | No effect | Increase |
| Mucositis | None | Anti-mucositis effect |
| Effects on STAT3 | Up-regulation | Down-regulation |
| Effects on cancer | Potential to lead to cancer progression | Anti-cancer, anti-metastasis activity |

$y = 0.1037e^{1.0658x}$

HaCaT cells

HaCaT cells

COMPOSITIONS FOR PREVENTION OR TREATMENT OF ACUTE RADIATION SYNDROME AND OTHER RADIATION EXPOSURE

CROSS-REFERENCE TO RELATED APPLICATION

This application is a continuation of U.S. application Ser. No. 16/888,716, filed May 30, 2016, which is a continuation-in-part of International Application PCT/IB2018/059538 filed Nov. 30, 2018 (published as WO2019/106632) which claims the benefit of US Provisional Patent Application No. 62/691,604, filed Jun. 28, 2018 and Korean Application No. 10-2017-0162404 filed Nov. 30, 2017, all of which applications are incorporated herein in their entireties and for all purposes.

FIELD

In one aspect, methods and compositions that comprise PLAG (1-palmitoyl-3-linoleoyl-3-acetylglycerol) are provided for preventing, treating, modulating or mediating acute radiation syndrome (ARS).

BACKGROUND

Acute radiation syndrome (ARS) is a disease that occurs when a large part of the human body is exposed to radiation; it is a fatal disease that ultimately leads to death by destroying immune, hematopoietic, neurologic and/or gastrointestinal systems. Nuclear explosion and nuclear accident may cause a radiation exposure that can cause the acute radiation syndrome.

A main treatment for patients exposed to radiation is to prevent and manage infection. Clinically, adjuvant therapies such as cytokines, antibiotic administration, and blood transfusions are performed in the early stage after the radiation exposure, and when the duration of neutropenia in patients is prolonged, risk of secondary infection also increases.

It thus would be desirable to have new therapies for acute radiation syndrome.

SUMMARY

In one aspect, we now provide new therapies for treatment and prevention of acute radiation syndrome that include PLAG (1-palmitoyl-2-linoleoyl-3-acetylglycerol).

In another aspect, new therapies are provided to treat a subject that has been exposed to ionizing radiation (particularly adverse exposure such as unintended and/or non-therapeutic exposure and/or therapeutic exposure (particularly adverse therapeutic exposure), and/or exposure to excessive ionizing radiation, including gamma radiation) which include administering to the subject an effective amount of PLAG (1-palmitoyl-2-linoleoyl-3-acetylglycerol).

In a yet further aspect, therapies are provided for treatment and prevention of one or more subsyndromes of acute radiation syndrome that include use of PLAG (1-palmitoyl-2-linoleoyl-3-acetylglycerol). ARS subsyndromes include hematopoietic, gastrointestinal, cutaneous and/or neurovascular.

In a still further aspect, therapies are provided for treatment and prevention of hematopoietic (bone marrow) acute radiation syndrome, gastrointestinal acute radiation syndrome, cutaneous acute radiation syndrome, cardiovascular acute radiation syndrome, and/or central nervous system (CNS) acute radiation syndrome.

In a further aspect, therapies are provided for treatment and prevention of radiation-induced coagulopathy.

In a yet further aspect, therapies are provided for treatment, including to reduce averse effects, from exposure galactic cosmic rays (GCR) and solar particle events (SPE) as may arise from a subject being in higher levels of the atmosphere or beyond the atmosphere (i.e. in space). Possible acute (in-flight) and late risks from galactic cosmic rays (GCR) and/or solar particle events (SPE) exposure include central nervous system (CNS) injury and are concerns for human exploration of space. Acute CNS risks may include altered cognitive function, impaired motor function, and behavioral changes, all of which may affect performance and human health. Late CNS risks may include neurological disorders such as Alzheimer's disease, dementia, or accelerated aging.

In an additional aspect, therapies are provides for treatment from adverse effects and/or protection from therapeutic radiation such as may be administered to a cancer patient.

In a further aspect, as discussed, therapies are provided for the treatment of cutaneous radiation syndrome, which may include administration of a present compound to subject in need thereof, such as a subject suffering from cutaneous radiation syndrome. Cutaneous radiation syndrome is recognized as referred to radiations effects on the skin, which may include inflammation, erythema, dry or moist desquamation, hair loss, blistering, reddening, ulceration, damage to sebaceous and sweat glands, atrophy, fibrosis, decreased or increased skin pigmentation, and/or necrosis.

In certain aspects, a subject being treated herein has not received any therapeutic radiation treatment, for example as may be administered for a cancer therapy, but has received adverse radiation from other sources/exposure.

PLAG (1-palmitoyl-2-linoleoyl-3-acetylglycerol) can alleviate, prevent and/or treat the reduction of immune cells such as leukocytes, neutrophils and lymphocytes by radiation exposure, and alleviate inflammatory diseases like oral mucositis, and further increase the survival rate and/or otherwise reduce injury to subjects exposed to radiation.

PLAG can be advantageously first administered to a subject even after an extended period has elapsed since the time the subject was exposed to the injurious radiation such as gamma radiation. That is, the subject can receive a therapeutic benefit, including increased survival times, even after such delayed treatment. See, for instance, the in vivo results set forth in the Examples which follow. This can be significant because first treatment of a subject suffering radiation exposure often can be delayed.

Thus, in certain aspects, PLAG is first administered (first dose to a subject) within 3, 6, 12, 18, 24, 36, 48, 60 or 72 hours after the subject suffered an injurious exposure to radiation (including gamma radiation exposure). In particular aspects, PLAG is first administered (first dose to a subject) between 3 and 12, 18, 48 or 72 hours, or between 6 and 18, 24 or 48 hours after the subject suffered an injurious exposure to radiation (including gamma radiation exposure). In certain aspects, an injurious exposure to radiation may be exposure to ionizing radiation such as gamma radiation of 1 Gy to 8 Gy or more for 1 second to 30, 60 or 120 seconds or more.

In a further aspect, a pharmaceutical composition is provided comprising PLAG (1-palmitoyl-2-linoleoyl-3-acetylglycerol) for preventing or treating acute radiation syndrome.

A pharmaceutical composition is also provided comprising PLAG (1-palmitoyl-2-linoleoyl-3-acetylglycerol) for preventing or treating a subject exposed to ionizing radiation, particularly a subject exposed to excessive ionizing radiation.

In a yet further aspect, kits are provided for use to treat or prevent acute radiation syndrome, or to treat or prevent exposure to excessive ionizing radiation.

Kits of the invention suitably may comprise 1) 1-palmitoyl-2-linoleoyl-3-acetylglycerol (PLAG); and 2) instructions for using the PLAG for treating or preventing acute radiation syndrome (ARS) of a subject, or for treating or preventing exposure to excessive ionizing radiation. Preferably, a kit will comprise a therapeutically effective amount of PLAG. The instructions suitably may be in written form, including as a product label.

The terms PLAG, EC-18 and 1-palmitoyl-2-linoleoyl-3-acetylglycerol are used interchangeably herein and designate the same compound herein.

In additional aspects, a compound of Formula 1 as set forth below may be employed in the methods, compostions and kits of the invention, particularly to treat a subject suffering from acute radiation syndrome or who have been exposed to adverse ionizing radiation.

Sources of radiation include radon gas, cosmic rays from outer space, medical x-rays, as well as from nuclear power generation and nuclear weapons. Radiation can be classified as ionizing or non-ionizing radiation, depending on its effect on atomic matter. A common use of the word "radiation" refers to ionizing radiation. Ionizing radiation has sufficient energy to ionize atoms or molecules, while non-ionizing radiation does not. Radioactive material is a physical material that emits ionizing radiation. There are three common types of radiation, alpha, beta and gamma radiation. They are all emitted from the nucleus of an unstable atom. X-rays produced by diagnostic and metallurgical imaging and security screening equipment are also ionizing radiation, as are neutrons produced by nuclear power generation and nuclear weapons.

Sources of radiation exposure include, but are not limited to, radiotherapy, nuclear warfare, nuclear reactor accidents, and improper handling of research or medical radioactive materials.

Radiation Dosage: The rad is a unit of absorbed radiation dose defined in terms of the energy actually deposited in the tissue. One rad is an absorbed dose of 0.01 joules of energy per kilogram of tissue. The more recent SI unit is the gray (Gy), which is defined as 1 joule of deposited energy per kilogram of tissue. Thus, one gray is equal to 100 rad.

Radiation poisoning, radiation sickness, acute radiation syndrome and other such disorders can involve damage to biological tissue due to excessive exposure to ionizing radiation. These terms generally refer to acute problems caused by a large dosage of radiation in a short period, though this also has occurred with long term exposure to lower levels of radiation. Symptoms of radiation poisoning, radiation sickness, acute radiation syndrome and other such disorders include: reduction of red and/or white blood cell count, decreased immune function (with increased susceptibility to infection), nausea and vomiting, fatigue, sterility, hair loss, tissue burns and necrosis, gastrointestinal damage accompanied by internal bleeding, and the like.

Radiation therapy is used in the treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment Other aspects are disclosed infra.

FIG. 13A is a schematic diagram of EC-18 treatment (17 days) in a radiation-induced Acute Radiation Syndrome animal model. FIG. 13B shows skin erythema in mice (BALB/c, 9 weeks old) administered with and without EC-18 (250 mg/kg/day PO) receiving lethal total body irradiation (8 Gy).

Figure 14A:
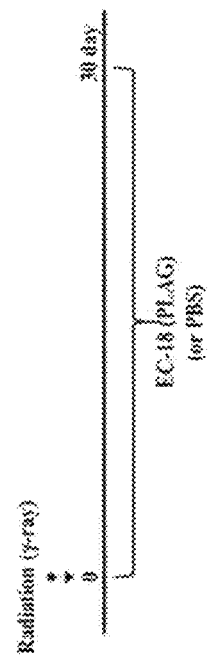
Figure 14B:
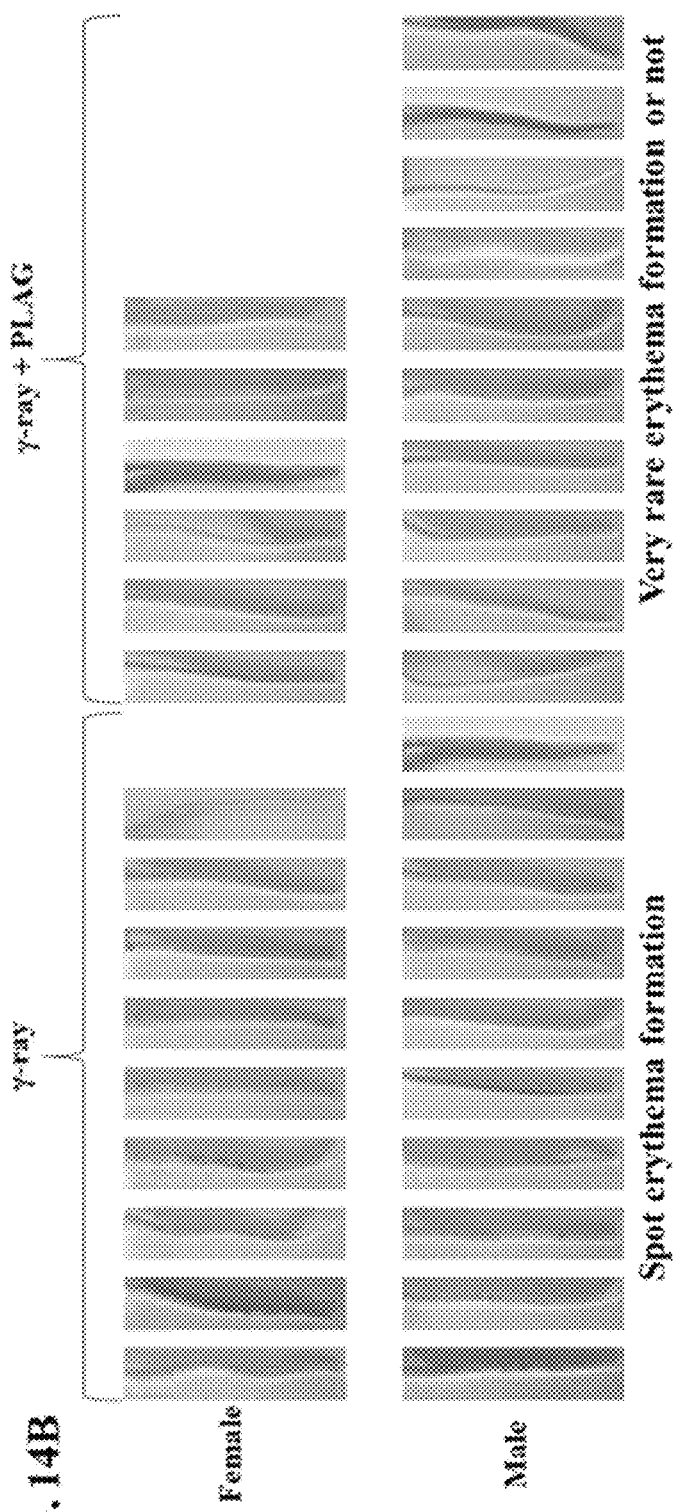

FIG. 14A is a schematic diagram of EC-18 treatment (30 days) in a radiation-induced Acute Radiation Syndrome animal model. FIG. 14B shows skin erythema in mice (BALB/c, 9 weeks old) administrated with or without EC-18 (250 mg/kg/day PO) receiving total body irradiation (6.5 Gy).

FIG. 15 shows skin erythema in mice (BALB/c, 11 weeks old) administrated with or without EC-18 (250 mg/kg/day PO) receiving total body irradiation (6.5 Gy) according to the diagram in FIG. 14A.

Figure 16:
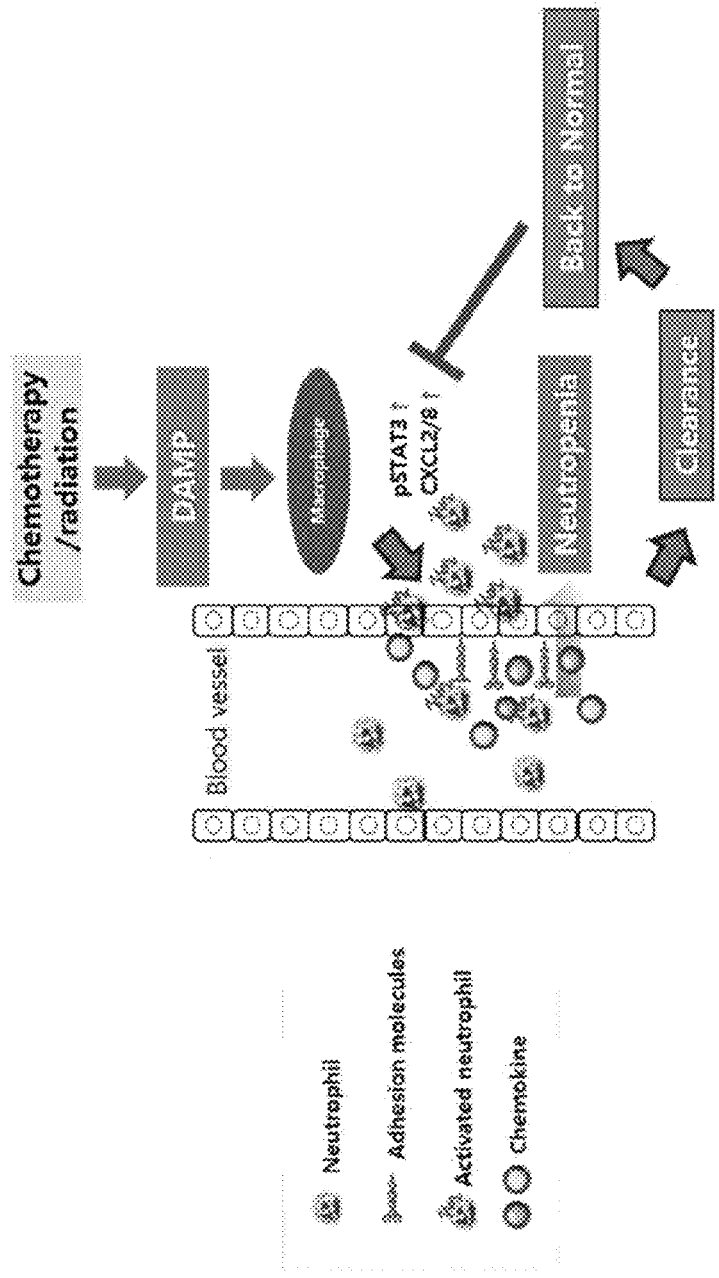

FIG. 16 illustrates a schematic mechanism of action of EC-18 in Radiation Induced Neutropenia (RIN), which illustrates that EC-18 promotes the removal of DAMP in a short period of time, inhibiting the continuous release of neutrophils from blood vessels.

Figure 17A:
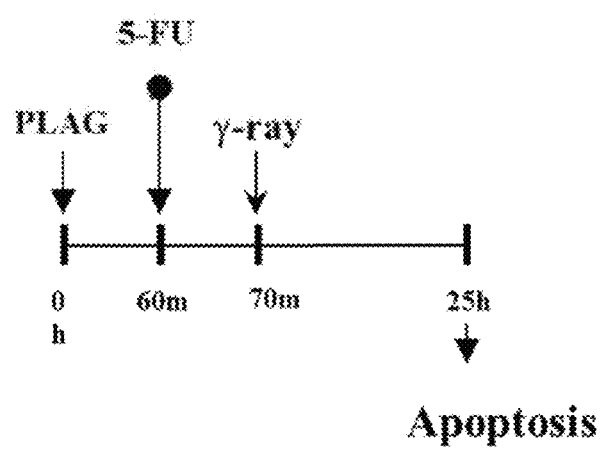

FIG. 17A depicts a schematic diagram of testing the effect of EC-18 on anti-apoptosis in HaCaT Cells. 5-FU and γ-ray-induced damage on HaCaT.

FIG. 17B shows cell number counts in the experiments depicted in FIG. 17A according to 5-FU dose, radiation and treatment with PLAG (EC-18).

FIG. 17C shows early apoptosis rate (%) in the experiments depicted in FIG. 17A according to 5-FU amount, radiation and the treatment with PLAG (EC-18).

Figure 5:
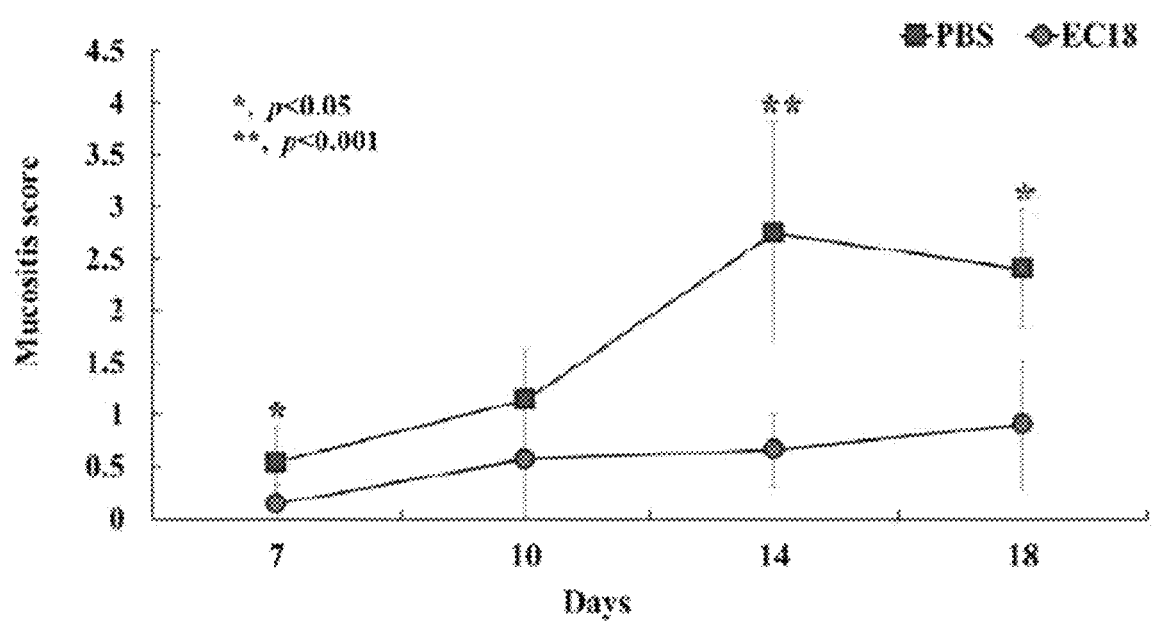
FIG. 5 shows the calculated mucositis score in PLAG (EC-18)-treated and untreated animals in an animal model of acute radiation syndrome accompanying oral mucositis.
Figure 17D:
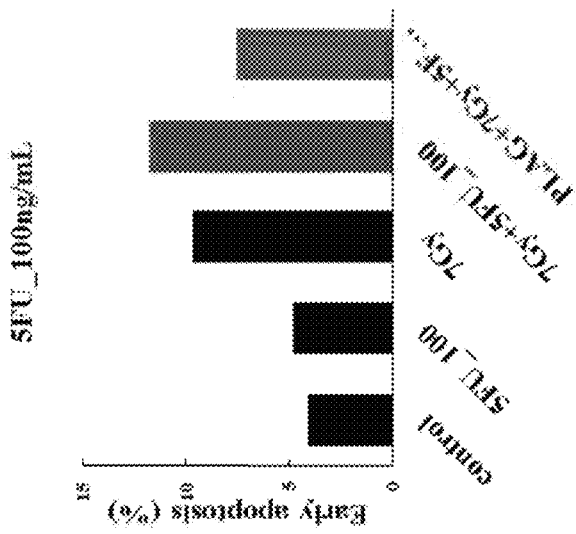

FIG. 17D shows early apoptosis rate (%) in the experiments depicted in FIG. 17A 5-at FU amount of 1 ng/mL according to radiation and the treatment with PLAG (EC-18).

Figure 17E:
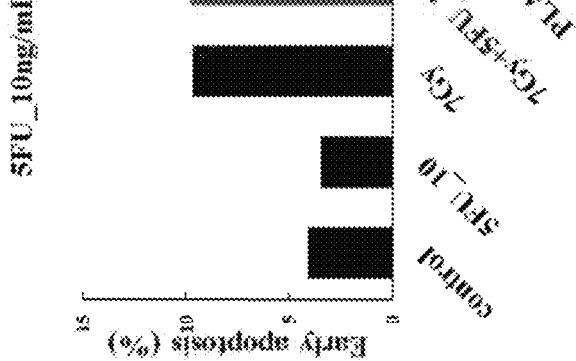

FIG. 17E shows early apoptosis rate (%) in the experiments depicted in FIG. 17A 5-at FU amount of 10 ng/mL according to radiation and the treatment with PLAG (EC-18).

Figure 17F:
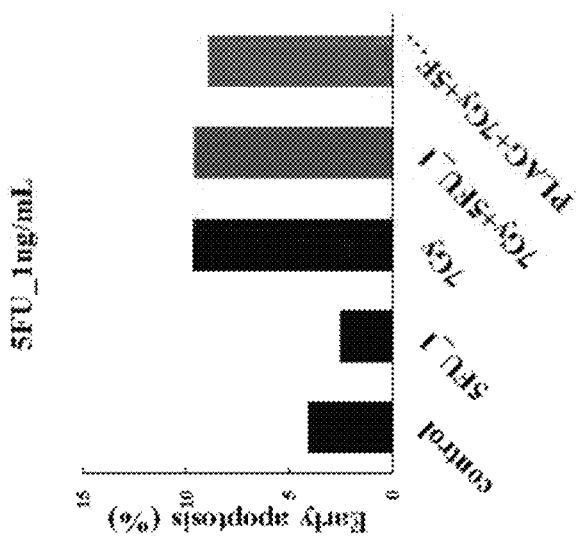

FIG. 17F shows early apoptosis rate (%) in the experiments depicted in FIG. 17A 5-at FU amount of 100 ng/mL according to radiation and the treatment with PLAG (EC-18).

FIG. 18A shows late apoptosis rate (%) in the experiments depicted in FIG. 17A according to 5-FU amount, radiation and the treatment with PLAG (EC-18).

FIG. 18B shows late apoptosis rate (%) in the experiments depicted in FIG. 17A 5-at FU amount of 1 ng/mL according to radiation and the treatment with PLAG (EC-18).

FIG. 18C shows late apoptosis rate (%) in the experiments depicted in FIG. 17A 5-at FU amount of 10 ng/mL according to radiation and the treatment with PLAG (EC-18).

FIG. 18D shows late apoptosis rate (%) in the experiments depicted in FIG. 17A 5-at FU amount of 100 ng/mL according to radiation and the treatment with PLAG (EC-18).

Figure 19A:
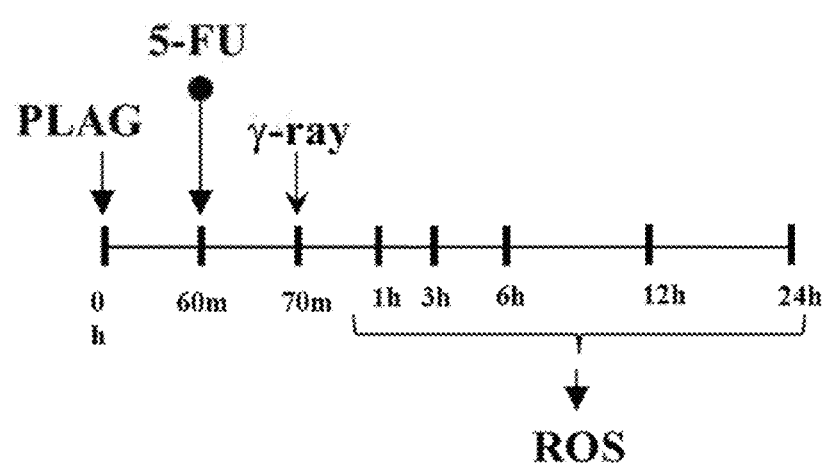

FIG. 19A illustrates a schematic diagram of testing the effect of EC-18 on intracellular ROS expressions in HaCaT Cells. 5-FU and γ-ray-induced damage on HaCaT.

Figure 19B:
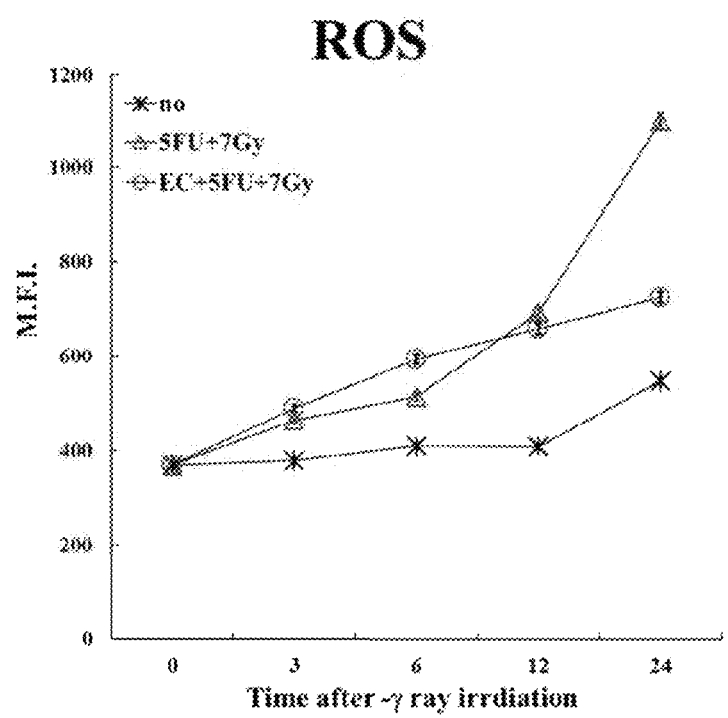

FIG. 19B shows ROS measurements in HaCaT Cells exposed to 7 Gy of γ-radiation after treatment of EC-18 after irradiation or without treatment.

FIG. 19C shows cell counts in HaCaT Cells against ROS expression when the cells were exposed to 7 Gy of γ-radiation after treatment of EC-18 after irradiation or without treatment (top: 6 hours after exposure, bottom: 24 hours after exposure).

Figure 20:
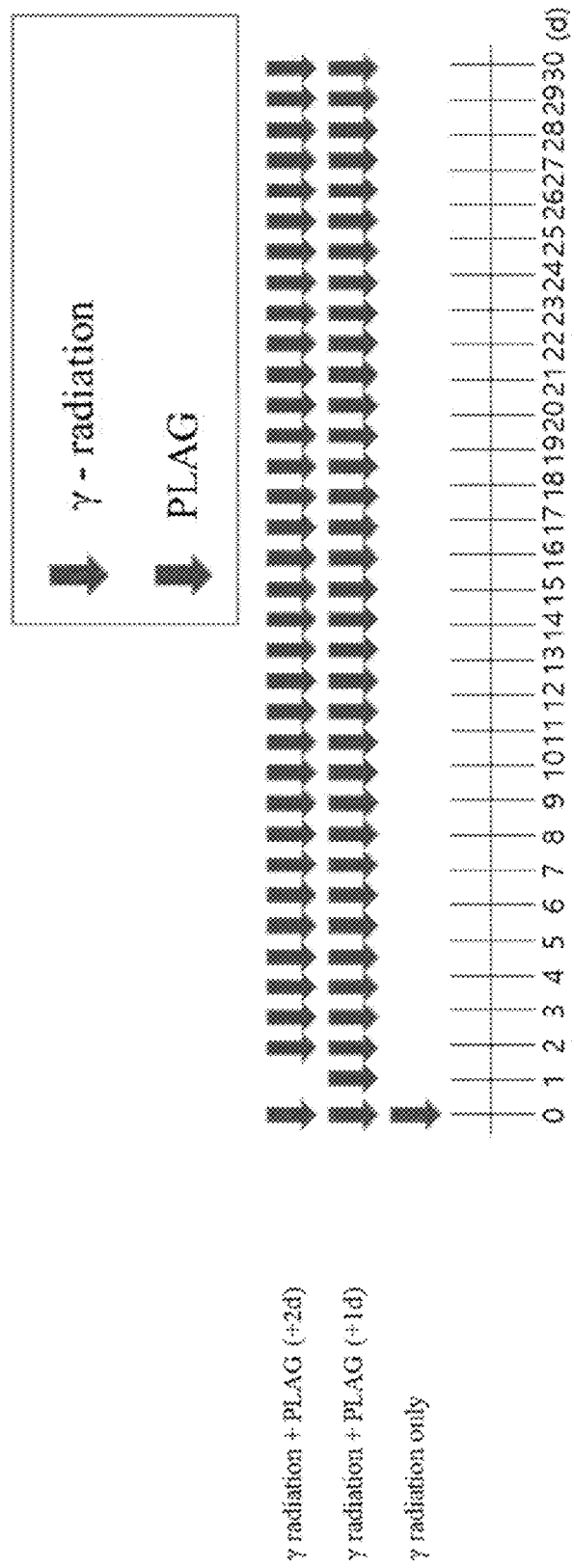

FIG. 20 illustrates a diagram for an exemplary experiment to test survival rates of treatment of EC-18 (PLAG) on 6.5 Gy of γ-radiation induced Acute Radiation Syndrome animal model (mouse, BALB/c, 11 weeks old).

Figure 21:
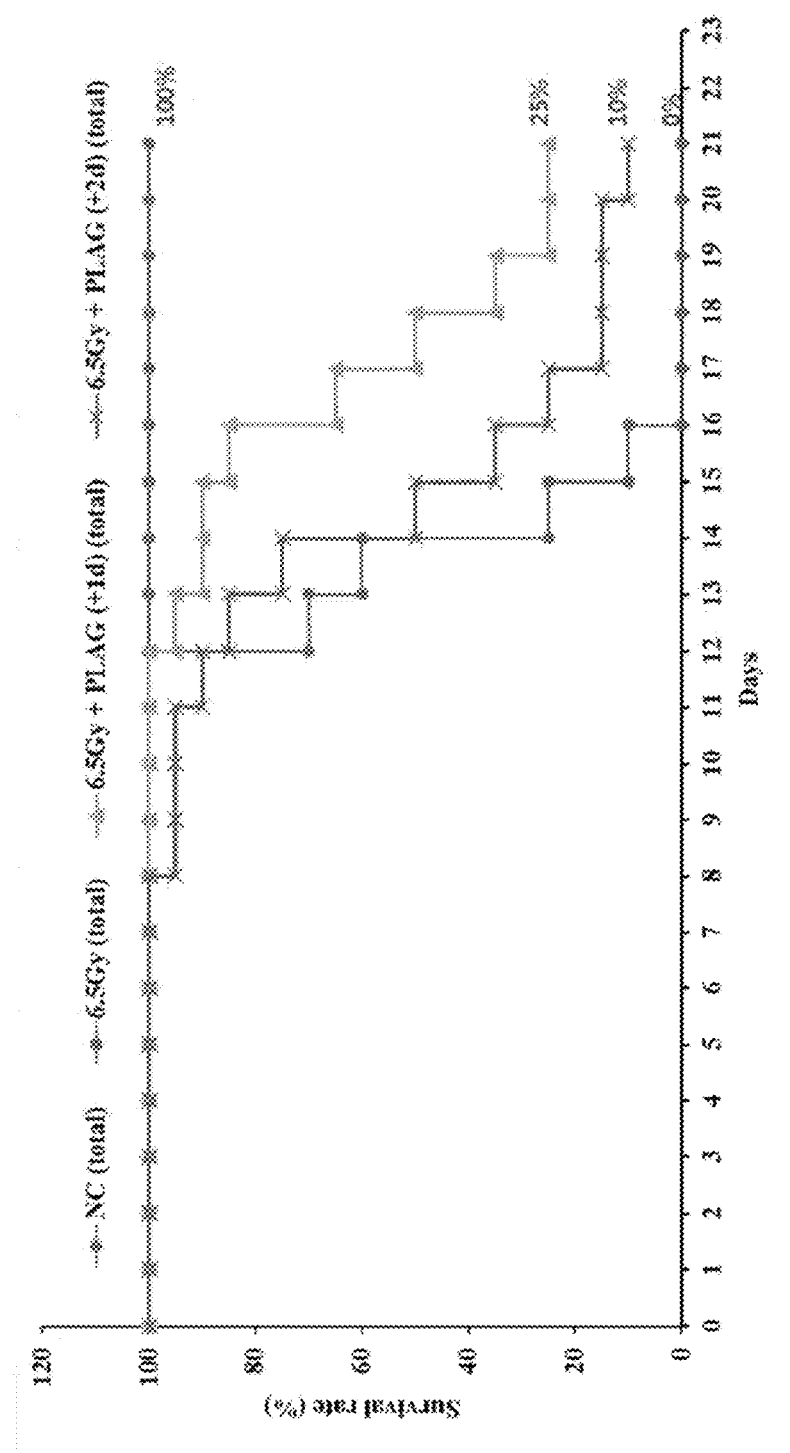

FIG. 21 shows survival curves for Balb/c mice (n=20 per group) not exposed to total body radiation (control), exposed to 6.5 Gy of γ-radiation (total body; non-treated) and treated with EC-18 beginning at day 1 (24 hours after radiation exposure) or day 2 (48 hours after radiation exposure).

Figure 22:
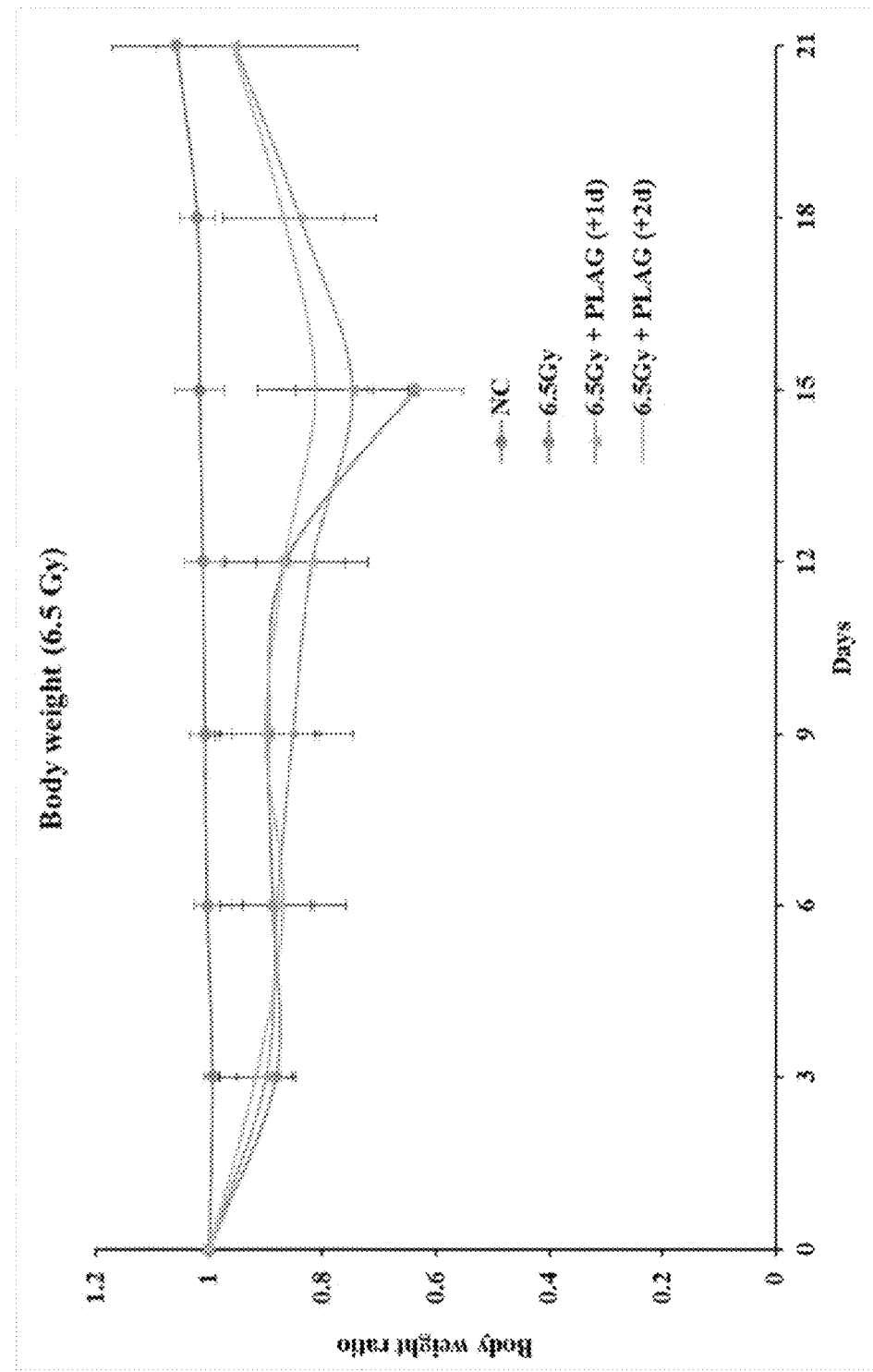

FIG. 22 shows the body weight of Balb/c mice not exposed, exposed to 6.5 Gy of γ-radiation, and exposed to 6.5 Gy of γ-radiation (total body) treated with EC-18 24 or 48 hours after irradiation.

Figure 23:
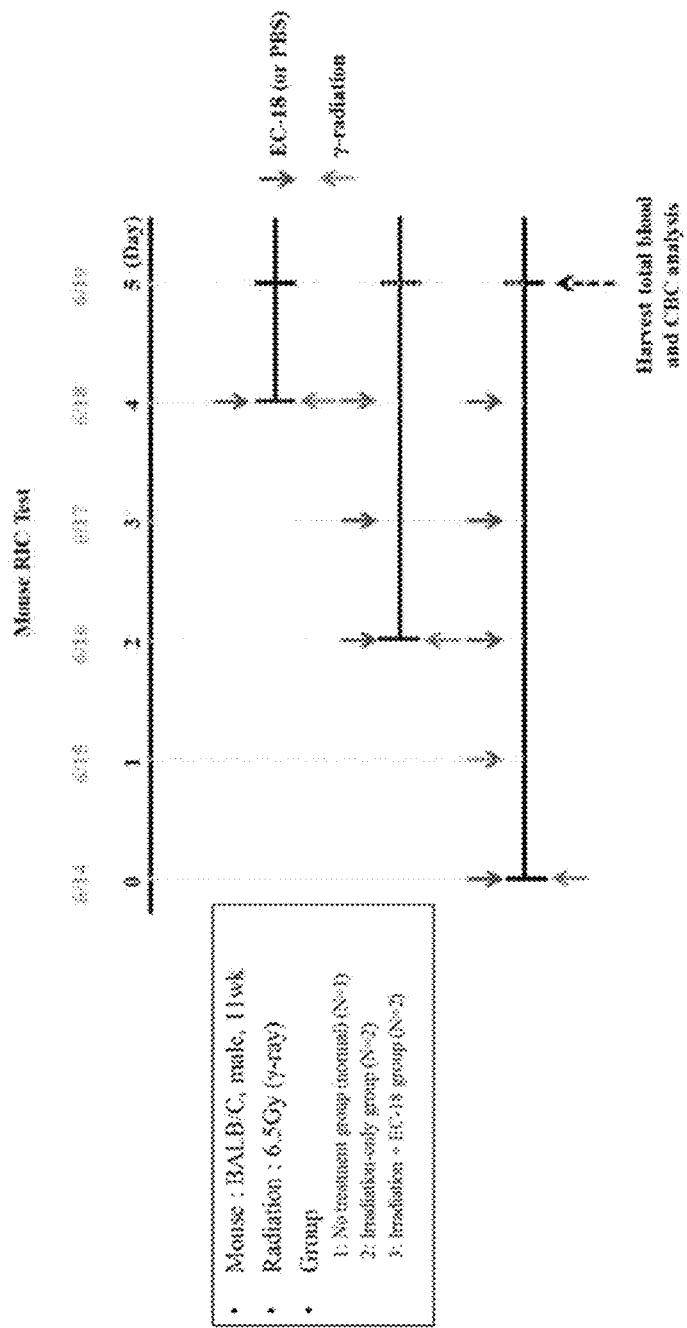

FIG. 23 is illustrates a diagram for an exemplary experiment to test radiation induced coagulopathyin a mouse model.

Figure 24:
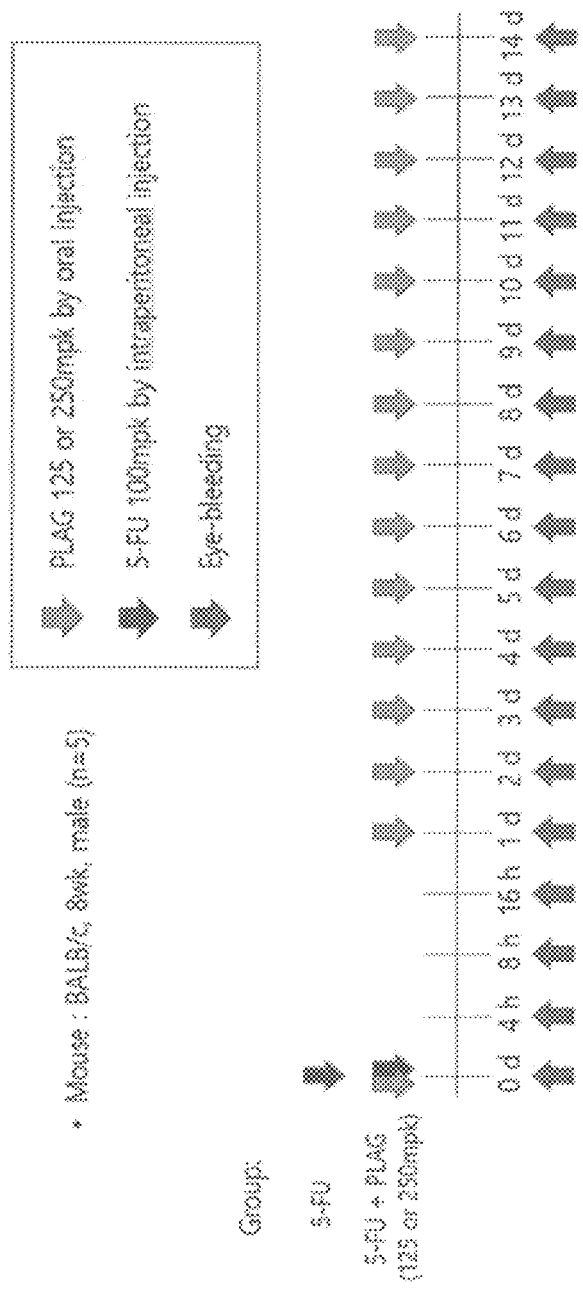

FIG. 24 depicts a diagram for an exemplary experiment including three groups (5-FU only, 5-FU+PLAG 125 mg/kg, 5-FU+PLAG 250 mg/kg) to check time kinetics of neutrophil in 5-FU (100 mg/kg) induced neutropenia.

Figure 25:
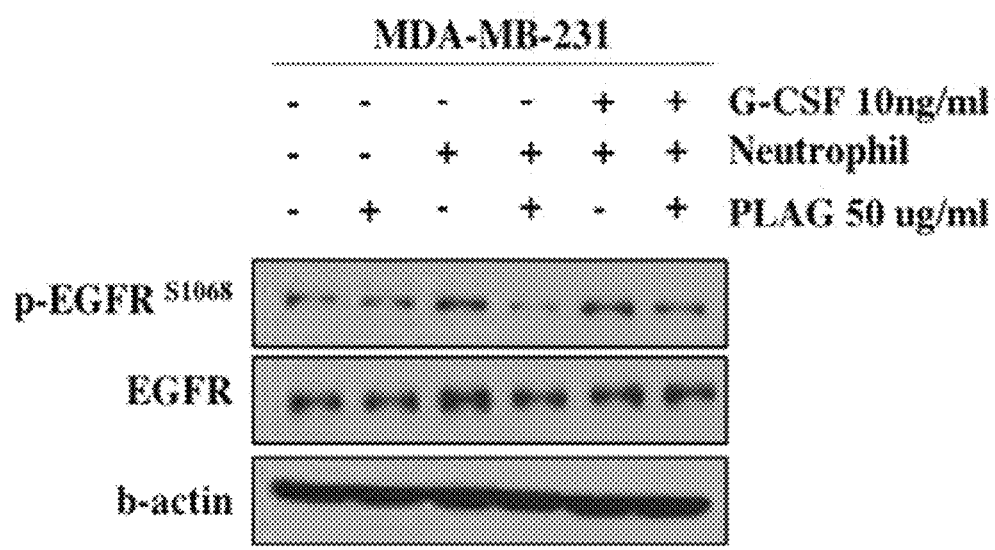

FIG. 25 shows in vitro experiments comparing the effects of EC-18 against G-CSF by western blot.

FIG. 26 is a table illustrating a comparison EC-18 with G-CSF.

Figure 27:
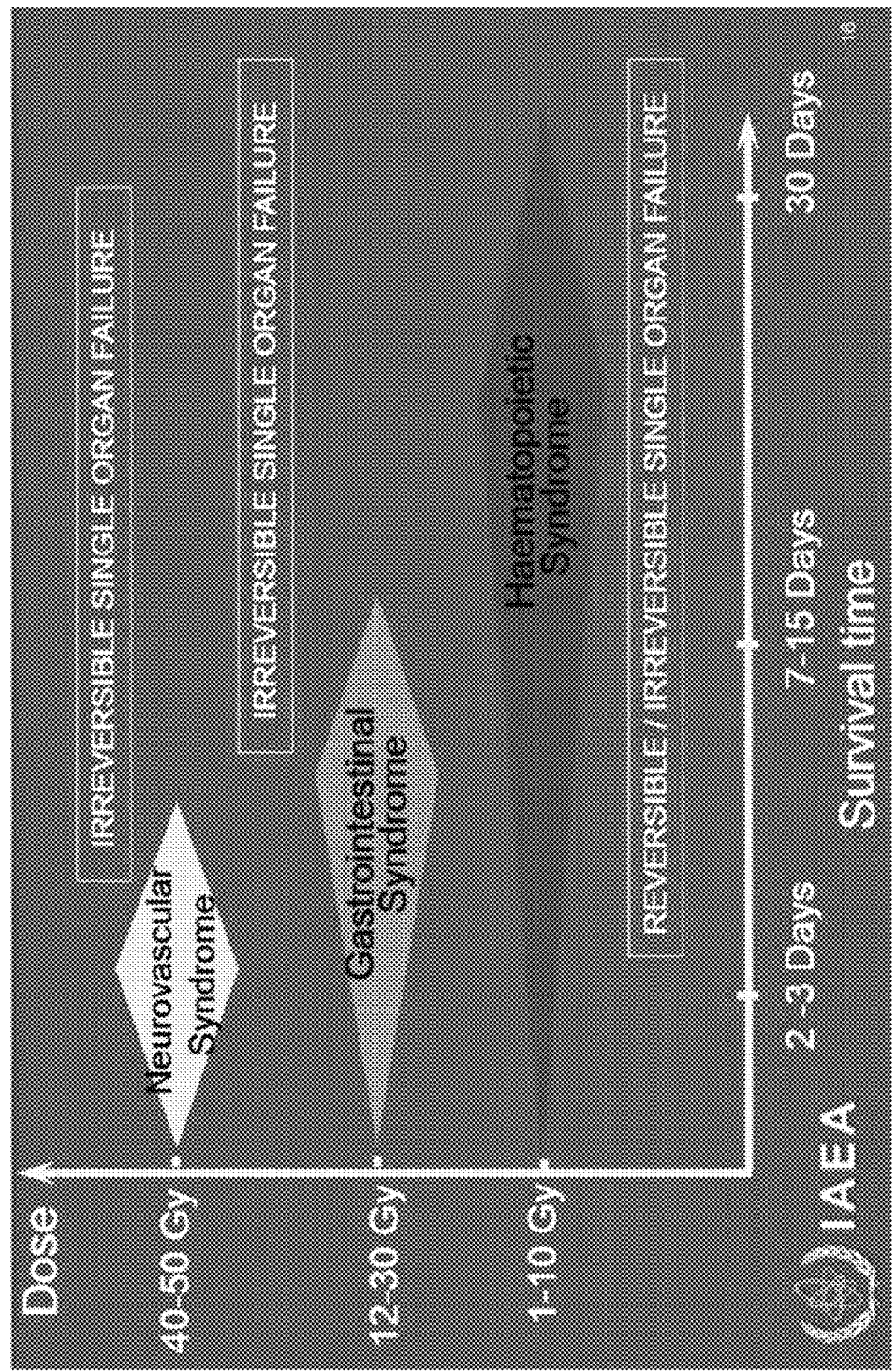

FIG. 27 depicts a diagram of survival time of patients exposed to radiation and various ARS subsyndromes.

Figure 28A:
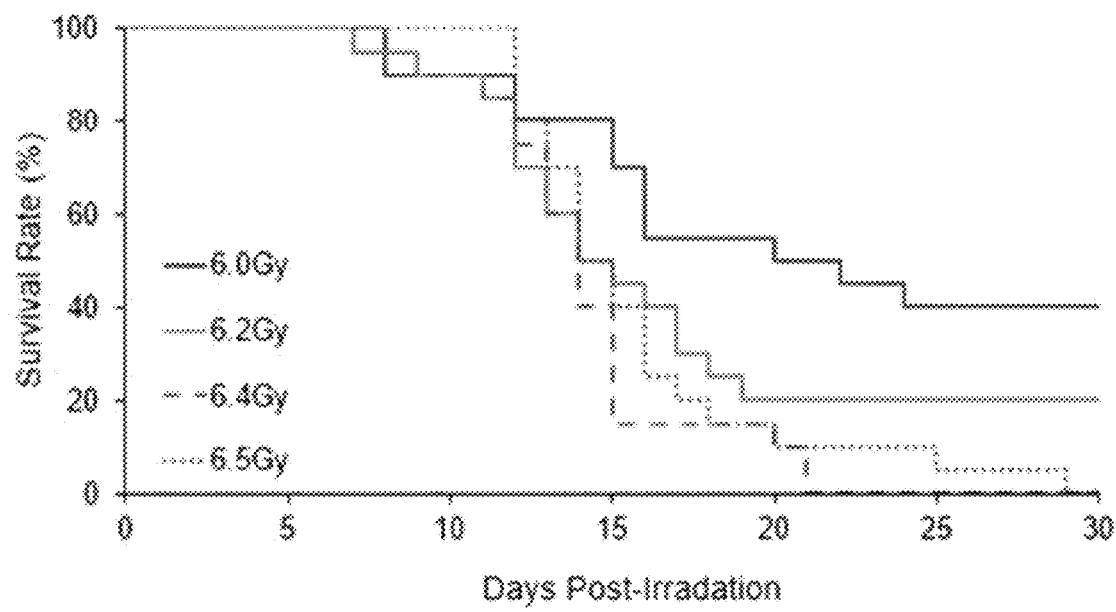
Figure 28B:
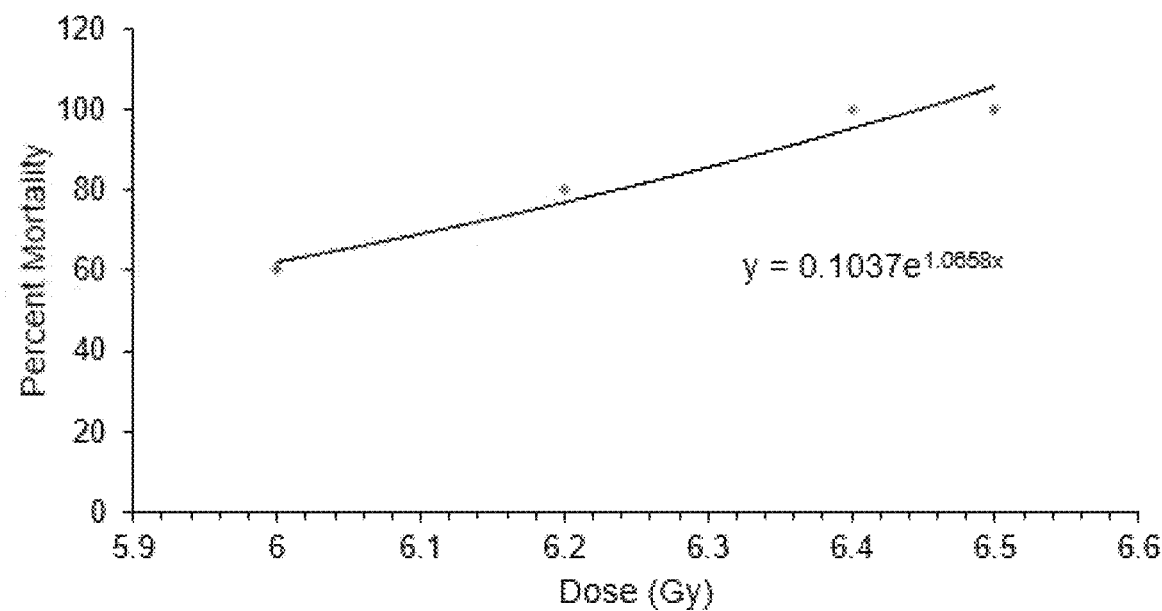

FIG. 28A shows survivability of irradiated mice with each γ-radiation dose over 30 days of observation. FIG. 28B shows radiation dose relationship (DRR) using probit models of BALB/c mice exposed to various doses of γ-radiation.

Figure 29:
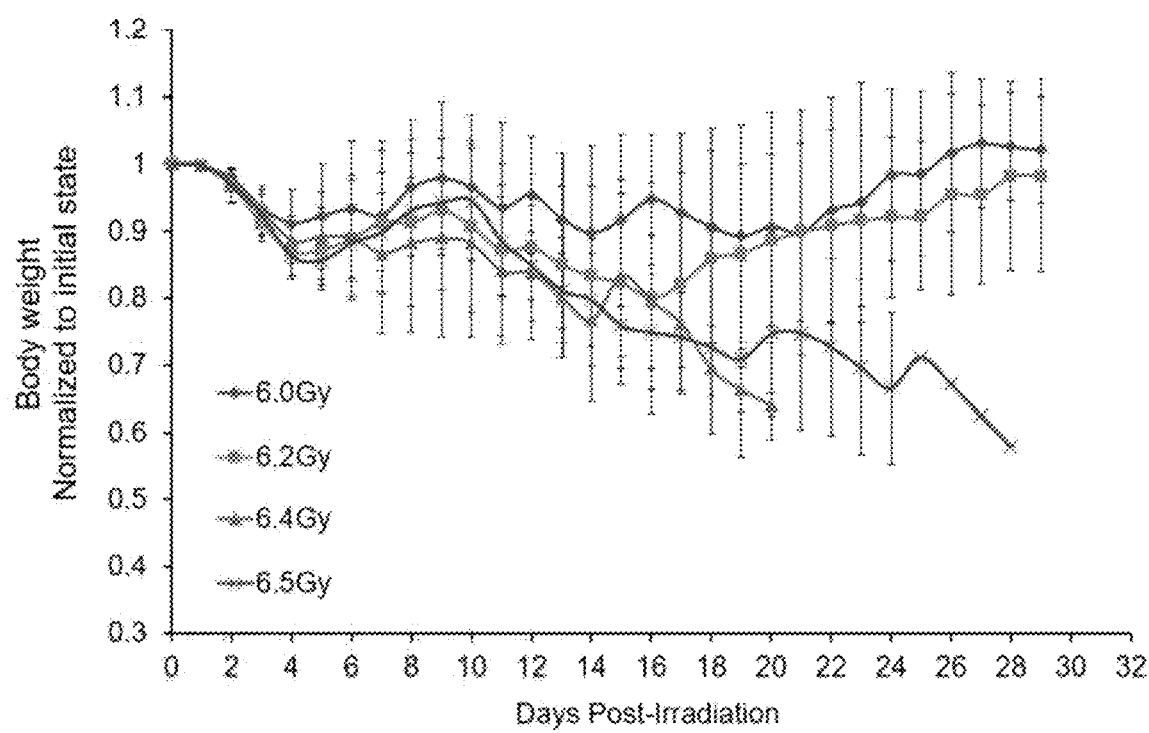

FIG. 29 shows that the normalized body weight changes of irradiated mice exposed to various doses of γ-radiation.

Figure 30A:
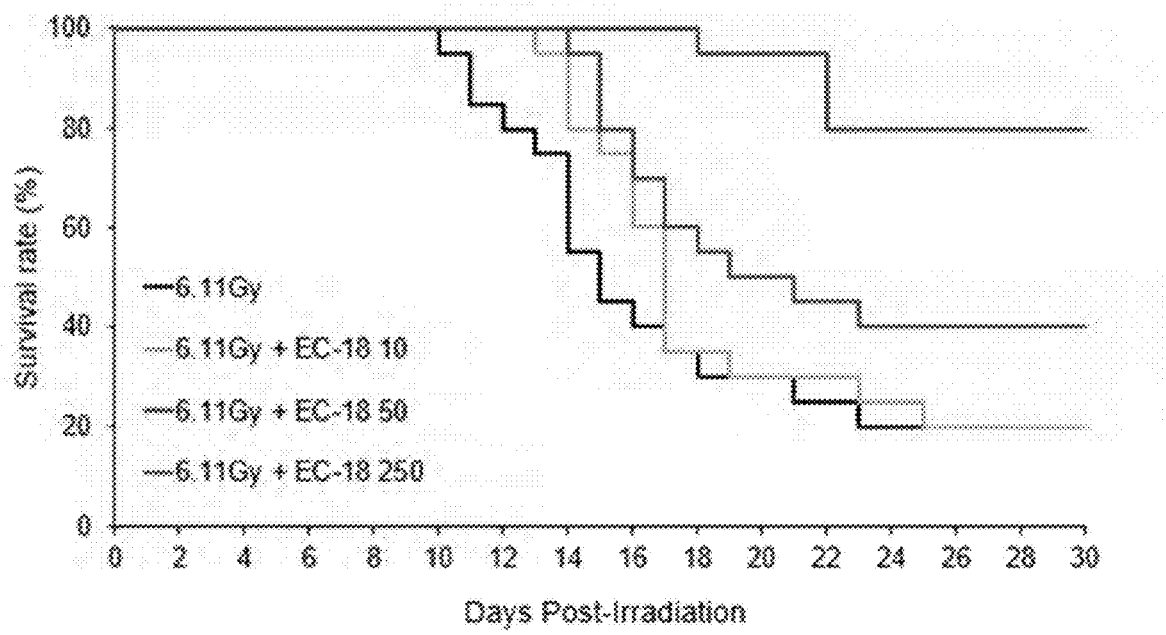
Figure 30B:
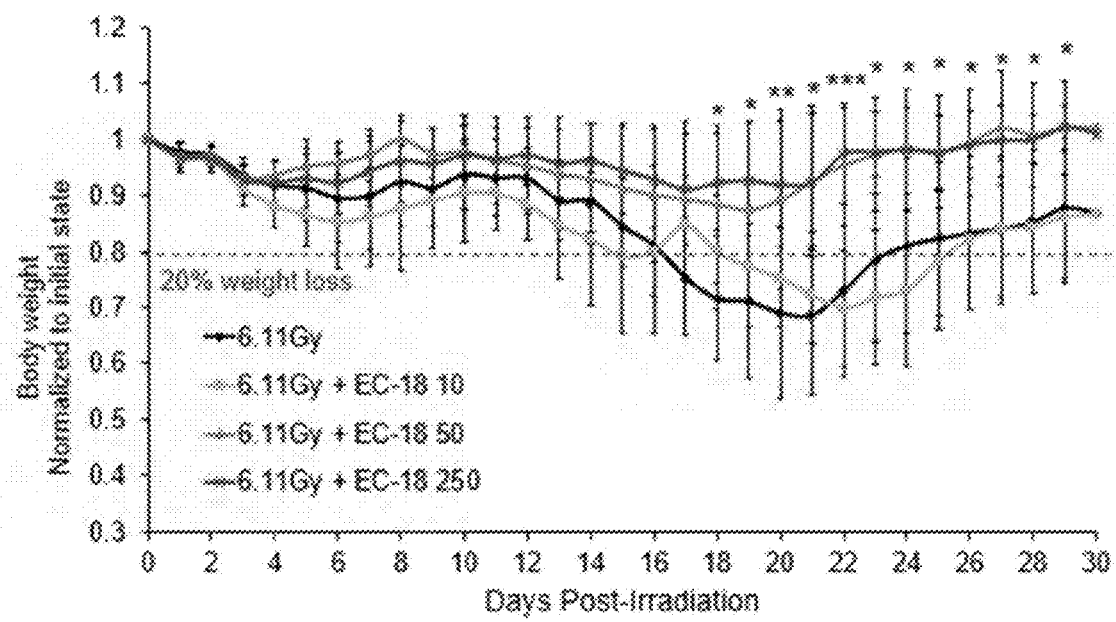

FIGS. 30A-B show therapeutic effect of EC-18 administration in γ-radiation-induced ARS. FIG. 30A shows the survival rate and FIG. 30B shows body weight loss of irradiated mice with a dose of 6.11 Gy of γ-radiation. * $p<0.05$,  $p<0.01$, * $p<0.005$, for 6.11Gy versus 6.11Gy+EC-18 250 mg/kg.

Figure 31A:
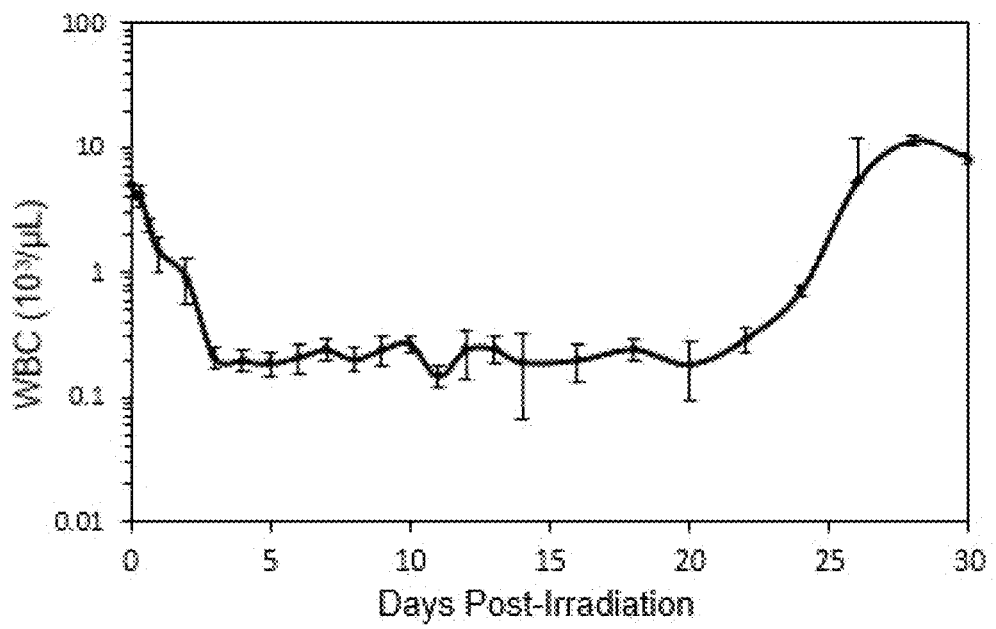
Figure 31B:
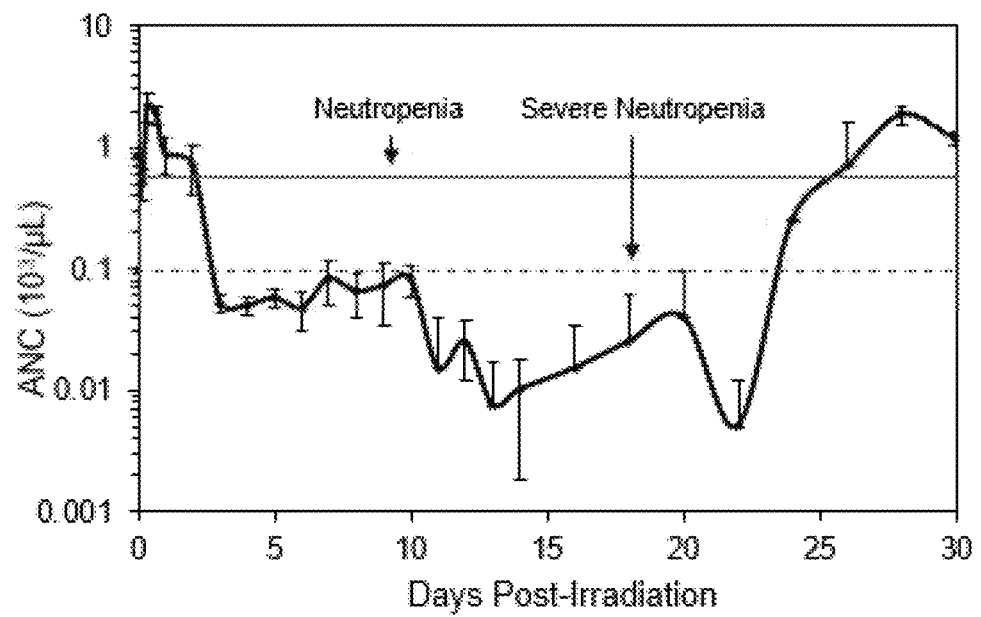
Figure 31C:
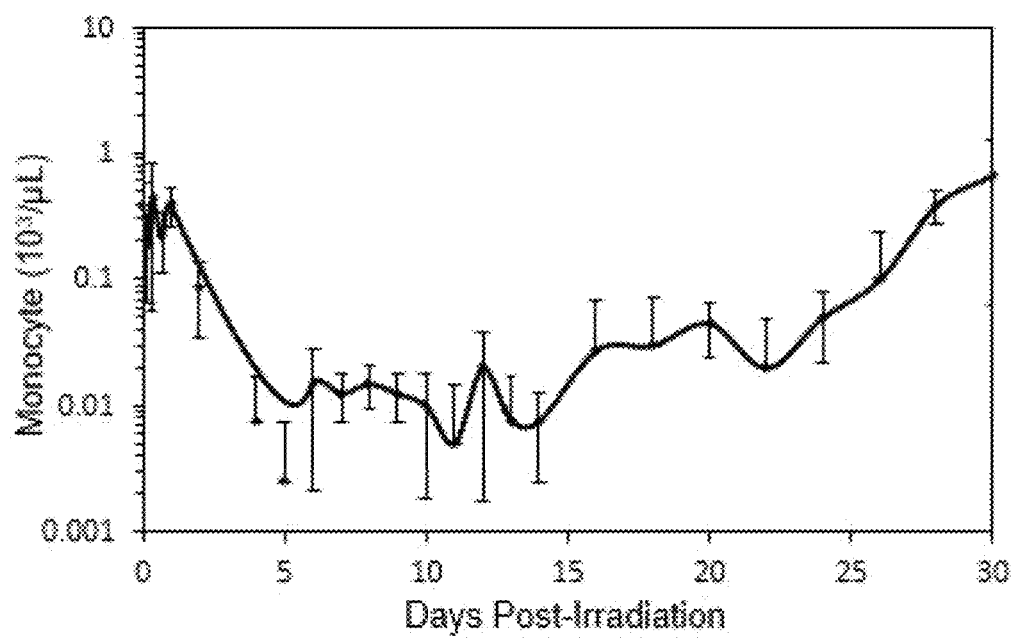
Figure 31D:
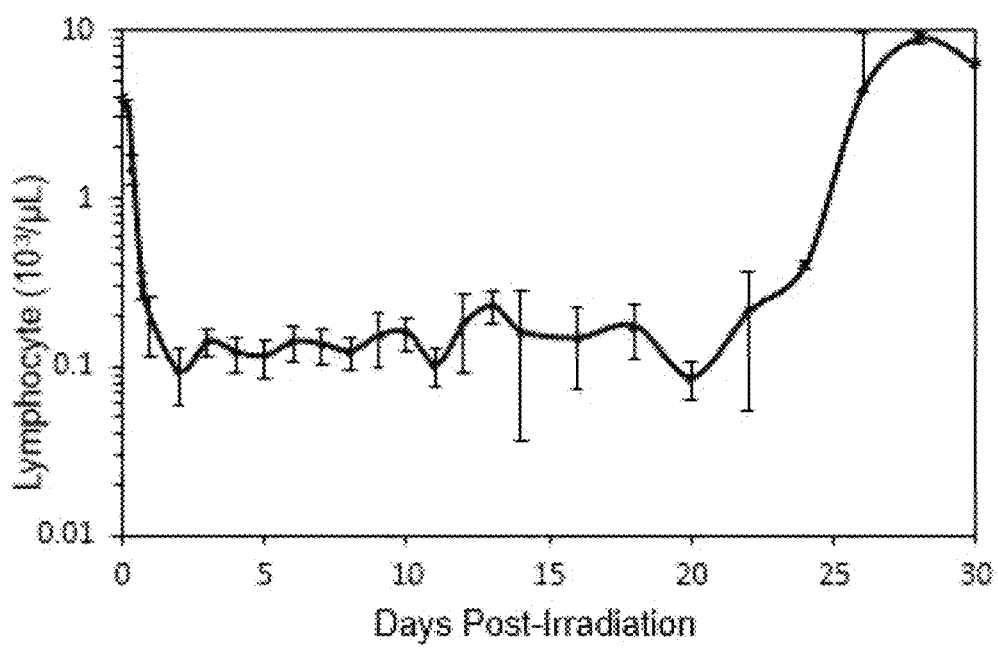
Figure 31E:
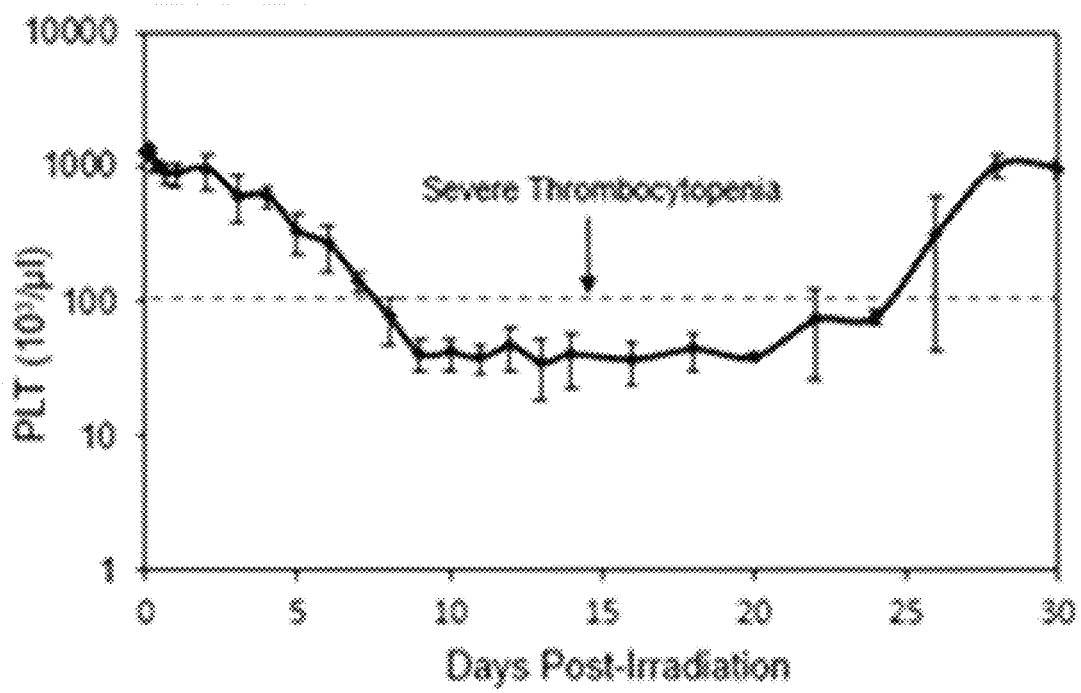
Figure 31F:
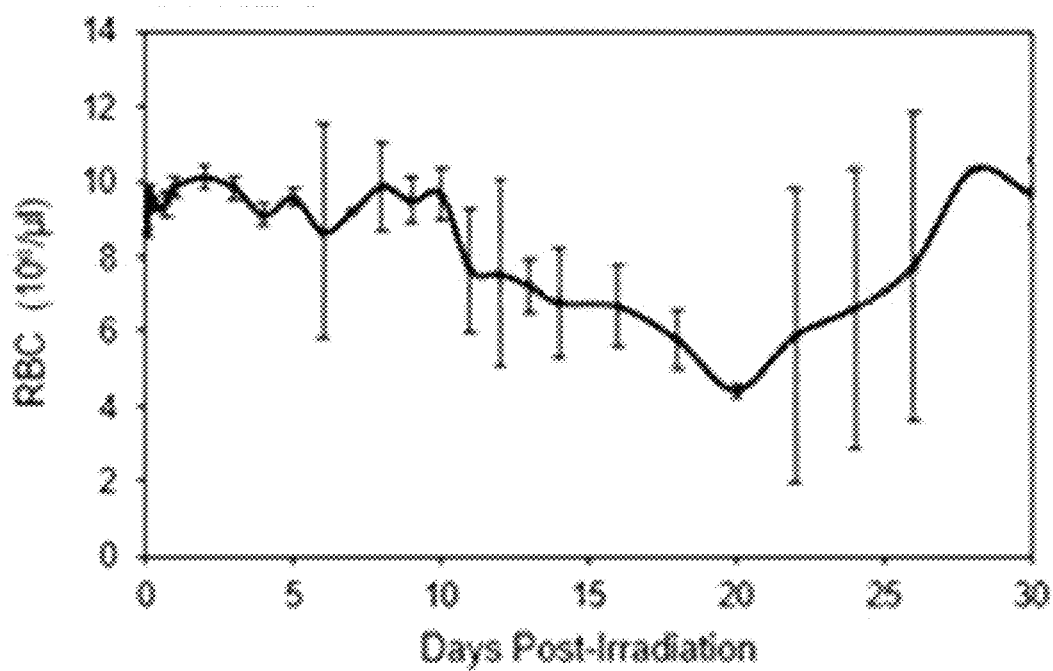

FIGS. 31A-F are CBC parameters in mice exposed to 6.11Gy of γ-radiation. FIGS. 31A through 31F show the white blood cell (WBC; FIG. 31A), absolute Neutrophil count (ANC; FIG. 31B), monocyte (FIG. 31C), absolute Lymphocyte count (ALC; FIG. 31D), platelet count (PLT; FIG. 31E) and red blood cell count (RBC; FIG. 31F), respectively. n=5 mice/cohort.

Figure 32A:
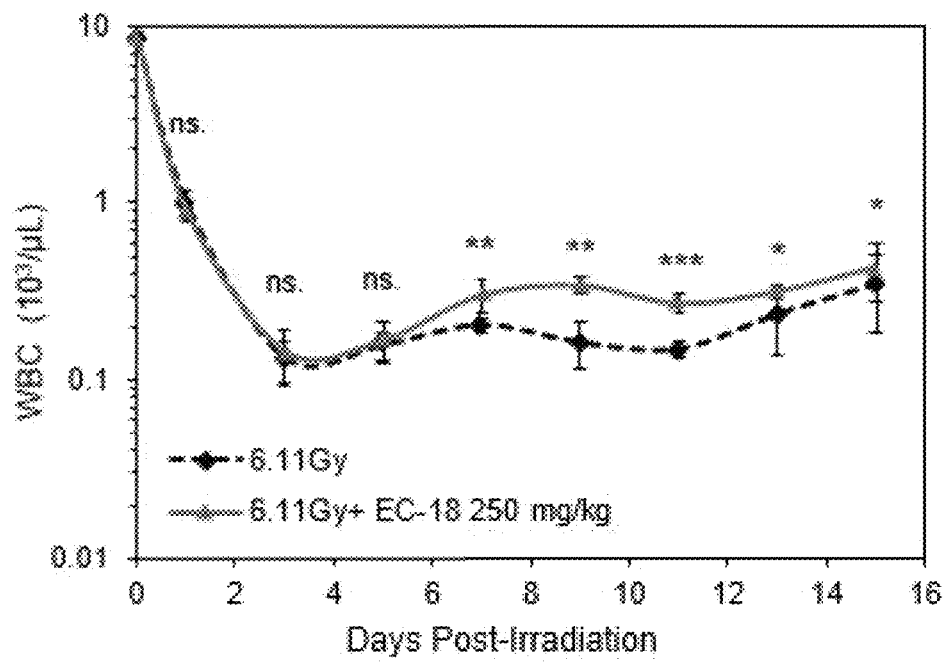
Figure 32B:
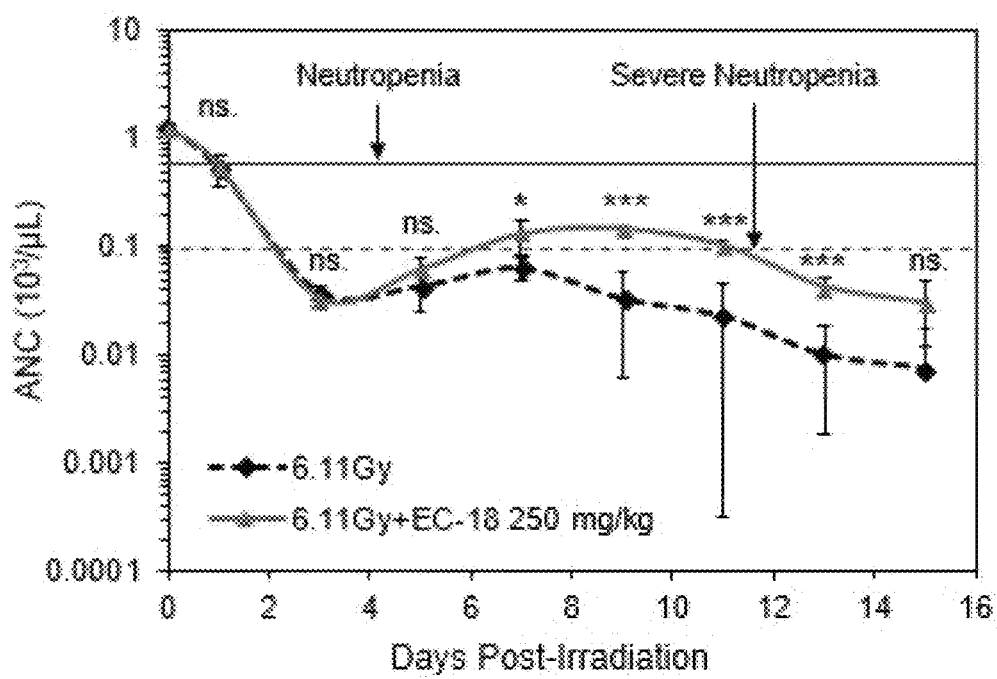
Figure 32C:
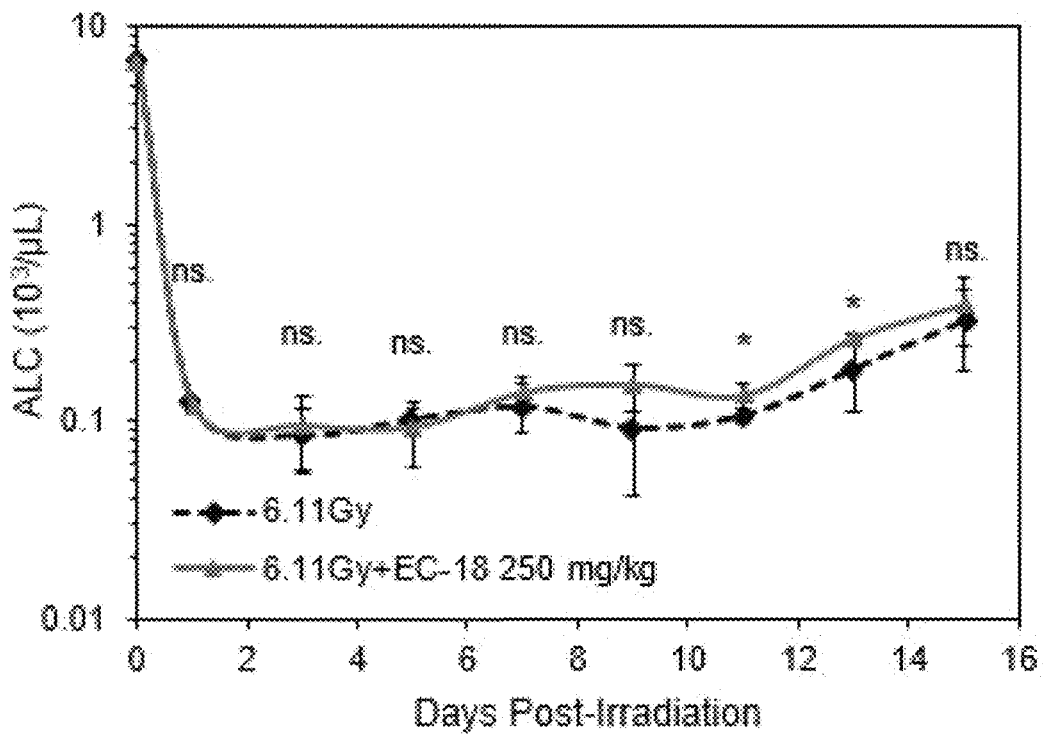
Figure 32D:
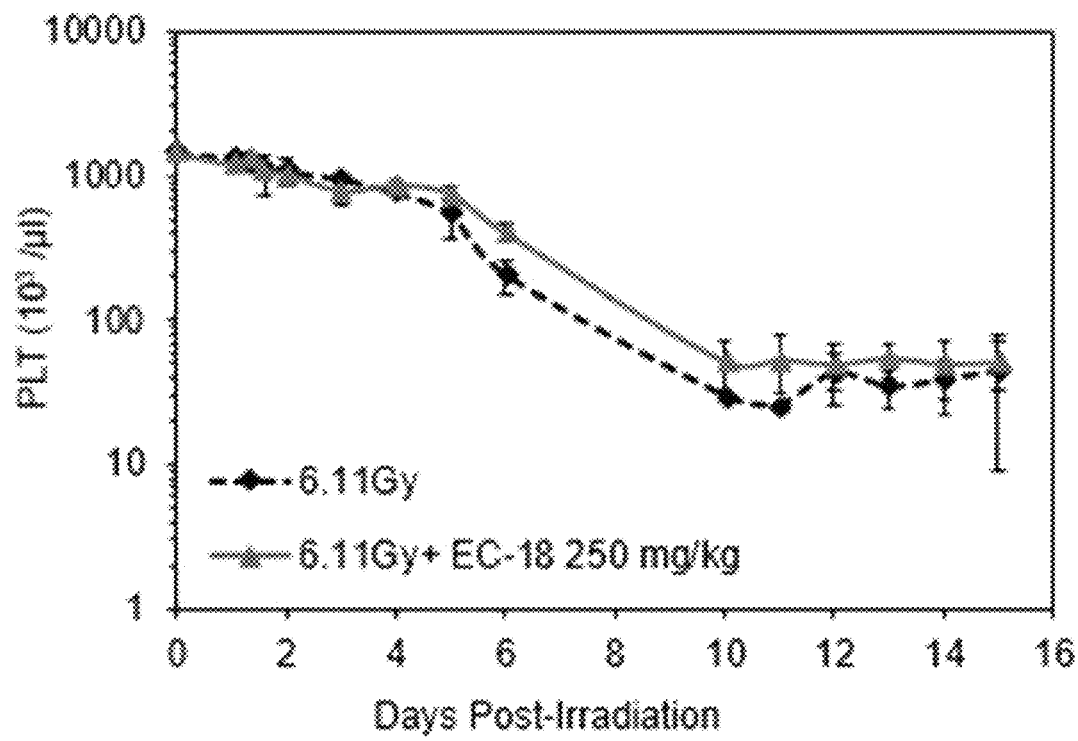
Figure 32E:
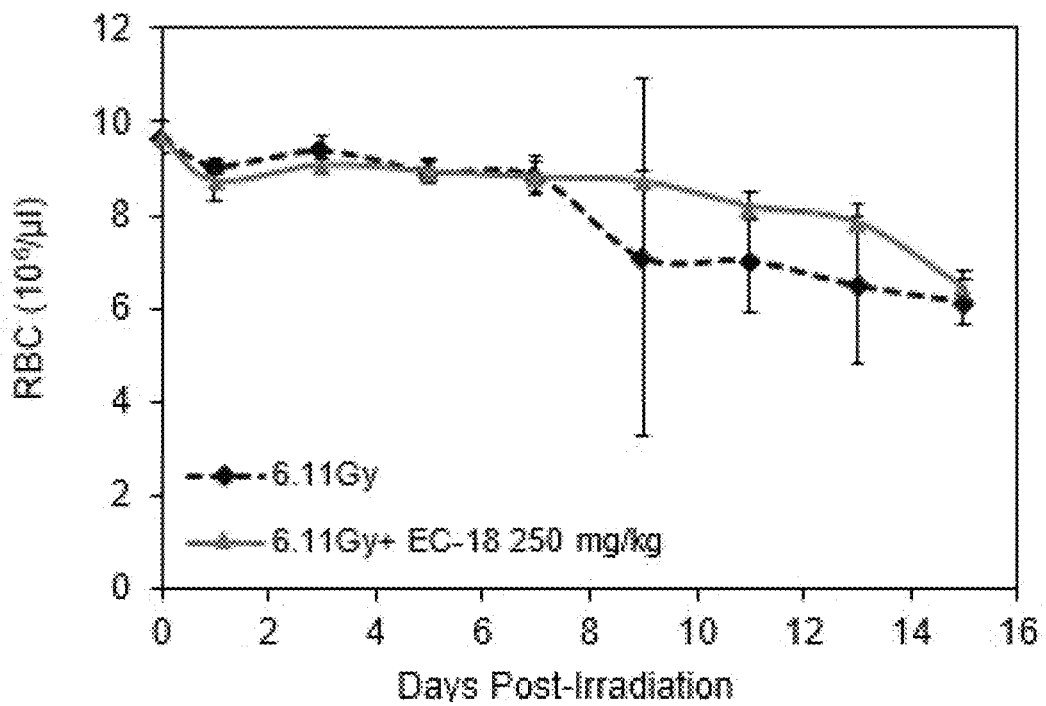
Figure 32F:
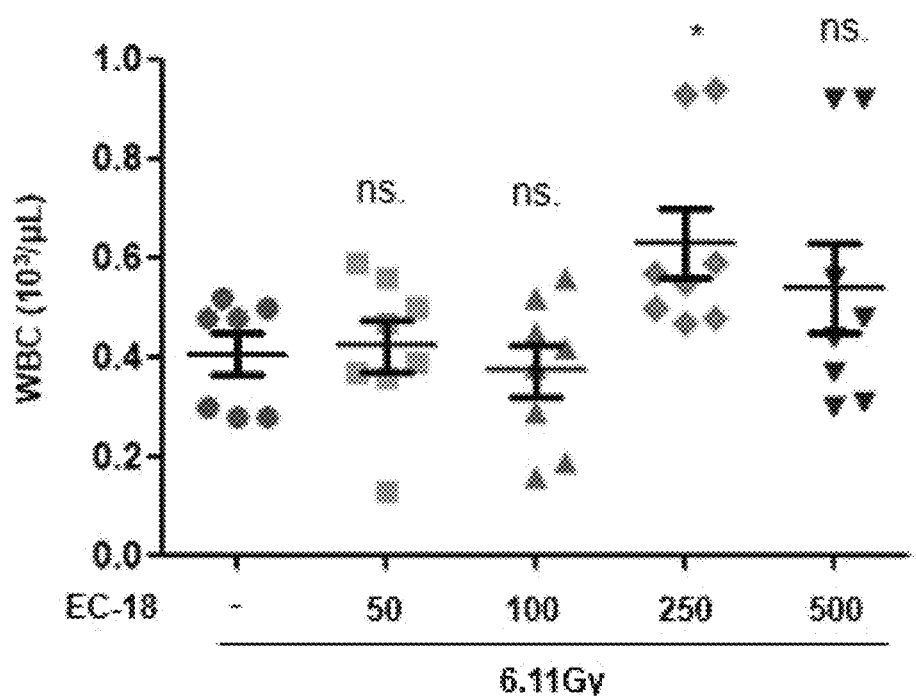
Figure 32G:
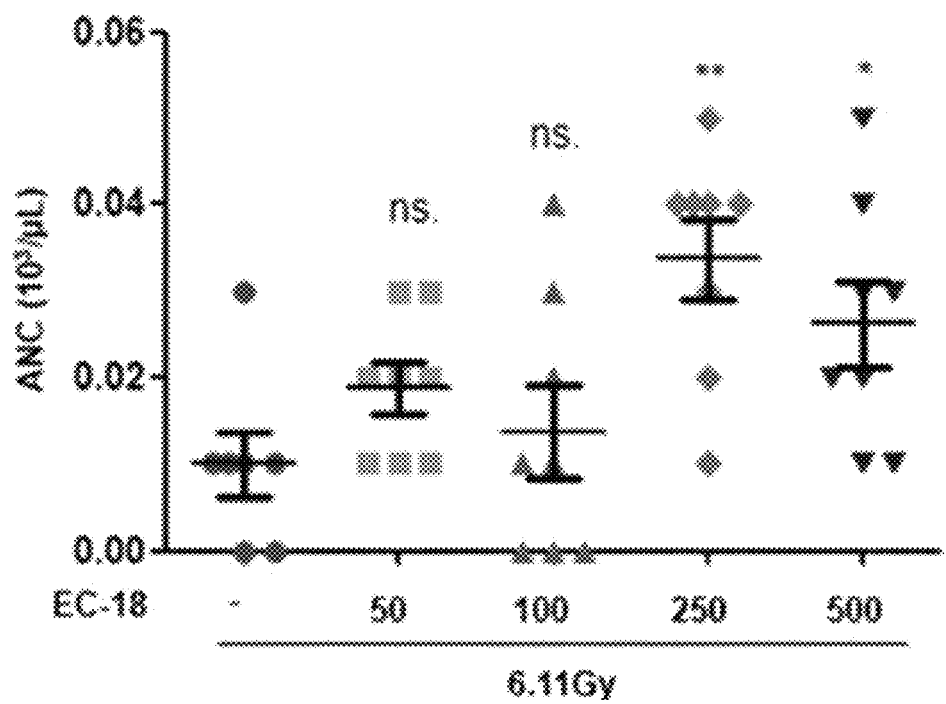
Figure 32H:
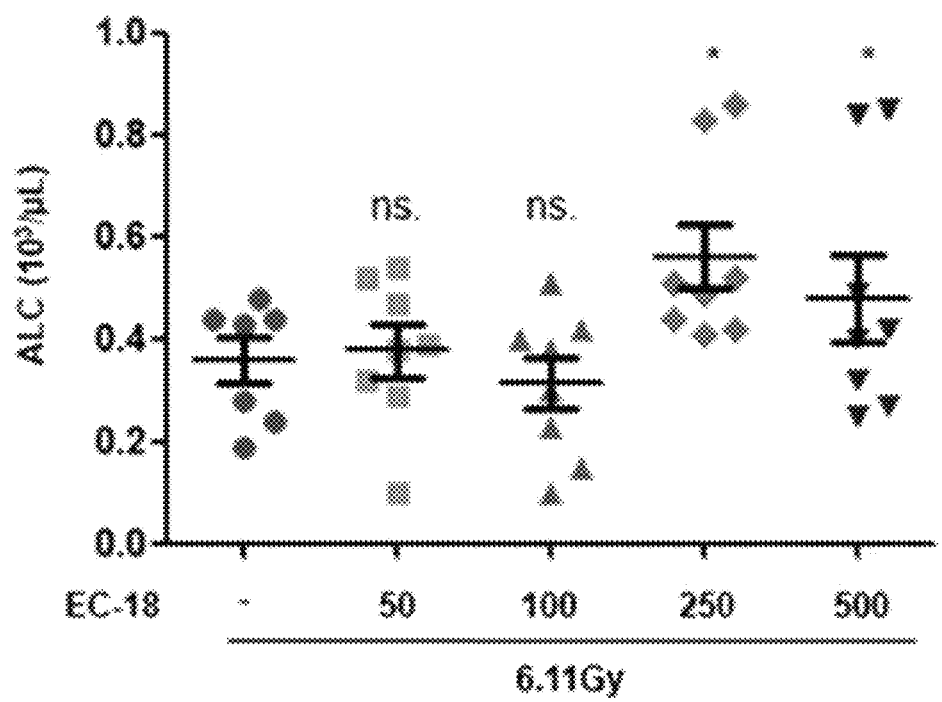
Figure 32I:
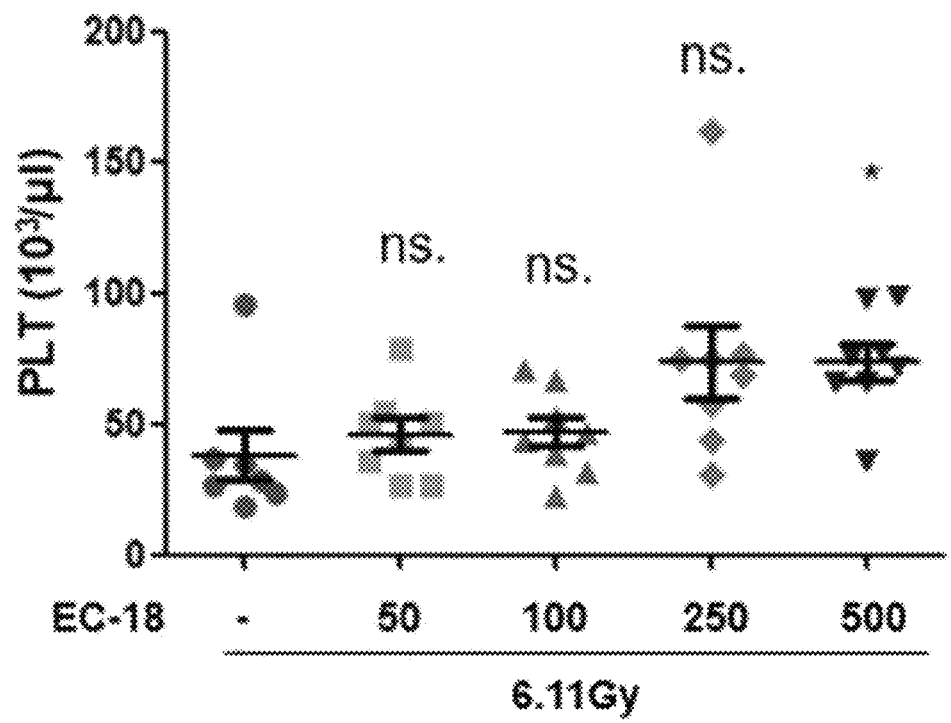
Figure 32J:
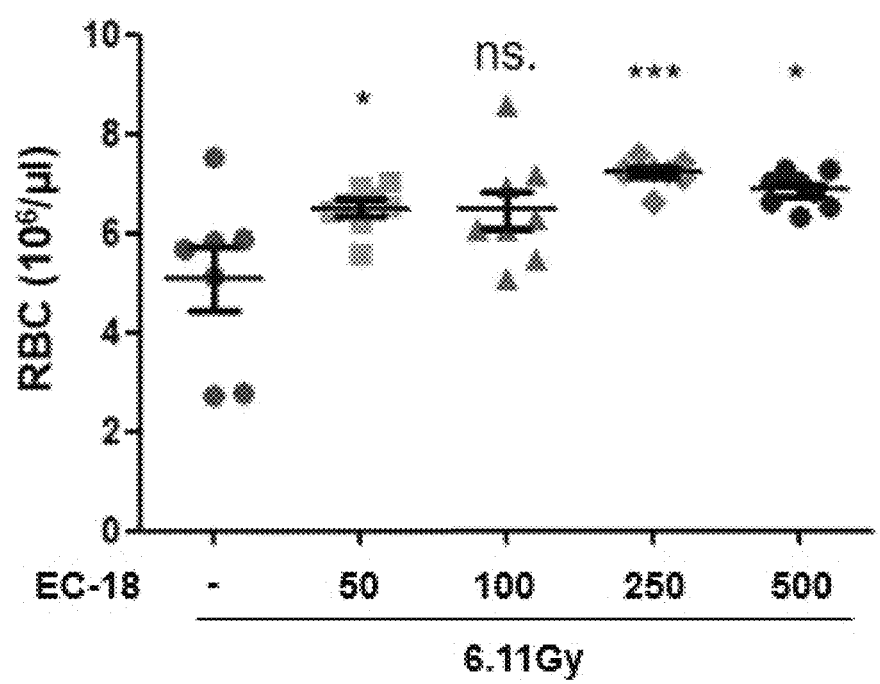

FIGS. 32A-J show therapeutic effect of EC-18 administration on CBC parameters in mice exposed to 6.11Gy of γ-radiation. FIGS. 32A through 32E show the time course of the white blood cell count (WBC; FIG. 32A), absolute Neutrophil count (ANC; FIG. 32B), absolute Lymphocyte count (ALC; FIG. 32C), platelet count (PLT; FIG. 32D) and red blood cell count (RBC; FIG. 32E) over 15 days, respectively. FIGS. 32F through FIG. 32J show the dose effect of EC-18 administration on WBC (FIG. 32F), ANC (FIG. 32G), ALC (FIG. 32H), PLT (FIG. 32I) and BRC (FIG. 32J) on day 15, respectively. ns; not significant, * $p<0.05$,  $p<0.01$, * $p<0.005$.

Figure 33A:
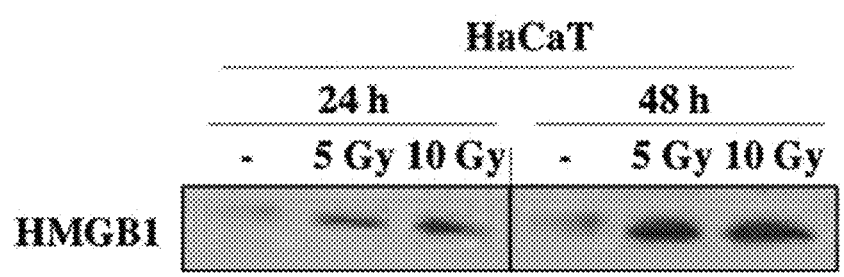
Figure 33B:
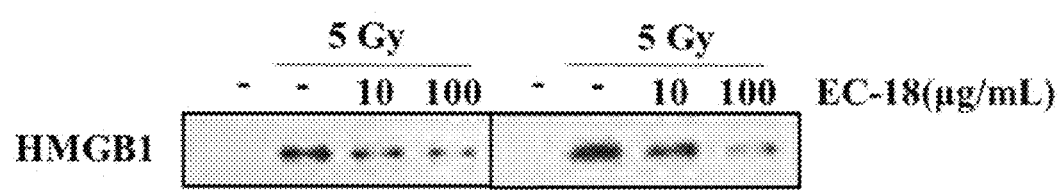

FIGS. 33A-33B show that EC-18 attenuates DAMP secretion. The radiation-induced DAMP removal was evaluated in HaCaT (human keratinocyte) cells exposed with γ-radiation from a $^{60}$Co radiation source (0.833 Gy/minute) without EC-18 (FIG. 33A) and with treatment EC-18 (FIG. 33B).

Figure 34:
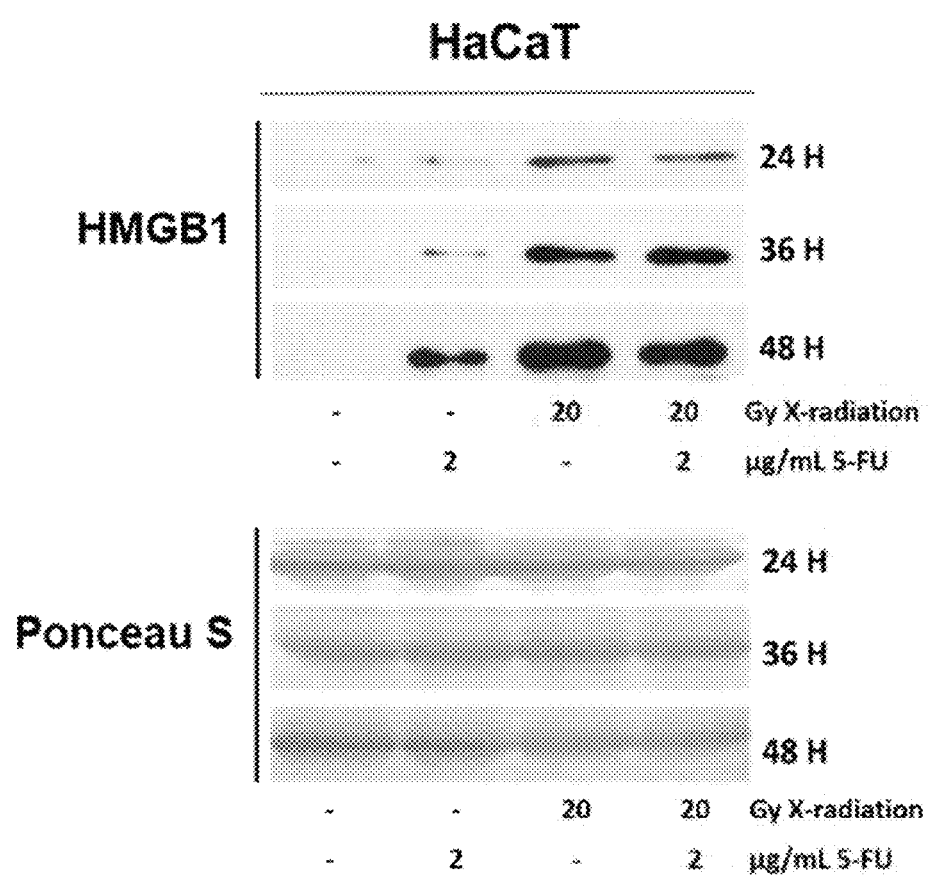

FIG. 34 shows that HMGB1 was released from HeCaT cells treated with X-radiation or anti-cancer drug (5-FU). Ponceau S staining was used to demonstrate comparable protein loading.

FIGS. 35A-35D show that EC-18 mitigates the necroptosis signaling pathway and the release of DAMPs.

Figure 36A:
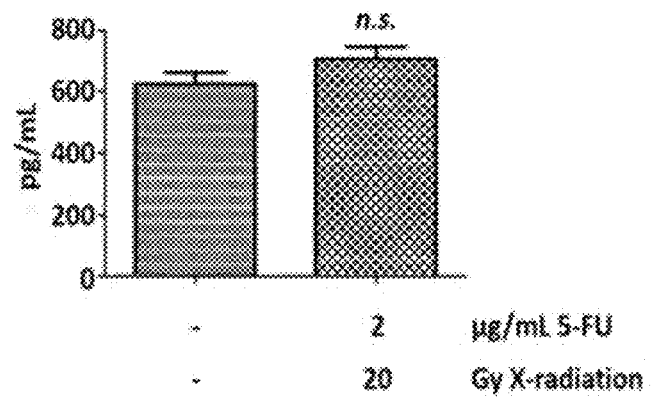
Figure 36B:
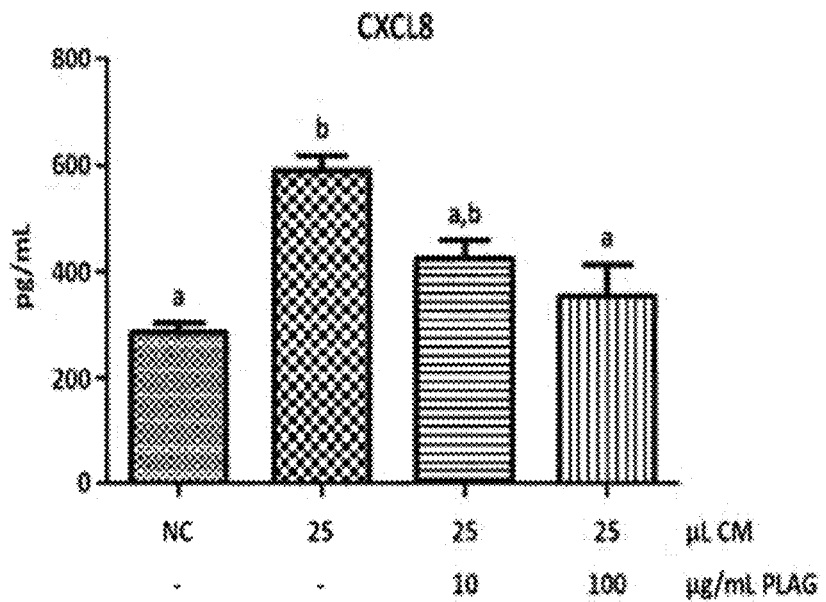
Figure 36C:
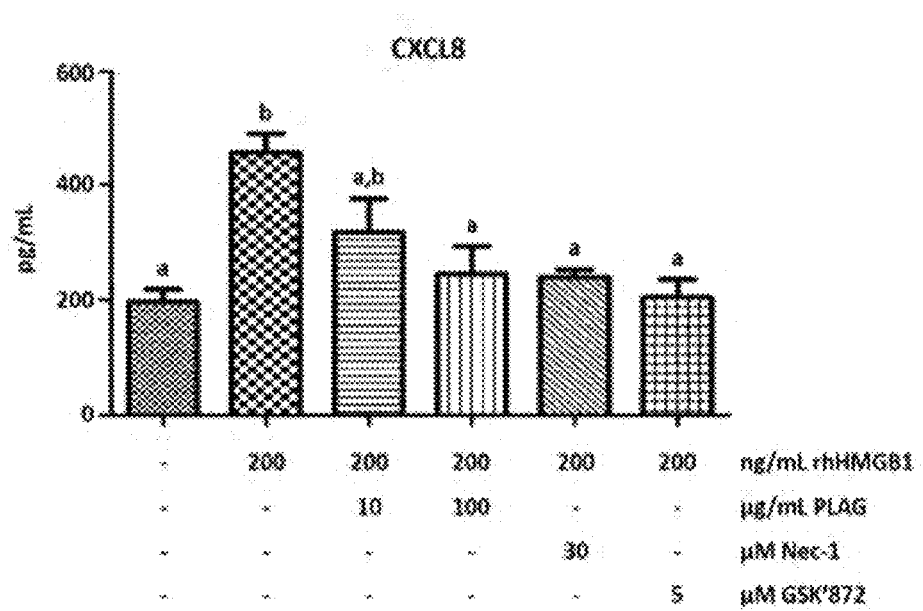

FIGS. 36A-36C show that EC-18 modulates the release of CXCL8 induced by CM and rhHMGB1.

Figure 37:
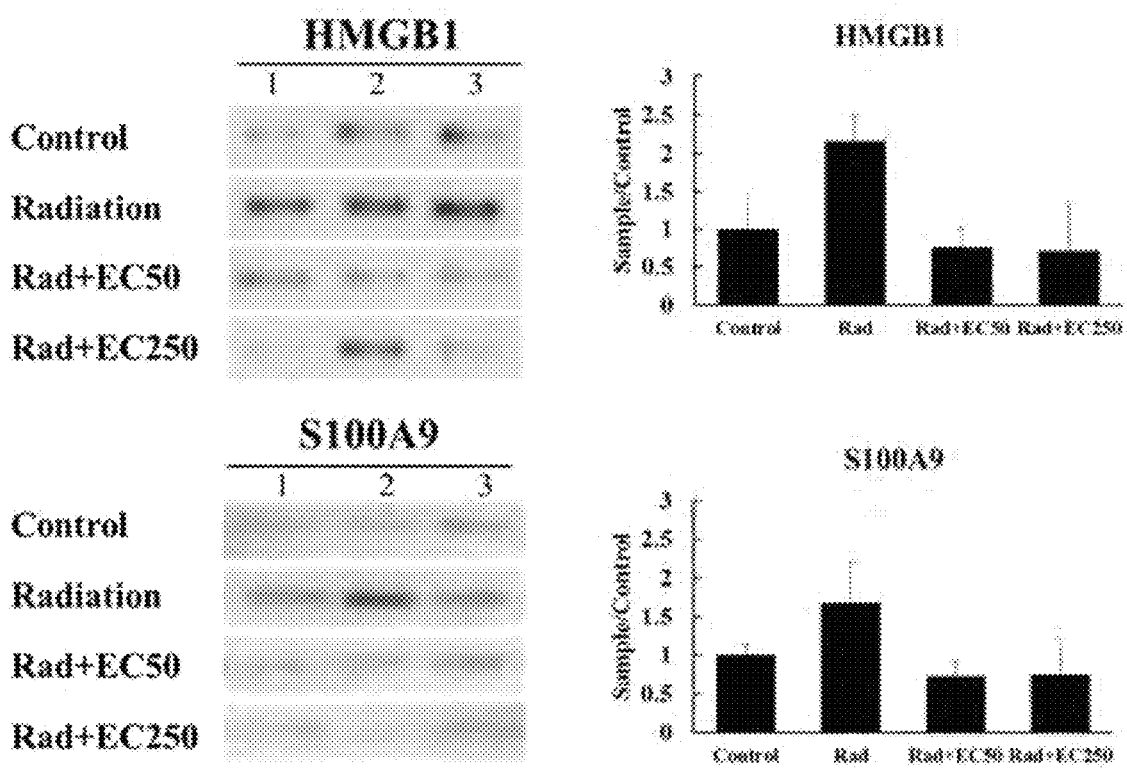

FIG. 37 shows that EC-18 attenuates the DAMP expression in an irradiated murine model.

Figure 38:
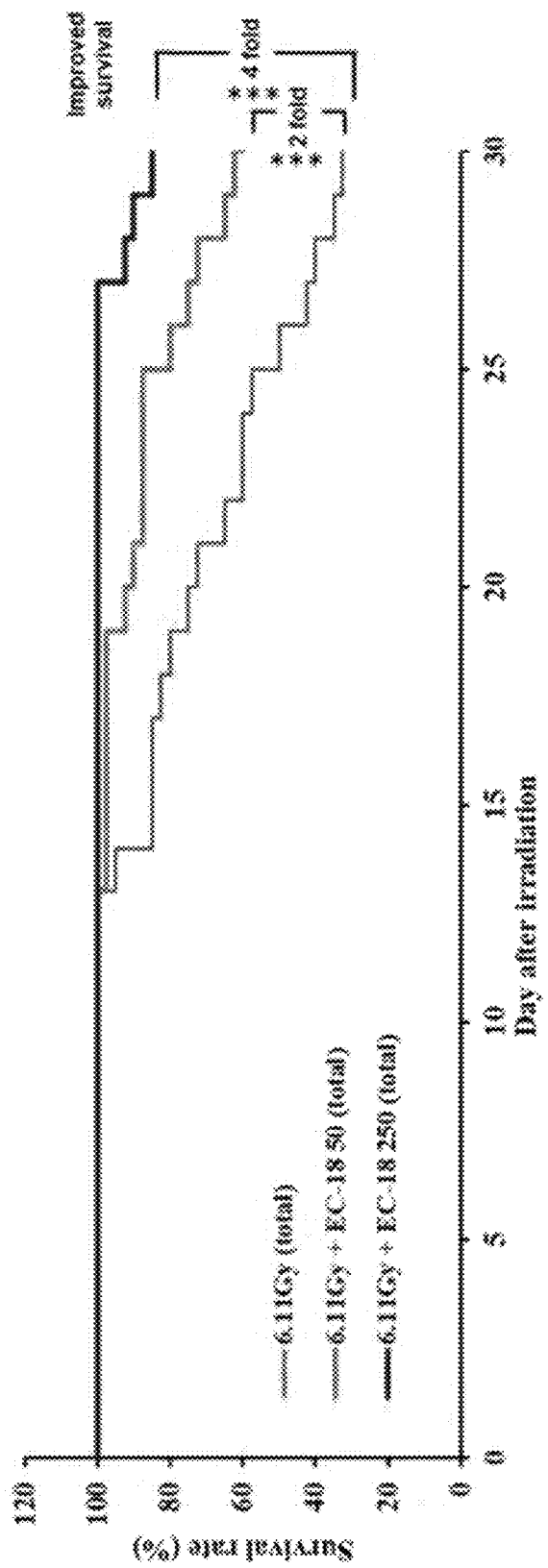

FIG. 38 shows survival of TBI (6.11 Gy) Balb/c mice treated with EC-18; ***denotes $p<0.001$ compared to the vehicle control group.

Figure 39A:
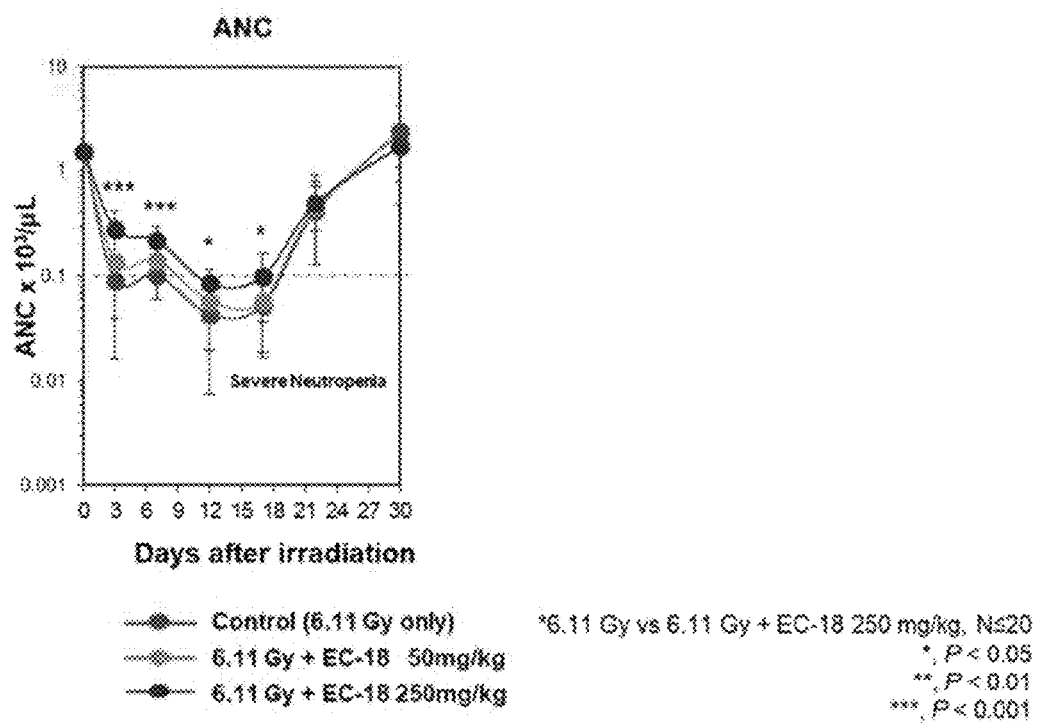
Figure 39B:
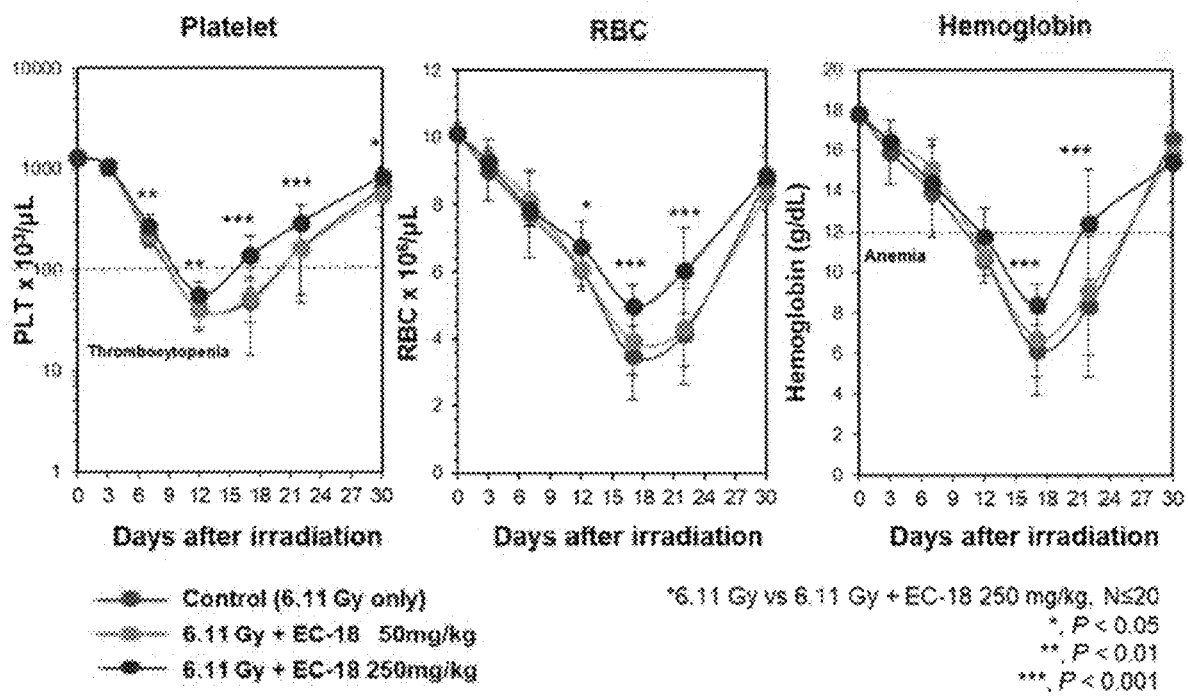

FIGS. 39A-39B shows effect of EC-18 on CBC parameters after TBI irradiation in Balb/c mice.

Figure 40:
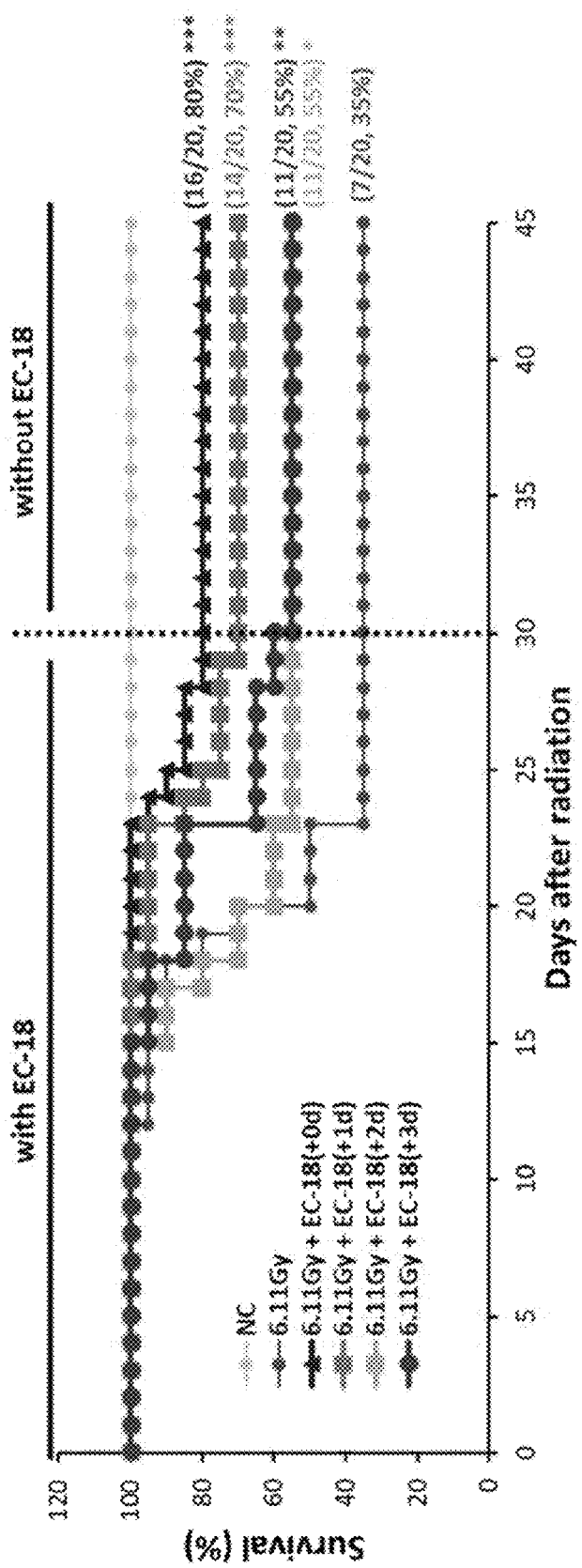

FIG. 40 shows dosing schedule finding study results with the durable efficacy study (with EC-18 withdrawal); *denotes $p<0.05$,  denotes $p<0.01$, and *denotes $p<0.001$, all compared to the vehicle control group.

Figure 41:
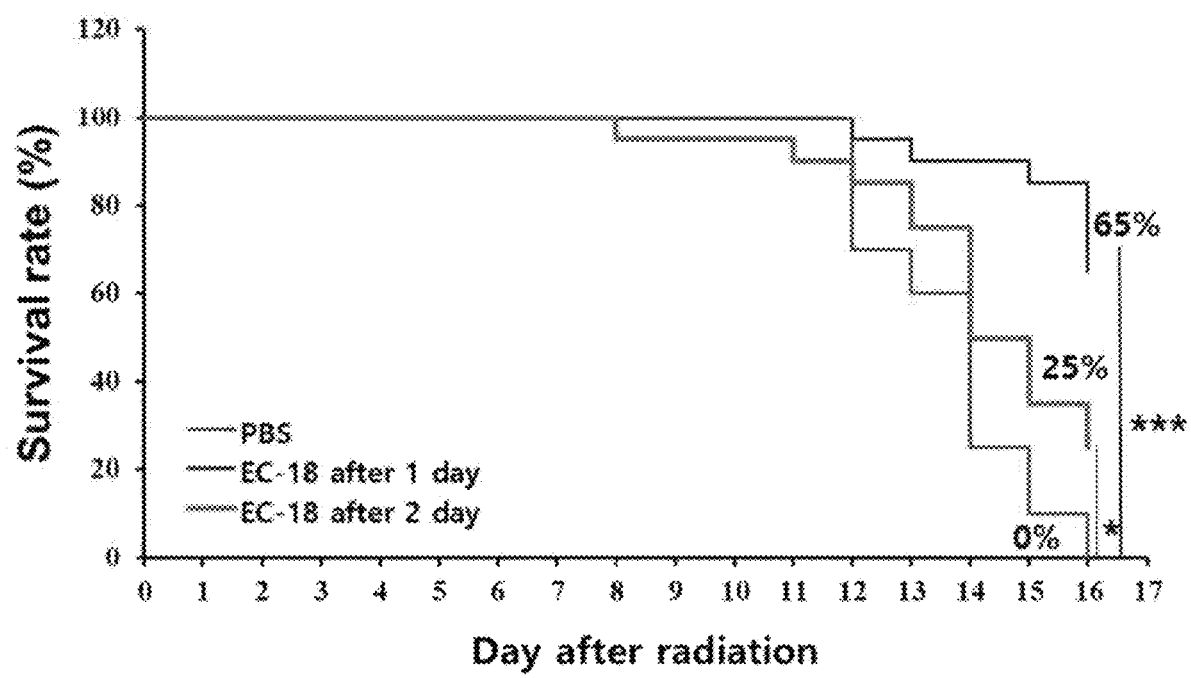

FIG. 41 shows effect of EC-18 on survival, starting at Day 1 or Day 2 post-irradiation, in mice exposed to 6.5 Gy (LD100/16); * denotes $p<0.05$ and *** denotes $p<0.001$, both compared to the vehicle control group.

Figure 42:
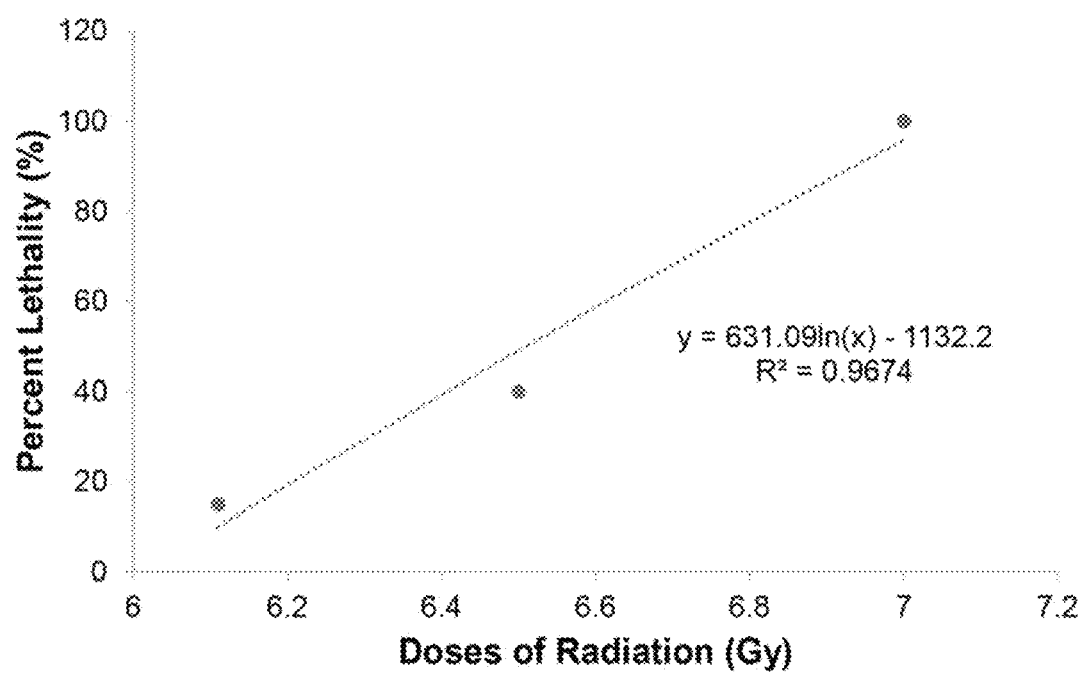

FIG. 42 shows dose reduction plot of EC-18 at 250 mg/kg with a linear trend line.

Figure 43:
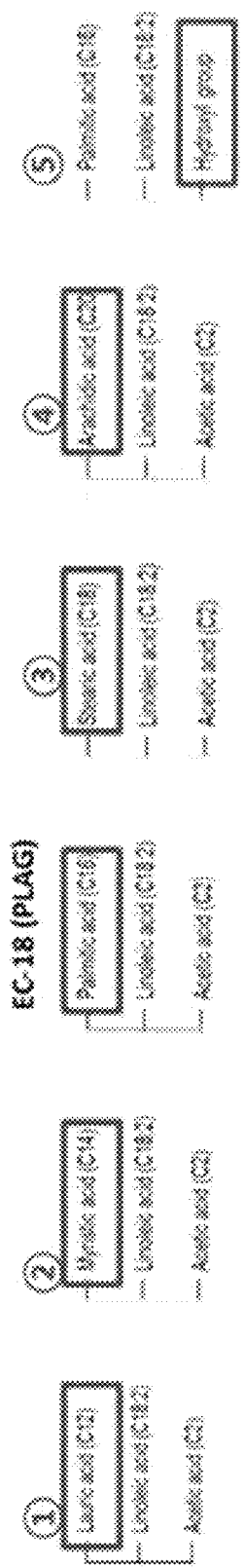

FIG. 43 shows structural analogs tested for optimizing the EC-18's activity.

Figure 44:
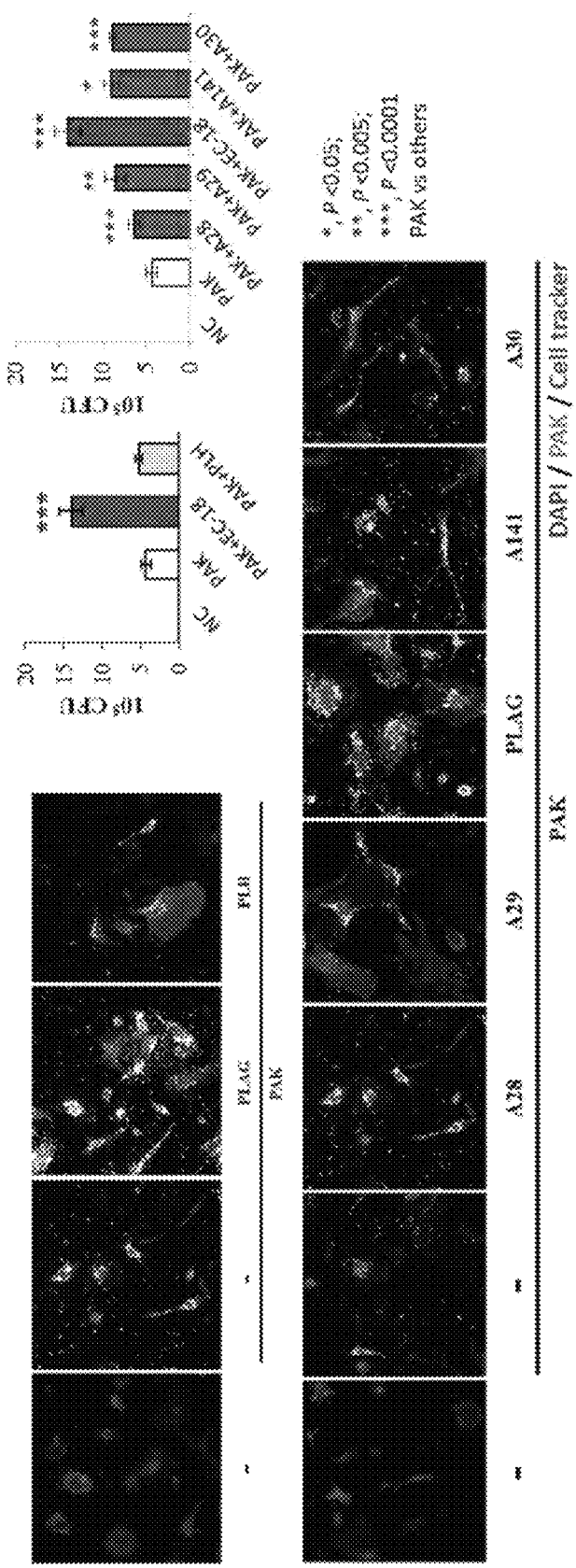

FIG. 44 shows CFU level comparisons in the co-culture test of monocytes with PAK after 1 hr.

Figure 45:
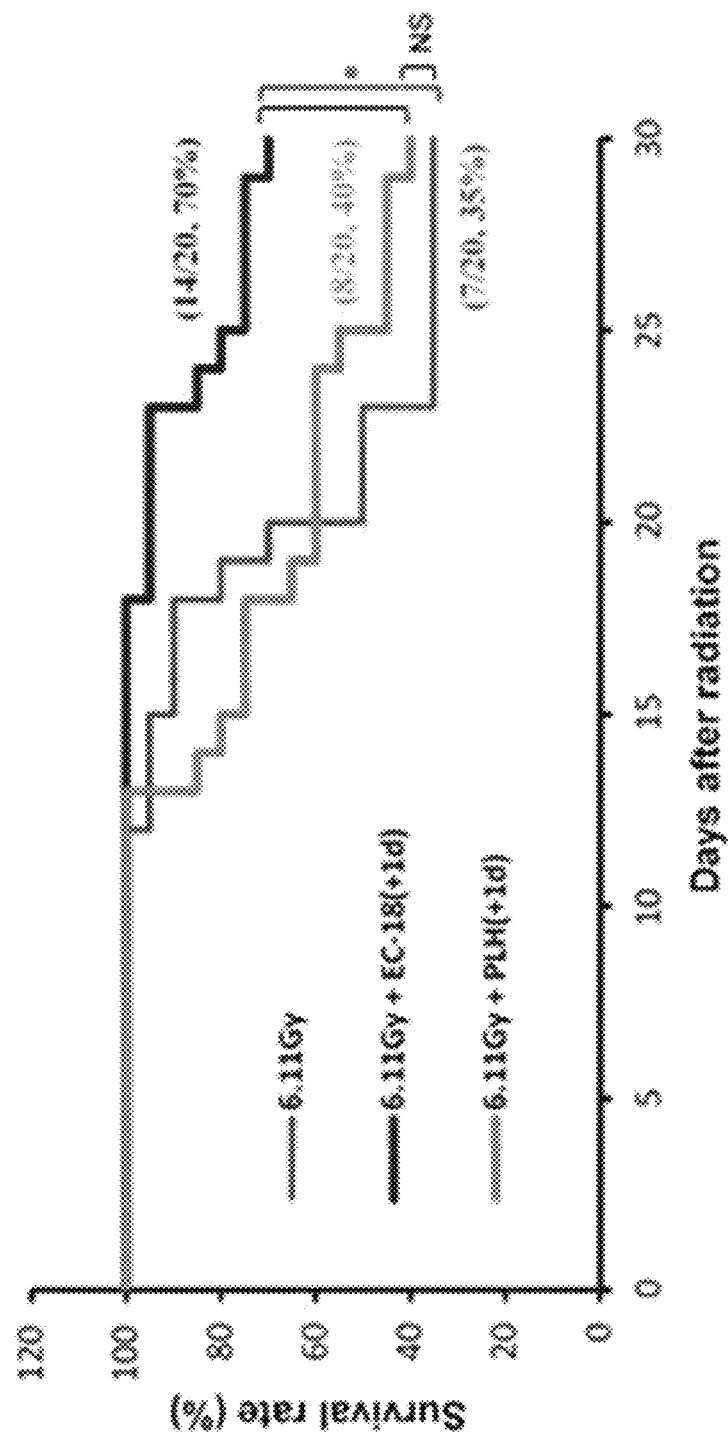

FIG. 45 shows comparison of survival in LD65/30 Balb/c model after treatment with EC-18 or the hydroxyl analog; * denotes $p<0.05$ and NS denotes statistically non-significant.

Figure 46:
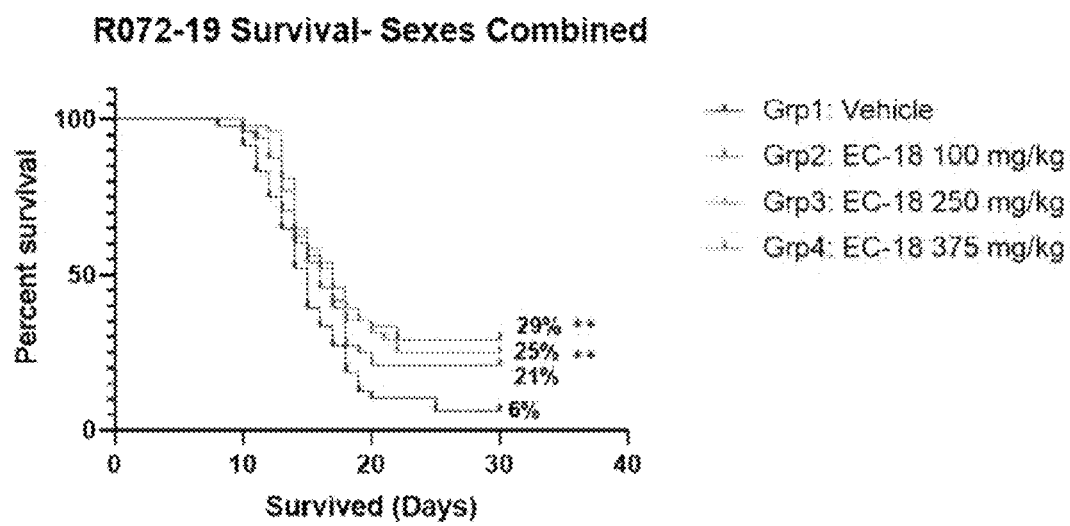

FIG. 46 shows Kaplan-Meier survival curve for all animals; **denotes $p<0.01$ compared to the vehicle group.

Figure 47:
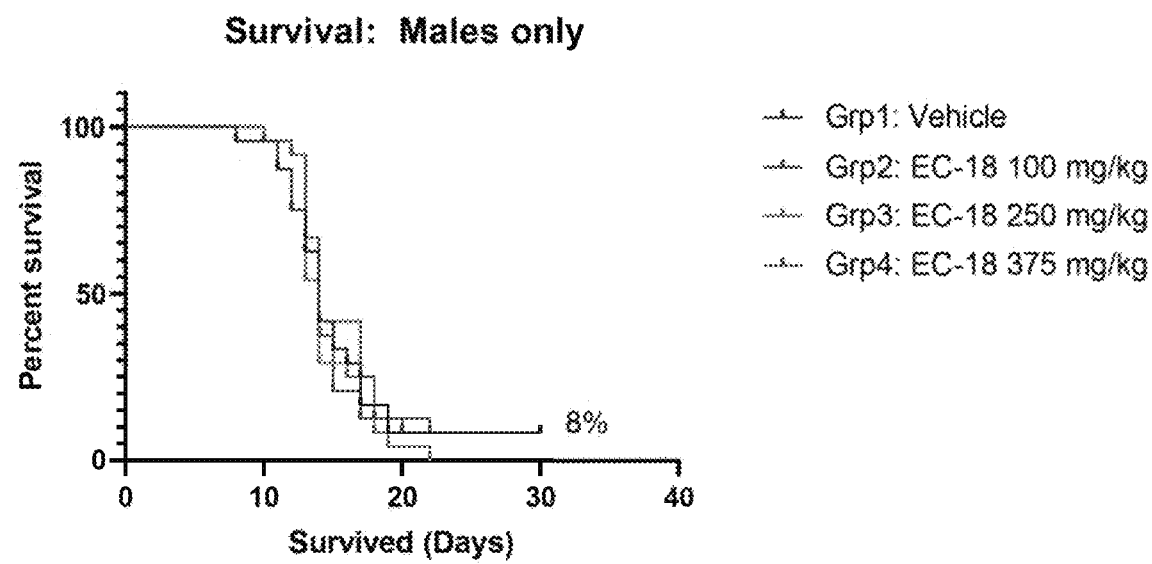

FIG. 47 shows Kaplan-Meier survival curve for males only.

Figure 48:
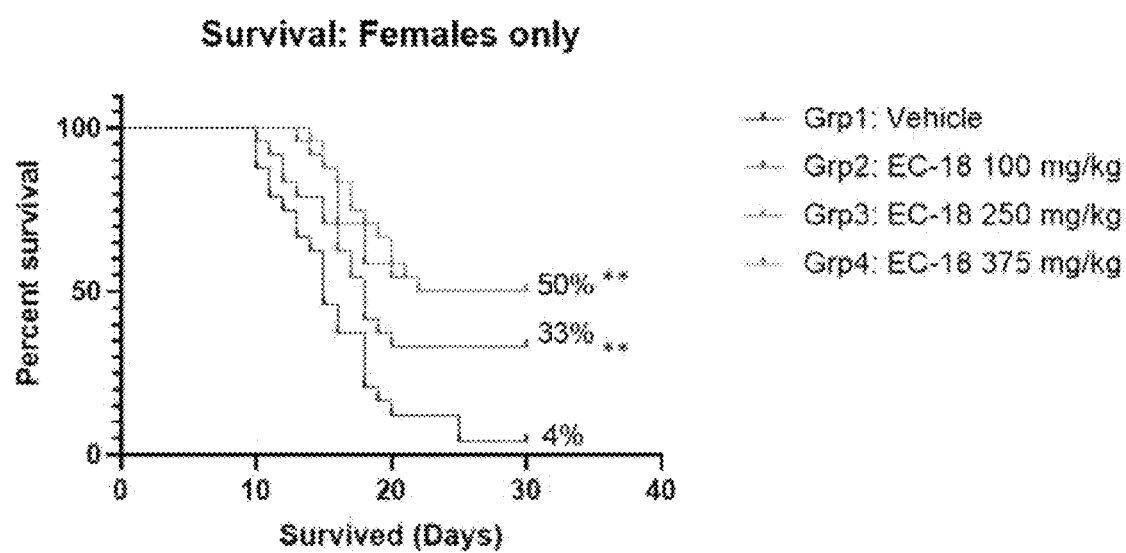

FIG. 48 shows Kaplan-Meier survival curve for females only; **denotes $p<0.01$ compared to the vehicle group.

Figure 49A:
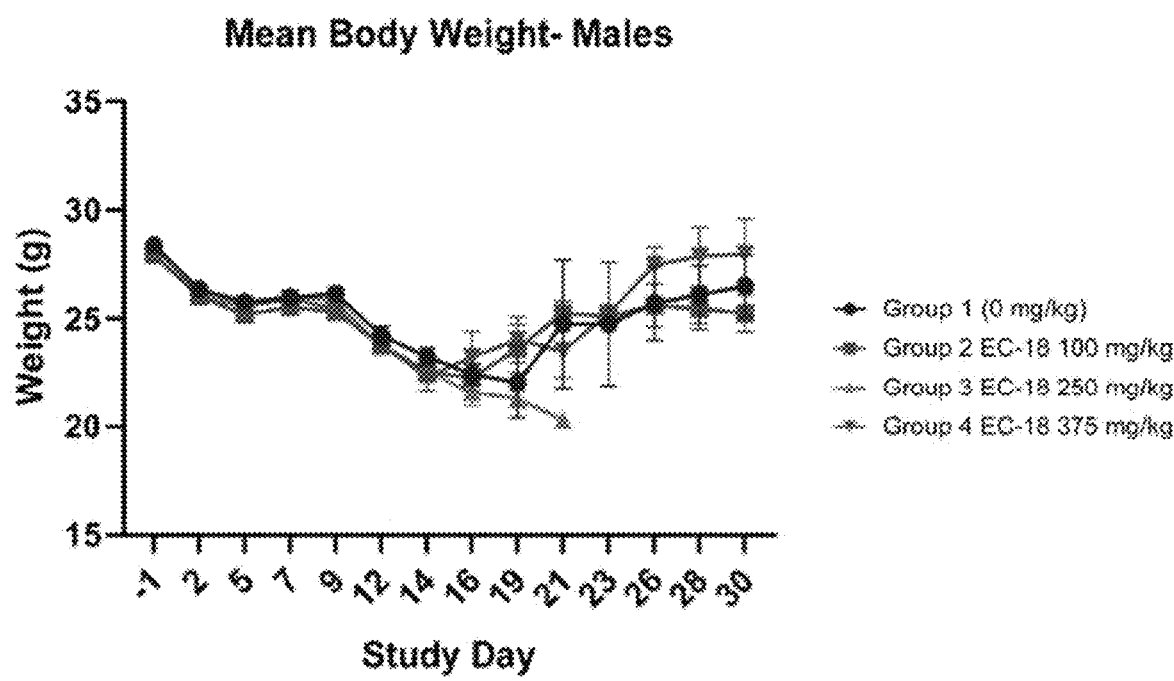
Figure 49B:
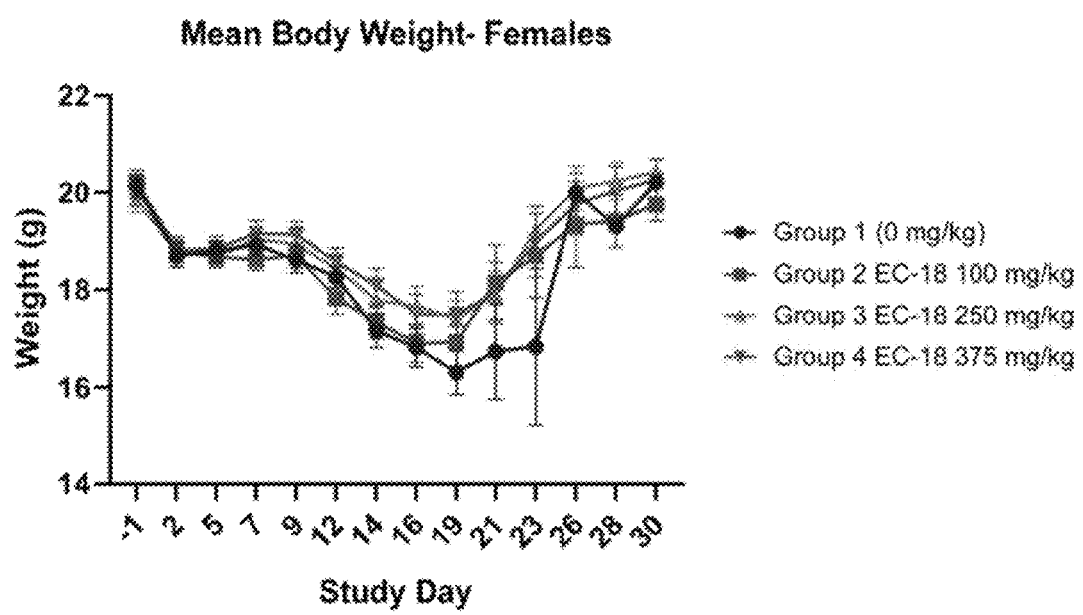

FIGS. 49A-49B show mean body weights for irradiated C57BL/6J mice treated with either EC-18 or PBS (vehicle); error bars represent the standard error of the mean.

Figure 50:
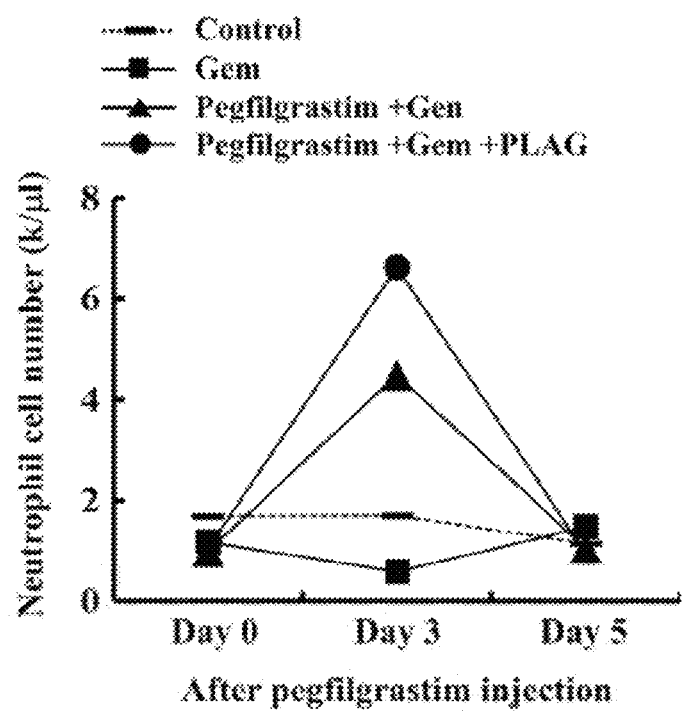

FIG. 50 shows that PLAG with pegfilgrastim increased the number of circulating neutrophils in the blood.

Figure 51:
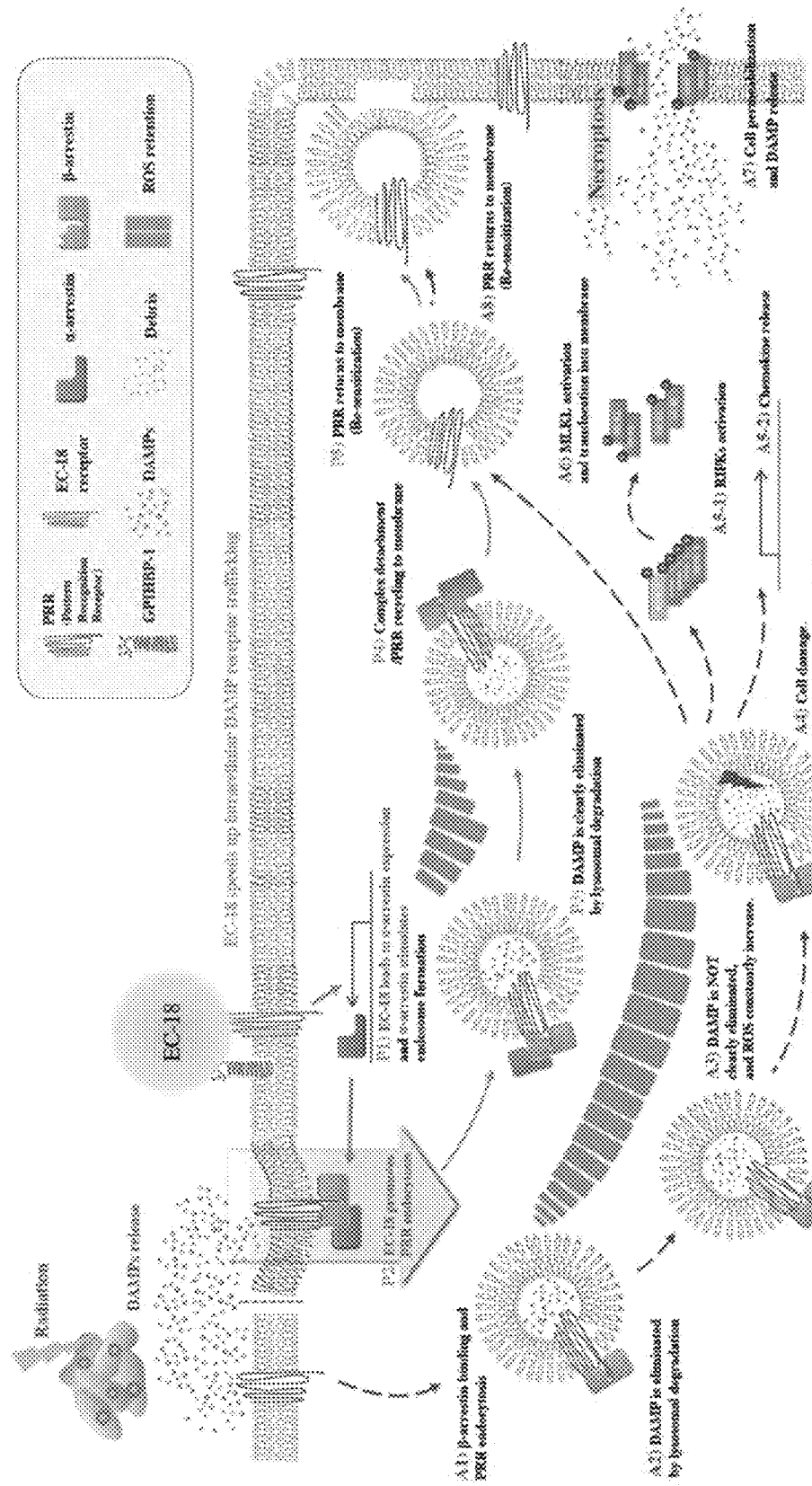

FIG. 51 shows that proposed mechanism of action of EC-18 in ARS.

FIGS. 52A-52G show assessment of the mitigating effect of EC-18 in CRIOM.

FIGS. 53A-53E show that EC-18 ameliorated the released pro-inflammatory cytokines and neutrophil infiltration.

Figure 54A:
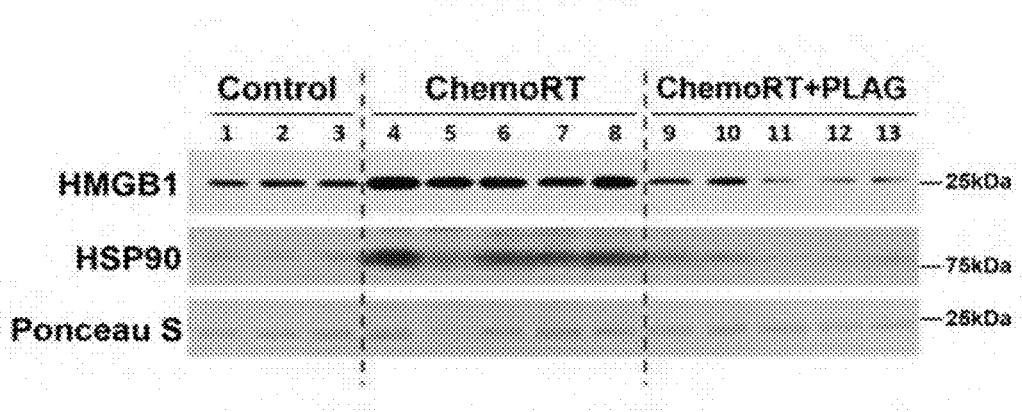
Figure 54B:
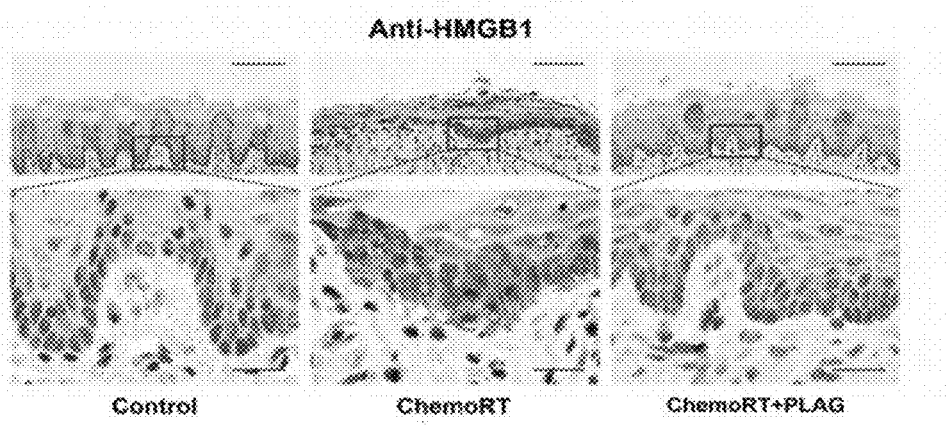

FIGS. 54A-54B show that the release of DAMPs was subsided by EC-18.

Figure 55A:
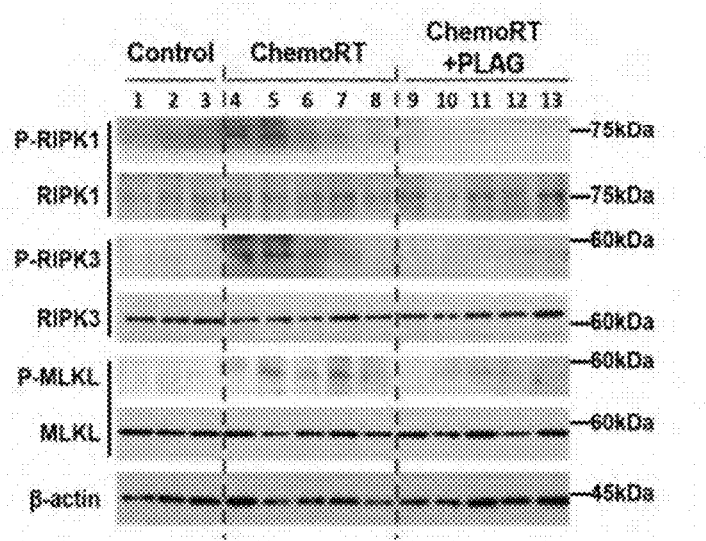
Figure 55B:
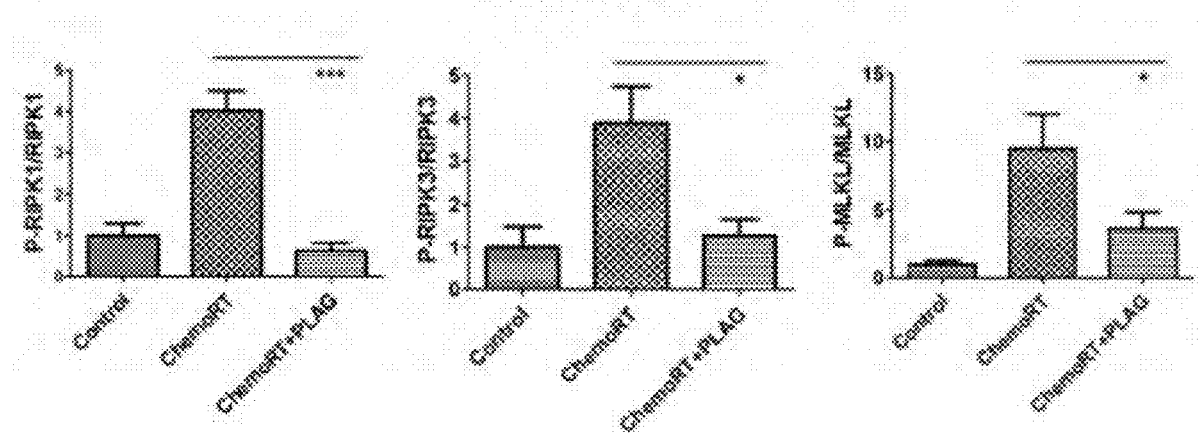
Figure 55C:
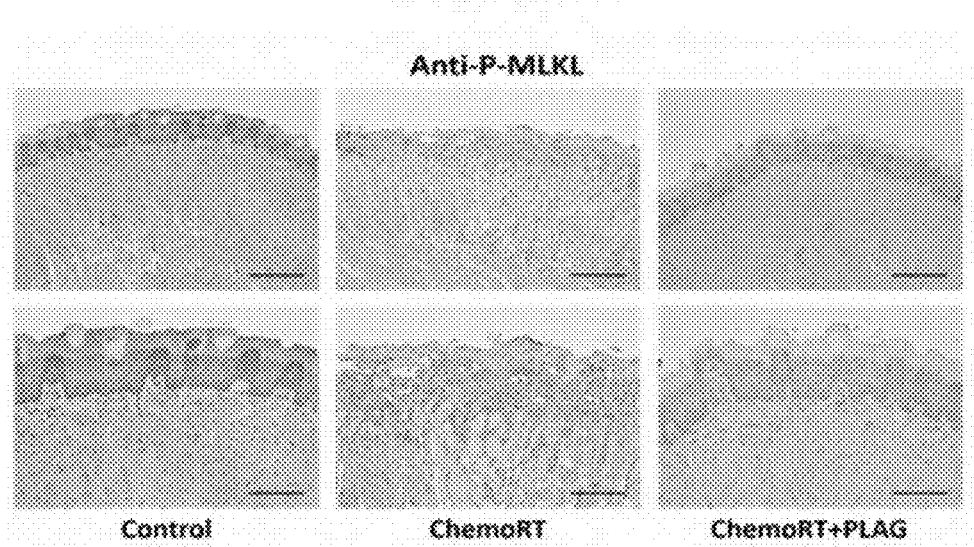

FIGS. 55A-55C show that EC-18 down-regulates necroptosis signaling in tongues with CRIOM.

Figure 56:
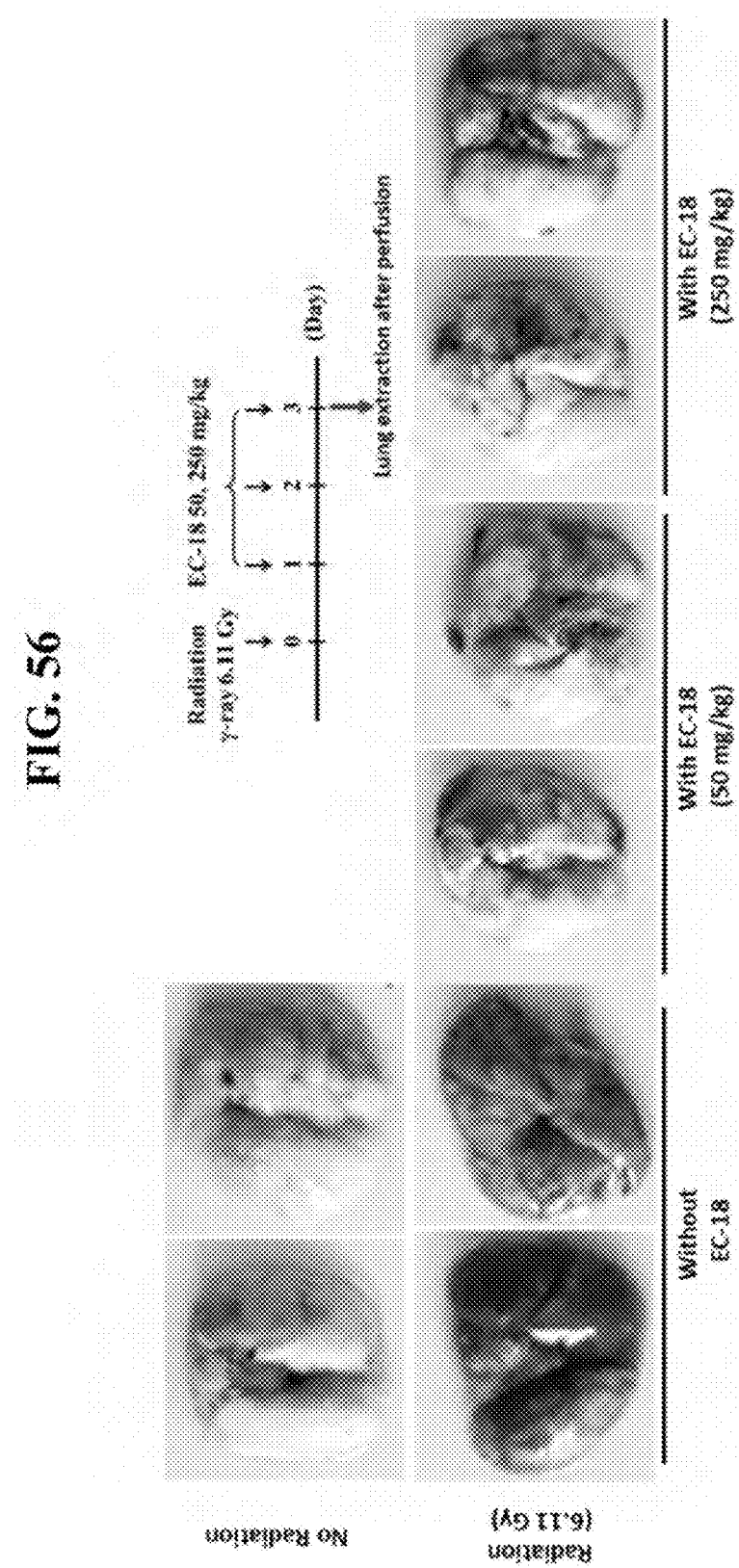

FIG. 56 shows EC-18 attenuates radiation-induced lung injury.

Figure 57:
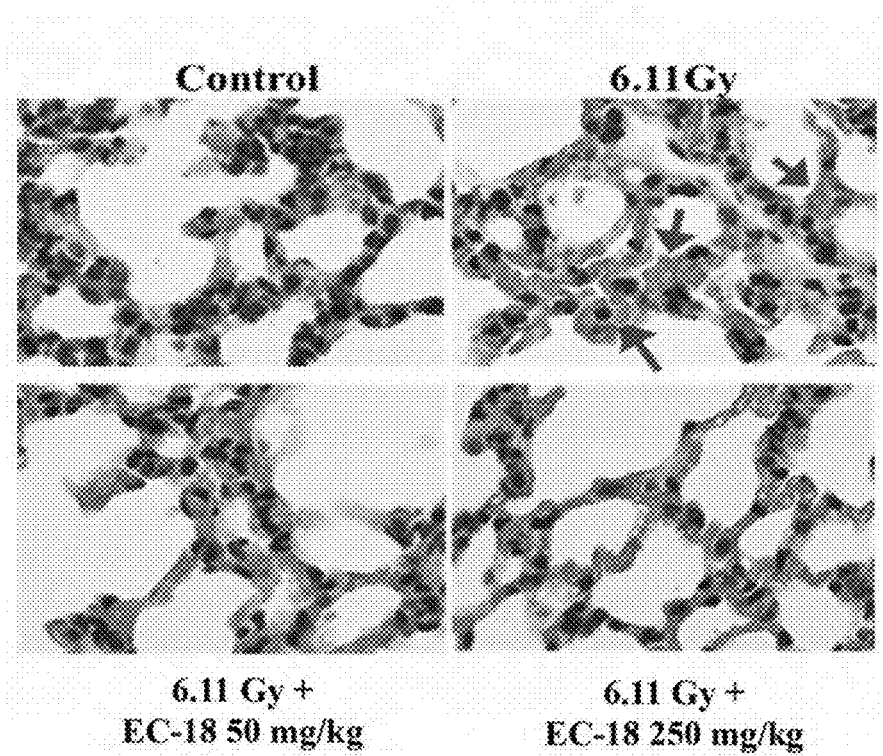

FIG. 57 shows microscopic analysis of H&E stained lung sections.

Figure 58A:
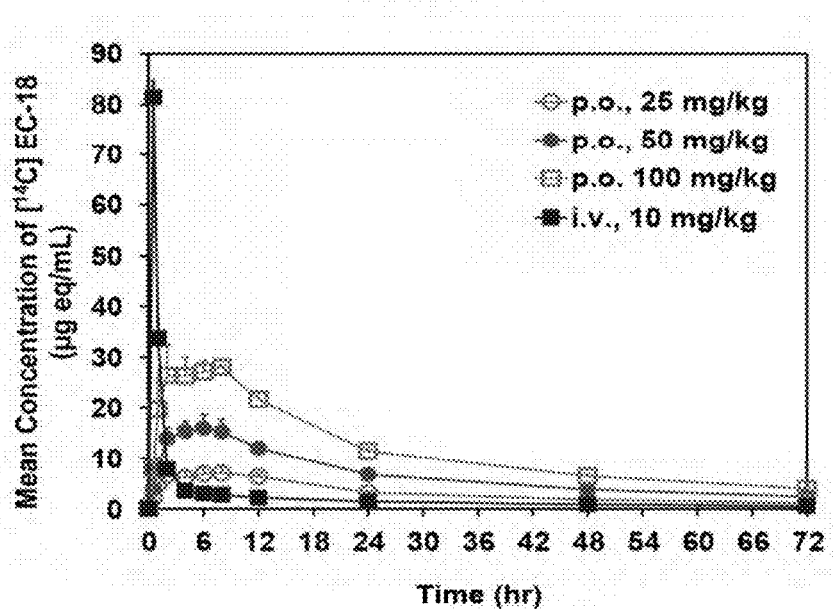
Figure 58B:
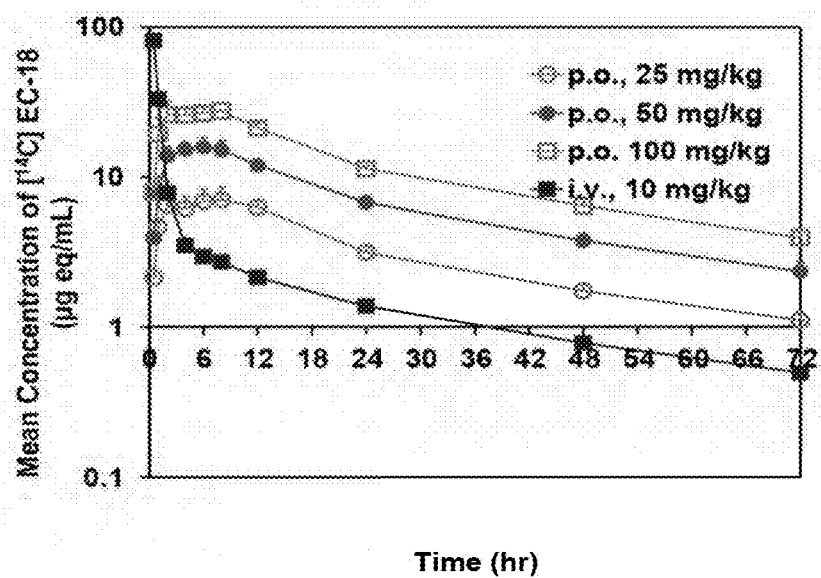

FIGS. 58A-58B show mean radioactive concentration in rat plasma after single IV or oral administration of [$^{14}$C] EC-18 (linear [FIG. 66A], logarithmic [FIG. 66B]).

Figure 59:
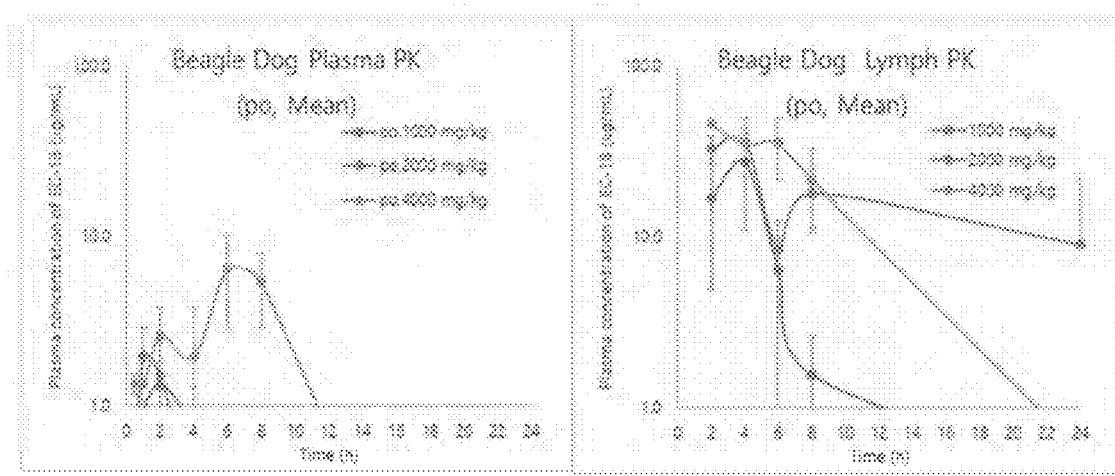

FIG. 59 shows semi-logarithmic concentrations vs. time plots in plasma (left) and lymph (right) of dogs after a single oral administration of EC-18.

Figure 60:
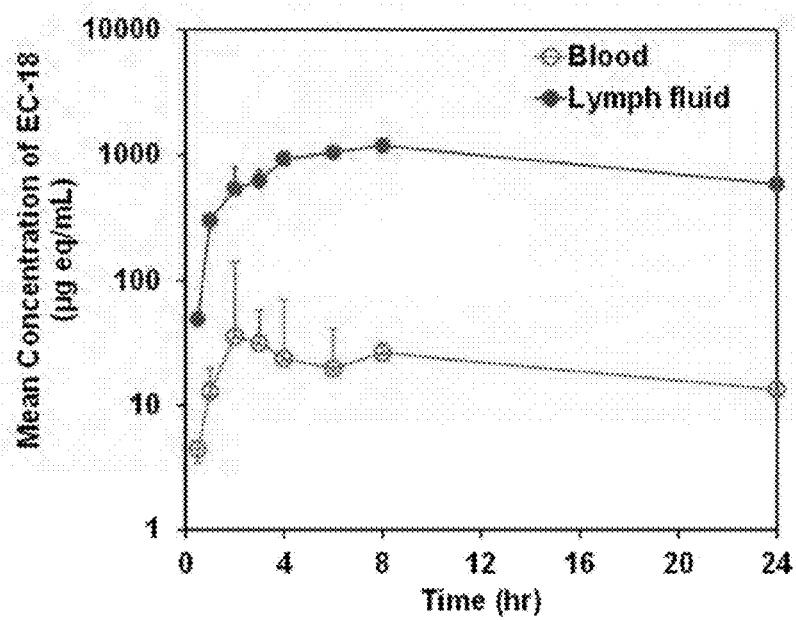

FIG. 60 shows Mean radioactive concentration in rat whole blood and lymphatic fluid after a single oral administration of [$^{14}$C]EC-18.

Figure 61:
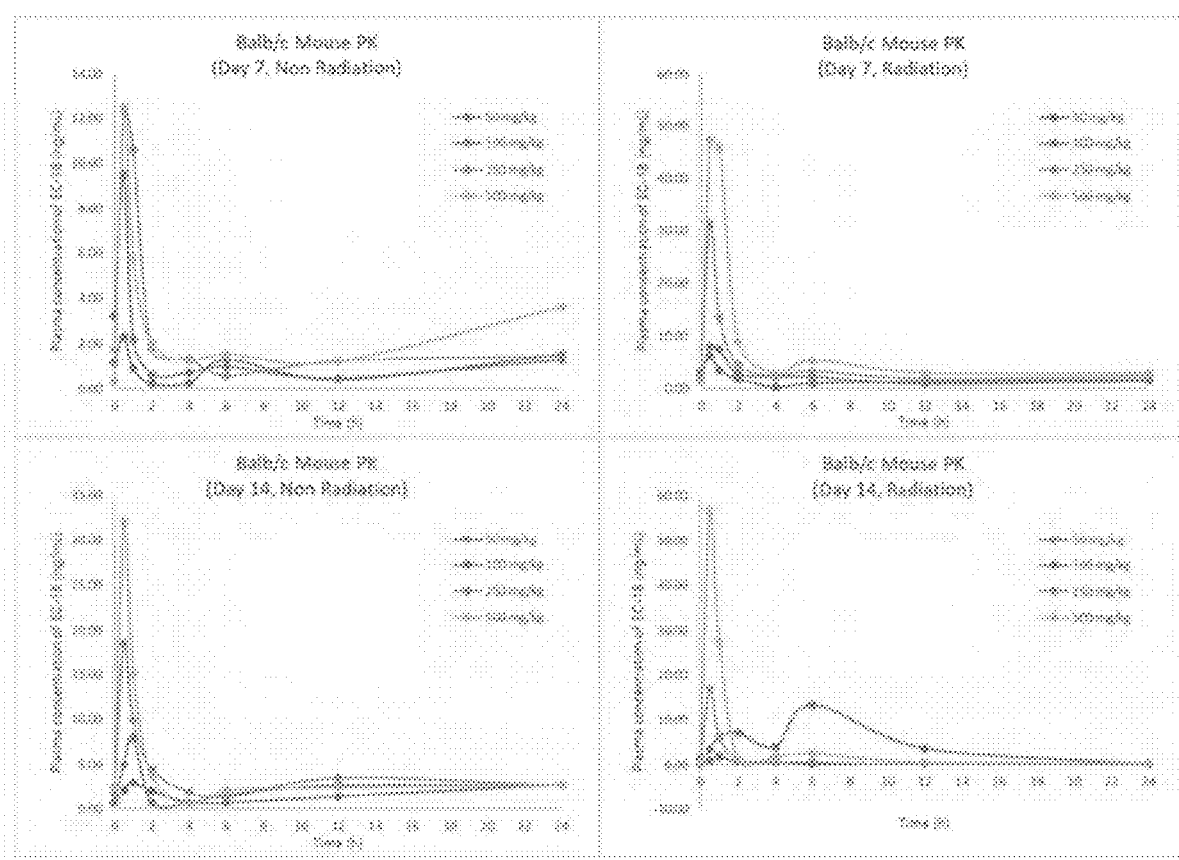

FIG. 61 shows mean PK profile in plasma concentration after 1 and 2 weeks repeat oral administration of EC-18 in non-irradiated and irradiated mice.

Figure 62:
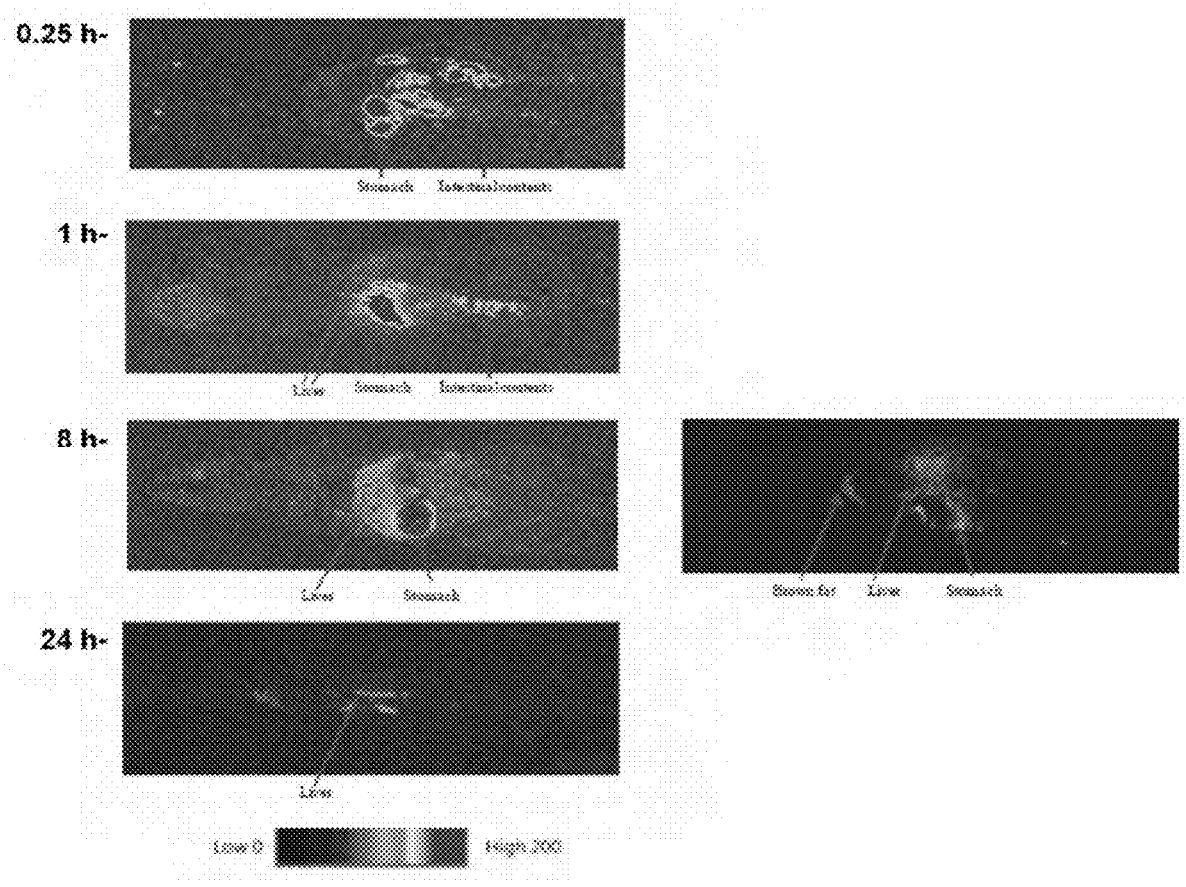

FIG. 62 shows whole-body autoradiography in rats after a single oral administration.

Figure 63:
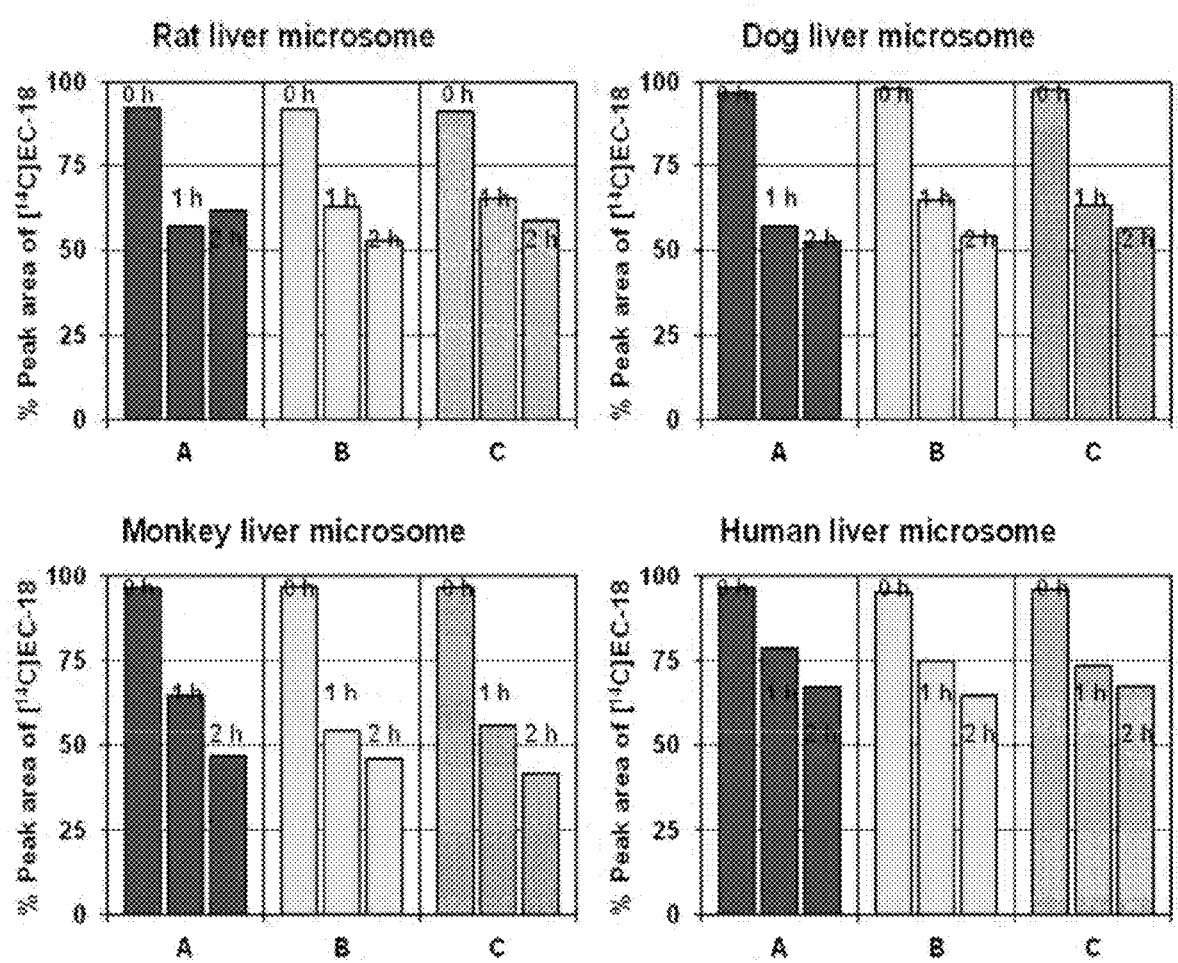

FIG. 63 shows relative residual radioactivity concentration at 1 µM of [$^{14}$C]EC-18 with rat, dog, monkey, and human liver microsomes for 2 hrs; (panel A) NADPH added, (panel B) NADPH, PAPS, and UDPGA added, and (panel C) no cofactor added (n=2).

Figure 64:
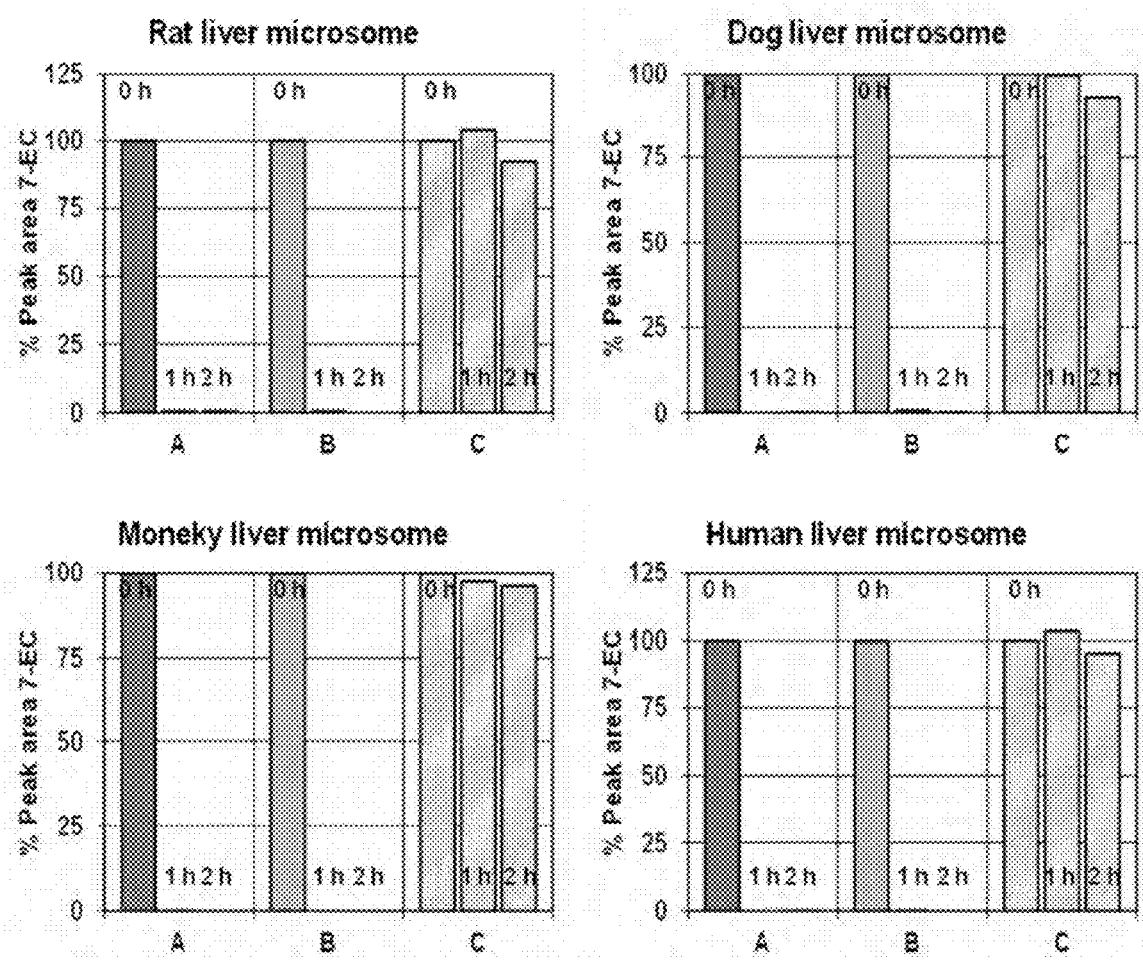

FIG. 64 shows Relative residual concentration at 100 µM of 7-EC with rat, dog, monkey, and human liver microsomes for 2 hrs; (Panel A) NADPH added, (Panel B) NADPH, PAPS, and UDPGA added, and (Panel C) no cofactor added (n=2).

Figure 65A:
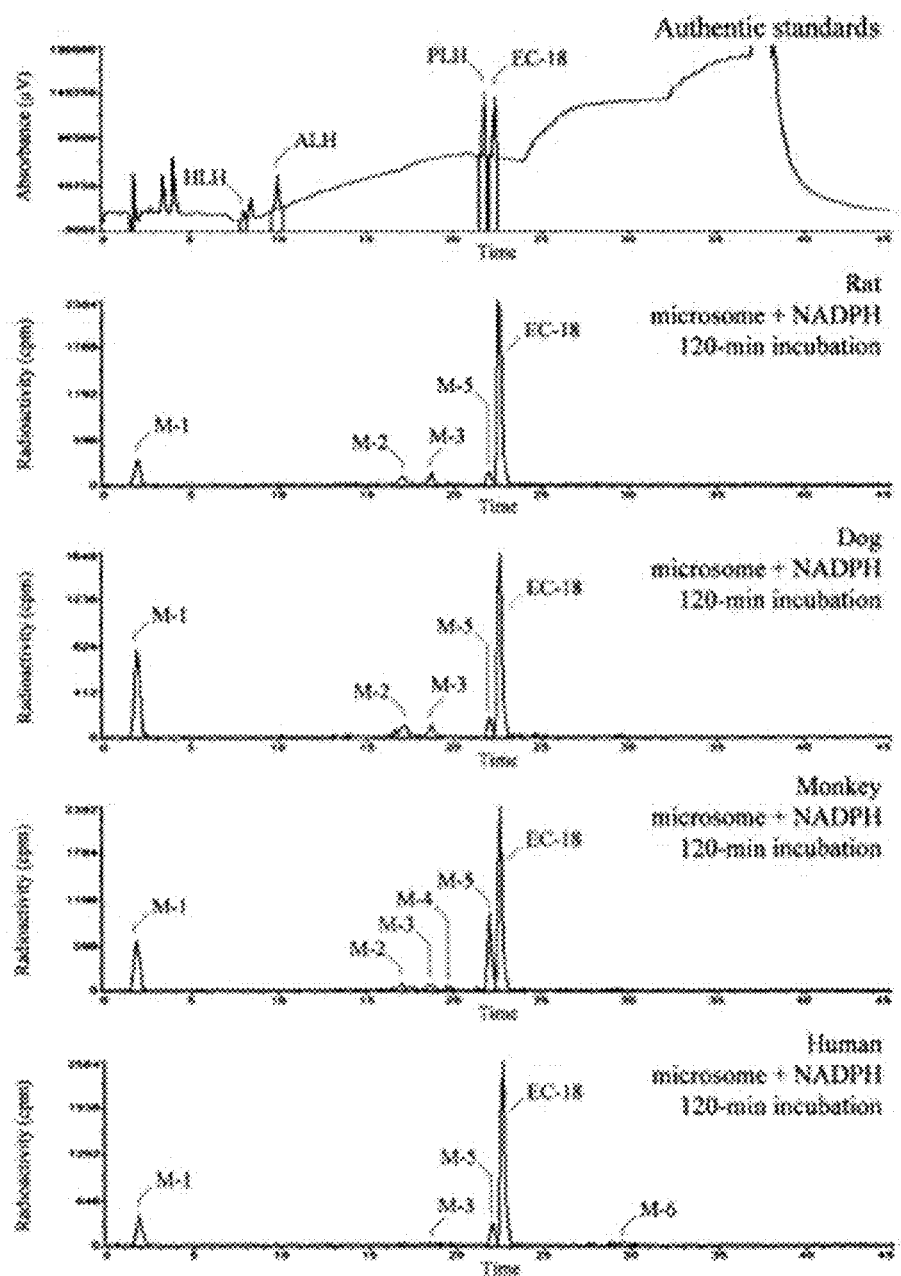
Figure 65B:
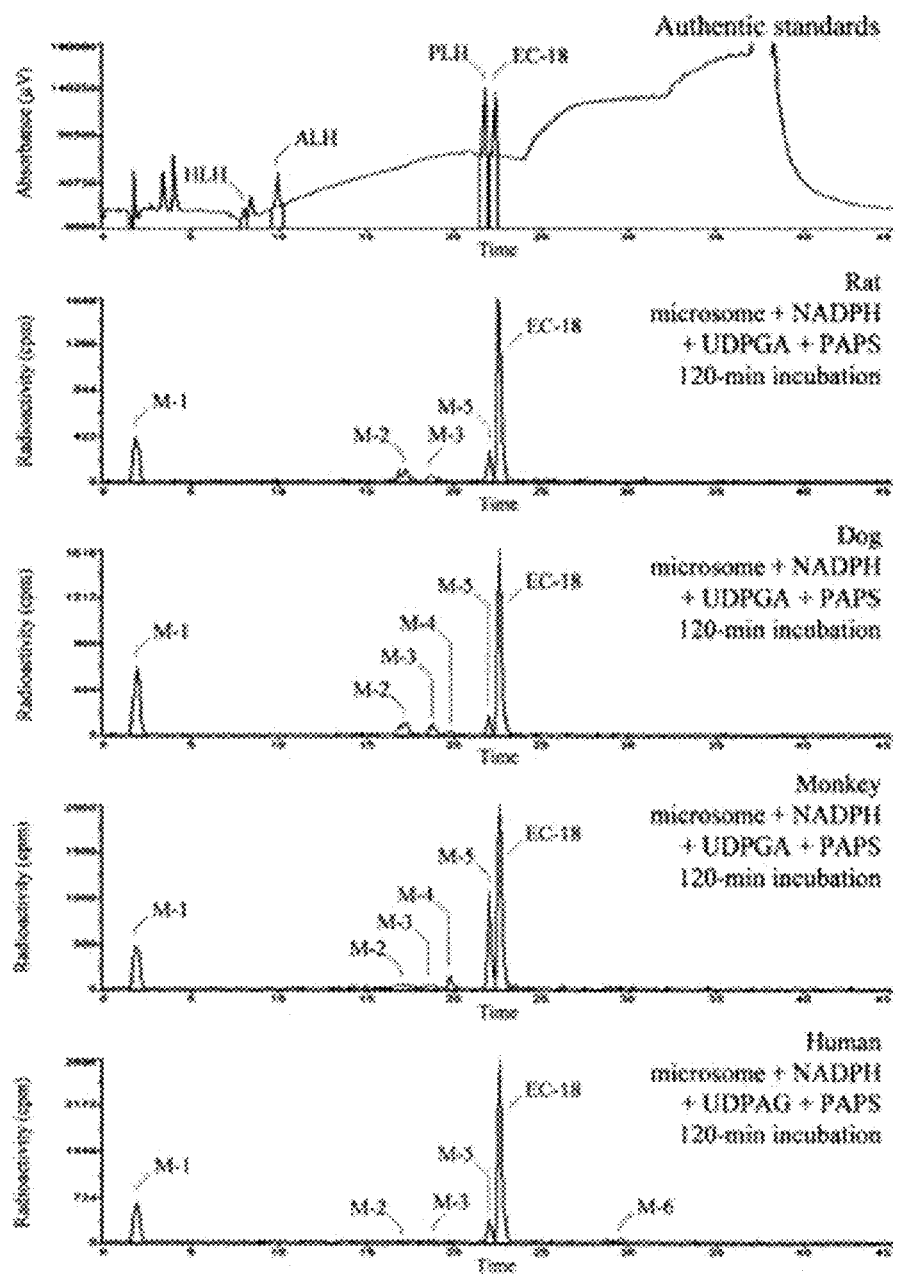
Figure 65C:
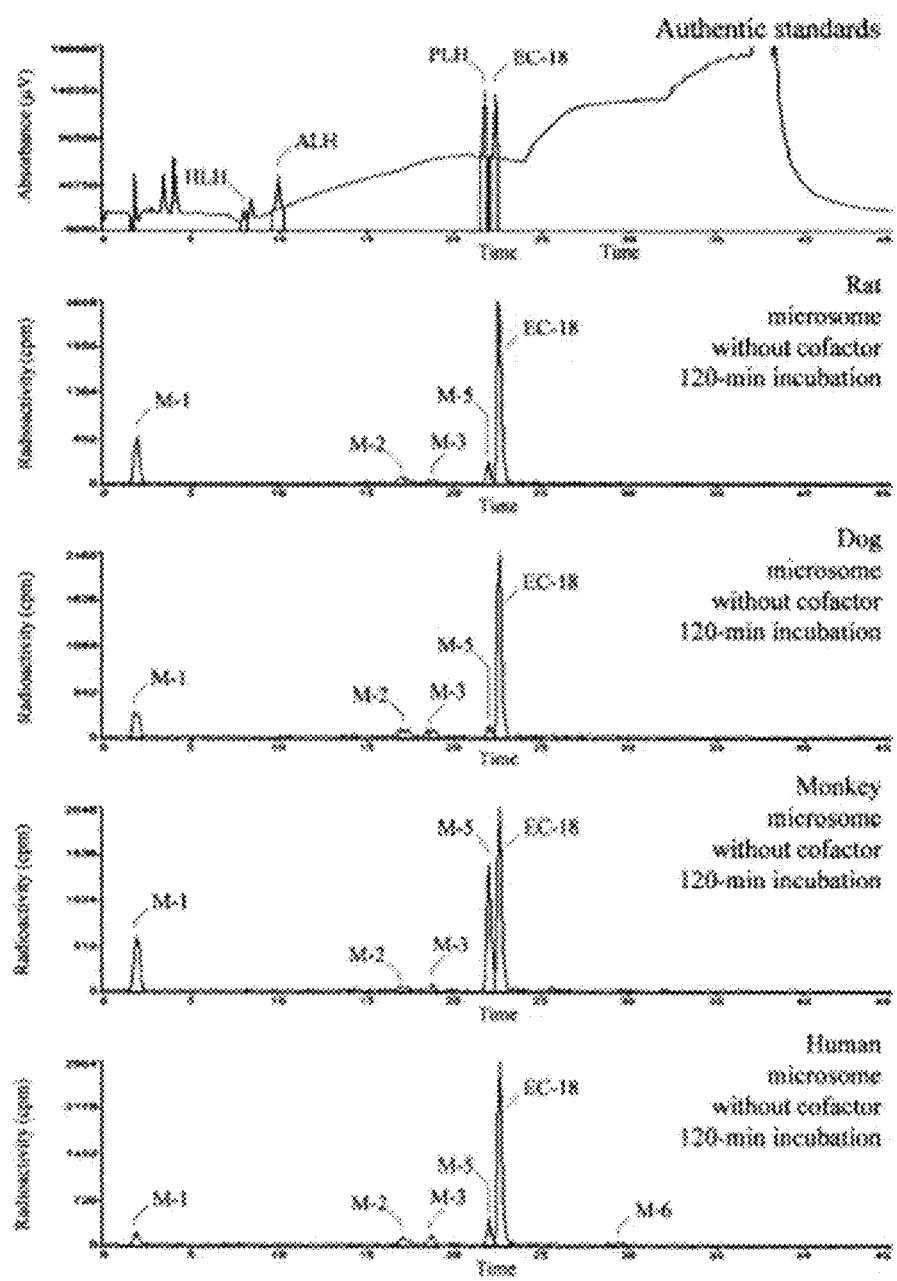

FIGS. 65A-65C show Relative residual concentration after reacting 100 µM of EC-18 with rat, dog, monkey, and human liver microsomes for 2 hrs. In FIG. 65A, NADPH is added, in FIG. 65B, NADPH, PAPS, and UDPGA added, and in FIG. 65C, no cofactor added (n=2).

Figure 66:
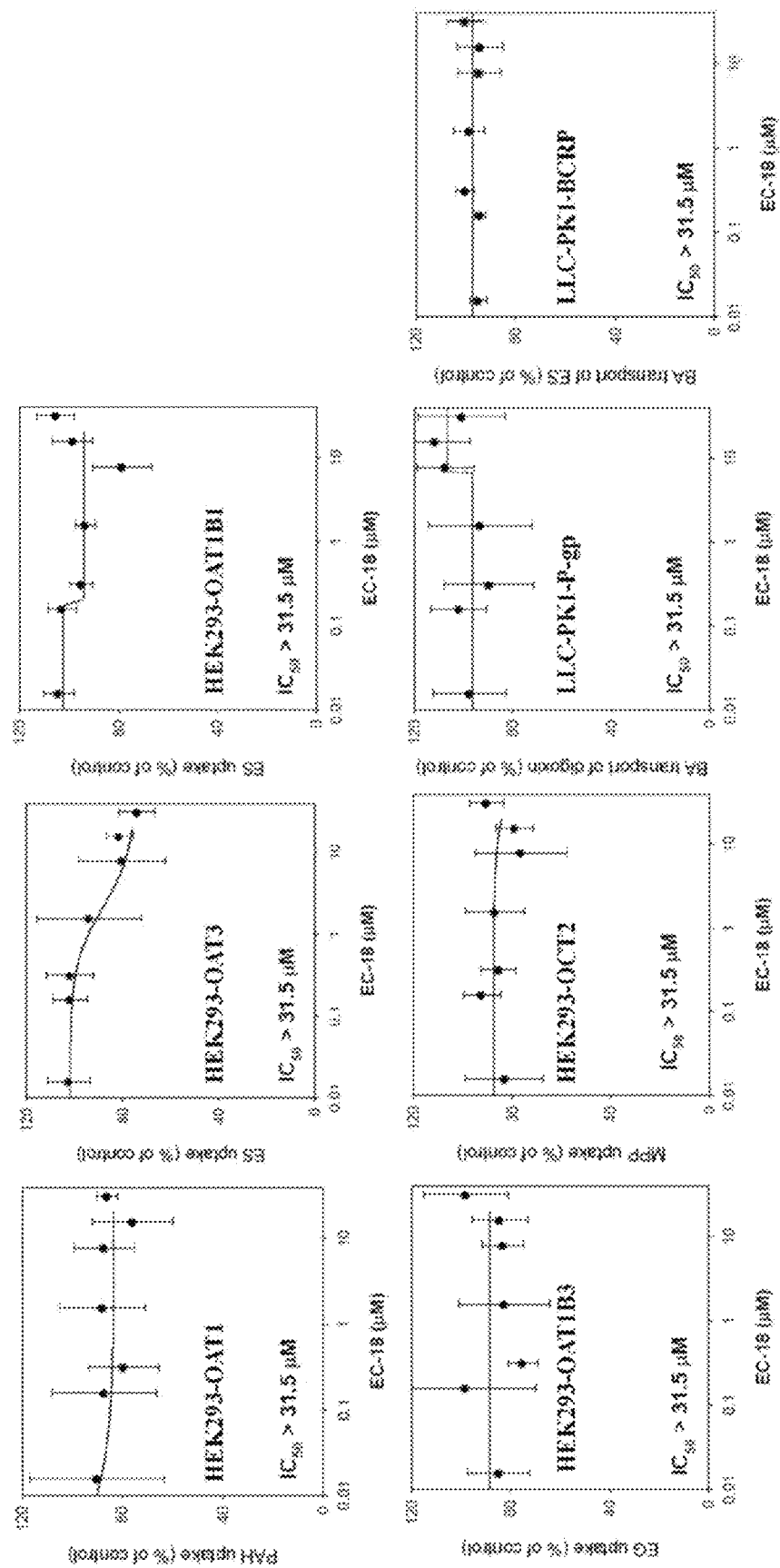

FIG. 66 shows cellular uptake or basolateral transport of substrate vs. EC-18 concentration.

Figure 67:
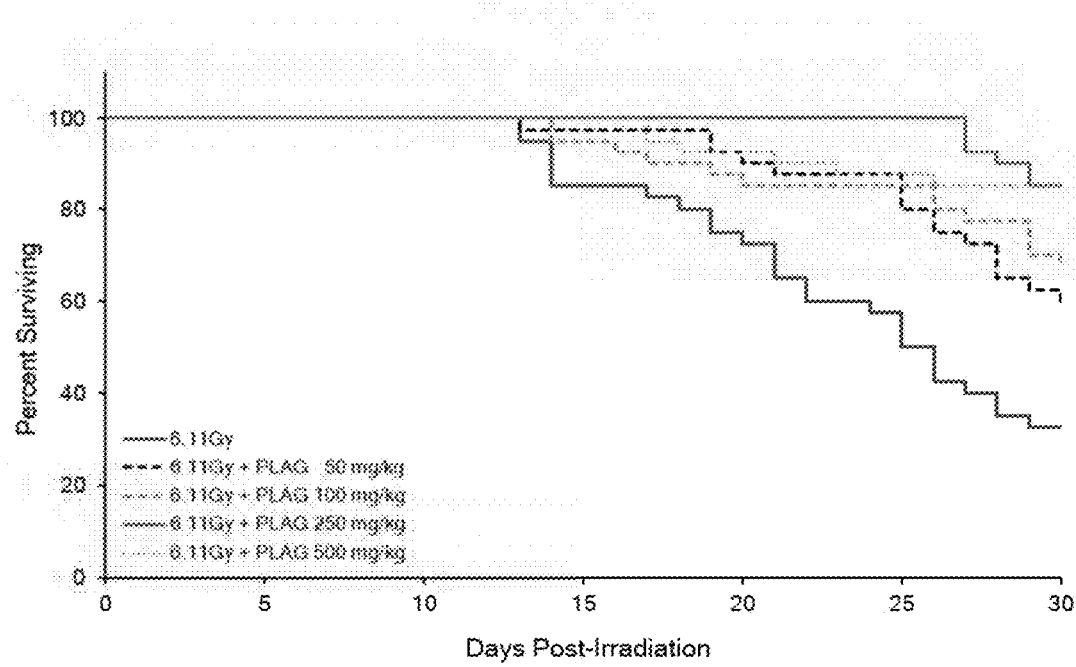

FIG. 67 shows dose optimization study of EC-18 based on the percent survival of the irradiated mice.

Figure 68:
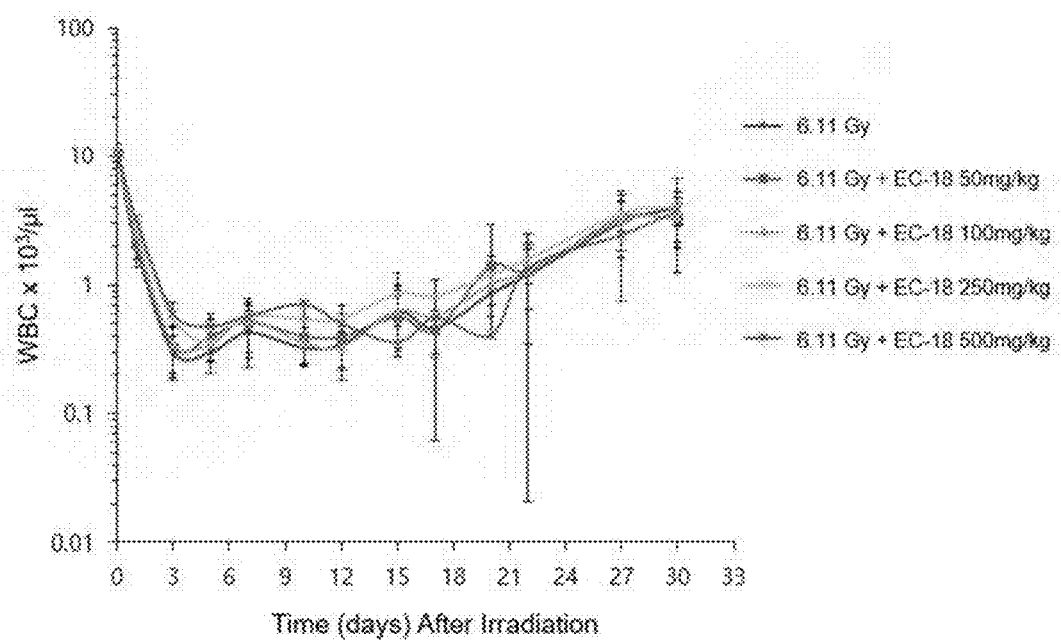

FIG. 68 shows effect of EC-18 on the kinetics of the mean WBC counts of the irradiated mice.

Figure 69:
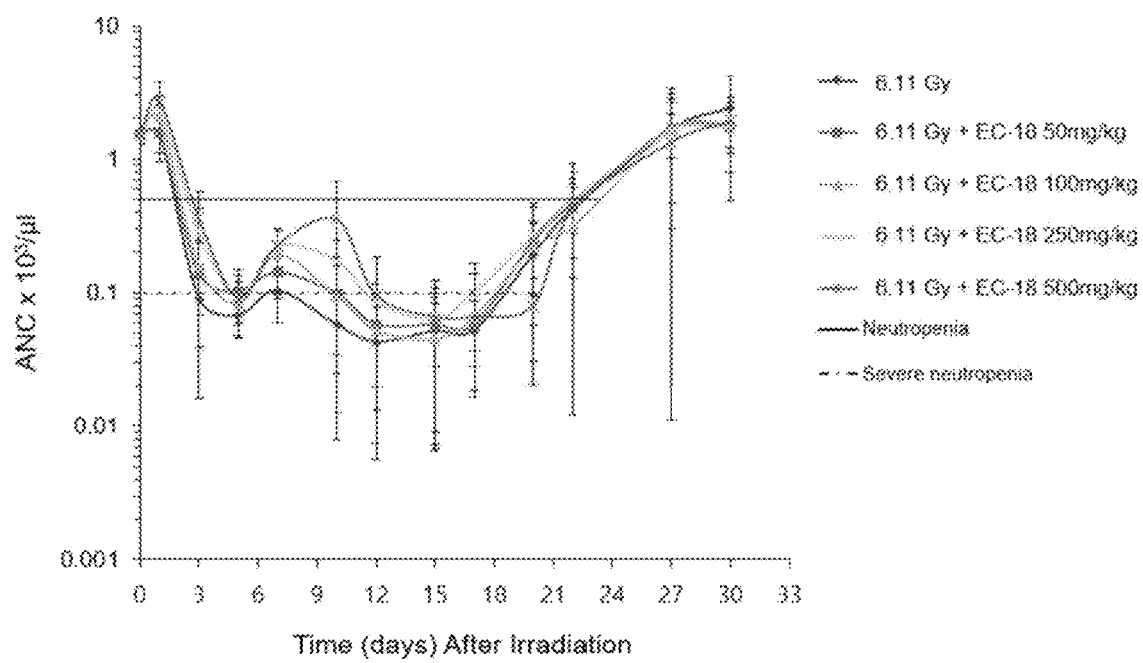

FIG. 69 shows effect of EC-18 on the kinetics of the mean ANCs of the irradiated mice.

Figure 70:
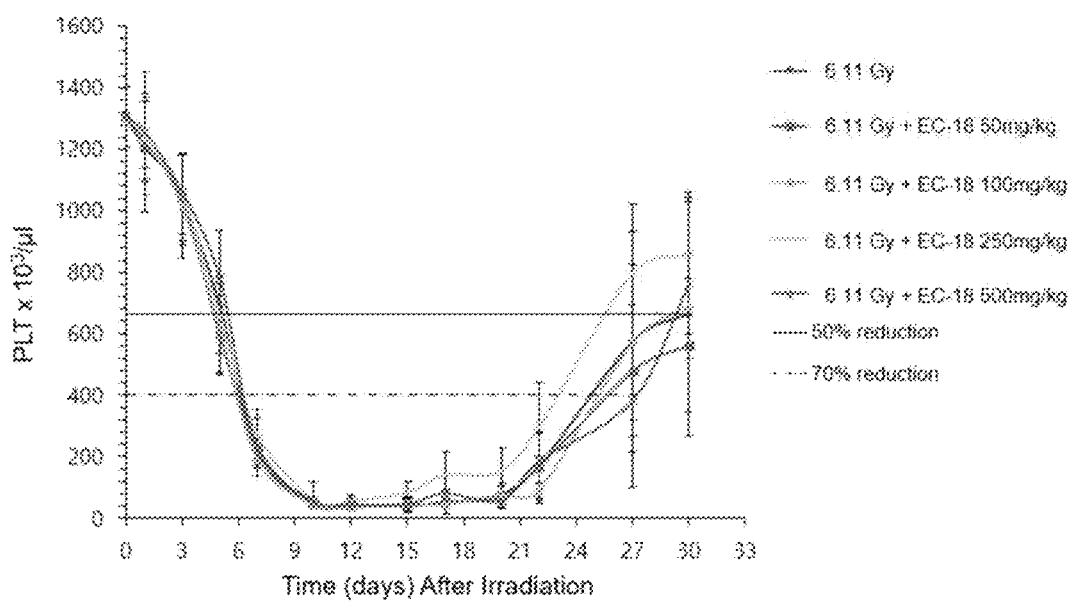

FIG. 70 shows effect of EC-18 on the kinetics of the mean PLT counts of the irradiated mice.

Figure 71A:
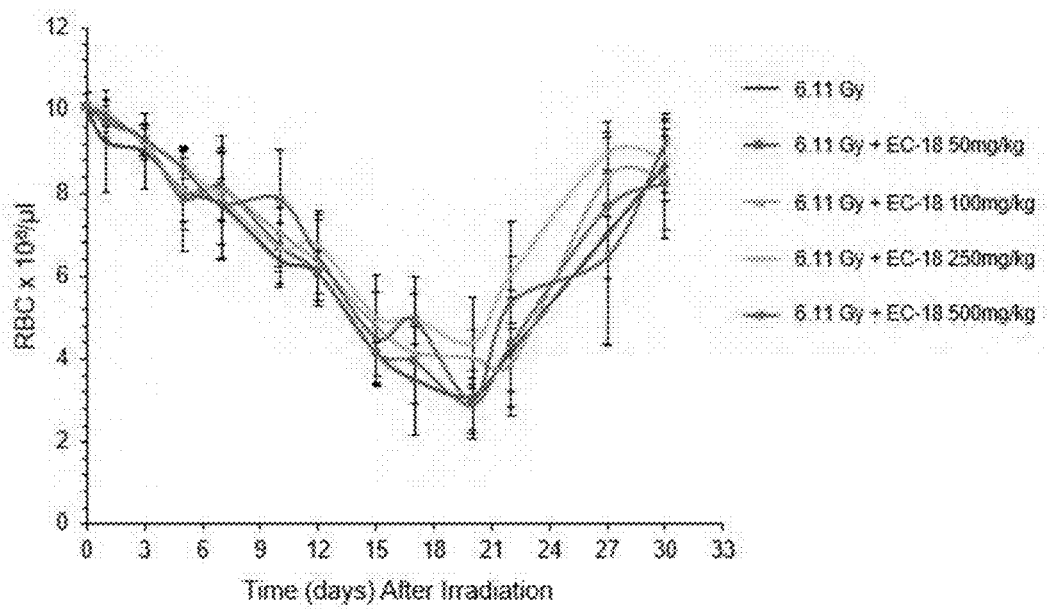
Figure 71B:
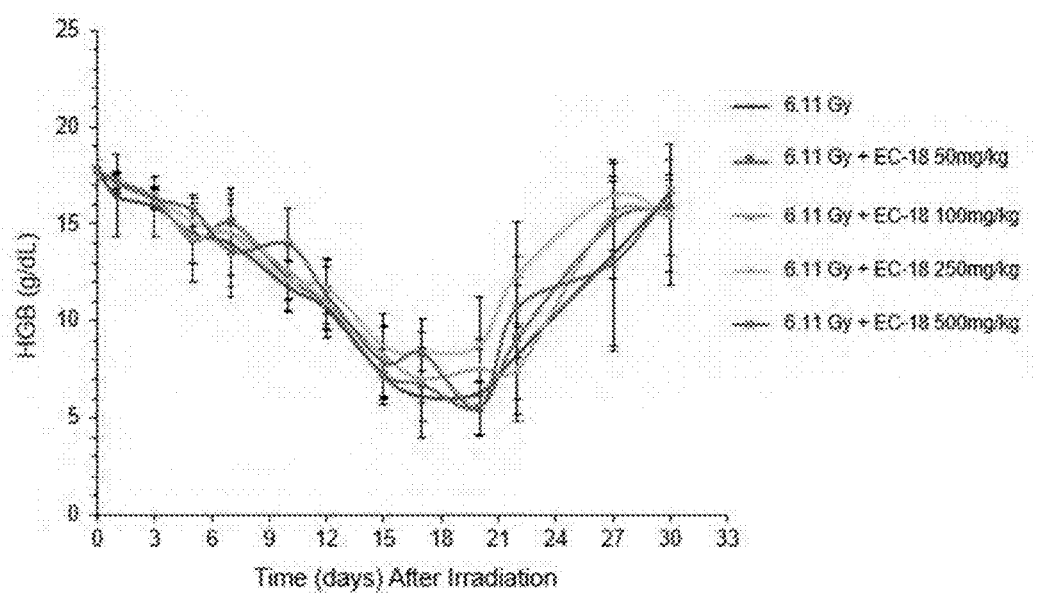

FIGS. 71A-71B show effect of EC-18 on the kinetics of the mean RBC counts and hemoglobin of irradiated mice.

Figure 72:
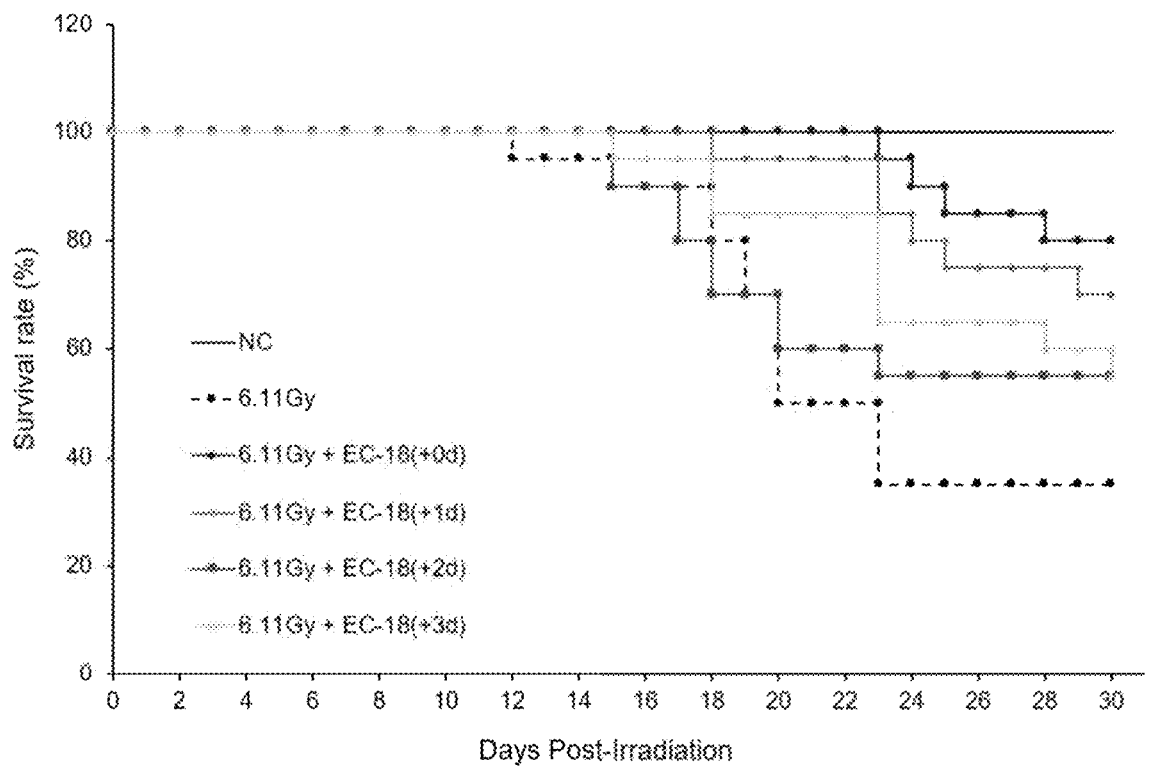

FIG. 72 shows effect of EC-18 (250 mg/kg) dosing schedule on the survival of the irradiated mice.

Figure 73:
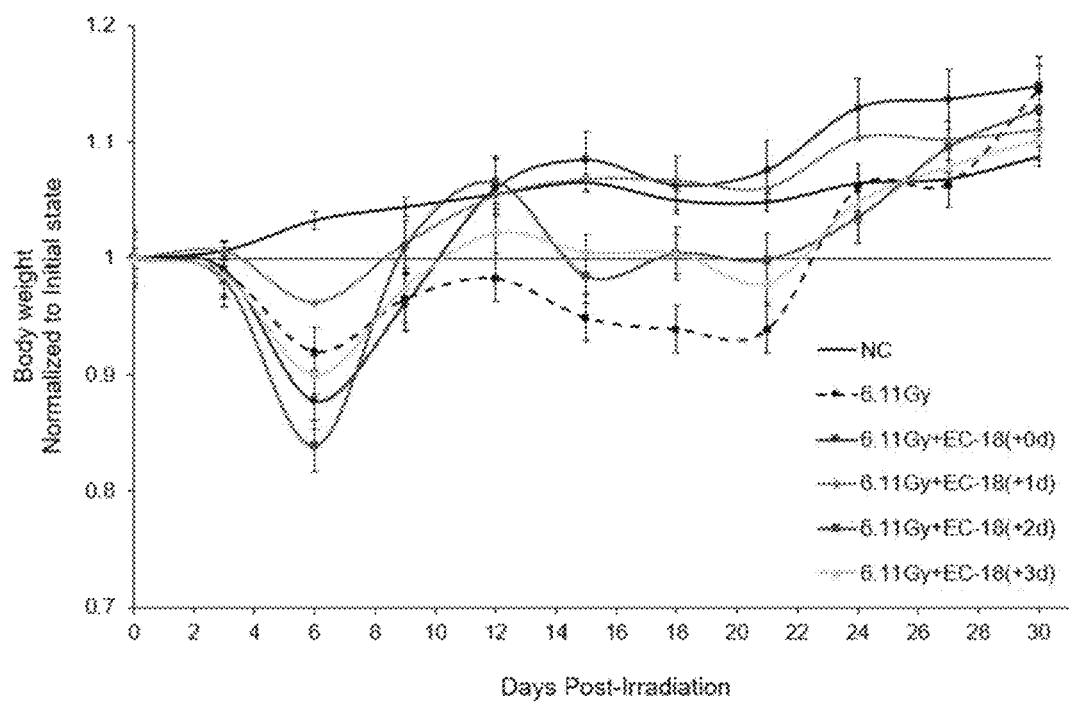

FIG. 73 shows effect of EC-18 (250 mg/kg) dosing schedule on the body weight loss of the irradiated mice.

Figure 74:
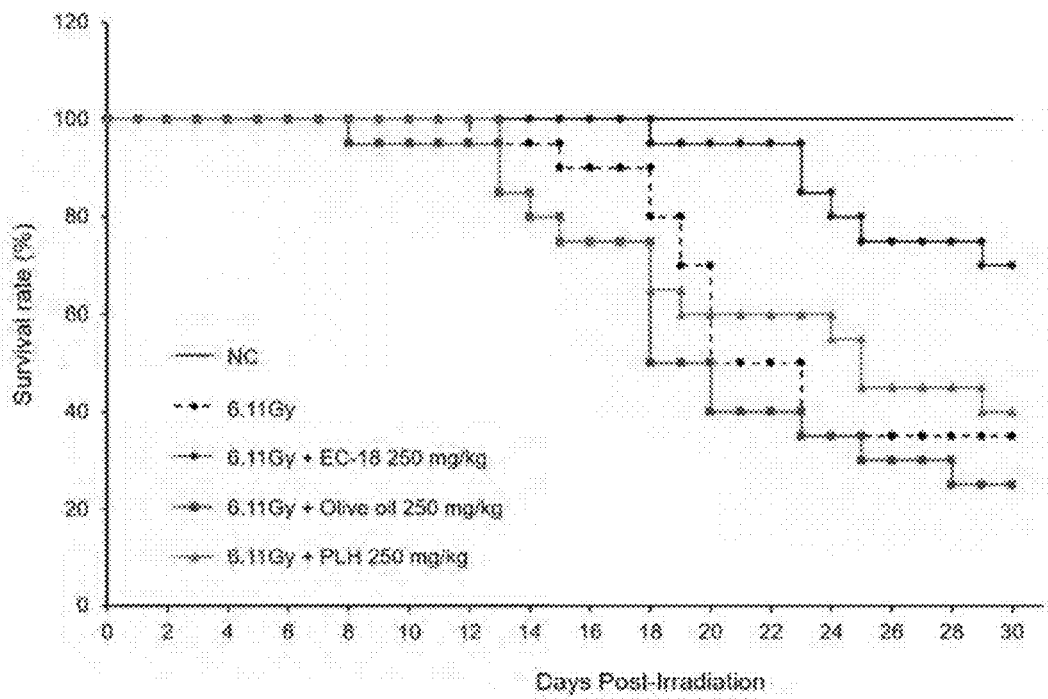

FIG. 74 shows effects of EC-18, olive oil, and PLH on the survival of the irradiated mice.

Figure 75:
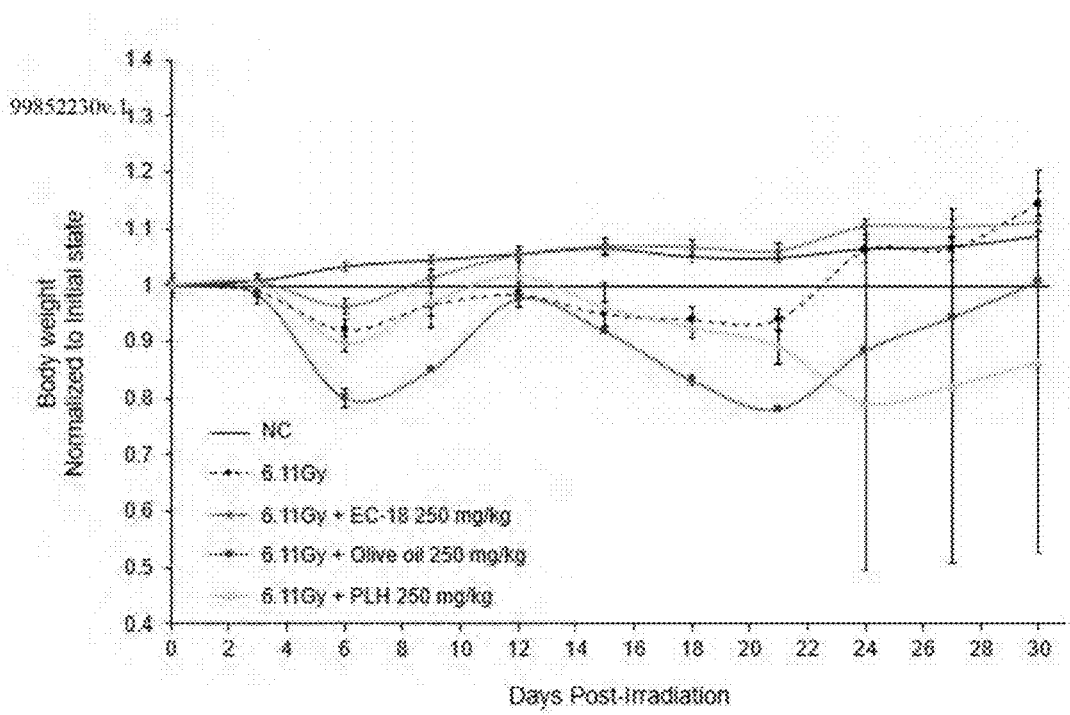

FIG. 75 shows effects of EC-18, olive oil, and PLH on the body weight loss of the irradiated mice.

DETAILED DESCRIPTION

Definitions

The abbreviations used herein have their conventional meaning within the chemical and biological arts. The chemical structures and formulae set forth herein are constructed according to the standard rules of chemical valency known in the chemical arts.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds disclosed herein may exist in tautomeric forms, all such tautomeric forms of the compounds being within the scope of the invention.

The terms "a" or "an," as used in herein means one or more. For example, the singular forms "a," "an" and "the" are intended to include the plural forms as well, unless the context clearly indicates otherwise. It will be further understood that the terms "comprise", "include", "have", etc. when used in this specification, specify the presence of stated features, regions, integers, steps, processes, operations, elements and/or components but do not preclude the presence or addition of one or more other features, regions, integers, steps, processes, operations, elements, components, and/or combinations thereof.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. The term "treating" and conjugations thereof, may include prevention of an injury, pathology, condition, or disease. In embodiments, treating is preventing. In embodiments, treating does not include preventing.

The term "prevent" refers to a decrease in the occurrence of disease symptoms in a patient. As indicated above, the prevention may be complete (e.g., no detectable symptoms) or partial, such that fewer symptoms are observed than would likely occur absent treatment.

The term "modulate" is used in accordance with its plain ordinary meaning and refers to the act of changing or varying one or more properties. "Modulation" refers to the process of changing or varying one or more properties. For example, a modulator of a disease decreases a symptom, cause, or characteristic of the targeted disease such as ARS and its subsyndromes.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient or subject is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a catabolic enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

A therapeutically effective amount of PLAG can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount" or "effective amount" as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the PLAG compound is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

"Disease", "disorder" or "condition" refer to a state of being or health status of a patient or subject capable of being treated with the compounds or methods provided herein. As used herein, the term "acute radiation syndrome" or "ARS" refers to a disease or disorder associated with radiation toxicity or radiation sickness (e.g., acute radiation syndrome (ARS) including hematopoietic (bone marrow) acute radiation syndrome, gastrointestinal acute radiation syndrome, cutaneous acute radiation syndrome, cardiovascular acute radiation syndrome, and/or central nervous system (CNS) acute radiation syndrome). The term the term "acute radiation syndrome" or "ARS" also may include radiation-induced coagulopathy. In certain embodiments, the disease is acute radiation syndrome (ARS). In certain embodiments, ARS occurs in a subject upon exposure to a radiation of about 0.1 Gy (or 10 rads) or greater, about 0.2 Gy (or 20 rads) or greater, about 0.3 Gy (or 30 rads) or greater, about 0.4 Gy (or 40 rads) or greater, about 0.5 Gy (or 50 rads) or greater, about 0.6 Gy (or 60 rads) or greater, about 0.7 Gy (or 70 rads) or greater, about 0.8 Gy (or 80 rads) or greater, about 0.9 Gy (or 90 rads) or greater, about 1 Gy (or 100 rads) or greater, about 2.0 Gy(or 200 rads), about 3.0 Gy(or 300 rads) or about 4.0 Gy (or 400 rads) or greater.

In certain embodiments, ARS may occur in a subject upon exposure to radiation (including gamma radiation) of about 1 Gy (or 100 rads) to about 8 Gy (or 800 rads) for any varying time periods such as at least 1, 2, 5, 10, 30, 60, 80, 120, 180, 240 or 300 seconds.

In certain embodiments, the methods and compositions disclosed herein to treat a subject that has been exposed to ionizing radiation (particularly exposure to excessive ionizing radiation, including gamma radiation)—which methods and compositions may include use or administering to a subject an effective amount of PLAG (1-palmitoyl-2-linoleoyl-3-acetylglycerol)—are suitably utilized where the subject has been exposed to radiation of about 1 Gy (or 100 rads) to about 8 Gy (or 800 rads) or more for any varying time periods such as at least 1, 2, 5, 10, 30, 60, 80, 120, 180, 240 or 300 seconds.

In certain embodiments, the disease or disorder includes cutaneous radiation syndrome such as skin damages, erythema, altered sensation, itching, edema, blistering, desquamation, ulcer, necrosis, hair loss, onycholysis, and the like. In certain embodiments, the disease or disorder includes neutrophil, or infection by reduced white blood cells. In certain embodiments, the disease or disorder includes hemorrhage. In certain embodiments, the disease or disorder includes diarrhea. In certain embodiments, the disease or disorder includes dehydration or electrolyte imbalance. In certain embodiments, the disease or disorder includes convulsion and/or coma.

As discussed, in certain embodiments, methods and compositions as disclosed herein are used to treat a subject that has been exposed to ionizing radiation. In particular aspects, the radiation exposure may be unintended or accidental. In additional aspects, the radiation exposure will not be for therapeutic purposes, for example the radiation exposure will not be radiotherapy as may be utilized for treatment of cancer or other therapy. In further aspects, at least a substantial portion (e.g. an entire limb and/or torso and/or entire head region) of a subject may be exposed to the radiation.

As referred to herein, together and any one of such unintended, accidental, non-therapeutic, and/or substantial body portion exposure may be referred to as "adverse" radiation exposure.

I. Compositions

As discussed, one aspect of the present invention provides a therapeutic pharmaceutical composition for preventing or treating Acute Radiation Syndrome comprising PLAG (1-palmitoyl-2-linoleoyl-3-acetylglycerol) (also referred to herein as EC-18) as an active ingredient.

As referred to herein, the term "acute radiation syndrome" is an acute disease caused by radiation exposure on the entire or on a substantial portion of the body; acute radiation syndrome is also known as radiation toxicity or radiation sickness. Radiation is the released energy when an unstable nucleus is converted into another nucleus. When radiation passes through the body, radiation energy is absorbed and can cause ionization in the tissue. At this time, $H_2O$ is ionized and can transformation of DNA of the subject.

Clinical characteristics of acute radiation syndrome include hematopoietic syndrome, gastrointestinal syndrome, cardiovascular syndrome and neurovascular syndrome.

As described above, acute radiation syndrome can damage radiation-sensitive systems, such as immune, hematopoietic, and gastrointestinal systems, and lead to death. Therefore, the most important factor to consider for preventive or therapeutic effect on acute radiation syndrome is the increase of survival rate of the subjects exposed to radiation. In the present invention, the acute radiation syndrome may be any of the symptoms of hematopoietic syndromes, gastrointestinal syndromes, cardiovascular syndromes and neurovascular syndromes, but at the same time the acute radiation syndrome is not limited to the above symptoms. The composition from this invention is effective in preventing, treating, or mediating the above symptoms and ultimately improves the survival rate of the subjects exposed to radiation.

Acute radiation syndrome usually progresses with four clinical stages: prodromal phase, latent phase, manifest phase, and recovery or death. Depending on the amount of radiation absorbed, the symptoms may appear within hours to weeks. The prodromal phase usually starts within 48 hours after radiation exposure, but may last up to 6 days after the exposure and symptoms may include nausea, vomiting, fatigue, autonomic nerve anxiety and loss of consciousness. The latent phase may last from several days to several weeks depending on the amount of radiation exposure, and clinical symptoms may not appear partially or completely. However, at this stage, symptoms such as lymphocytopenia, granulocytopenia, and myelogenous deficiency may occur. Symptoms from the manifest phase may occur with several weeks delay. Symptoms from the manifest phase may include hematopoietic syndrome, gastrointestinal syndrome, cardiovascular syndrome, and neurovascular syndrome depending on the amount of radiation exposure. Patients exposed to extreme amounts of radiation can experience all four of these steps within a few hours and die within a short period of time.

Among the acute radiation syndrome, the hematopoietic syndrome may be affected, induced or caused by radiation dose of about 0.7-10 Gy, gastrointestinal syndrome may be affected, induced or caused by radiation dose of about 10-30 Gy, and cardiovascular/neurovascular syndrome may be affected, induced or caused by radiation dose of about 50 Gy. In exemplary embodiments of the present invention, acute radiation syndrome includes syndromes affected, induced or caused, by radiation dose of about 0.1 to 100 Gy, about 0.1 to 80 Gy, about 0.1 to 70 Gy, about 0.1 to 60 Gy, about 0.1 to 50 Gy or about 0.7 or 50 Gy, and may be affected, induced or caused by radiation dose of about 0.1 Gy, about 0.5 Gy, about 0.7 Gy, about 1.0 Gy, about 2.0 Gy, about 3.0 Gy or about 4.0 Gy or greater, which may cause death in a specially exposed subject (Reports of Practical Oncology and Radiotherapy, 2011, 16 (4): 123-130), but is not limited thereto.

In additional exemplary embodiments, acute radiation syndrome includes syndromes affected, induced or caused, by radiation dose of about 1 Gy (or 100 rads) to about 8 Gy (or 800 rads) for any varying time periods such as at least 1, 2, 5, 10, 30, 60, 80, 120, 180, 240 or 300 seconds.

The term "prevention" as used herein means any action that inhibits or delays the occurrence, spread or reoccurrence of a specified disorder or disease such as acute radition syndrome upon administration of a compound or composition as disclosed herein. The term "treatment" as used herein means any act that improves or alleviates the symptoms of a specified disorder or disease such as acute radition syndrome upon administration of a compound or composition as disclosed herein.

In certain aspects, the compound administered to a subject is of the following Formula 1:

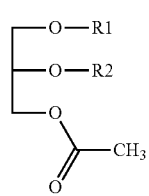

Formula 1 wherein $R_1$ and $R_2$ are independently a fatty acid residue of 14 to 20 carbon atoms.

The glycerol derivatives of Formula 1 above are sometimes referred to herein as monoacetyldiacylglycerols (MDAG). Fatty acid residue refers to the acyl moiety resulting from formation of an ester bond by reaction of a fatty acid and an alcohol. Non-limiting examples of $R_1$ and $R_2$ thus include palmitoyl, oleoyl, linoleoyl, linolenoyl, stearoyl, myristoyl, arachidonoyl, and so on. Preferable combinations of $R_1$ and $R_2$ ($R_1/R_2$) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyldiacylglycerol derivatives of Formula 1 can be (R)-form, (S)-form or a racemic mixture, and may include their stereoisomers. In certain aspects, in compounds where $R_1$ and/or $R_2$ substituents are unsaturated fatty acid residues, one or more double bonds that are present suitably may have the cis configuration. In other aspects, one or more double bonds $R_1$ and/or $R_2$ substituents may be present in a trans configuration. In certain aspects, such one or more double bonds will be present only in cis configuration.

In a certain preferred aspect, the compound administered to as subject is PLAG (1-palmitoyl-2-linoleoyl-3-acetylglycoerol) having a structure of the following Chemical Formula 2 (the compound also sometimes referred to herein as EC-18):

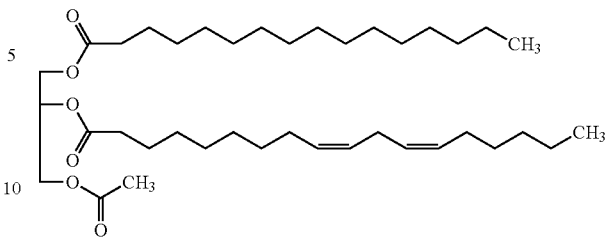

Chemical Formula 2

Further, in the present invention, PLAG can include all of the above-mentioned compounds of Chemical Formula 2 and other obvious derivatives from the industry known chemical transformation. For example, additions and substitution reactions for increasing the stability of the compound or for formulation of the compound can be carried out within a range not affecting the pharmacological effect of PLAG, and these chemical derivatives are all included within the scope of this invention.

PLAG has been known to have therapeutic effects on neutropenia, thrombocytopenia, and mucositis caused by anti-cancer chemotherapy. However, efficacy of PLAG on preventing or treating acute radiation syndrome, including whether it can increase the survival rate of individuals with acute radiation syndrome has not been reported.

Figure 2A:
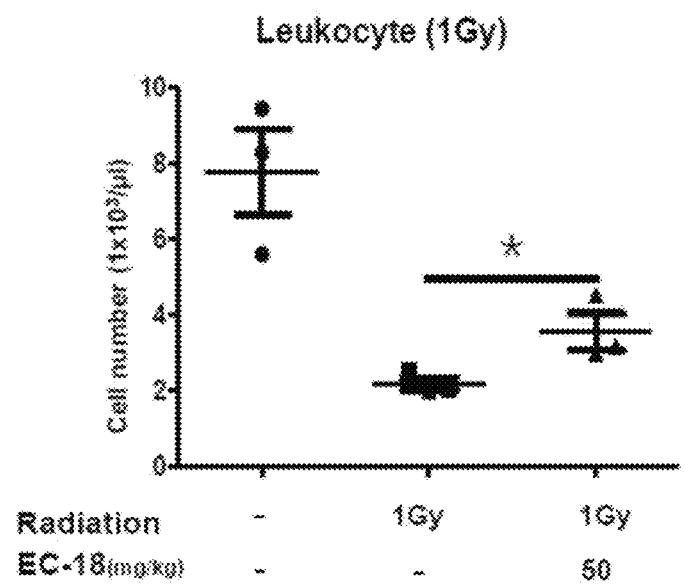
FIGS. 2A-2C show the level of blood leukocyte (FIG. 2A), neutrophil (FIG. 2B) and lymphocyte (FIG. 2C) counts after PLAG (1-palmitoyl-2-linoleoyl-3-acetylglycerol) administration in an animal model of acute radiation syndrome.
Figure 2B:
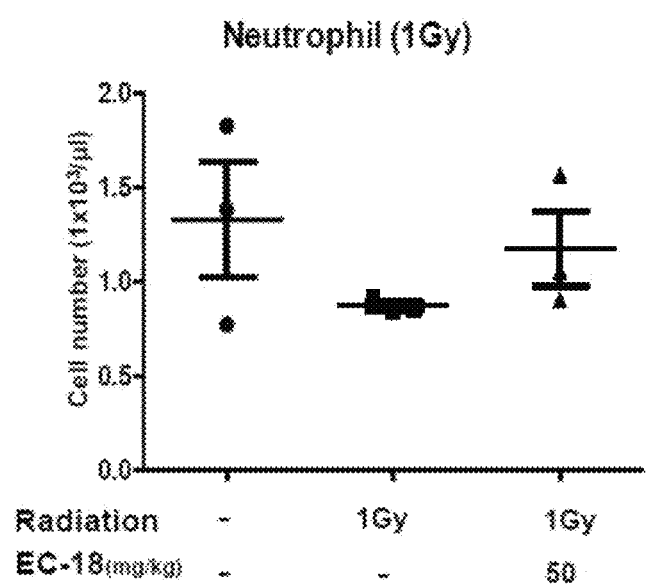
Figure 2C:
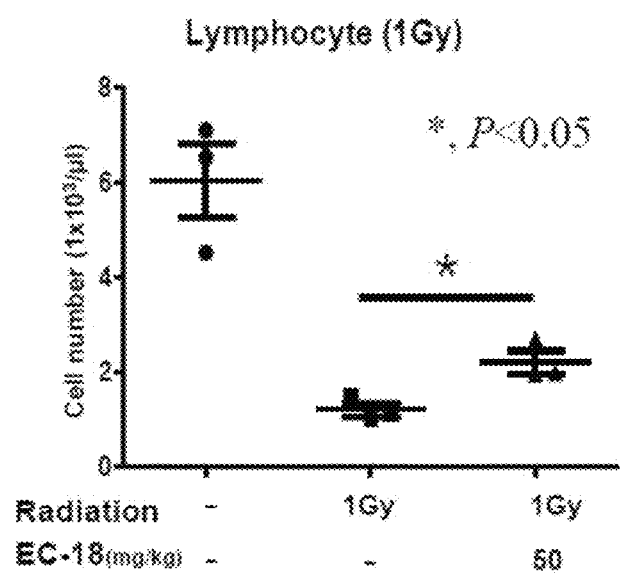
Figure 3:
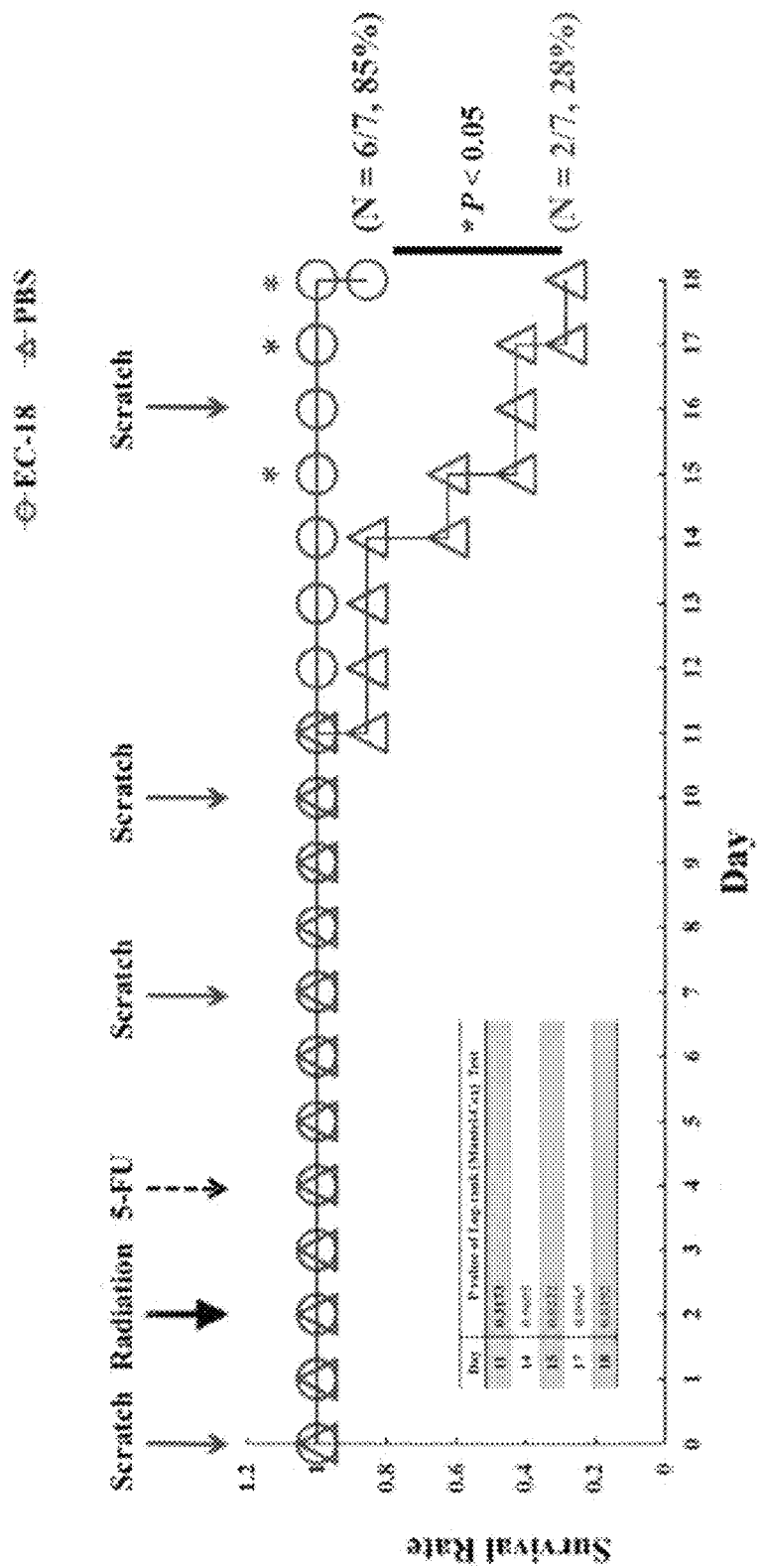
FIG. 3 shows the survival rate with PLAG administration in an animal model with acute radiation syndrome accompanying oral mucositis.
Figure 4:
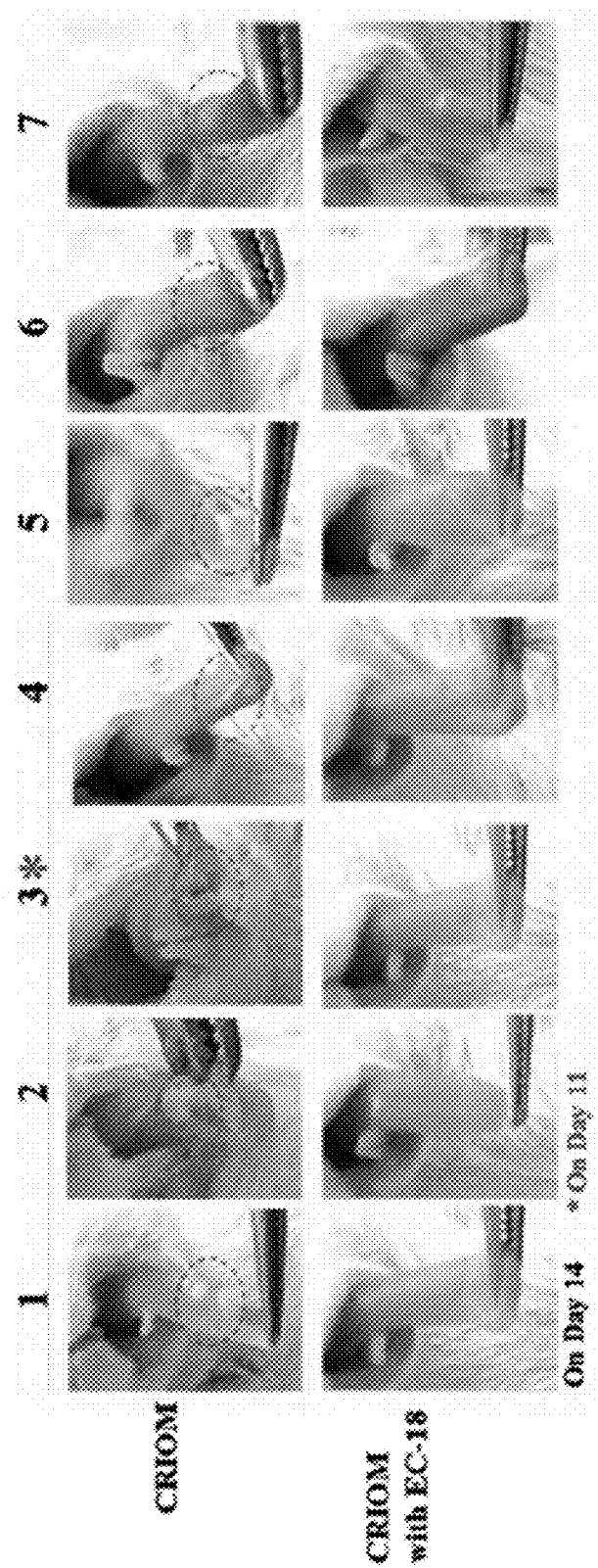
FIG. 4 shows the state of mucositis after PLAG administration in an animal model of acute radiation syndrome.

In an exemplary embodiment, PLAG was found to significantly increase the numbers of leukocyte, neutrophil and lymphocyte counts in blood of subjects with radiation exposure (Table 1 and FIG. 2), and improved mucositis from the animal study model with severe acute radiation syndrome where oral mucositis was induced from the chemoradiotherapy (FIGS. 4 and 5) and increased neutrophils in the blood (FIG. 6), and as a result PLAG dramatically increased the survival rate of the study subjects (FIG. 3). Therefore, the composition of the present invention has an excellent effect as a therapeutic pharmaceutical composition for preventing or treating acute radiation syndrome.

The therapeutic pharmaceutical composition of the present invention may be administered within 1 hour, within 2 hours, within 3 hours, within 4 hours, within 5 hours, within 6 hours, within 7 hours, within 8 hours, within 9 hours, within 10 hours, within 12 hours, within 16 hours, within 20 hours, within 30 hours, within 40 hours, or within 48 hours after the radiation exposure, but is not limited thereto, as discussed above.

Also, the above composition may be administered as an individual therapeutic agent or may be administered in combination with another drug that is known to have an efficacy on treating acute radiation syndrome. For example, the above composition may be administered with one or more of therapeutic agents including proteins, small molecule drugs, nucleic acids or the like. For example, the composition may be administered with a therapeutic agent including granulocyte-colony stimulating factor (G-CSF), but the administration is not limited thereto. Further, the above composition can be administered together with analgesics, anti-ulcer agents, antidiarrheic, antibiotics, antipyretics, nutritional supplements and antioxidants, which can help preventing or treating acute radiation syndrome.

The term "administration" in the present invention means introducing a therapeutic pharmaceutical composition of the present invention to a patient by any suitable method, and the administration route of the composition of the present invention may be administered via various routes whether orally or non-orally. The therapeutic pharmaceutical composition of the present invention can be manufactured into various formulations depending on the administration methods.

The frequency of administration of the composition of the present invention is not particularly limited, but it may be administered once a day or several times a day with divided dosage.

The therapeutic pharmaceutical composition of the present invention can be used as a single medication, and can be used as a combined medication containing another drug, and can be formulated with using a pharmaceutically acceptable carrier, excipient or diluent to make a single-dose unit or a unit with a multi-dose container.

The term "pharmaceutical composition" as referred to herein indicates a composition prepared for the purpose of preventing or treating diseases, and can be formulated into various forms according to ordinary methods. For example, it can be formulated into oral administration formulations such as powders, granules, tablets, capsules, suspensions, emulsions and syrups, and can be formulated in the form of external use, suppositories, and sterilized injection solutions.

In addition, the pharmaceutical composition of the present invention may be manufactured with additional pharmaceutically acceptable carrier for each formulation. As used herein, the term "pharmaceutically acceptable carrier" may refer to a carrier or diluent that does not stimulate organism and not inhibiting biological activity and characteristic of the injected compound. The type of the carrier that can be used in the present invention is not particularly limited, any carrier conventionally used in the area of industry and pharmaceutically acceptable may be used.

Saline, sterilized water, IV fluids, buffer saline, albumin injection solution, dextrose solution, maltodextrin solution, glycerol, ethanol are non-limiting examples of the usable carriers. These carriers may be used alone or in combination of two or more. The carrier may include a non-naturally occurring carrier. If necessary, other conventionally used additives like an antioxidant, a buffer and/or a bacteriostatic agent may be added and used. It may be formulated with diluent, a dispersant, a surfactant, a bonding agent, a lubricant to make an injection solution like aqueous solution, suspension, emulsion, and pills, capsules, granules or tablets, and the like.

In addition, the pharmaceutical composition of the present invention may contain a pharmaceutically effective amount of PLAG. The term "pharmaceutically effective amount" in the present invention means an amount sufficient to treat a disease at a reasonable benefit or risk ratio applicable to medical treatment and is generally in the range of about 0.001 to 5000 mg/kg, preferably of about 0.05 to 1000 mg/kg, may be administered once a day or several times a day with divided dosage. However, for the purposes of the present invention, the specific therapeutically effective amount for a particular patient will depend upon the nature and extent of the reaction to be achieved, the particular composition, including whether or not other agents are used, the age, weight, sex and diet of the patient, the time of administration, the route of administration and the proportion of the composition, the duration of the treatment, the drugs administered or co-administered with the specific composition, and similar compounds well known in the medical industry.

As discussed, kits are also provided. For instance, in this aspect, a PLAG compound suitably can be packaged in suitable containers labeled, for example, for use as a therapy to treat a subject suffering from acute radiation sickness, or a subsyndrome thereof, or exposure to excessive ionizing (e.g. gamma) radiation. The containers can include a PLAG compound or composition and one or more of a suitable stabilizer, carrier molecule and/or the like, as appropriate for the intended use. In other embodiments, the kit further comprises one or more therapeutic reagents that alleviate some of the symptoms or secondary infections or disorders that may be associated with acute radiation sickness, or a subsyndrome thereof, or exposure to excessive ionizing (e.g. gamma) radiation. Accordingly, packaged products (e.g., sterile containers containing one or more of the compositions described herein and packaged for storage, shipment, or sale at concentrated or ready-to-use concentrations) and kits, including a PLAG compound, and instructions for use, are also within the scope of the invention. A product can include a container (e.g., a vial, jar, bottle, bag, or the like) containing a PLAG compound or composition. In addition, an article of manufacture or kit further may include, for example, packaging materials, instructions for use, syringes, delivery devices, for treating or monitoring the condition for which prophylaxis or treatment is required.

The product may also include a legend (e.g., a printed label or insert or other medium describing the product's use (e.g., an audio- or videotape)). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents and/or an additional therapeutic agent. Alternatively, the compositions for example can be provided in a concentrated form with a diluent and instructions for dilution.

Another aspect of the present invention is a health functional food composition of food supplement for preventing or ameliorating Acute Radiation Syndrome comprising PLAG (1-palmitoyl-2-linoleoyl-3-acetylglycerol) as an active ingredient.

In the present invention, the term "improvement" means all actions that at least reduce the degree of symptom associated with the condition being treated. Herein, the health functional food composition may be used simultaneously or separately with the medicament for treatment before or after the occurrence of the disease to prevent or improve the acute radiation syndrome.

PLAG does not show notable toxicity to cells and shows improvement effect on acute radiation syndrome, so PLAG can be manufactured and be taken in the form of a health functional food composition.

Functional food is the same term as food for special health use (FoSHU). It refers to foods that have been processed so that the biological control function appears more efficient in addition to nutritional value. The food may be prepared in various forms such as tablets, capsules, powders, granules, liquids, rings and the like in order to obtain a useful effect on skin regeneration.

For that, the content level of PLAG contained in the health functional food is not particularly limited, but may be 0.01 to 100% by weight, specifically 1 to 80% by weight based on the total weight of the health functional food.

The health functional food composition of the present invention may also contain a pharmaceutically acceptable carrier.

There is no particular limitation on the kind of health functional foods including PLAG from the present invention, and examples thereof include drinks, gums, tea, vitamin complex, health supplement foods and the like. The food may be supplemented with other ingredients that do not interfere with the improvement effect on acute radiation syndrome, and the kind thereof is not particularly limited. For example, various herbal extracts, sitology-acceptable food supplementary or other natural carbohydrates may be added as an additional ingredient.

The food-aid additive described above is added to produce the health functional food of each formulation and can be appropriately selected and used by a person skilled in the relevant field of technology. For example, various nutrient additives, vitamins, minerals (electrolytes), synthetic flavors and natural flavors, colorants and fillers, pectic acid and its salts, alginic acid and its salts, organic acids, protective colloid thickeners, pH controller, stabilizer, preservative, glycerin, alcohol, carbonating agent used in a carbonated drink, and the like, but the kind is not limited by the above.

In addition, the health functional food described above may contain additional ingredients which are commonly used in food to improve smell, taste, visual appearance and the like. For example, vitamins A, C, D, E, B1, B2, B6, B12, niacin, biotin, folate, panthotenic acid and the like can be included. In addition, it may include minerals such as zinc (Zn), iron (Fe), calcium (Ca), chromium (Cr), magnesium (Mg), manganese (Mn) and copper (Cu) and the like. It may also contain amino acids such as lysine, tryptophan, cysteine, valine and the like.

In addition, the described health functional food may include one or more preservatives (such as potassium sorbate, sodium benzoate, salicylic acid, and sodium dehydroacetate), bactericides (such as bleaching powder and high bleaching powder, sodium hypochlorite), antioxidants (butylhydroxyanilide (BHA), butylhydroxytoluene (BHT), etc.), coloring agents (such as tar pigments), color formers (such as sodium nitrite and sodium acetates), bleaching agents (sodium sulfite), seasonings (such MSG, sodium glutamate), sweeteners (such as dulcin, cyclamate, saccharin, sodium), flavorings (vanillin, lactones, etc.), swelling agents (alum, potassium hydrogen D-tartrate), fortifier, emulsifiers, thickeners, encapsulating agents, gum bases, foam inhibitors, solvent, improver, and the like. The above additives are selected according to the type of food and used in an appropriate amount.

The health functional food composition of the present invention can be prepared by a method commonly used in the industry and can be prepared by adding raw materials and ingredients which are conventionally added in the industry. In addition, unlike general medicine, the health functional food may have an advantage, fo example, as there can be no side effect from a long-term use and have better portability.

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch.1, p.1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, PA) and WO 96/05309, the teachings of both of which are hereby incorporated by reference.

III. Methods of Treatment

Another aspect of the present invention is a method for preventing or treating Acute Radiation Syndrome comprising the step of administering PLAG (1-palmitoyl-2-linoleoyl-3-acetylglycerol) to a subject.

Definition of PLAG (also referred to herein as EC-18) and acute radiation syndrome are described above.

Since PLAG has preventive and therapeutic effects on acute radiation syndrome, it is possible to prevent or treat the acute radiation syndrome by administering a composition containing PLAG to the individual.

PLAG (1-palmitoyl-2-linoleoyl-3-acetylglycerol) has an excellent effect in preventing and treating acute radiation syndrome by increasing the survival rate of subjects with radiation exposure. Accordingly, the pharmaceutical composition and the health functional food composition containing the PLAG as an active ingredient of the present invention can be effectively used for preventing, treating or improving acute radiation syndrome.

IV. Examples

Although the foregoing section has been described in some detail by way of illustration and example for purposes of clarity of understanding, it is apparent to those skilled in the art that certain minor changes and modifications will be practiced in light of the above teaching. Therefore, the description and examples should not be construed as limiting the scope of any invention described herein.

All references cited herein, including patent applications and publications, are hereby incorporated by reference in their entirety.

Example 1: Effect of PLAG (1-Palmitoyl-2-Linoleoyl-3-Acetylglycerol) on the Reduction of Immune Cell Levels in the Blood of an Animal Model of Acute Radiation Syndrome (ARS)

Balb/c mice (9-week-old male) were purchased from Koatech (Pyeongtaek, Republic of Korea) and maintained in a specific pathogen-free (SPF) environment to establish an animal model of acute radiation syndrome. In order to evaluate the effect of PLAG on the reduction of immune cells by radiation, the following three groups were constructed for this study. (1) normal control group (positive control); (2) Radiotherapy-Radiation induced leukopenia (RIL) group (negative control group); And (3) RIL+PLAG treated group (experimental group).

Figure 1:
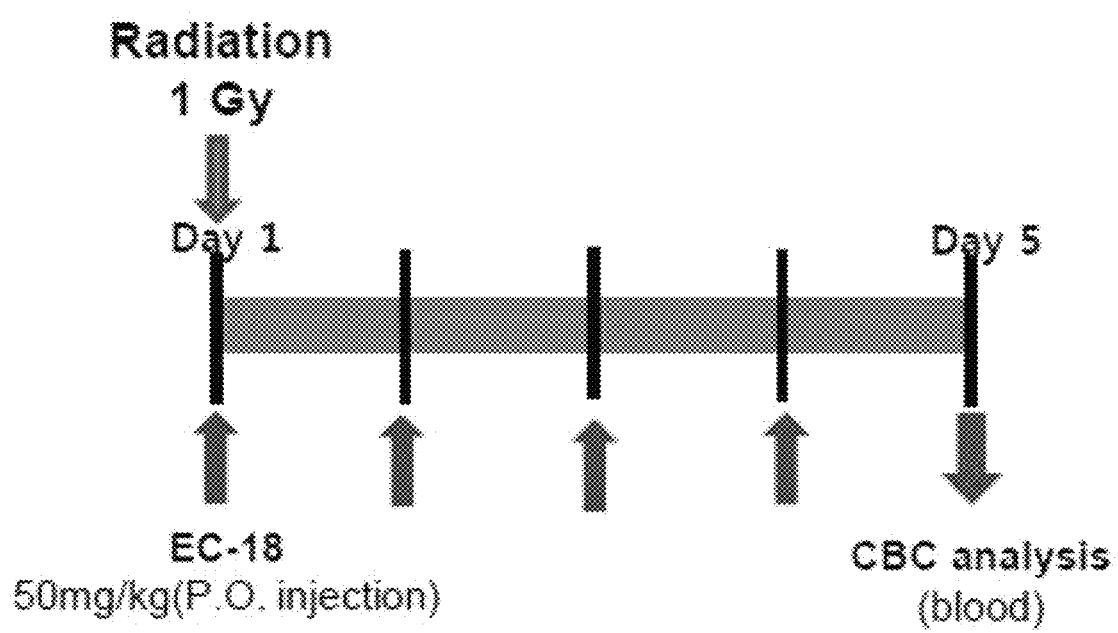
FIG. 1 shows a schematic experimental design diagram related to radiation-induced Acute Radiation Syndrome in an animal model.

Specifically, mice treated with RIL and RIL+PLGA were exposed to whole body radiation at 1 Gy (100 rad=1.06 min). For the RIL+PLAG treatment group, 50 mg/kg/day of PLAG (Enzychem Lifesciences Co., Daejeon, Republic of Korea) was orally administered daily for 4 consecutive days after irradiation. The normal controls were not exposed to radiation. On the 5th day after irradiation, blood samples were collected, and then Complete Blood Count (CBC) was measured using a Mindray BC-5300 auto hematology analyzer (Shenzhen Mindray Bio-medical Electronics, China) so that the number of blood leukocytes, neutrophils and lymphocytes in blood could be counted (FIG. 1).

As a result, in the RIL+PLAG treated group, the blood level of leukocyte, neutrophil and lymphocyte counts were 63% (2.18±0.31 vs 3.56±0.84), 34% (0.87±0.04 vs. 1.17±0.35) and 85%±0.25 vs. 2.2±0.42) (Table 1 and FIG. 2) increased in statistically significant manners.

TABLE 1

|  | Normal Control (n = 3) | RIL (n = 3) | RIL + PLAG (n = 3) |
| --- | --- | --- | --- |
| White blood cells ($10^3/\mu L$) | 7.76 ± 1.96 | 2.18 ± 0.31 | 3.56 ± 0.84 |
| Neutrophils ($10^3/\mu L$) | 1.32 ± 0.53 | 0.87 ± 0.04 | 1.17 ± 0.35 |
| Lymphocyte ($10^3/\mu L$) | 6.05 ± 1.36 | 1.19 ± 0.25 | 2.2 ± 0.42 |

Therefore, it can be seen from the above results that PLAG exhibits an effect of inducing an increase of various immune cells levels which were reduced by radiation treatment in the ARS study model.

Example 2: The Effect of PLAG on Survival Rate in Acute Radiation Syndrome (ARS) Animal Model In order to further confirm the effect of PLAG on the acute radiation syndrome, an animal model of radiation-induced oral mucositis was prepared and tested as an acute radiation syndrome animal model with severer conditions than those in Example 1 above. First, Balb/c mice (8-week-old female) were purchased from Koatech (Republic of Korea) and maintained in a specific pathogen-free (SPF) environment to establish a radiation-induced oral mucositis model. In this example, first group of oral mucositis induced group (negative control) was compared to the second group where PLAG was orally administered to animals with induced oral mucositis.

Specifically, mice were exposed to 1 Gy whole body gamma radiation and scars of 0.2 cm on the mice tongue were scratched at 0, 7, 10 and 16 days with the same force and depth using an 18 gauge needle. On day 2 post-irradiation, 5-Fluorouracil (50 mg/kg/day) was intraperitoneally administered and PLAG was administered orally at 250 mg/kg/day for 18 days (Table 2).

TABLE 2

|  | OM induced group | OM induced + PLGA administered group |
| --- | --- | --- |
| Number of subjects | 7 (female) | 7 (female) |
| Scratch on tongue (0, 2, 10 and 16 days) | 0.2 cm | 0.2 cm |
| Gamma ray (day 2) | 1 Gy | 1 Gy |
| dosage/day | PBS | PLAG (250 mg/kg) |
| Method of administration/days | Oral 0 or 18 days | Oral 0 or 18 days |
| CBC analysis/schedule | 7 and 10 days | 7 and 10 days |

As a result, in the oral mucositis-induced group, the survival rate was only 28% (2/7, 72%) at day 18, whereas 85% (6/7, 15% (FIG. 3) survival rate was reported from OM-induced+PLAG administration Group. These results suggest that PLAG treatment significantly increased the survival rate of mice despite with the reduction of hematopoietic cells from the gamma ray exposure and 5-Fluorouracil treatment and the increased risk of infection caused by oral wounds with scratch on tongue. It further suggests that PLAG exhibits excellent prophylactic and therapeutic effects.

Example 3: Effect of PLAG on Each Symptom Affecting Survival Rate in an Animal Model of Acute Radiation Syndrome For the animal model used in Example 2 above, oral mucositis level and neutrophil count in blood were determined.

Oral mucositis level was determined by counting the ulcer formation and edema of the tongue and the incidence of wound atrophy, and calculating the score of oral mucositis by a total of 5 blinded observers. On the 7th and 10th day, the blood of the experimental groups was collected and the number of neutrophils in the blood was measured by measuring the Complete Blood Count (CBC) using a Mindray BC-5300 auto hematology analyzer (Shenzhen Mindray Bio-medical Electronics, China).

Figure 6A:
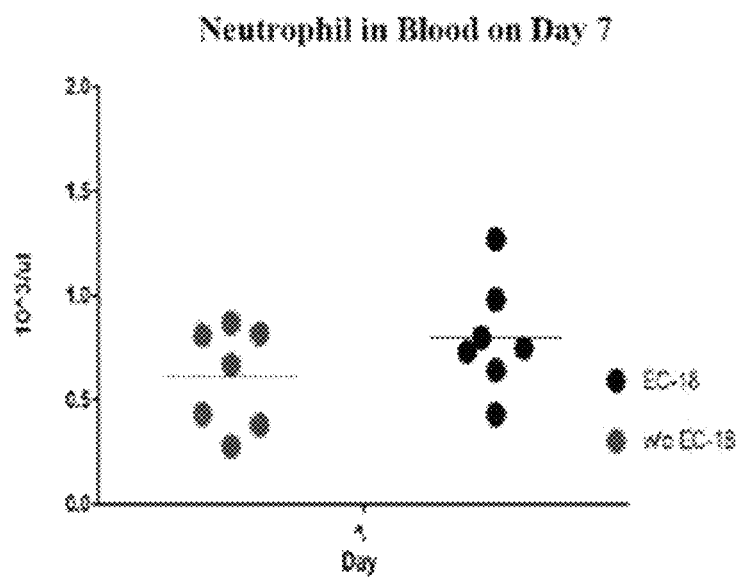
FIGS. 6A-6B show the level of neutrophil counts in the blood following PLAG administration in an animal model of acute radiation syndrome accompanying oral mucositis after 7 days (FIG. 6A) and after 10 days (FIG. 6B).
Figure 6B:
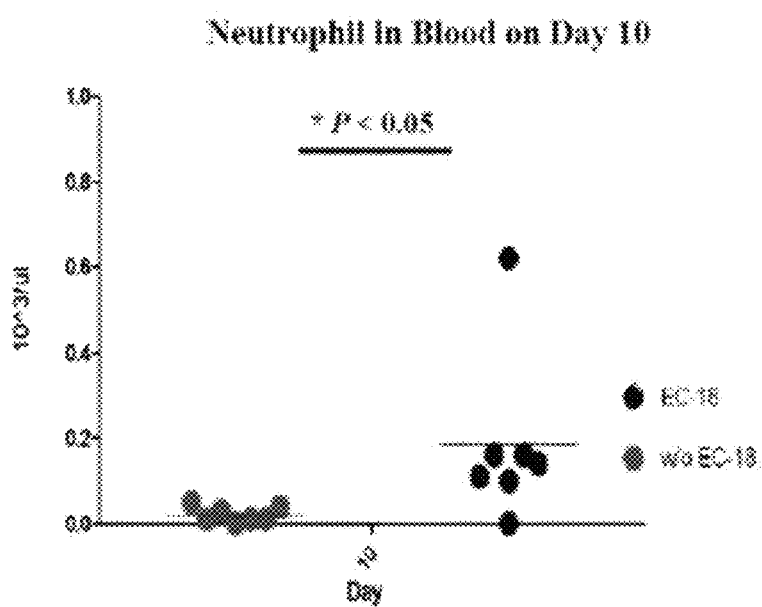

As a result, visually confirmed oral mucositis levels were significantly reduced in the PLAG-treated group compared to the non-PLAG-treated group with less ulcer formation and edema of the tongue and the lower incidence of wound atrophy. (FIG. 4) The oral mucositis score was also significantly decreased (FIG. 5) On the 7th and 10th days, neutrophil counts in the blood were decreased by approximately 95% in the blood from radiation-induced oral mucositis animal group at 10 days, but neutrophil number was significantly increased in the group administered with PLAG daily (FIG. 6).

Example 4: Improvement of Survival Rate

In order to evaluate effects of PLAG on survival rates of animal models exposed to radiation, the following test groups were constructed as shown in Table 3 and results are shown in FIG. 7B, and FIG. 8-12. As discussed in Examples above, the first group of untreated group (negative control) of ARS-induced mice after radiation was compared to the second group of treated group of ARS-induced mice with PLAG after radiation.

TABLE 3

Figure 7A:
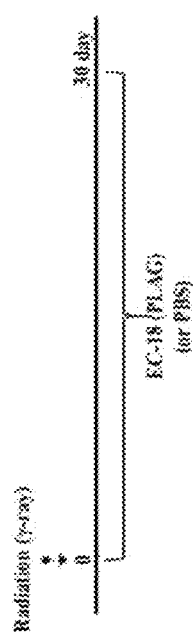
FIG. 7A is a schematic diagram of EC-18 treatment (30 days) in a radiation-induced Acute Radiation Syndrome animal model.
Figure 7B:
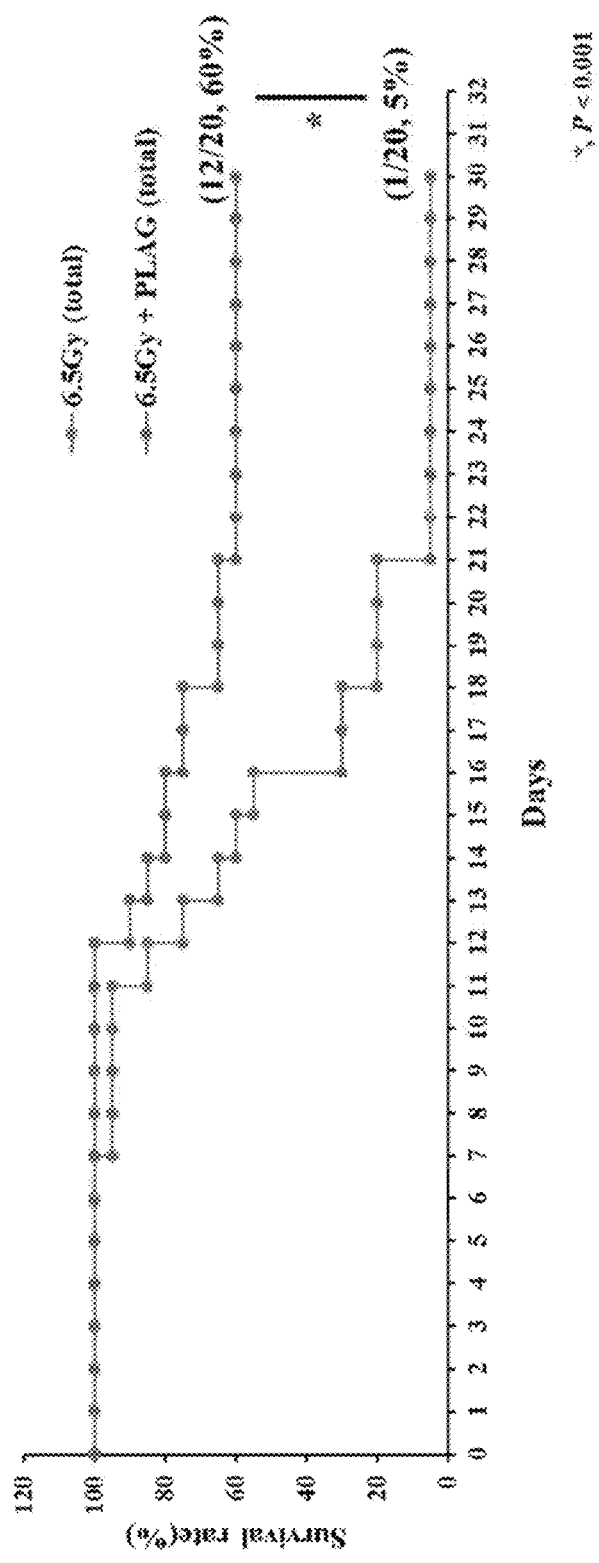
FIG. 7B shows a survival rate of mice (BALB/c, 11 weeks old) administered with or without EC-18 (250 mg/kg/day PO) receiving total body irradiation (6.5 Gy). The survival rate in mice administered with EC-18 is improved compared to the untreated (without EC-18) mice.

| Test Groups | |
| --- | --- |
| FIG. 7B | Balb/c: 11 weeks, male (n = 10) or Female (n = 10) γ-Radiation: 6.5Gy (100 rad = 1.06 min), TBI EC-18: 250 mg/kg/day (P.O.) Group: 1) untreated group after radiation 2) EC-18 group treated group after radiation |

TABLE 3-continued

Figure 8:
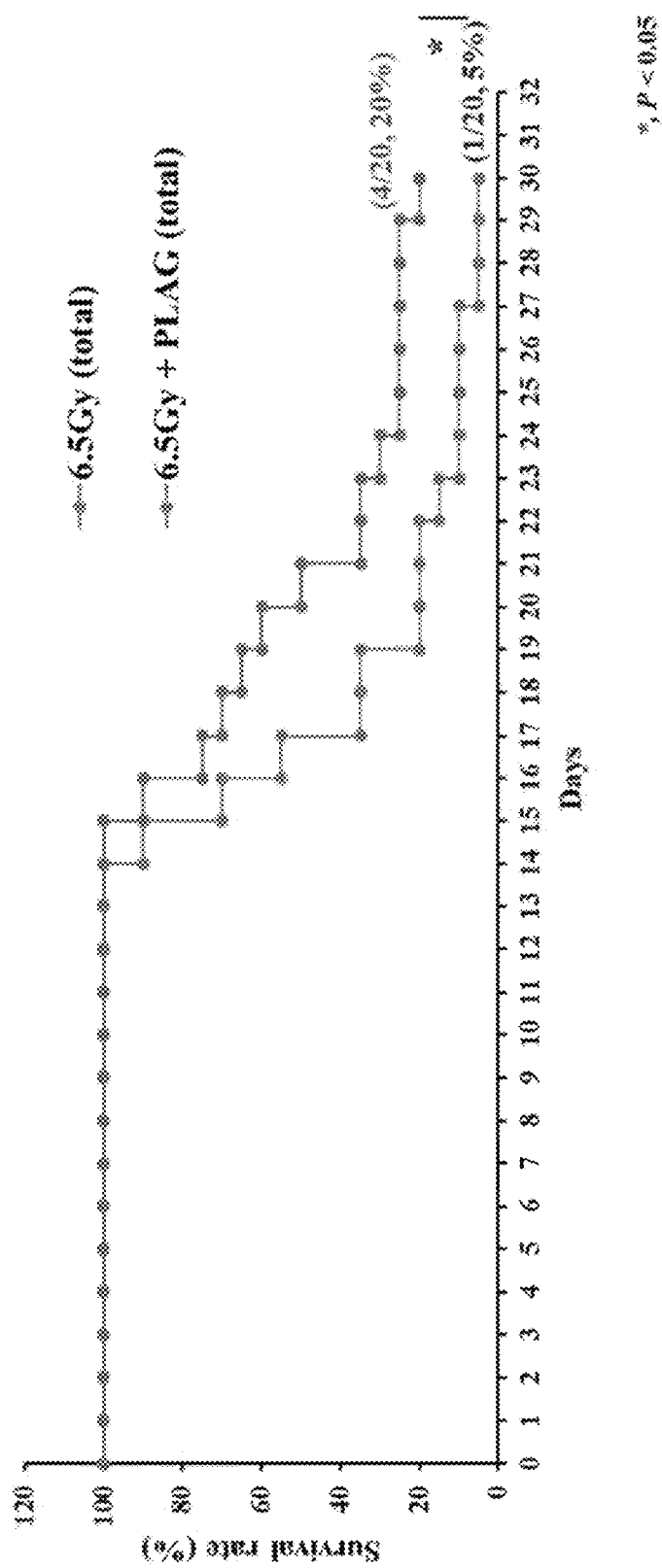
FIG. 8 shows a survival rate of mice (BALB/c, 9 weeks old) administered with (n=20) or without (n=20) EC-18 (250 mg/kg/day PO) receiving total body irradiation (6.5 Gy) according to the diagram in FIG. 7A. Survival rate of mice treated with EC-18 is improved compared to the untreated (without EC-18) mice.
Figure 9:
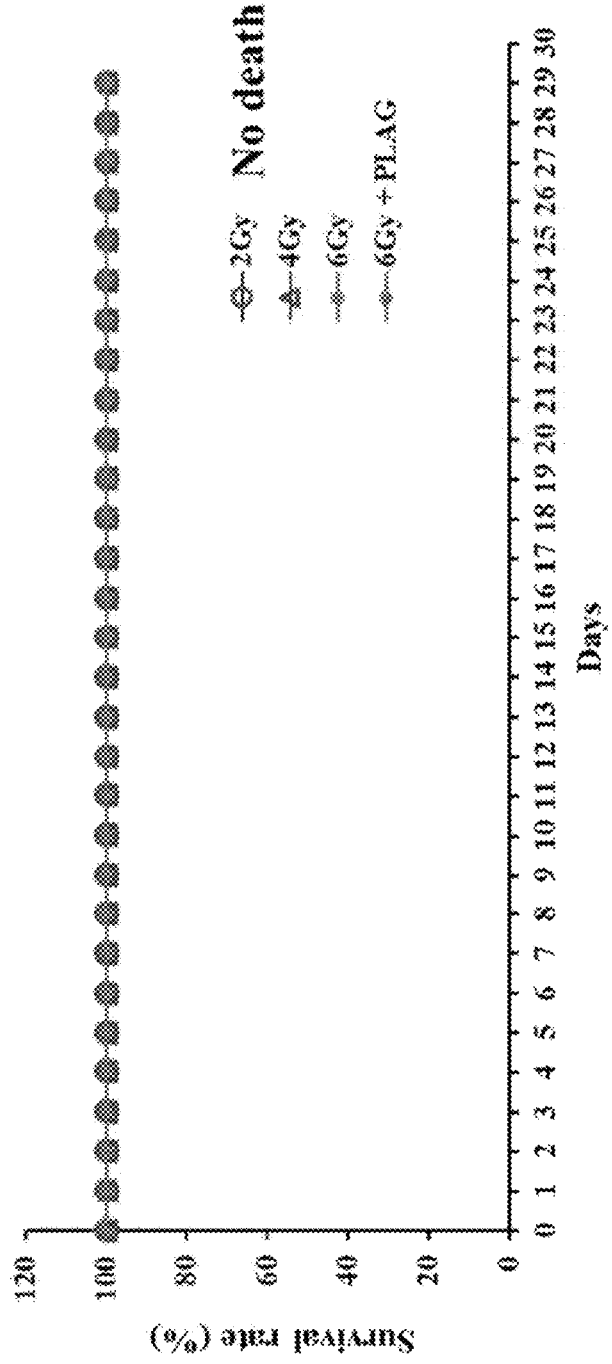
FIG. 9 shows survival curves of mice (BALB/c, 9 weeks old) receiving total body irradiation (2, 4, and 6 Gy) without EC-18 treatment and with EC-18 treatment (250 mg/kg/day PO) in mice receiving total body irradiation at 6 Gy according to the diagram in FIG. 7A.
Figure 10A:
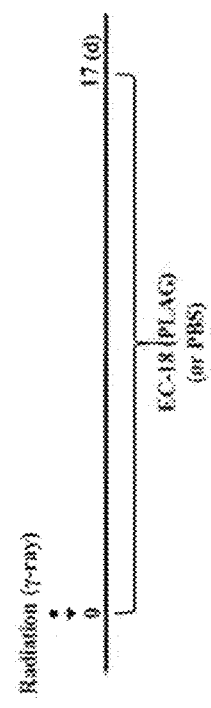
FIG. 10A is a schematic diagram of EC-18 treatment (17 days) in a radiation-induced Acute Radiation Syndrome animal model.
Figure 10B:
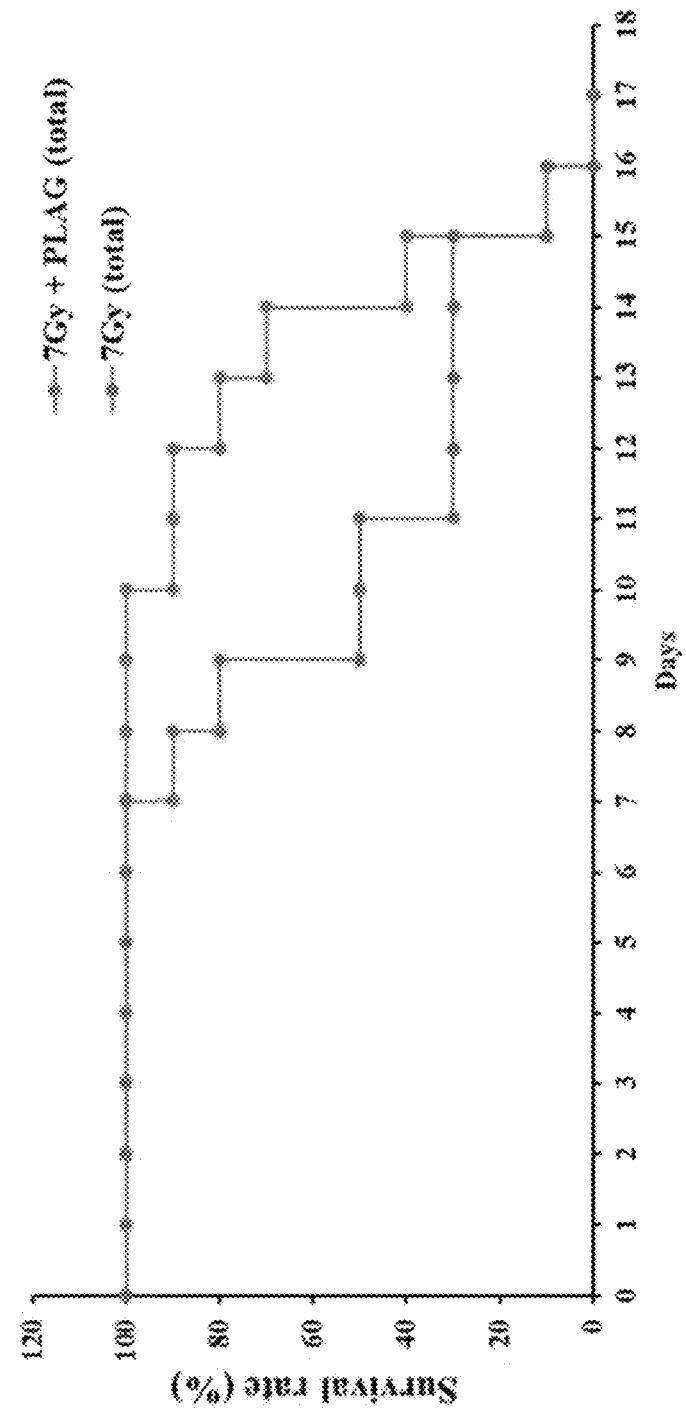
FIG. 10B shows survival rate of mice (BALB/c, 9 weeks old) administered with or without EC-18 (250 mg/kg/day PO) receiving lethal today body irradiation (7 Gy). Survival rate of mice administered with EC-18 receiving lethal irradiation is improved until about day 15 compared to untreated (without EC-18) mice.
Figure 11:
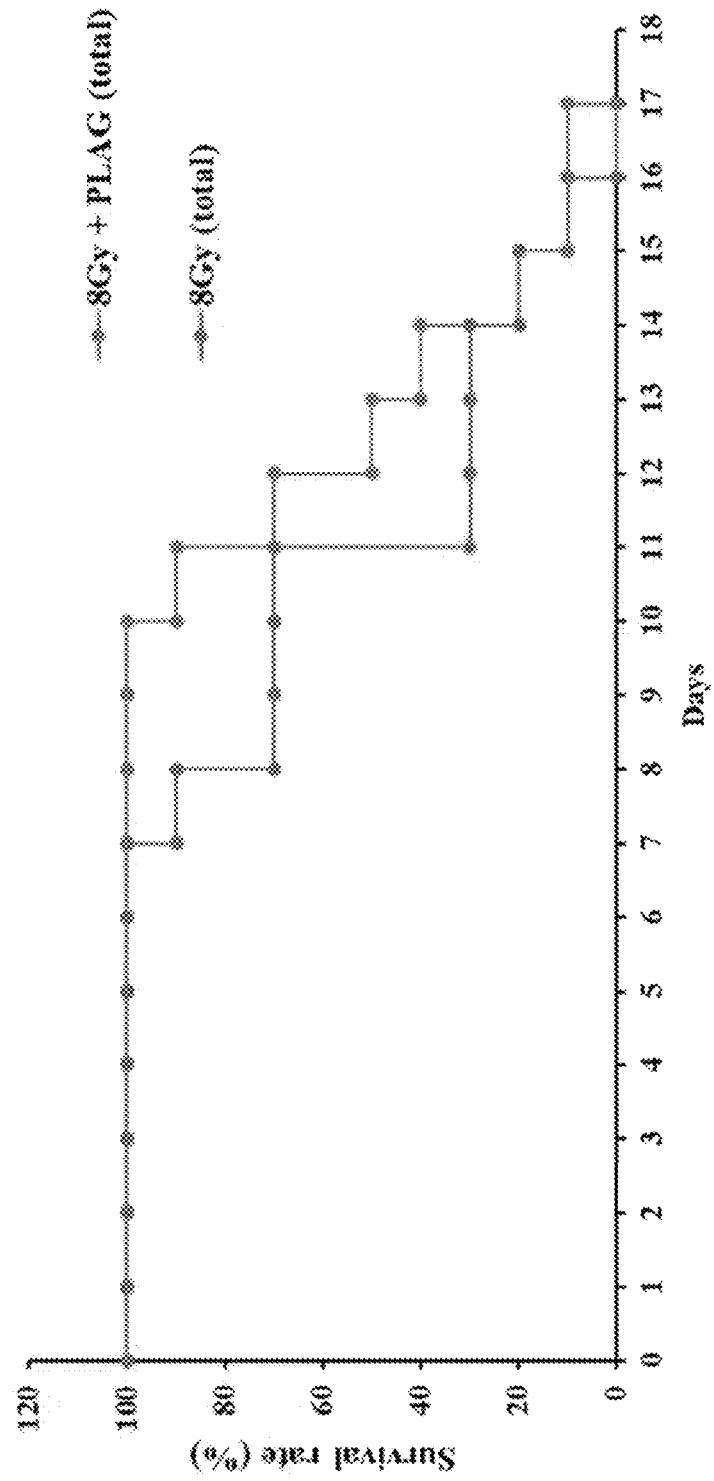
FIG. 11 shows survival rate of mice (BALB/c, 9 weeks old) administered with or without EC-18 (250 mg/kg/day PO) receiving lethal total body irradiation (8 Gy). Survival rate of mice administered with EC-18 receiving irradiation is improved until about day 14 compared to untreated (without EC-18) mice according to the diagram in FIG. 10A.
Figure 12A:
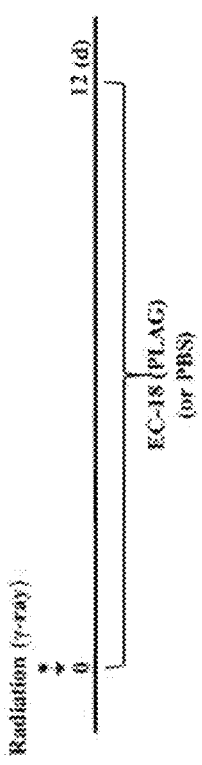
FIG. 12A is a schematic diagram of EC-18 treatment (12 days) in a radiation-induced Acute Radiation Syndrome animal model.
Figure 12B:
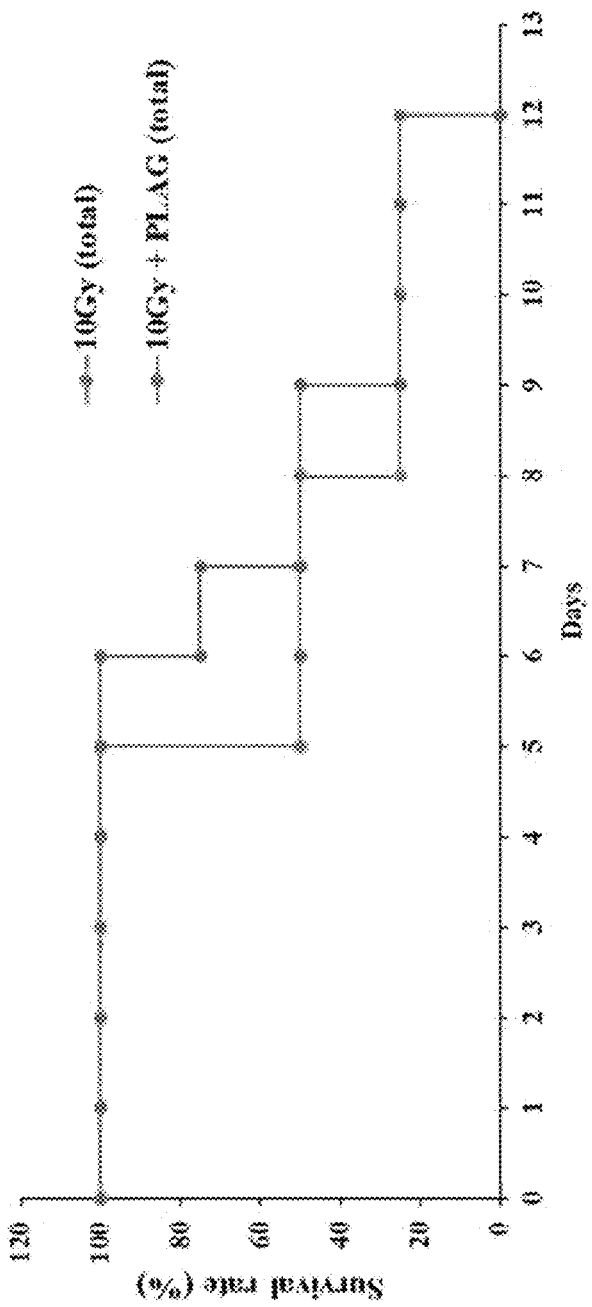
FIG. 12B shows survival rate of mice (BALB/c, 9 weeks old) administered with or without EC-18 (250 mg/kg/day PO) receiving lethal total body irradiation (10 Gy). Survival rate of mice administered with EC-18 receiving irradiation is improved until about day 9 compared to the untreated (without EC-18) mouse according to the diagram in FIG. 12A.

| | Test Groups |
|---|---|
| FIG. 8 | Balb/c: 9 weeks, male (n = 10) or Female (n = 10)<br>γ-Radiation: 6.5Gy (100 rad = 1.06 min), TBI<br>EC-18: 250 mg/kg/day (P.O.)<br>Group: 1) untreated group after radiation<br>2) EC-18 group treated group after radiation |
| FIG. 9 | Balb/c: 9 weeks, male (n = 5) or Female (n = 5)<br>γ-Radiation: 2, 4, 6 Gy (100 rad = 1.06 min), TBI<br>EC-18: 250 mg/kg/day (P.O.)<br>Group: 1) untreated group after radiation (2 Gy)<br>2) untreated group after radiation (4 Gy)<br>3) untreated group after radiation (6 Gy)<br>4) EC-18 group treated group after radiation (6 Gy) |
| FIG. 10B | Balb/c: 9 weeks, male (n = 5) or Female (n = 5)<br>γ-Radiation: 7 Gy (100 rad = 1.06 min), TBI<br>EC-18: 250 mg/kg/day (P.O.)<br>Group: 1) untreated group after radiation<br>2) EC-18 group treated group after radiation |
| FIG. 11 | Balb/c: 9 weeks, male (n = 5) or Female (n = 5)<br>γ-Radiation: 8 Gy (100 rad = 1.06 min), TBI<br>EC-18: 250 mg/kg/day (P.O.)<br>Group: 1) untreated group after radiation<br>2) EC-18 group treated group after radiation |
| FIG. 12 | Balb/c: 9 weeks, male (n = 2) or Female (n = 2)<br>γ-Radiation: 10 Gy (100 rad = 1.06 min), TBI<br>EC-18: 250 mg/kg/day (P.O.)<br>Group: 1) untreated group after radiation<br>2) EC-18 group treated group after radiation |

Example 5: Treatment of Erythema

In order to evaluate effects of PLAG on recovery skin damage of animal models exposed to radiation, the following test groups were constructed as shown in Table 4 and results are shown in FIGS. 13-15. As discussed in Examples above, the first group of untreate group (negative control) of mice after radiation was compared to the second group of treated group of mice with PLAG after radiation.

TABLE 4

| | Experiment Group |
|---|---|
| FIG. 13B | Balb/c: 9 weeks, male (n = 5) or Female (n = 5)<br>γ-Radiation: 8 Gy (100 rad = 1.06 min), TBI<br>EC-18: 250 mg/kg/day (P.O.)<br>Group: 1) untreated group after radiation<br>2) EC-18 group treated group after radiation |
| FIG. 14B | Balb/c: 9 weeks, male (n = 10) or Female (n = 10)<br>γ-Radiation: 6.5Gy (100 rad = 1.06 min), TBI<br>EC-18: 250 mg/kg/day (P.O.)<br>Group: 1) untreated group after radiation<br>2) EC-18 group treated group after radiation |
| FIG. 15 | Balb/c: 11 weeks, male (n = 10) or Female (n = 10)<br>γ-Radiation: 6.5 Gy (100 rad = 1.06 min), TBI<br>EC-18: 250 mg/kg/day (P.O.)<br>Group: 1) untreated group after radiation<br>2) EC-18 group treated group after radiation |

Example 6: Effect on Anti-Apotosis of HaCaT Cells

In order to evaluate effects of PLAG on HaCaT cells exposed to radiation, test groups were constructed as follows and results are shown in FIGS. 17B-18D.

HaCaT: human keratinocyte

PLAG: 100 μg/mL for 1 hr pretreatment

5-FU: 1, 10, 100 ng/mL

Gamma radiation: 7 Gy apoptosis check after 24 hours

Cell counting after Trypan blue staining

Apoptosis (Annexin V+7AAD)

Example 7: Effect on Reactive Oxygen Species (ROS) of HaCaT Cells

In order to evaluate effects of PLAG on HaCaT cells exposed to radiation, test groups were constructed as in Example 6 and results are shown in FIGS. 19A-19C.

Example 8: Improvement of Survival Rate

FIG. 20 is an exemplary diagram for testing survival rates of treatment on 6.5 Gy of γ-radiation induced Acute Radiation Syndrome animal model (mouse, BALB/c, 11 weeks). FIG. 21 shows the results of survival curves for Balb/c mice exposed to 6.5 Gy of γ-radiation in the daily treatment of EC-18 after irradiation. NC represents untreated control without radiation; 6.5 Gy is the survival rate of the mouse radiated with 6.5 Gy of γ-radiation; 6.5 Gy+PLAG (+1 d) is the survival rate of the mouse radiated with 6.5 Gy of γ-radiation and treated with PLAG for 1 day; and 6.5 Gy+PLAG (+2 d) is the survival rate of the mouse radiated with 6.5 Gy of γ-radiation and treated with PLAG for 2 day. FIG. 22 shows changes in body weights of Balb/c mice in FIG. 21.

Various tests to measure survival rates after γ-radiation to animal models can be set. For instance, FIG. 23 depicts an exemplary diagram for an exemplary experiment to test survival rate in the mouse models. FIG. 24 depicts an exemplary diagram for an exemplary experiment including three groups (5-FU only, 5-FU+PLAG 125 mg/kg, 5-FU+PLAG 250 mg/kg) to check time kinetics of neutrophil in 5-FU (100 mg/kg) induced neutropenia.

Example 9: Effects of PLAG Measured In Vitro (Western Blot)

The effects of EC-18 in comparison to G-CSF to cells after γ-radiation were measured by western blot (FIG. 25). The experiment can i) show correlation between EGFR activity and the abnormal growth and metastasis induction of breast cancer cells in the TAN environment and ii) confirm inhibitory effect mechanism by PLAG treatment in this condition. In fact, it was confirmed that EGFR activity was increased in the groups stimulated with neutrophil or G-CSF-activated neutrophils, however, the activity of EGFR (Phosphorylation of EGFR) was decreased in the group treated with PLAG. FIG. 26 can show effects of PLAG in comparison to G-CSF.

Example 10: Survival Time of Various Radiation Syndrome

FIG. 27 depicts a diagram of survival time of patients exposed to radiation and various ARSs.

Example 11: EC-18 for the Treatment of Acute Radiation Syndrome

We investigated the efficacy of EC-18 for the development of a medical countermeasure for Acute Radiation Syndrome (ARS) by analyzing IR-induced mortality and morbidity.

MATERIALS AND METHODS

Animals

Specific-pathogen-free male and female BALB/c mice (10 weeks of age) were obtained from Koatech Co. (Pyongtaek, Republic of Korea). Upon receipt, the mice were housed, 5 per cage, in a specific pathogen-free facility and acclimatized for 1 week under conditions of consistent temperature and normal light cycles. All the animals were fed a standard mouse diet with water allowed ad libitum. All experimental procedures were approved by the Institutional Animal Care and Use Committee of the Korea Research Institute of Bioscience and Biotechnology and were performed in compliance with the National Institutes of Health guidelines for the care and use of laboratory animals and Korean national laws for animal welfare.

Determination of Lethality Dose (LD) of Total Body γ-Radiation (TBI)

Whole-body irradiation of the animals was carried out with Gamma Irradiator (J. L. Shepherd & Associates, San Fernando, USA) with a $^{60}$Co source (exposure rate 0.833 Gy/min). For the experiments to determine survival rate following γ-irradiation, mice were grouped 20 (10 males and 10 females) per treatment cohorts; 6.0 Gy-exposed cohort, 6.2 Gy-exposed cohort, 6.4 Gy-exposed cohort and 6.5 Gy-exposed cohort. The survival and body weight of the animals was recorded daily for 30 days.

Establishment of a Murine Model of γ-Radiation-Induced Acute Radiation Syndrome (ARS)

For the experiments to determine survival rate following LD70/30 dose 6.11 Gy of γ-irradiation (TBI, $^{60}$Co, 0.833 Gy min-1), mice were grouped 20 (10 males and 10 females) per treatment cohorts; γ-radiation only cohort (positive control), γ-radiation with EC-18 10 mg/kg cohort, γ-radiation with EC-18 50 mg/kg cohort, and γ-radiation with EC-18 250 mg/kg cohort. EC-18 (Enzychem Lifesciences, Jaecheon, Republic of Korea) was suspended in PBS and orally administrated once a day, starting 1 day after irradiation. The positive control group was administrated PBS. The survival and body weight of the animals were recorded daily for 30 days.

For the time course analysis of hematopoietic ARS (H-ARS), female mice were grouped 5 per treatment cohorts; γ-radiation only cohort (positive control) and γ-radiation with EC-18 250 mg/kg cohort. For the analysis of dose effect of EC-18 administration on H-ARS, mice were grouped 8 (5 males and 3 females) per treatment cohorts; γ-radiation only cohort (positive control), γ-radiation with EC-18 50 mg/kg cohort, γ-radiation with EC-18 100 mg/kg cohort, γ-radiation with EC-18 250 mg/kg cohort and γ-radiation with EC-18 100 mg/kg cohort. The whole blood was collected from the orbital sinuses using EDTA-free capillary tubes (Kimble Chase Life Science and Research Products LLC, Fla., USA) and collection tubes containing K3E-K3EDTA (Greiner Bio-One International, Kremsmünster, Austria). The blood cells were counted and classified by complete blood count (CBC) analysis using Mindray BC-5000 auto-hematology analyzer (Shenzhen Mindray Biomedical Electronics, Guangdong Sheng, China). The values of the blood cells of the animals were recorded daily for 30 days.

Statistical Analyses

All data are presented as the mean±standard deviation (SD). A paired Log rank (Mantel-Cox) test of survival curve was applied to estimate the significance on survival rate and to compare the duration of neutropenia between control and EC-18-treated cohorts. Average life span was calculated as the sum of the life span for all mice/total number of mice. For comparison of the statistical differences of more than two groups, one-way ANOVA test was used. All other statistical analyses were performed using a Student's paired t test and p values <0.05 were considered statistically significant.

Results

Radiation Dose-Response Relationship (DRR) and LDXX/30

Radiation dose is a significant predictor of mortality and morbidity with increasing doses. FIG. 28A shows the survival rate of BALB/c mice exposed to various doses of $^{60}$Co γ-radiation. The dose of 6.0, 6.2, 6.4 and 6.5 Gy led to 60, 80, 100 and 100% mortality, respectively, after 30 days of observation. FIG. 28B shows the radiation dose relationship (DRR) using probit models. The mean survival time of decedents for each radiation dose cohort was 15.30±4.98, 13.69±3.26, 14.15±3.48 and 15.85±4.42 days, respectively (Table 5). Thirty-day survival was calculated at each radiation dose and is shown as percent mortality on the Y-axis. Based on the probit model, we determined the LD30/30, LD50/30, LD70/30, and LD95/30 with 95% confidence intervals around each dose (Table 6). The LD70/30 was determined to be 6.11 Gy, and was used to evaluate several biological indicators (e.g. survivability, body weight reduction, and reduction of hematopoietic cells) in subsequent studies.

TABLE 5

30-Day Mortality of BALB/c Mice After γ-Radiation

| Radiation dose (Gy) | Mortality | Survival time of decedents (days) | |
|---|---|---|---|
| | | Mean ± SD | Median |
| 6.00 | 12/20 (60%) | 15.30 ± 4.98 | 15.50 |
| 6.20 | 16/20 (80%) | 13.69 ± 3.26 | 13.50 |
| 6.40 | 20/20 (100%) | 14.15 ± 3.48 | 14.00 |
| 6.50 | 20/20 (100%) | 15.85 ± 4.42 | 14.50 |

TABLE 6

Estimated Radiation Dose in BALB/c mice After γ-Radiation

| LD XX/30 | LD estimate (Gy) | Lower 95% CI (Gy) | Upper 95% CI (Gy) |
|---|---|---|---|
| LD30/30 | 5.31 | 4.98 | 5.56 |
| LD50/30 | 5.79 | 5.59 | 5.96 |
| LD70/30 | 6.11 | 5.98 | 6.22 |
| LD95/30 | 6.39 | 6.30 | 6.48 |

The γ-radiation also caused a substantial reduction of body weight of the irradiated mice (FIG. 29). It was difficult to find a strict relationship between radiation dose and the loss of body weights in the initial stage (0-10 day), but the body weights of lower dose cohorts (6.0 and 6.2Gy) were restored to the normal range at the end of the observation period.

Therapeutic effect of EC-18 administration on survivability, average life span and body weights of irradiated mice with LD70/30 of TBI We next investigated the therapeutic effect of EC-18 on survivability of irradiated mice with LD70/30 (6.11 Gy) of TBI over 30 days of the observation period. The survival rate of the positive control cohort was 20% while that of EC-18 10, 50 and 250 mg/kg-treated cohorts was 20, 40 and 80%, respectively (FIG. 30A). Moreover, EC-18 significantly increased the average life span of irradiated mice in a dose-dependent manner (Table 7). The respective average life span of EC-18 10, 50 and 250 mg/kg-treated cohorts was 19.3, 22.3 and 28.2 days as compared to 17.9 days of the positive control cohort.

TABLE 7

Dose-effect of EC-18 administration on survivability and average life duration of irradiated mice.

| | No. of mice that survived/total | Survivability | Average life span | Median survival, days | Log-rank test p* |
|---|---|---|---|---|---|
| Control | 16/20 | 80% | 28.2 | 30 | <0.0001 |
| EC-18 10 mg/kg | 8/20 | 40% | 22.3 | 20 | 0.0464 |

TABLE 7-continued

Dose-effect of EC-18 administration on survivability
and average life duration of irradiated mice.

|  | No. of mice that survived/ total | Surviv- ability | Average life span | Median survival, days | Log-rank test p* |
|---|---|---|---|---|---|
| EC-18 50 mg/kg | 4/20 | 20% | 19.3 | 17 | 0.4425 |
| EC-18 250 mg/kg | 4/20 | 20% | 17.9 | 15 |  |

The administration of EC-18 also effectively prevented γ-radiation-induced severe weight loss (FIG. 30B). In particular, EC-18 250 mg/kg-tread cohort significantly reduced γ-radiation-induced weight loss from the 18th day after irradiation to the end of the experiment as compared to the positive control cohort. In addition, the number of mice experiencing a 20% body weight loss from the baseline value sharply decreased as the dose of EC-18 increased (Table 8).

TABLE 8

Dose-effect of EC-18 administration on
body weight loss in irradiated mice.

|  | ≥10% Body Weight Loss | | ≥20% Body Weight Loss | |
|---|---|---|---|---|
|  | n | % | n | % |
| Control | 16 | 80 | 8 | 40 |
| EC-18 10 mg/kg | 17 | 85 | 14 | 70 |
| EC-18 50 mg/kg | 11 | 55 | 7 | 35 |
| EC-18 250 mg/kg | 3 | 15 | 3 | 15 |

Based on the observations in this study, we concluded that EC-18 has therapeutic potential for improving survivability and preventing body weight loss in γ-radiation-induced ARS.

Therapeutic Effect of EC-18 Administration on γ-Radiation-Induced H-ARS

A single TBI of γ-radiation (6.11Gy) rapidly exhausted all kinds of hematopoietic cells including the absolute neutrophil counts (ANC), monocytes, absolute lymphocyte count (ALC), platelet counts (PLT) and red blood cell counts (RBC) within 3 days after irradiation (FIG. 31). The mean first day of neutropenia was 2.8±0.45 day, and the duration of neutropenic state was 18.0±1.41 days. All individuals in the irradiated cohort experienced severe neutropenic state (ANC<100 cells/μL), and the duration of severe neutropenic state was 16±0.00. The mean nadir of ANC after γ-ray irradiation was 0.0±0.00 cells/μL, and the time of recovery to an ANC≥500 or 1000 cells/μL was both 27±1.41 days. Moreover, γ-radiation induced greater than 90% reduction in PLT within 7 days after irradiation, and started to recover at 26 days after irradiation. RBC gradually decreased and started to recover at 22 days after irradiation.

The therapeutic effect of EC-18 administration on H-ARS was then evaluated. The administration of EC-18 significantly attenuated γ-radiation-induced depletion of the white blood cell counts (WBC), absolute neutrophil counts (ANC) and absolute lymphocyte counts (ALC) in the irradiated mice (FIGS. 32A-J). Groups of BALB/c mice (n=5, female for FIG. 32A through FIG. 32E and n=8, 5 male, 3 female for FIG. 32F through FIG. 32J) were exposed to 6.11 Gy of γ-radiation and various doses of EC-18 were orally administered once daily to day 15, or remained untreated. FIGS. 32A through 32E show the time course of the white blood cell count (WBC; FIG. 32A), absolute Neutrophil count (ANC; FIG. 32B), absolute Lymphocyte count (ALC; FIG. 32C), platelet count (PLT; FIG. 32D) and red blood cell count (RBC; FIG. 32E) over 15 days, respectively. FIGS. 32F through FIG. 32J show the dose effect of EC-18 administration on WBC (FIG. 32F), ANC (FIG. 32G), ALC (FIG. 32H), PLT (FIG. 32I) and BRC (FIG. 32J) on day 15, respectively. ns; not significant, *p<0.05, p<0.01, *p<0.005.

The administration of EC-18 substantially reduced γ-radiation-induced reduction of ANC. The mean first day of neutropenia (ANC<500 cells/μL) of control and EC-18-treated cohorts was 1.8±1.09 and 2.2±1.09 days (two-sided P value=0.62), respectively. Although EC-18 did not protect the irradiated mice from experiencing severe neutropenia, it effectively reduced the duration of severe neutropenia from 13.0 days to 7.2±1.79 days. In addition, EC-18 significantly increased the mean nadir of ANC after γ-ray irradiation from 4.0±5.48 cells/μL to 20.0±10.00 cells/μL (two-sided P value=0.035). The administration of EC-18 attenuated the reduction of PLT and RBC induced by a single TBI (FIGS. 32D, 32E and FIGS. 32I, 32J). Based on the observations, we concluded that EC-18 may have therapeutic potential for attenuating the reduction of blood cells in γ-radiation-induced ARS.

Example 12:

The radiation-induced DAMP removal was evaluated in HaCaT (human keratinocyte) cells exposed with γ-radiation from a $^{60}$Co radiation source (0.833 Gy/minute). As one type of DAMPs, high-mobility group box 1 (HMGB1) was used as a biomarker to establish the mitigating effect of EC-18 against radiation. HMGB1 proportionally secreted as the radiation dosage (5 to 10 Gy) and exposure time (24 to 48 hrs) increased (FIG. 33A). As well-demonstrated, this extracellularly released HMGB1 could bind to its neighboring cells' receptors to trigger inflammation and lead to cell death (Sonis 2010, Vasconcelos et al., 2016). With the EC-18 treatment, it was confirmed that HaCaT cells had less HMGB1 released in a dose-dependent manner (FIG. 33B).

A similar study was conducted with the addition of a chemotherapeutic drug, 5-FU. At 24-hr post irradiation (with 20 Gy exposure), DAMPs were released from radiation- and/or 5-FU treated-cells and increased in a time-dependent manner compared to Ponceau S as a control (FIG. 34).

Necroptosis is an inflammatory cell death featuring apoptosis and necrosis (Davidovich et al., 2014). Various stimuli through different receptors induce such type of cell death (Pasparakis and Vandenabeele, 2015). Necroptosis is identified with a signaling axis involving RIPK1, RIPK3, and MLKL. As RIPK1 and RIPK3 are phosphorylated, they form necrosome and necrosomal RIPK3 phosphorylates MLKL, which oligomerizes and translocates to the plasma membrane (Petrie et al., 2019). As a result, endogenous molecules and massive DAMPs are released and consequently, inflammation response initiates (Pasparakis and Vandenabeele, 2015). Thus, the therapeutic target of opportunity for attenuating of necroptosis will likely be 24 hrs or longer after irradiation.

Figure 35A:
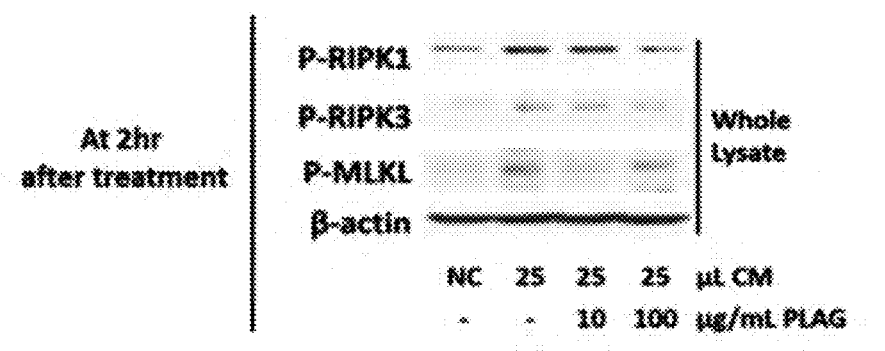
Figure 35B:
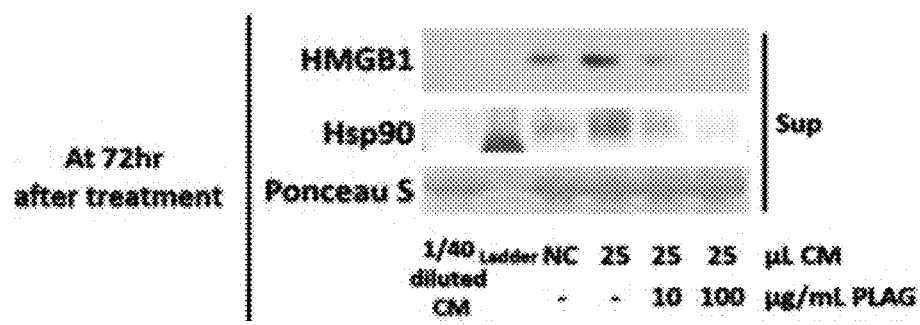
Figure 35C:
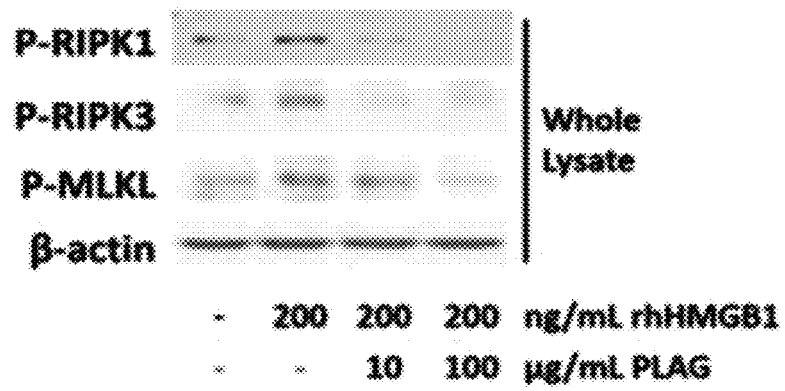
Figure 35D:
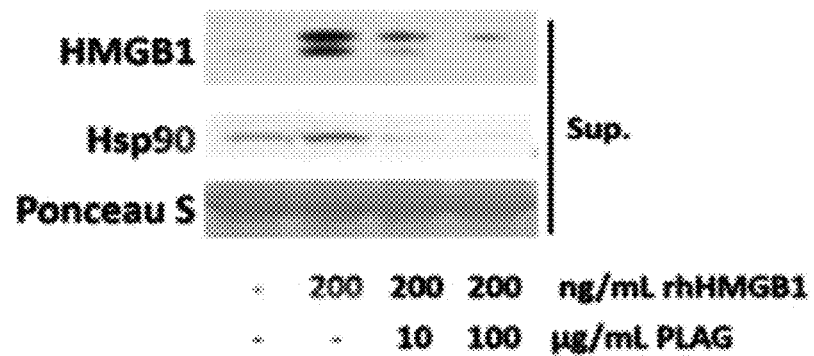

An additional experiment was tested for assessing whether EC-18 treatment leads to early termination of the RIPK1/3-MLKL-mediated downstream necroptosis pathway. This was performed by using DAMP-containing conditioned media (CM) harvested from HaCaT cells, irradiated for 48 hrs, and analyzed after 2 or 72 hrs of EC-18 treatment. CM containing DAMPs induced the phosphorylation of RIPK1, RIPK3, and MLKL (FIG. 35A) and subsequently increased the release of HMGB1 and the heat shock protein 90 (HSP90), another type of DAMPs (FIG. 35B). To further confirm that DAMPs in CM contribute to the activation of a necroptosis signaling pathway in a paracrine manner, recombinant human HMGB1 (rhHMGB1) was treated directly to the normal HaCaT cells. The rhHMGB1 elevated the phosphorylation of RIPK1/3 and MLKL after 2 hrs and subsequently released HMGB1 and HSP90 (FIGS. 35C-35D). To evaluate whether EC-18 mitigates the activation of RIPK1/3 and MLKL, 10 or 100 µg/mL of EC-18 was treated before the addition of CM or rhHMGB1. As a result, EC-18 lowered the phosphorylation of RIPK1/3 and MLKL in both CM- and rhHMGB1-treated cells after 2 hrs. Release of HMGB1 and Hsp90 was also subsided by EC-18 after 72 hrs of post addition of CM or rhHMGB1 to the cells (FIGS. 35A-35D).

TLR4-induced necroptosis signaling pathway caused by DAMP release produces cytokines, such as CXCL8, a chemotactic cytokine for neutrophils. As CXCL8 increases upon tissue damage, it was measured in cells treated with CM or rhHMGB1 as a measure of inflammation. CXCL8 of CM from cells treated with chemo and radiotherapy was used for this evaluation. Chemo- and radiotherapy-treated cells did not significantly elevate the CXCL8 expression compared with control (FIG. 36A). CM-treated cells had elevated CXCL8 levels than the negative control and with the EC-18 treatment, the CXCL8 level decreased in a dose-dependent manner (FIG. 36B). Moreover, rhHMGB1 increased the production of CXCL8, modulated by EC-18. Necrostin-1 (Nec-1, a RIPK1 kinase inhibitor) and GSK872 (a RIPK3 kinase inhibitor) demonstrated a significant reduction of CXCL8 than rhHMGB1-treated group (FIG. 36C), indicating that CXCL8 release is related to the activation of RIPK1 and RIPK3.

To confirm the proposed mechanism of EC-18 in the in vivo model, female Balb/c mice were irradiated with a gamma-ray of 6.11 Gy on day 0. Then, EC-18 (50 and 250 mg/kg) or PBS was orally administered for 3 consecutive days from day 1 and the mice were sacrificed on the third day. Gamma-ray irradiation resulted in increased DAMP release (HMGB1 and S100A9) in the blood (FIG. 37). While, from the EC-18-treated group, the amount of DAMP reduced compared to the control group, supporting the proposed mechanism of EC-18.

Establishment of a Balb/C Mouse Model for ARS

For the study of the hematopoietic syndrome, most researchers have used, in addition to canine models and NHPs, inbred mouse strains, including Balb/c, C3H/HeN, B6D2F1/J and C57BL/6. Of these strains, Balb/c is the most sensitive to radiation, and C57BL/6 is the most resistant (Williams et al., 2010). Because radiation directly affects single- and double-stranded DNA breaks and/or impairment of DNA-damage repair machinery (Lai and Singh, 1996), the relatively high sensitivity of Balb/c mice to radiation can be attributed to defects in double-stranded DNA repair (Okayasu et al., 2000). In early studies, Balb/c mice were used to evaluate the effect of EC-18, since it was believed that this strain, due to its inherent genetic defects, would more apparently exhibit radiation-induced systemic inflammatory response by releasing DAMPs. However, we have subsequently evaluated EC-18 in C57BL/6J because of strain variables with respect to radiation response and have also observed significant levels of mitigation induced by EC-18 in this relatively radiation-resistant mouse model.

Establishment f Radiation Lethality Curve In The Ars Model

To establish the lethal dose-response curve in mice, Balb/c mice (n=10/sex/group) were exposed to the approximate LD70/30 dose of total body γ-radiation (TBI, $^{60}$Co, 0.833 Gy min$^{-1}$). Radiation dose was a significant predictor of mortality with increasing doses. Before the PLAG efficacy test, we first investigated the relationship between gamma-ray dose and lethality of mice to determine the lethality dose (LD) of gamma-ray irradiation during the 30-day survival observation.

FIG. 28A shows Kaplan-Meier survival curves of Balb/c mice irradiated at various doses of $^{60}$Co gamma rays; increasing radiation dose significantly decreased the overall survival time. The mean survival time (MST) of decedents for each radiation dose cohort ranged from 13.69 to 15.30 days, with the overall MST of decedents across all dose cohorts being 14.38 days.

FIG. 28B shows the radiation DRR using a probit model. Thirty-day survival was calculated at each radiation dose and is shown as percentage mortality on the y-axis. Based on the probit model in FIG. 28B, we determined LDXX/30 with 95% confidence intervals around each dose. The LD30/30, LD50/30, LD70/30, and LD95/30 values were 5.45, 5.85, 6.11, and 6.35 Gy, respectively (Table 9). The established LD70/30 in this experiment was applied in subsequent experiments to determine PLAG efficacy.

TABLE 9

Estimated radiation dose in Balb/c mice after γ-radiation

| LDXX/30 | LD estimate (Gy) | Lower 95% CI (Gy) | Upper 95% CI (Gy) |
| --- | --- | --- | --- |
| LD30/30 | 5.44 | 5.17 | 5.65 |
| LD50/30 | 5.85 | 5.68 | 5.99 |
| LD70/30 | 6.11 | 6.00 | 6.21 |
| LD95/30 | 6.35 | 6.27 | 6.42 |

To establish the predictability of the mouse ARS model for the human disease, the progression of neutropenia, considered a secondary endpoint, was established in irradiated animals For 30 days, white blood cell counts (including differentials) were assessed in female Balb/c mice (n=5/ sacrifice time) exposed to lethal radiation (6.11 Gy). This radiation was used for all the LD70/30 studies unless otherwise mentioned.

The WBC counts, ANC and absolute lymphocyte counts (ALC) rapidly decreased following irradiation and did not begin to recover until after Day 24 (FIGS. 31A, 31B, and 31D, respectively). PLTs exhibited a slower decline (FIG. 31E), and red blood cell (RBC) count was even slower to reach the nadir (FIG. 31F). In the case of PLT counts, severe thrombocytopenia started to appear on Day 8, and anemia occurred after 2 weeks. All CBC parameters including RBC, WBC, ANC, ALC, and PLTs recovered to almost normal levels by Day 30.

The data on ARS cell recovery kinetics are lacking in untreated humans after irradiation because supportive medical care, such as hematopoietic growth factor, hydration, and antibiotics, are almost always provided. In humans, the onset of radiation-induced cytopenia is variable and dose-dependent; the time to onset and duration of the nadir are variable. Interestingly, the time course of CBC response in mice exposed to 6.11 Gy radiation (FIGS. 31A-31F) is similar to that of animal studies conducted by other researchers in terms of onset and recovery of neutropenia and thrombocytopenia. Interestingly, the ANC profile demonstrated above showed an increase before decline; this is termed an 'abortive' rise, a finding that may be clinically helpful because it may indicate a more survivable exposure. Overall, the effects noted in mice following radiation exposure are comparable to those exhibited in humans. Although the timeframe to the onset of changes is shorter in mice than humans, this is anticipated given the difference in size between the species.

Preliminary ars Efficacy Studies in Ld70/30 Balb/C Model

To investigate the therapeutic effects of EC-18, it was daily administered to Balb/c mice (n=20/sex/group) 24 hrs after irradiation at 0, 50, or 250 mg/kg/day for 30 days. In this study, mortality in the control group was 67.5% (LD67/30). These data demonstrate that EC-18 dose-dependently attenuated γ-radiation-induced mortality in mice and significantly improved survival at the EC-18-treated group (FIG. 38). Compared to the control group, daily dosing of EC-18 at 250 mg/kg significantly improved survival by 4-fold, while EC-18 administered at 25 mg/kg significantly improved survival by 2-fold.

Body weight was obtained for each mouse every day. Radiation alone caused a substantial decrease in the body weight of the mice (FIG. 30B). The administration of the two higher doses of EC-18 significantly prevented severe weight loss. The number of mice experiencing a 20% loss in body weight from baseline value decreased sharply as the EC-18 dose increased (Table 10). For EC-18-treated at 250 mg/kg, statistically significant differences from the 18th day after irradiation to the end of the experiment were noted compared to the control group ($p<0.05$). Unpaired student t-test was used for the body weight data to evaluate the significance of the difference between the EC-18 administrated groups and the radiation control group.

TABLE 10

Occurrence and severity of body weight loss in mice exposed to 6.11 Gy radiation dose followed by EC-18 treatment.

| Treatment | ≥10% Body Weight Loss | | ≥20% Body Weight Loss | |
| --- | --- | --- | --- | --- |
| | N | % | N | % |
| Control | 16 | 80 | 8 | 40 |
| EC-18 50 mg/kg/day | 11 | 55 | 7 | 35 |
| EC-18 250 mg/kg/day | 3 | 15 | 3 | 15 |

Before evaluating the effect of EC-18 on CBC parameters through 30 days post-TBI, the effects of EC-18 were evaluated for a shorter duration. Mice (20/20 male/female; 40 mice per group) were monitored at least twice daily for survival for 30 days. For assessment of blood cell kinetics, the mice were divided into two cohorts of 20 mice/cohort based on blood collection time. Blood collection schedules were as follows. Cohort 1 collection was performed on days 1, 5, 10, 15, 20 and 27; cohort 2 collection was performed on days 3, 7, 12, 17, 22 and 30. Since the mice died from radiation injury, the number of blood samples taken from the mice was different as the study progressed. The blood cells were counted and classified by CBC analysis using a Mindray BC-5000 auto-hematology analyzer. The numbers of blood cells were recorded at the appointed dates for 30 days.

Using CBC analysis, it was investigated whether enhanced survivability by EC-18 results from the increase in nadir values. A single-dose of TBI rapidly diminished the ANC within 3 days after irradiation (FIG. 39A). In particular, the administration of EC-18 (50 and 250 mg/kg) significantly attenuated radiation-induced depletion of ANC in mice in a dose-dependent manner (FIG. 39A). The timing of nadirs for neutrophils, PLTs, red blood cells, and hemoglobin is unchanged (FIG. 39B). However, the severity of the nadir is diminished, which is consistent with EC-18's hypothesized mechanism of action (FIGS. 39A-39B). That is, EC-18 modulates the inflammatory process, reducing the severity of the response to acute radiation exposure.

Ec-18 Dosage and Schedule (Dose Regimen) Optimization (1) Dosage Optimization

The dosage optimization study was conducted in a total of 40 Balb/c mice (20 males and 20 females) in the LD70/30 ARS model. Then, EC-18 was administered daily in-life at the dosages of 50, 250, and 500 mg/kg 1 day after irradiation. Based on the 24-hr delayed dose-ranging study, the survival rates of the irradiated mice treated with EC-18 at the dosages of 50, 250 and 500 mg/kg were 60%, 85%, and 85%, respectively. Moreover, the average life spans of the decedents were 24.3, 27.8 and 20.3 days, respectively. Collectively, there was a significant improvement (~4-fold) in survival for the EC-18-treated group with 250 and 500 mg/kg compared to the control group and the survival rate significantly improved in a dose-dependent manner (FIG. 38 and Table 11). From these data, 250 mg/kg was as selected as an optimal dosage for the 24-hr delayed treatment as no difference was noticed between 250 and 500 mg/kg dosage in terms of improvement in survival. Based on this result, the future studies tested dosages only up to 250 mg/kg.

TABLE 11

Effect of EC-18 on survivability and average life duration of irradiated mice

| | No. of mice that survived/ total | Surviv- ability | Survival time of decedents (days) | | Log-rank test $p^*$ |
| --- | --- | --- | --- | --- | --- |
| | | | Mean ± SEM | Median | |
| Control Radiation only | 13/40 | 32.5 | 21.2 ± 1.0 | 21.0 | |
| Radiation + EC-18 50 mg/kg | 24/40 | 60 | 24.3 ± 1.2 | 25.5 | 0.0041 |
| Radiation + EC-18 250 mg/kg | 34/40 | 85 | 27.8 ± 0.4 | 27.5 | <0.0001 |
| Radiation + EC-18 500 mg/kg | 34/40 | 85 | 20.3 ± 1.5 | 19.5 | <0.0001 |

(2) Dosing Schedule Optimization

The dosing schedule optimization study was conducted in a total of 20 Balb/c mice (10 males and 10 females) in the LD70/30 model. EC-18 was administered daily in-life with its optimal dosage (250 mg/kg) at 0, 1, 2, and 3 days after irradiation on Day 0. To examine the durable efficacy of EC-18, the survival was examined 15 days after the in-life phase without the daily treatment of EC-18.

Upon EC-18 administration, the survival significantly improved for the EC-18-treated groups (even up to 3-day-delayed treatment regimen) compared to its negative control (NC) (FIG. 40). However, the optimal therapeutic outcome of the dosing schedule was achieved by the treatment of EC-18 at Day 0. It is also important to note that the withdrawal of EC-18 extended the survival of animals for an extra 15 days after the LD70/30 study ended. To the best of our knowledge, we are not aware of any other radiation MCM candidates that demonstrated improved survival even with the 72-hr delayed treatment.

Survival Benefits of EC-18 in An Extreme Ld100 Tbi Murine Model

To investigate the therapeutic effects of EC-18 in a higher lethality with extreme radiation, the experiment was conducted in Balb/c mice (n=10/sex/group) exposed to TBI of 6.5 Gy followed by the treatment with EC-18 at 24- and 48-hr post-irradiations. Animals were treated orally with phosphate-buffered saline or EC-18 at 250 mg/kg/day for 16 days.

The vehicle control group resulted in no survival by Day 16 and the average lifespan was 13.65 days. In comparison, treatment with EC-18 for 16 days resulted in 65 and 25% survival when it was administered at 24- and 48-hr post-irradiation, respectively (FIG. 41). Even under this more stringent model, the offered survival benefits by EC-18 were statistically significant compared to the control group (with 100% mortality by Day 16). Furthermore, the signs of subcutaneous hemorrhage were markedly improved, providing the systemic effect to maintain the viability throughout the body. Therefore, it was demonstrated that EC-18 effectively mitigated the γ-radiation-induced mortality in mice, while the efficacy decreased with the delayed treatment.

Estimation of Dose Reduction Factor for EC-18 In Balb/C Mouse Model

Analysis of several TBI, 24-hr delayed administration of EC-18 at 250 mg/kg in Balb/c mice yields an estimate of the dose reduction factor (DRF) of EC-18. Data used in the calculation of DRF are shown in Table 12.

TABLE 12

Comparison of γ-radiation-induced lethality in the absence and presence of EC-18

| Radiation dose (Gy) | Lethality | |
|---|---|---|
| | Absence of EC-18 | Presence of EC-18 |
| 4.0 | 0/20 (0%) | |
| 6.0 | 12/20 (60%) | |
| 6.11 | 27/40 (67.5%) | 6/40 (15%) |
| 6.2 | 16/20 (80%) | |
| 6.5 | 19/20 (95%) | 8/20 (40%) |
| 7 | 10/10 (100%) | 10/10 (100%) |
| 8 | 10/10 (100%) | 10/10 (100%) |
| 10 | 4/4 (100%) | 4/4 (100%) |

Table 13 presents the calculated DRFs at different lethality levels. The DRF is 1.30 at LD50/30 and 1.18 at LD70/30. The dose reduction plot is shown in FIG. 42.

TABLE 13

Estimated radiation dose in BALB/c mice after γ-radiation in the absence or the presence of EC-18

| | LD Estimate (Gy) | | |
|---|---|---|---|
| LDXX/30 | Absence of EC-18 | Presence of EC-18 | DRF |
| LD30/30 | 3.62 | 5.26 | 1.45 |
| LD50/30 | 4.22 | 5.50 | 1.30 |
| LD70/30 | 4.87 | 5.76 | 1.18 |
| LD95/30 | 5.78 | 6.09 | 1.05 |

Structural-Activity Relationship Work of EC-18

To assess the optimal structure of EC-18, structural-activity relationship work was examined A total of five structural analogs of EC-18 were selected by changing one fatty acid chain structure (red boxes in FIG. 43) and evaluated in bone marrow-derived monocytes co-cultured with Pseudomonas aeruginosa K (PAK). All analogs along with EC-18 were inoculated with PAK at the multiplicity of infection (MOI) of 50 for 30 mins and then, treated for 1 hr at the dosage of 100 µg/mL.

As a measure of cell proliferation, the colony-forming units (CFUs) from each group were examined. As shown in blue bar graphs in FIG. 44 below, the EC-18-treated group achieved significantly higher CFUs than other analogs or the control groups. Fluorescent images also support this result by showing more PAK populations in fluorescent green being phagocytosed by the red-labeled monocytes in culture. These quantitative and qualitative results demonstrate that EC-18 has the most optimal structure to preserve the cell function and viability by actively facilitating the PAK clearance.

Similarly, a structural analog efficacy study was conducted to identify the optimally functional molecule in the ARS murine model. The study was performed with the structural analog in which the acetyl group in EC-18 is replaced with a hydroxyl group (yielding palmitic linoleic hydroxyl glycerol, PLH) in 20 Balb/c mice (10 female and 10 male) per group. Mice were irradiated with TBI of 6.11 Gy at day 0 and 250 mg/kg of EC-18 or PLH were given daily in-life. As shown in FIG. 45, the EC-18-treated group exhibited a significant increase (2-fold increase) in survival compared to both control and PLH-treated group. Furthermore, there were no statistically significant differences in the survival of the PLH-treated group compared to that of the control group (FIG. 45). The deacetylation abolished the function of EC-18 and this demonstrates that the acetyl group is crucial to maintain the activity of EC-18.

ARS Efficacy Studies in LD/30 C57BL/6J Mice

The objective of this study was to evaluate the 30-day survival benefit of EC-18 in male and female C57BL/6J mice when administered by daily oral gavage at doses ranging from 100-375 mg/kg/day, for 30 consecutive days beginning approximately 24 hrs after a single LD70/30 dose (680 cGy) of TBI. The study had 4 dose groups, each with 24 animals of each sex, Group 1 animals were administered sterile PBS, Groups 2, 3, and 4 were administered EC-18 at 100, 250, and 375 mg/kg/day, respectively. Dose volumes were determined using the most recently recorded body weight. Survival was monitored for 30 days post irradiation, with early removal criterion used to determine morbidity. Clinical observations were recorded daily before administration of vehicle or test article. Gavage checks were performed on all animals found dead or moribund, and no animals were found to be injured or moribund due to improper gavage technique. Body weights were recorded minimally 3 times per week, daily for animals with weight loss of ≥15%, or twice daily for animals with ≥20% weight loss. The experimental design is shown in Table 14.

TABLE 14

Dose range-finding LD70/30 survival study design

| Group | Rad. Dose (cGy)[a] | Treatment | Dose Regimen (Days) | Dose Level (mg/kg)[b] | Dose Conc. (mg/ml) | Dose Vol. (ml/kg)[c] | Total No. of Animals |
|---|---|---|---|---|---|---|---|
| 1 | 680 | Vehicle control | 1-30 | 0 | 0 | 10 | 24M/24F |
| 2 | 680 | EC-18 | 1-30 | 100 | 10 | 10 | 24M/24F |
| 3 | 680 | EC-18 | 1-30 | 250 | 25 | 10 | 24M/24F |
| 4 | 680 | EC-18 | 1-30 | 375 | 37.5 | 10 | 24M/24F |

[a]Single dose of TBI delivered on Day-1 corresponding to SRI's estimated LD70/30 dose for C57BL/6J mice.
[b]All oral gavage dose administration volumes will be delivered based on each animal's most recent body weight.
[c]An oral gavage volume of 250 μl would be delivered for a body weight of 25 g. Day 1 oral gavage to occur 24-28 h post-irradiation.

Results are shown in FIGS. 46, 47, and 48, and Table 15. Improvement in survival for both sexes combined was modest, driven almost entirely by survival in the female EC-18 treated animals. EC-18 did not appear efficacious in male animals, however, it notably improved survival in the females. Specifically, in Groups 3 and 4, EC-18-treated females experienced a 46% increase in survival when compared to vehicle-treated female controls.

TABLE 15

Mortality results

| Group | Males | | Females | | All Animals | |
|---|---|---|---|---|---|---|
| | N | Dead/Moribund | N | Dead/Moribund | N | Dead/Moribund |
| Grp 1: Vehicle only | 24 | 22 (92%) | 24 | 23 (96%) | 48 | 45 (94%) |
| Grp 2: 100 mg/kg EC-18 | 24 | 22 (92%) | 24 | 16 (67%) | 48 | 38 (79%) |
| Grp 3: 250 mg/kg EC-18 | 24 | 24 (100%) | 24 | 12 (50%) | 48 | 36 (75%) |
| Grp 4: 375 mg/kg EC-18 | 24 | 22 (92%) | 24 | 12 (50%) | 48 | 34 (71%) |

EC-18 provided a statistically significant improvement in survival for all 3 dose groups of EC-18 treated females. Female vehicle-treated animals (Group 1) had 4% survival, whereas Group 2 females had an increased survival of 29% above control, and Group 3 and 4 females had a survival of 46% above control. Therefore, the dose-dependent increase in survival seen when data from both sexes were combined is the result of the increased survival of EC-18 treated female mice. The highest dose, 375 mg/kg, did not provide any additional survival benefit, therefore EC-18 at 250 mg/kg represents the minimal dose to achieve the maximal therapeutic effect for the three doses tested in this study.

Moribund sacrifices occurred between study Days 10-22 for both male and female animals, based on each animal's health status, using standardized early removal criteria. Four males and four females were found dead in the vehicle control group (Days 8-16) while five males and no females were found dead in the EC-18-treated groups (on Days 12-14). Commonly observed clinical findings consistent with radiation exposure included hunched posture, dehydration, hypoactivity, and ruffled fur. Hunched posture was the most prevalent finding and was observed in nearly all animals regardless of sex. Other radiation-associated findings included dyspnea and alopecia. Dehydration, hypoactivity, ruffled fur, and dyspnea were slightly more prevalent in males, and the time to onset was generally 1-3 days later in the EC-18-treated females, particularly in Groups 3 and 4. There were no statistically significant differences in mean body weights between the vehicle and EC-18-treated animals on any study day (FIGS. 49A-49B). EC-18-treated female mice had slightly higher body weights than vehicle controls at the nadir on Day 19, and EC-18-treated Group 3 and 4 females had higher body weights than vehicle controls between Days 14 and 26. Survival for Group 1 irradiated animals treated with a vehicle was similar for both sexes, with a combined sex survival rate of 6%. While this was lower than the targeted survival of 30% based on the LD70/30 for both sexes combined, the additional stress of 30 consecutive days of handling and gavage dose administration likely accounted for the increased mortality. In the combined sex survival analysis, EC-18 provided a dose-dependent survival benefit with 21, 25, and 29% combined sex survival seen for Groups 2, 3, and 4, respectively, compared with 6% survival in the controls. The improved survival in Groups 3 and 4 was statistically significant when compared with Group 1 controls. EC-18 provided no survival improvement in male mice. Survival for Group 2-4 males (0-8%) was identical or lower than that in the vehicle controls (8%).

This study is being repeated with improved animal handling techniques. It was agreed upon by all parties involved that the high mortality observed in male mice was likely due to handling stress during oral gavage.

Synergistic Effect of EC-18 With Pegfilgrastim

In this work, neutrophil counts were compared in four groups of mice: control mice, gemcitabine-treated mice, gemcitabine/pegfilgrastim-treated mice, and gemcitabine/pegfilgrastim/PLAG-treated mice. Gemcitabine was administered intraperitoneally to induce neutropenia. On Day 0, pegfilgrastim was administered subcutaneously. PLAG (50 mg/kg) was orally administered every day during the treatment course. Blood was taken from the orbital sinuses on Days 0, 3, and 5, and neutrophils were counted. The CBC analysis showed that the group treated with PLAG experienced dramatically increased neutrophil counts on the third day following pegfilgrastim treatment (FIG. 50). Pegfilgrastim is polyethylene glycol (PEG)-conjugated granulocyte colony-stimulating factor (PEGylated-G-CSF, pegfilgrastim).

PLAG did not affect blood cell apoptosis and neutrophil release from bone marrow. Additionally, pegfilgrastim-induced CXCR2 expression in neutrophils was markedly decreased in PLAG-treated animals. These results suggest that PLAG plays a role in inhibiting neutrophil extravasation, giving rise to an increased number of circulating neutrophils when used with pegfilgrastim during gemcitabine treatment. These data support the potential for PLAG to be used with pegfilgrastim to treat or prevent chemotherapy-induced neutropenia by modulating neutrophil transmigration. From the data, one can infer that EC-18 may be similarly synergistic with pegfilgrastim in treating neutropenia resulting from acute radiation exposure.

Secondary Measures of EC-18's Efficacy in the Mouse Models of the Radiation-Induced Symptoms The effectiveness of EC-18 has been probed via secondary measures and the proposed mechanism of action of EC-18 for the symptoms associated with ARS is portrayed in FIG. 51. EC-18 is a GPCR agonist and acts as a PRR endocytic trafficking accelerator (PETA). Upon binding to GPCR, it upregulates CD14 and α-arrestin, accelerating the removal process of the danger signals in the following order: 1) CD14 acts as a co-receptor of one of the PRRs, TLR4, and facilitates the endocytosis of DAMPs and PAMPs while α-arrestin promotes the GPCR-mediated endocytosis; 2) these lead to the early formation of endosome results in prompt production of ROS as well as faster clearance of danger signals, thereby shortening the duration of ROS exposure; 3) this downregulates the expression of transcriptional factors involved in pro-inflammatory chemokine (CXCL8) and cytokine (IL-6) expression and terminates the necroptosis pathway early; 4) By obviating the need to excessively recruit neutrophils to the inflamed site, EC-18 may play a pivotal role in preventing of radiation-induced inflammatory disease. It is also demonstrated that EC-18 mitigates sub-syndromes in multiple organ systems that are associated with ARS.

(1) Efficacy Assessment of EC-18 on Skin Damage in Lethal ARS Mouse Models

In addition to the ARS survival studies that have been conducted in mice, a series of studies that probe secondary measures of efficacy in radiation-induced skin damage in the Balb/c mice (n=10/sex/group). They were exposed to 6.5 Gy (LD100/30) at Day 0 and treated with EC-18 daily at 250 mg/kg/day for 30 days. The development of skin damage (erythema and reddening) on the tails were evaluated. The EC-18-treated group demonstrated a substantial reduction of tail erythema compared to the PBS-treated group (FIG. 15).

In the following study, Balb/c mice (n=5 females/group) were exposed with a supra-lethal radiation dosage of 8 Gy and treated with EC-18 daily at 250 mg/kg/day for 17 days. The resulting skin damage (necrosis, ulceration, blistering, and hair loss) on tails and feet was extensively reduced by the EC-18 treatment as compared to the PBS control cohort (FIG. 13B). Overall, these results suggest that EC-18 treatment would have significant efficacy in enhanced survival to include severe neutropenic conditions induced by high lethal TBI. This may suggest that EC-18 may be effective in cutaneous radiation syndrome as well.

(2) Efficacy Assessment of EC-18 on Oral Mucositis in a CRIOM Murine Model

Radiation-Induced Coagulopathy is worsened in more severe syndromes including mucositis in the oral cavity and GI. As described above, exposure to radiation stimulates DAMP release and DAMP recognized by PRR results in an inflammatory response that causes apoptosis, mucosal atrophy, and ulceration. Specifically, TLR-4 has been identified as a major PRR, which plays a critical role in the pathogenesis of mucosal injury (Vasconcelos et al., 2016). To investigate the mitigating effect of EC-18 against CRIOM, different doses of EC-18 were administered to mice daily. CRIOM mouse model was established using concurrent treatments with 5-FU (100 mg/kg, i.p.) and X-radiation (20 Gy) on heads and necks of mice. PBS or EC-18 (100 and 250 mg/kg, p.o.) was administered daily (n=5 for each group). The body weights of mice were observed, and the mice were sacrificed on day 9.

Figure 52A:
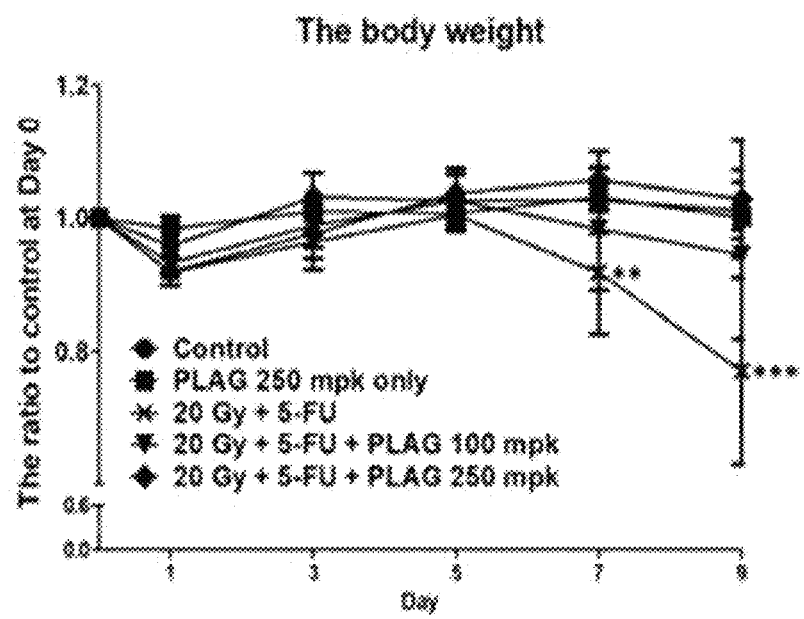
Figure 52B:
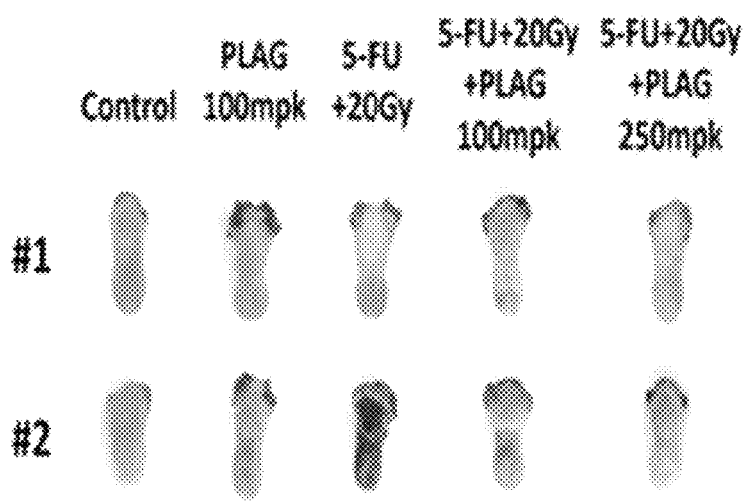
Figure 52C:
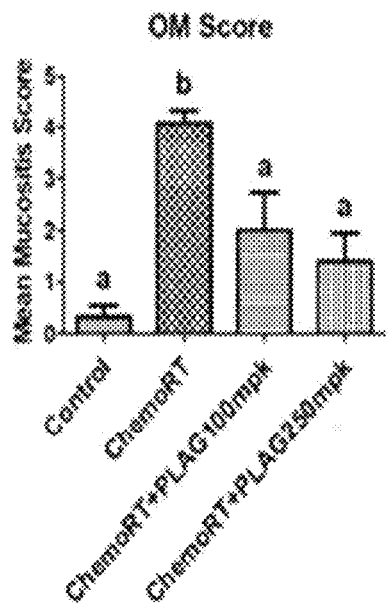
Figure 52D:
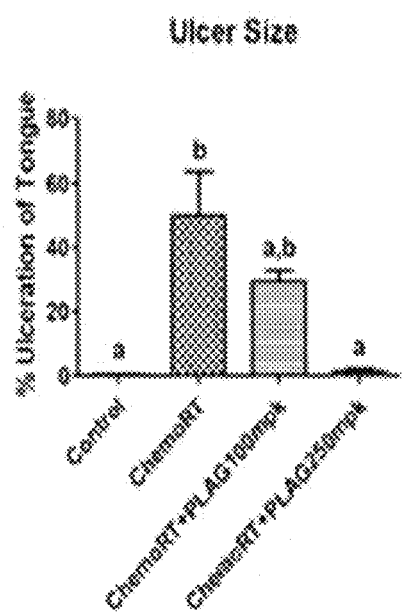
Figure 52E:
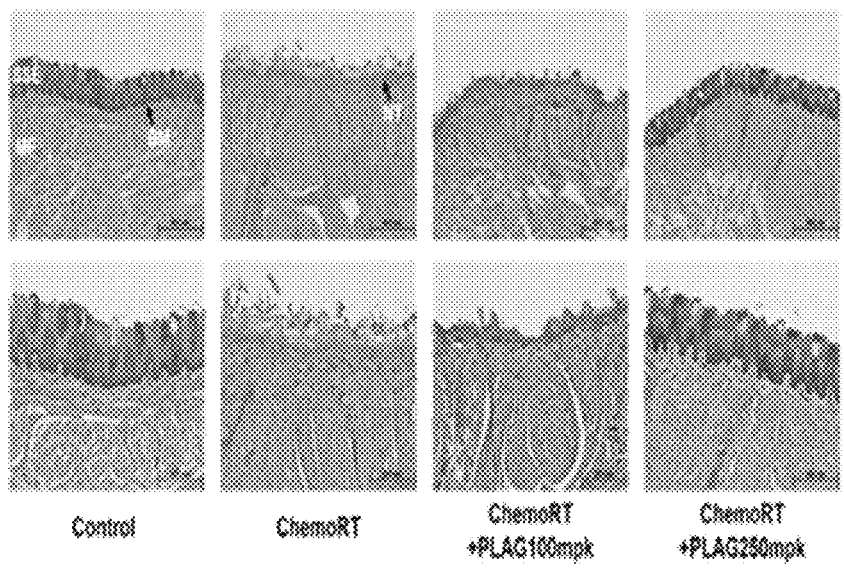
Figure 52F:
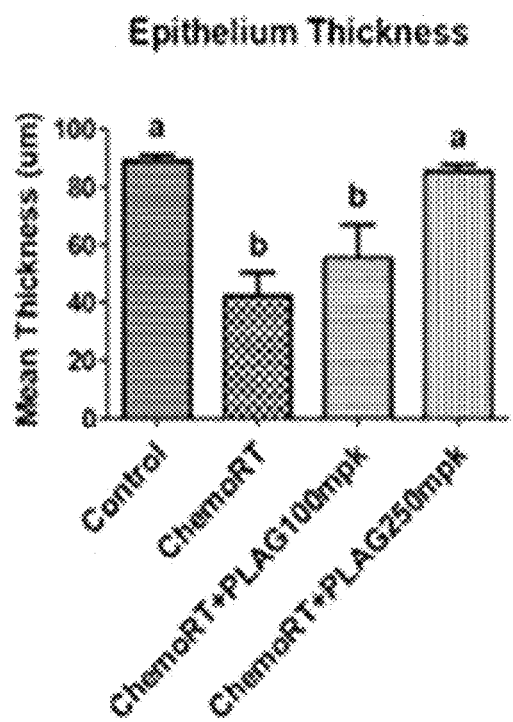
Figure 52G:
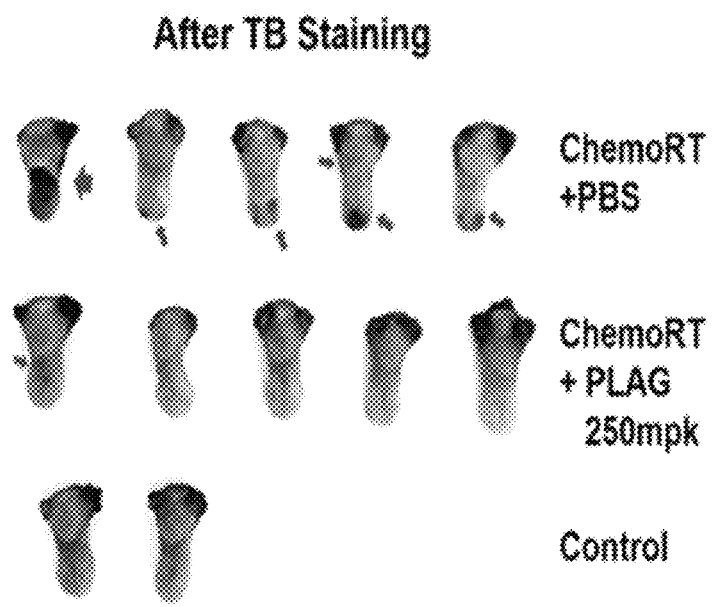

The result showed that EC-18 (100 and 250 mg/kg)-treated mice did not exhibit a significant weight loss as the chemoradiation-treated group did (FIG. 52A). The mice only treated with EC-18 250 mg/kg, kept their body weights similar to the control ones throughout the experiment. chemoradiation-treated (ChemoRT) group developed ulceration and erosions on their tongues. However, ChemoRT+EC-18-treated mice exhibited less severe ulcerations. The protective effect was more noticeable in ChemoRT+EC-18 250 mg/kg group than 100 mg/kg-treated mice. The group treated only with EC-18 showed no difference from the control group (FIG. 52B). For the assessment of OM, three following markers were used: the mean OM scores, areas of ulceration and epithelium thickness. ChemoRT group had the most severe OM, a higher rate of ulceration and the loss of epithelium of their tongues among all the groups compared. However, EC-18-administered groups had statistically improvement of OM score and lower rates of ulceration dose-dependently (FIGS. 52C-52D). ChemoRT+EC-18 250 mg/kg mice had their epithelium of the tongues protected. The thickness of the oral epithelium was measured using H&E samples (FIG. 52E). The result indicated that the ChemoRT group had extensively thinner epithelium than the control group, but EC-18 demonstrated a protective effect against the damage (FIG. 52F). Overall, EC-18 250 mg/kg treatment on chemoradiation-applied mice exhibited the most recognizable results against CRIOM (FIG. 52G). Therefore, further experiments were conducted by comparing ChemoRT and ChemoRT+EC-18 250 mg/kg groups.

Figure 53A:
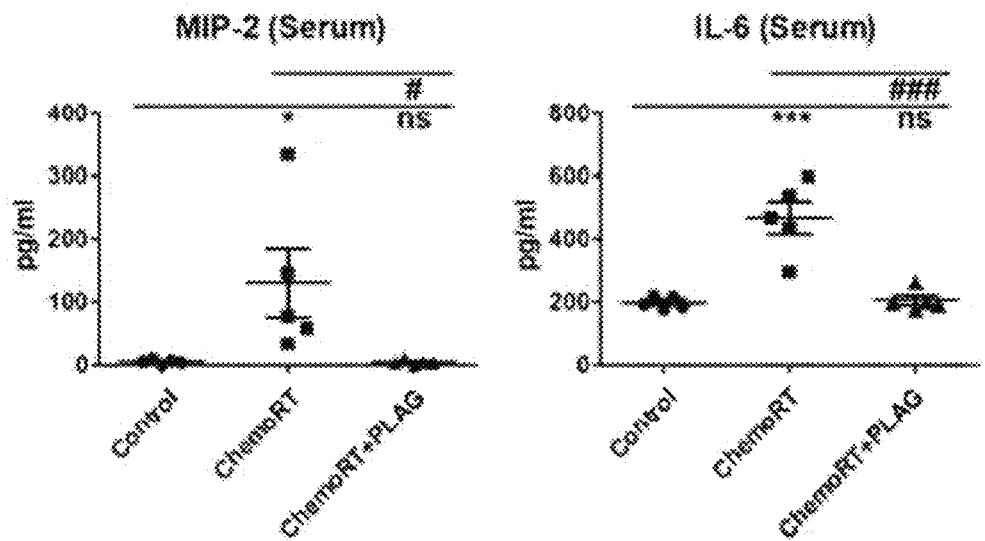
Figure 53B:
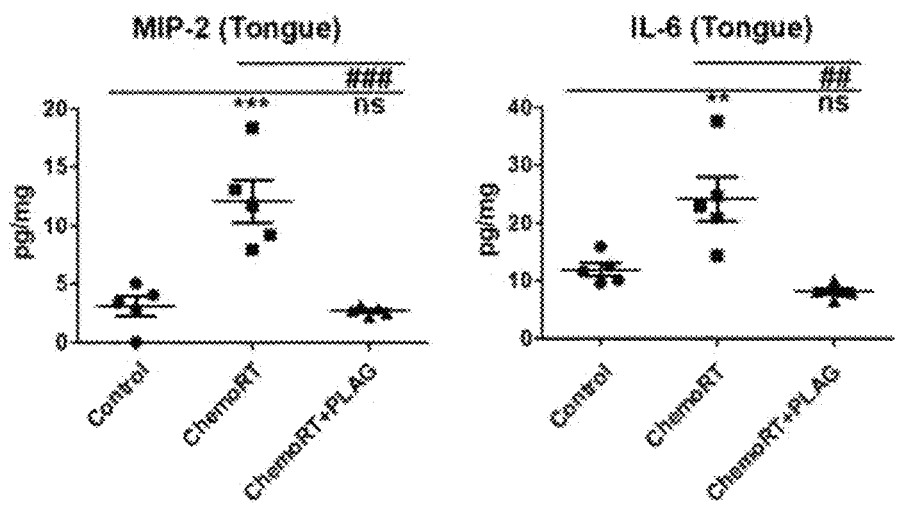
Figure 53C:
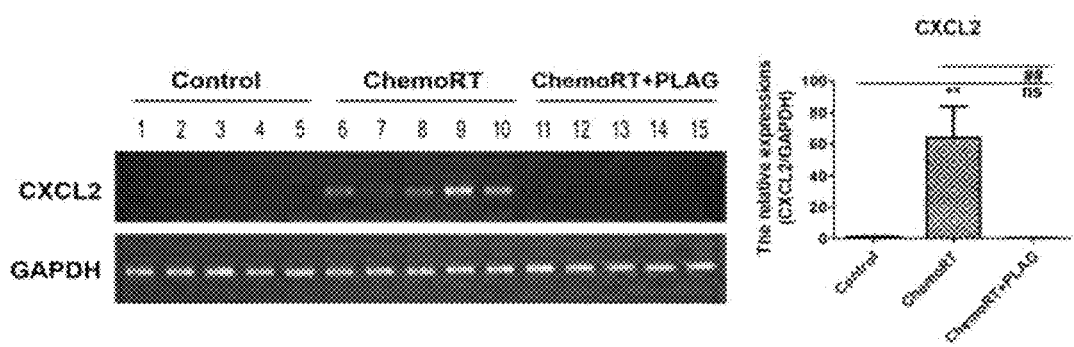
Figure 53D:
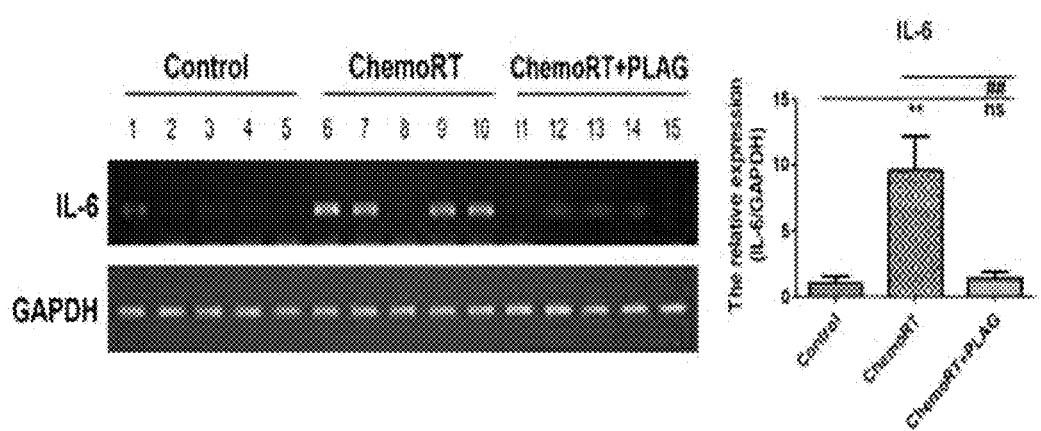
Figure 53E:
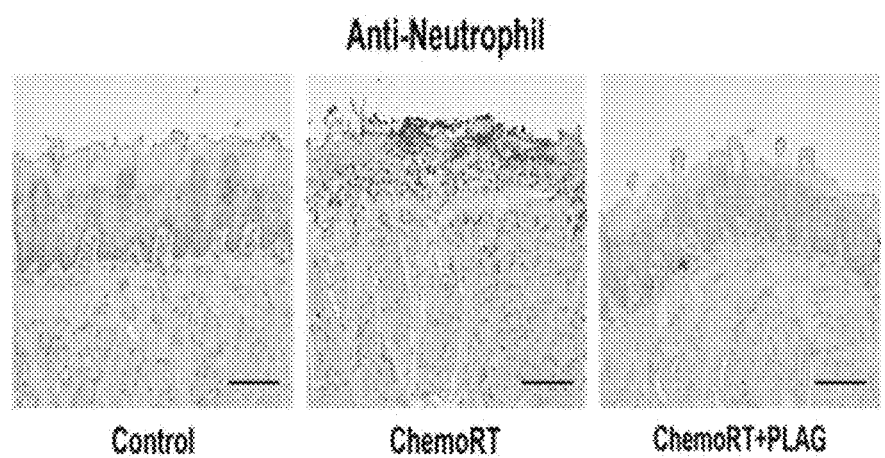

To dissect the effect of OM in the inflammatory response, the levels of pro-inflammatory cytokines were examined ChemoRT group had significantly elevated levels of MIP-2 and IL-6 in their serum than the normal group (FIG. 53A). Nonetheless, EC-18-treated mice had substantially less systemic inflammation. To confirm whether the systemic inflammation in the ChemoRT group was caused by OM, the tongue-specific protein extracts were measured as well. The result showed the same pattern as the result of the serum (FIG. 53B). Also, the mRNA levels of IL-6 and MIP-2 were noticeably elevated in tongues of ChemoRT mice. However, the EC-18-treated group had a downregulated expression level of CXCL2 and IL-6 (FIG. 53C and FIG. 53D). To detect neutrophil infiltration on the oral epithelium, tissue slides were stained with anti-neutrophil antibody (NIMP-R14) for immunohistochemistry (IHC). Tongues of the ChemoRT group had neutrophils recruited at their oral epithelium, while the EC-18-treated mice did not (FIG. 53E).

To further evaluate the systemic inflammation and its relation to the necrotic epithelium, DAMPs in serum were examined Levels of high mobility group Box1 (HMGB1) and heat shock protein 90 (HSP90) were observed using western blotting (FIG. 64A). The result inferred that the ChemoRT group had higher levels of DAMPs than the control group, but EC-18-treated mice showed subsided levels of DAMPs. Further, to determine whether HMGB1 detected in serum came from the oral mucosa, the tongue tissue slides were stained with anti-HMGB1 for IHC (Im et al., 2019). FIG. 64B demonstrated the translocation of HMGB1 from the nucleus to the cytoplasm as the cytoplasmic HMGB1 was positively stained in the ChemoRT group. However, EC-18-treated mice showed their intact HMGB1 remaining in nuclei.

To confirm whether the observed inflammatory responses were associated with the necroptotic damages on the oral mucosa, the necroptosis signaling pathway was examined in tongue lysates using western blotting (FIG. 55A). The result indicated that the ChemoRT group had phosphorylation of RIPK1, RIPK3, and MLKL in their tongues. However, in EC-18-administered mice, the necroptotic signaling axis was significantly modulated (FIG. 55B). This was verified with histological observations using IHC. ChemoRT mice had a higher level of phosphorylated MLKL in their epithelial and connective tissues than the control and the PLAG-treated groups (FIG. 55C).

From the findings in this study, we summarized our results and proposed a schematic for the pathogenesis of CRIOM and the roles of PLAG. On day 9, exposure of ChemoRT to mice resulted in OM as an acute response. Therefore, DAMPs and pro-inflammatory cytokines were released from the damaged oral mucosa, and they led to systemic necro-inflammation via the circulatory system. Also, neutrophils were recruited to the oral epithelium due to the elevated level of MIP-2 and passively released DAMPs. With further investigation, the tongue tissues of ChemoRT-treated mice were discovered to have activated the necroptotic signaling axis. This confirms the inflammatory response in mice was highly related to necroptosis. However, PLAG ameliorated OM by lowering levels of pro-inflammatory cytokines and DAMPs via modulating the necroptosis signaling pathway.

(3) Efficacy Assessment of EC-18 on Lung Damage in Radiation-induced Pneumonitis Mouse Model To examine the effect of EC-18 on the lung damage in pneumonitis, female Balb/c mice (n=3/group) were exposed to 6.11 Gy of gamma-radiation at Day 0. EC-18 at 50 or 250 mg/kg was administered daily from Day 0 to 3. To verify the vascular leakage of the lung due to radiation exposure, Evans blue staining was diluted with PBS and injected i.v. into mice 30 mins before sacrificing them on Day 3 (FIG. 56).

It was observed that red blood cells infiltrated between pneumocytes consisting of pulmonary alveoli in the lung after perfusion for the irradiated lung group. This was caused by the damage of endothelial cells induced by lethal irradiation. In contrast, EC-18 mitigated the vascular leakage, thereby not having infiltrated red blood cells into the pulmonary alveoli of the lung for the EC-18-treated group. Both 50 and 250 mg/kg of EC-18-treated lungs looked comparable to the normal lung without radiation.

The further microscopical analysis was conducted by extracting the lung after sacrificing the mice. The perfused lung tissues were fixed in 10% buffered formalin for 24 hrs, embedded in paraffin, sectioned at 4 µm, and stained with hematoxylin and eosin (H&E) staining. From the intricate morphology of lung tissues, only the irradiated tissues showed intercalated RBCs between the alveolar cells (FIG. 57, arrows). In contrast, the infiltration of the RBCs into the lung tissues was not observed in both the EC-18-treated group. These results indicate that EC-18 limits the early destruction of endothelium induced by radiation through attenuating the vicious inflammatory cascades, which may lead to pneumonitis.

EC-18 Safety, Toxicity, and ADME

Safety assessment of EC-18 in the five clinical trials showed that there were no adverse events (AEs) that could be considered serious or severe. AEs that were observed involved mild symptoms unrelated to EC-18 administration. With single- and multiple-dose administration of EC-18 in a range from 500 to 4000 mg, no accumulation with repeated-dosing was observed, and there were no statistically significant differences in the safety profile between administration before and after a meal. In the clinical studies with pancreatic cancer patients, there were no SAEs associated with EC-18 administered twice daily (BID) for a total of 1000 mg/day. These data confirm that EC-18 is safe and well-tolerated for both healthy and cancer patients.

In addition to the clinical data, Enzychem has performed safety pharmacology studies, including repeat-dose toxicity, genetic toxicity, and dose-ranging embryofetal development studies, on EC-18. Additional toxicology studies have been performed including fertility and early embryonic development study and definitive embryofetal development studies. The data confirm that EC-18 produces no evidence of genetic toxicity or teratogenic risk.

(1) Pharmacokinetics and Pharmacodynamics

Method Validation for Quantitative Analysis of EC-18 or [$^{14}$C]EC-18 in Plasma or Biological Samples EC-18 concentrations in animal plasma or biological samples were measured using LC-MS/MS. Method validation was carried out in compliance with the "Guideline on Bioanalytical Method Validation" (the Ministry Food and Drug Safety, 2013) and "Bioanalytical Method Validation: Guidance for Industry" (Food and Drug Administration, 2001). The LC-MS/MS method for determination of EC-18 in human plasma was validated for selectivity, accuracy, precision, the linearity of a calibration curve, and sensitivity and lower limit of quantification (LLOQ). The validation parameters were within acceptance criteria, which indicated that the LC-MS/MS method can ensure good reliability and reproducibility.

(2) Safety Pharmacology

GLP-compliant safety pharmacology studies have been conducted on EC-18 assessing the core organ systems.

CNS Function in Mice (Irwin Test)

ICR mice (n=8 males/group) orally received a single dose of EC-18 at 0 (vehicle), 500, 1000 and 2000 mg/kg and general behaviors were observed with the Irwin test method up to 4 hrs to assess potential CNS effects.

Through 4-hr post-dose, no individual animal in the control and study groups showed any TA-related effects on cognition, mood, mobility, ocular signs, general signs, or secretory signs corresponding with behavioral changes. The results indicated that EC-18 did not affect the CNS function in mice up to single oral doses of 2000 mg/kg.

Effects of EC-18 on the Central Nervous System of Rats (FOB)

Sprague-Dawley rats (n=8 males/group) received control material (olive oil) or EC-18 at 500, 1000, and 2000 mg/kg. The functional observational battery test, which included observations inside the cage, in open space, and while holding in the hands, along with sensory-motor function, and body temperature measurements were performed before EC-18 administration and 0.5, 1, 3, 6, and 24 hrs after control or EC-18 administration. All EC-18-treated groups showed no changes in any of the parameters after its administration. Based on these findings, it was found that EC-18 did not affect the CNS up to doses of 2000 mg/kg.

In Vitro hERG Channel Inhibition

The effects of EC-18 on hERG channel currents at concentrations of 125, 250, 500 and 1000 μM were evaluated in HEK-293 cells. As a positive control, E-4031 (N-[4-[1-[2-(6-Methylpyridin-2-yl) ethyl]piperidine-4-carbonyl]phenyl]) a selective Ikr blocker, was used at a concentration of 0.1 μM.

By assessing hERG channel currents in hERG gene-transfected HEK-293 cells, EC-18 achieved the hERG channel current suppression rate (compensated suppression rate) of 1.39, 2.97, 2.54, and 2.90% at 125, 250, 500 and 1000 μM, respectively, and IC50 was not calculated as the maximum suppression rate was below 50%. The positive control, E-4031, was exposed to each one of finished recording cells of the vehicle control group or test substance group on each experimental day and hERG channel currents were recorded. The compensated suppression rate of hERG channel currents of the positive control, E-4031, was 92.11% confirming the suitability of the test system. The results indicated that EC-18 did not inhibit the hERG channel current in vitro at concentrations up to 1000 μM.

Cardiovascular Function in Conscious Dogs

CA was administered to one unanesthetized and unrestrained telemetered male Beagle dog and EC-18 (500, 1000, or 2000 mg/kg) was administered to each of three unanesthetized and unrestrained telemetered male Beagle dogs (1:1:1:1) weekly for 4 weeks. Cardiovascular effects were evaluated based on the behavioral observations, BP, HR, and ECG, from 1-hr pre-dose to 24-hr post-dose. The results indicated that EC-18 administered group had no cardiovascular effects at doses up to 2000 mg/kg.

Respiratory Function in Rats

EC-18 was orally administered to Sprague Dawley rats (n=6 males/group) at single doses of 0, 500, 1000 and 2000 mg/kg. Tidal volume, respiration rate per minute and minute volume were measured with whole-body plethysmograph at 0 (pre-dose), 1, 2 and 4-hr post-dose. The results indicated that EC-18 did affect the respiratory function in rats up to single oral doses of 2000 mg/kg.

(3) Absorption

Plasma and Lymphatic Concentrations of EC-18 in Rats After Single Oral Administration After administering a single oral dose of 500 or 2000 mg/kg of EC-18 (vehicle: olive oil) to male SD rats, the EC-18 concentration in the sampled plasma and lymphatic fluid was measured to generate the values of PK parameters (Table 16). After a single oral administration, EC-18 was absorbed within 2 hrs, and its systemic exposure was found to be dose-dependent. The rate of increase in plasma $C_{max}$ and $AUC_{last}$ was lower than the rate of increase of the administered dosage.

At all administered doses, the EC-18 concentrations were detected at the below quantitative limit (BQL) between 6 and 10 h after administration. EC-18 reached the lymphatic system within 3 h after administration, and lymphatic exposure to EC-18 increased proportionally to the administered dose. After oral administration, the $C_{max}$ and $AUC_{last}$ in the lymphatic fluid were 11 to 20 and 59 to 129 times higher than those in plasma (Table 16). The PK parameters in plasma and lymphatic fluid showed statistically significant differences in each animal (>20%). Following administration of 500-2000 mg/kg to rats, the mean absolute bioavailability (BA) was <0.3%.

TABLE 16

Mean PK parameters in plasma and lymph after a single oral dose of EC-18 in male rats

| Sample | Group/Dose (mg/kg) | Mean PK Parameters (Mean ± S.D., n = 3) | | | |
|---|---|---|---|---|---|
| | | $AUC_{last}$ (ng · hr/mL) | $C_{max}$ (ng/mL) | $T_{max}$ (hr) | $t_{1/2}$ (hr) |
| Plasma | G2/500 | 6.97 ± 8.20 | 6.87 ± 6.12 | 0.50 ± 50 | NC* |
| | G3/2000 | 44.53 ± 39.53 | 12.13 ± 6.66 | 1.67 ± 0.58 | 3.07 ± 0.87 |
| Lymph | G2/500 | 902.96 ± 271.52 | 78.11 ± 34.06 | 3.33 ± 1.15 | NC |
| | G3/2000 | 2634.51 ± 1129.73 | 244.87 ± 54.20 | 3.00 ± 2.65 | 12.31 ± 5.08 |

*NC = Not Calculated

Plasma Concentrations of Radioactivity in Rats After Single Oral or Intravenous Administration of [$^{14}$C]EC-18

Male SD rats in the fed state were administered a single oral dose of 25, 50, or 100 mg/kg (vehicle: olive oil) or a single IV injection of 10 mg/kg of [$^{14}$C]EC-18 (EC-18 with radioactive isotope $^{14}$C attached). Subsequently, the PK parameters were assessed. The concentration of radioactivity in rat plasma was measured by liquid scintillation counting (LSC) method after adding a scintillator (Clear-Sol I, Nacalai Tesque, Inc). The PK parameters of EC-18 after a single IV or oral administration are summarized in Table 17.

EC-18 orally administered to rats in fed condition reached $C_{max}$ within 4-7 hrs. The $C_{max}$ and $AUC_{last}$ increased proportionally to the increase in administered dose, while all administered doses showed similar $t_{1/2}$ values and linear PK parameters (r>0.99) (FIGS. 58A-58B). The differences in plasma concentration of EC-18 between the animals were relatively lower in the fed condition than in the fasted condition. The absolute bioavailability (BA) was approximately 46%. Based on these results, it was determined that the oral absorption rate and plasma exposure of EC-18 were increased by food intake.

TABLE 17

Mean PK parameters after a single administration of [$^{14}$C] EC-18 in male rats

| Route | Dose (mg/kg) | Mean Plasma PK Parameters (Mean ± S.D., n = 3) | | | | |
|---|---|---|---|---|---|---|
| | | $AUC_{last}$ (μg eq · hr/mL) | $C_{max}$ (μg eq/mL) | $T_{max}$ (hr) | $t_{1/2}$ (hr) | F (%) |
| IV | 10 | 215 ± 11 | 81.5 ± 3.4* | — | 32.5 ± 1.2 | |
| Oral | 25 | 224 ± 30 | 7.2 ± 1.4 | 7.3 ± 5.0 | 32.0 ± 3.1 | 46 |
| | 50 | 473 ± 53 | 16.6 ± 1.4 | 4.7 ± 2.3 | 31.4 ± 1.8 | 49 |
| | 100 | 830 ± 29 | 29.6 ± 2.7 | 6.0 ± 3.5 | 31.7 ± 3.5 | 42 |

*$C_{max}$ = $C_0$

Plasma and Lymphatic Concentrations of EC-18 in Beagle Dogs After Single Administration A single dose of EC-18 (1000, 2000, 4000 mg/kg by mouth or 100 mg/kg IV) was administered to male beagle dogs in fed condition and the concentration of EC-18 in plasma and lymph was measured using UHPLC-MS/MS. The PK parameters are summarized in Table 18 and the drug concentrations versus time plots are shown in FIG. 59.

When EC-18 was administered orally to a beagle dog, the mean $C_{max}$ and $AUC_{0-last}$ of plasma increased proportionally to the dose (Table 18). The $T_{max}$ was 1.3 hrs at 1000 and 2000 mg/kg and 6.7 hrs at 4000 mg/kg. Thereafter, EC-18 drastically disappeared.

The PK parameters showed that the lymph exposure to EC-18 was much greater than the plasma exposure. $C_{max}$ and $AUC_{0-last}$ of EC-18 in lymph increased proportionally to the increase in dose. The median $T_{max}$ was 4 hrs at 1000 and 2000 mg/kg and 2 hrs at 4000 mg/kg. Thereafter, EC-18 drastically disappeared. Based on the canine model results, EC-18 may be mainly transported to the lymph system and becomes available via systemic circulation.

TABLE 18

Mean PK parameters in plasma and lymph in dogs after a single administration of EC-18

| Dose, Route | PK parameter | Plasma | Lymph |
|---|---|---|---|
| 100 mg/kg, IV | $AUC_{last}$ (µg · h/ml) | 7.540 ± 1.860 | |
| | $C_{max}$ (µg/ml) | | |
| | $T_{max}$ (hr) | | |
| | $T_{1/2}$ (hr) | 13.94 ± 2.3 | |
| 1000 mg/kg, po | $AUC_{last}$ (µg · h/ml) | 5.80 ± 2.81 | 118 ± 16.7 |
| | $C_{max}$ (µg/ml) | 1.75 ± 0.71 | 35.1 ± 5.16 |
| | $T_{max}$ (hr) | 1.3 ± 0.5 | 3.3 ± 0.9 |
| | $T_{1/2}$ (hr) | NC | NC |
| | F (%) | 7.8 | |
| 2000 mg/kg, po | $AUC_{last}$ (µg · h/ml) | 9.493 ± 3.852 | 389 ± 125 |
| | $C_{max}$ (µg/ml) | 2.11 ± 0.75 | 40.1 ± 8.62 |
| | $T_{max}$ (hr) | 1.3 ± 0.5 | 3.3 ± 0.9 |
| | $T_{1/2}$ (hr) | NC | NC |
| | F (%) | 6.3 | |
| 4000 mg/kg, po | $AUC_{last}$ (µg · h/ml) | 71.1 ± 31.7 | 431 ± 81.3 |
| | $C_{max}$ (µg/ml) | 6.76 ± 3.33 | 46.6 ± 1.73 |
| | $T_{max}$ (hr) | 6.7 ± 0.9 | 3.3 ± 1.9 |
| | $T_{1/2}$ (hr) | NC | 3.3 ± 0.2 |
| | F (%) | 23.6 | |

Plasma and Lymphatic Concentrations of Radioactivity After a Single Oral Administration of [$^{14}$C]EC-18

After inserting a cannula into the intestinal tract of male SD rats, the rats in fed condition were given a single dose of [$^{14}$C]EC-18 (oral dose of 50 mg/kg; vehicle: olive oil), and samples were collected after 0.5, 1, 2, 4, 6, and 8 hrs of administration. In parallel, lymphatic fluid samples were collected from conscious rats up to 8 hrs after administration. The radioactive concentrations in rat plasma and lymphatic fluid were measured by LSC after adding a scintillator, and the quantified data are shown in Table 19.

The radioactive concentration (17.5 µq/mL) measured in rat plasma for 8 h after administration of [$^{14}$C]EC-18 was approximately 28% of the administered dose, while the mean radioactive concentration in the lymphatic fluid collected up to 8 hrs after administration was around 23%. Based on these findings, it was determined that the EC-18 was absorbed through the small intestine and lymphatic vessels once EC-18 was orally administered.

TABLE 19

Mean radioactive concentration in male rat plasma and lymphatic fluid after a single oral administration of [$^{14}$C]EC-18

| Time (hr) | Radioactive Concentration in Plasma in µg eq/mL (Mean ± S.D., n = 3) | Relative Radioactive Concentration Measured in Lymphatic Fluid (Versus Administered Dose) |
|---|---|---|
| 0 | — | 23.4 ± 14.1% |
| 0.5 | 0.096 ± 0.096 | |
| 1 | 0.689 ± 0.796 | |
| 2 | 2.09 ± 1.65 | |
| 4 | 6.51 ± 2.21 | |
| 6 | 10.2 ± 2.7 | |
| 8 | 17.5 ± 4.9 | |

Whole Blood and Lymphatic Concentrations of Radioactivity in Rats After a Single Oral Administration of [$^{14}$C]EC-18

Male SD rats in fasted condition were administered a single dose of [$^{14}$C]EC-18 (oral dose of 100 mg/kg; vehicle: olive oil), and the radioactive concentration of the EC-18 was measured in whole blood samples at 0.5, 1, 2, 3, 4, 6, and 8 hrs after its administration. In parallel, male rats with a cannula inserted into the intestinal tract were administered a single dose of [$^{14}$C]EC-18 (oral dose of 100 mg/kg; vehicle: olive oil) and the concentration of EC-18-related radioactivity was measured in lymphatic fluid collected in conscious rats at 0.5, 1, 2, 3, 4, 6, and 8 hrs after its administration (FIG. 60). Then, the values of PK parameters were calculated using the quantitative data from whole blood and lymphatic fluid samples (Table 20). Following a single oral administration of [$^{14}$C]EC-18 concentration in the lymphatic fluid of rats was 10 to 53 times higher than that in whole blood (FIG. 60). Moreover, $C_{max}$ and $AUC_{0-last}$ of EC-18 in the lymphatic fluid were higher by 31 and 41 times than those in whole blood, respectively. The $C_{max}$ of radioactivity in whole blood and lymphatic fluid at 24 hrs after EC-18 administration was 34 and 48%, respectively, and $T_{max}$ was 3.8 and 7.0 hrs, respectively.

Whole blood and lymphatic concentrations of radioactivity in rats after a single oral administration of [$^{14}$C]EC-18, it was determined that orally administered EC-18 is absorbed through the small intestine and lymphatic vessels, and the oral absorption rate is affected by the food intake status.

TABLE 20

Mean PK parameters in whole blood and lymphatic fluid after a single oral administration of [$^{14}$C] EC-18 in male rats

| PK Parameters | Radioactive Concentration (Mean ± S.D., n = 3) | |
|---|---|---|
| | Whole Blood | Lymphatic Fluid |
| $AUC_{0-last}$ (µg eq · hr/mL) | 496 ± 69 | 20400 ± 600 |
| $AUC_{0-inf}$ (µg eq · hr/mL) | 819 ± 130 | 53900 ± 39100 |
| $C_{max}$ (µg/mL) | 38.8 ± 9.5 | 1210 ± 200 |
| $T_{max}$ (hr) | 3.8 ± 2.9 | 7.0 ± 2.0 |
| $t_{1/2}$ (hr) | 16.8 ± 1.9 | 29.7 ± 28.1 |

Plasma Concentrations of EC-18 in non-irradiated and irradiated mice

A day after 6.11 Gy gamma-radiation, both irradiated and non-irradiated male Balb/c mice (n=5) were orally administered daily with 50, 100, 250 or 500 mg/kg of EC-18 up to 14 days and analyzed for PK parameters on days 7 and 14 post-radiation (Table 21).

All groups that EC-18 was administered for a week had similar results on their PK parameters. The EC-18 administered irradiated mice had the $T_{max}$ reached within 1 h (FIG. 61) and the $C_{max}$ and $AUC_{last}$ increased proportionally to EC-18's dosage. The group fed with EC-18 for 2 weeks also had similar results on their PK parameters compared to those from the one week fed group. However, the irradiated mice fed with EC-18 at the dosage of 50 and 250 mg/kg had relatively low the plasma concentration of EC-18.

This study will facilitate the identification of effective EC-18 concentrations in the blood and lymph to aid in the design and evaluation of delivery/mitigation effects in the NHP model.

TABLE 21

Mean PK parameters in plasma concentration after 1 and 2 weeks of daily administration of EC-18 in non-irradiated and irradiated mice

| Day | Dose (mg/kg) | Radiation | $AUC_{last}$ (ng · hr/mL) | $C_{max}$ (ng/ml) | $T_{max}$ (h) |
|---|---|---|---|---|---|
| 7 | 50 | Non-irradiated | 21.6 ± 11.7 | 2.7 ± 1.4 | 2.8 ± 2.4 |
|  |  | Irradiated | 39.5 ± 14.8 | 7.8 ± 3.4 | 0.4 ± 0.3 |
|  | 100 | Non-irradiated | 25.3 ± 7.1 | 9.7 ± 4.7 | 5.2 ± 8.6 |
|  |  | Irradiated | 41.3 ± 12.1 | 9.8 ± 2.9 | 0.7 ± 0.2 |
|  | 250 | Non-irradiated | 40.7 ± 23.4 | 16.4 ± 11.2 | 0.6 ± 0.2 |
|  |  | Irradiated | 73.9 ± 27.1 | 31.4 ± 14.9 | 0.6 ± 0.2 |
|  | 500 | Non-irradiated | 57.1 ± 39.7 | 14.2 ± 3.0 | 5.2 ± 8.6 |
|  |  | Irradiated | 122.8 ± 17.8 | 60.7 ± 14.6 | 0.7 ± 0.2 |
| 14 | 50 | Non-irradiated | 38.5 ± 10.3 | 4.1 ± 1.4 | 7.8 ± 8.4 |
|  |  | Irradiated | 8.6 ± 3.7 | 1.9 ± 0.6 | 3.1 ± 4.5 |
|  | 100 | Non-irradiated | 51.3 ± 22.6 | 12.8 ± 9.9 | 7.6 ± 8.5 |
|  |  | Irradiated | 80.8 ± 123.8 | 17.2 ± 23.3 | 1.8 ± 2.1 |
|  | 250 | Non-irradiated | 76.6 ± 9.8 | 19.4 ± 12.3 | 2.8 ± 4.2 |
|  |  | Irradiated | 16.2 ± 7.8 | 17.9 ± 17.5 | 0.6 ± 0.2 |
|  | 500 | Non-irradiated | 75.9 ± 16.0 | 32.1 ± 8.0 | 0.5 ± 0 |
|  |  | Irradiated | 67.3 ± 34.1 | 61.0 ± 42.1 | 0.6 ± 0.2 |

(4) Distribution

Plasma Protein Binding and In Vitro Plasma Stability of EC-18

To assess the stability of EC-18 in plasma, the test material, or the standard reference material (test concentration 1 μM) was mixed with rat and human plasma and allowed to react for 1 hr at 37° C. Then, the residual EC-18 concentration was measured by LC-MS/MS. As standard reference materials, albendazole (a drug with high plasma stability) and vinpocetine (a drug with low plasma stability) were tested in parallel. The plasma stability of EC-18 and the standard reference materials in rats and humans are summarized in Table 22. When allowed to react with rat and human plasma for 1 hr, the residual EC-18 concentration in both rat and human plasma was >99% of the initial dose. These findings were comparable to those of albendazole, which is a plasma stability marker, indicating that EC-18 has high stability in rat and human plasma.

TABLE 22

Relative residual concentration of EC-18 and comparators at 1 hr (37° C.) in human and rat plasma

| Test or Standard Reference Material | Final Test Concentration (μM) | Residual Concentration Relative to the Initial Dose After Reaction for 1 hr in Plasma (%, n = 3) | |
|---|---|---|---|
|  |  | Humans | Rats |
| EC-18 | 1 | >99 | >99 |
| Albendazol (high plasma stability reference) | 1 | >99 | >99 |
| Vinpocetin (low plasma stability reference) | 1 | 85.3 ± 3.8 | 52.4 ± 7.2 |

The plasma protein binding ability of EC-18 was tested by rapid equilibrium dialysis (RED). The chamber separated by a dialysis tubing membrane (cut-off: 8 kDa) was filled on one side with rat or human plasma mixed with phosphate buffer and on the other side with rat or human plasma mixed with the test or standard reference material (test concentration: 1 μM). After 4 hrs of reaction, the free-drug (unbound) concentration was measured by LC-MS/MS. As standard reference materials, warfarin (high plasma protein binding) and atenolol (low plasma protein binding) were used. The plasma protein binding rates of EC-18 and the standard reference materials in rats and humans are summarized in Table 23. The plasma protein binding rate of EC-18 was ≥99% in both humans and rats. These findings were comparable to the binding rate of 99% shown by warfarin (in both humans and rats), indicating that EC-18 has a high binding affinity to plasma proteins.

TABLE 23

Plasma protein binding rates of EC-18 and comparators in humans and rats

| Test or Standard Reference Material | Final Test Concentration (μM) | Plasma Protein Binding Rate (%, n = 3) | |
|---|---|---|---|
|  |  | Humans | Rats |
| EC-18 | 1 | >99 | 98.8 ± 0.5 |
| Warfarin (high plasma protein binding) | 1 | 99.2 ± 0.2 | 99.1 ± 0.3 |
| Atenolol (low plasma protein binding) | 1 | 1.7 ± 1.2 | 9.2 ± 2.1 |

Whole-Body Autoradiography of Rats After a Single Oral Administration of [$^{14}$C]EC-18

Male albino rats in fasted conditions were administered a single dose of [$^{14}$C]EC-18 (oral dose of 200 mg/kg, vehicle: olive oil). The distribution and levels of radioactivity in the body were observed by whole-body autoradiography performed at 0.25, 1, 8, and 24 hrs after [$^{14}$C]EC-18 administration.

At 0.25 hr after administration, the highest radioactivity was observed in the stomach and small intestine. After 1 hr of administration, the highest radioactivity was observed in the stomach and small intestine, while low radioactivity was observed in the liver. After 8 hrs of administration, the highest radioactivity was observed in the inner walls of the stomach, and radioactivity was observed in the adipose tissues and the liver. After 24 hrs of administration, low radioactivity was observed in the liver. Over the 24-hr period since the administration of [$^{14}$C]EC-18, radioactivity was not observed in any other organ FIG. 62. These results indicated that EC-18 is strictly distributed to organs and eliminated within 24 hrs after administration.

In Vitro Metabolic Stability

[$^{14}$C]EC-18 or the positive control (7-ethoxycoumarin; 7-EC) reacted with microsomes prepared from hepatocytes of rats, dogs, monkeys, and humans, with or without cofactors, for 60 and 120 min. Then, the residual EC-18 concentration over time was measured by LC-RID ([$^{14}$C]EC-18) or LC-MS/MS (7-EC) (FIG. 63 and FIG. 64). The test systems used to assess the in vitro metabolic stability of EC-18 are shown in Table 24.

TABLE 24

| In vitro metabolic stability test system | | | | |
|---|---|---|---|---|
| Test | Concentration (µM) | | Cofactor | |
| System | EC-18 | 7-EC | | (µM) |
| A | 1 | 100 | NADPH* | (500) |
| B | 1 | 100 | NADPH* | (500) |
|   |   |   | PAPS** | (0.28) |
|   |   |   | UDPGA*** | 2 |
| C | 1 | 100 | — | |

*NADPH = Nicotinamide adenine dinucleotide phosphate
**PAPS = 3'-phosphoadenosine 5'-phosphosulfate
***UDPGA = Uridine 5'-diphosphoglucuronic acid When the microsomes from the four species were allowed to react for 1 hr with EC-18 and nicotinamide adenine dinucleotide phosphate (NADPH) (test system A); EC-18, NADPH, and/or 3'-phosphoadenosine 5'-phosphosulfate (PAPS) and uridine 5'-diphosphoglucuronic acid (UDPGA) (test system B); and EC-18 alone (test system C), residual EC-18 concentration ≥50% of the initial concentration was found in all species. When reacted for 2 hrs, the residual EC-18 concentration was in the order of human>rat and dog>monkey. In all species, except monkeys, the residual EC-18 concentration after 2 hrs of the reaction was ≥50% in all test systems.

Each test system was designed to examine phase 1 metabolic reaction (test system A), phase 2 metabolic reaction (test system B), and non-enzymatic degradation. There were no statistically significant differences in the residual concentrations of EC-18 reacted in the test systems of all species. Therefore, these results suggest that EC-18 is degraded by enzymatic metabolism or non-enzymatic reaction. The elimination rate of EC-18 measured in each test system after reaction with human microsomes was as follows: for 1-hr reaction, A (Phase 1 metabolic reaction) =21.2%; B (Phase 2 metabolic reaction)=25.5%; and C (non-enzymatic degradation)=26.5%; for 2-hr reaction, A=32.8%, B=35.4%, and C=32.6% (FIG. 63).

When the positive control 7-EC was reacted in the same in vitro test settings as EC-18, ≥99% of the initial concentration was eliminated after reaction for 1 hr in test systems A and B of rats, dogs, monkeys, and humans, whereas ≥92% of the initial concentration was retained even after reaction for 2 hrs in test system C (FIG. 64). These results proved the validity of this test method.

In Vitro Metabolite Screening

The LC-RID chromatographic profiles of radioactive metabolites produced in the 2-hr incubation reaction mixtures of the same test systems A, B, and C used to assess the metabolic and non-metabolic elimination rates of EC-18 were compared to the LC-UV chromatographic profiles of the synthetic reference material. The chromatograms revealed 5-7 major peaks of metabolites as compared with the reference chromatogram, and the most abundant peak was identified as EC-18 in all species. The relative radioactivity of EC-18 accounted for 42-67% of total radioactivity. The peaks designated as M2, M3, and M5 were also determined in all species, and their relative radioactivity accounted for 12-34% of total radioactivity. The peaks of M4 and M6 were determined in monkeys and humans. M1 was abundantly detected in all species, but it was assumed to be a peak of early elution. The LC-UV chromatograms of reaction mixtures in each test system (FIGS. 65A-65C) and the relative radioactivity of the screened metabolites are shown in Table 25.

TABLE 25

The relative quantitative value of radioactive metabolites measured after reacting [$^{14}$C] EC-18 with rat, dog, monkey, and human liver microsomes for 2 hrs; (A) NADPH added, (B) NADPH, PAPS, and UDPGA added, and (C) no cofactor added (n = 2)

| | Mean Peak Area in LC-RID (%) (N = 2) | | | | | | | | | | | |
|---|---|---|---|---|---|---|---|---|---|---|---|---|
| | A | | | | B | | | | C | | | |
| Screened | Rat | Dog | NHP | Human | Rat | Dog | NHP | Human | Rat | Dog | NHP | Human |
| M-1 | 13.0 | 24.9 | 18.7 | 12.3 | 18.8 | 21.2 | 16.2 | 15.4 | 14.6 | 16.5 | 16.6 | 6.3 |
| M-2 | 5.9 | 7.3 | 3.2 | 1.4 | 6.7 | 7.6 | 3.9 | 1.8 | 5.3 | 8.1 | 2.4 | 5.5 |
| M-3 | 3.6 | 3.6 | 2.6 | 1.9 | 3.0 | 4.4 | 1.8 | 1.5 | 3.5 | 5.4 | 2.3 | 4.3 |
| M-4 | ND* | ND | 0.8 | ND | ND | 1.0 | 2.1 | ND | ND | ND | ND | ND |
| M-5 | 4.7 | 4.9 | 21.8 | 8.8 | 6.8 | 4.0 | 22.7 | 9.0 | 6.6 | 4.7 | 29.3 | 8.2 |
| EC-18 | 61.8 | 52.6 | 46.8 | 67.2 | 51.9 | 54.3 | 46.0 | 64.6 | 58.8 | 56.6 | 41.8 | 67.4 |
| M-6 | ND | ND | ND | 1.8 | ND | ND | 0.6 | 1.9 | ND | ND | ND | 1.7 |
| Others | 11.2 | 6.8 | 6.4 | 6.7 | 13.0 | 7.7 | 6.8 | 5.9 | 11.5 | 6.8 | 7.8 | 6.8 |

Validation Test on CYP Enzyme Induction by EC-18

This test was performed to determine if EC-18 was capable of inducing CYP1A2 and CYP3A4 activities in human primary hepatocytes. As shown in Table 26, the relative activities of CYP1A2 and CYP3A4 did not increase relative to the normal control when treated with EC-18 up to concentrations of 100 µM. The results indicated that EC-18 had no potential to induce CYP1A2 and CYP3A4.

TABLE 26

Effects of EC-18 on CYP1A2 induction

| Test Articles (μM) | Enzyme Activity (pmol/106 Cells/Min) (Mean ± S.D, n = 3) | |
|---|---|---|
| | CYP1A2 | CYP3A4 |
| NC* | 0.29 ± 0.04 | 2.41 ± 0.41 |
| PC** | 6.56 ± 2.86 | 25.6 ± 9.67 |
| EC-18    1 | 0.33 ± 0.04 | 3.44 ± 0.73 |
| 10 | 0.38 ± 0.06 | 3.11 ± 0.25 |
| 100 | 0.33 ± 0.04 | 3.61 ± 0.28 |

*NC: Negative Control, PC: Positive control
**PC: Positive Control, 50 μM omeprazole for CYP1A2 and 25 μM rifampin for CYP3A4

Validation Test on CYP Enzyme Inhibition

CYP1A2, CYP2C9, CYP2C19, CYP2D6, and CYP3A4 are the CYP subfamily, which plays a critical role in the metabolism of most drugs. In this study, EC-18 and the selective inhibitors of each subfamily were incubated with human liver microsomes in the presence of NADPH and the substrate as follows: phenacetin for CYP1A2, diclofenac for CYP2C9, S-mephenytoin for CYP2C19, dextromethorphan for CYP2D6, and midazolam for 3A4. The inhibitory effects were measured by IC50 values that were the concentration of inhibitors reducing metabolite levels by a half: acetaminophen by CYP1A2, 4'-hydorxydiclofenac by CYP2C9, 4'-hydroxymephenytoin by CYP2C19, dextrorphan by CYP2D6, and 1'-hydroxymidazolam by CYP3A4. The inhibitory effect of EC-18 on each subfamily was determined by comparing IC50 values between the selective inhibitors and EC-18. The IC50 values are summarized in Table 27. The obtained IC50 values of EC18 showed no inhibitory effects of EC-18 on the CYP subfamilies, which means no clinical significance in drug interaction.

TABLE 27

IC$_{50}$ values of reference compounds and EC-18 on CYP subfamilies

| Test Compound | IC$_{50}$ (μM) | | | | |
|---|---|---|---|---|---|
| | CYP1A2 | CYP2C9 | CYP2C19 | CYP2D6 | CYP3A4 |
| Reference* | 1.7 | 0.2 | 6.0 | 67.9 | 28.8 |
| EC-18 | 24398 | 7992 | 83.61 | 67.9 | 26.8 |

*Reference compounds: 7-ethoxycoumarin for CYP1A2, sulfaphenazole for CYP2C9, omeprazole for CYP2C19, promethazine for CYP2D6, and fluconazole for CYP3A4

Study of Effects of EC-18 on Drug Transporters

This study examined the potential of EC-18 to interact with the transporter proteins that have been known to be involved in the absorption of commercially available drugs. EC-18 was pre-incubated with HEK-293 cells and LLC-PK1 cells that were transfected with the genes of most drug transporters as follows: OATP1B1, OATP1B3, OAT1, OAT3 and OCT2, and BCRP and P-gp, respectively. The inhibitory effect of EC-18 on each transporter was determined by the values of IC50 that was the concentration of EC-18 reducing the cellular uptake of the $^3$H-labeled substrate by half as follows: 100 nM [$^3$H] para-aminohippuric acid for OAT1, 100 nM [$^3$H] estrone-3-sulfate for OAT3 and OATP1B1, 100 nM [$^3$H] estradiol-17β-D-glucuronide for OATP1B3, 100 nM [$^3$H] methyl-4-phenylpyridinium for OCT2, [$^3$H] digoxin for P-gp and 100 nM [$^3$H] estrone-3-sulfate for BCRP, and the concentration-dependent transported substrates are depicted in FIG. 66. The IC50 values of EC-18 were obtained in a two order of magnitudes of micromolar (>32 μM), which suggested that EC-18 has no significant inhibitory effects on these drug transporters.

(6) Excretion

Pathway of Excretion in Rats after a Single Administration of [$^{14}$C]EC-18

To assess the routes of EC-18 excretion, male rats were administered a single dose of [$^{14}$C]EC-18 (oral dose of 50 mg/kg), after which, radioactive concentrations were measured in urine, feces, and exhaled air in the chamber of the animals for 168 hrs, and in the body after the autopsy.

With respect to the total cumulative radioactive concentration shown in, approximately 76% of the total administered dose was excreted within 24 hrs after EC-18 administration; approximately 83% by 72 hrs; and 96% by 168 hrs. The cumulative radioactive concentration relative to the total administered dose in exhaled air, feces, and urine was approximately 71, 3, and 2% at 24 hrs; 77, 4, and 2% at 72 hrs; and 79, 4, and 2% at 168 hrs (in live animals) after EC-18 administration, respectively (Table 28).

Moreover, the cumulative radioactive concentration relative to the total administered dose measured in the body was approximately 10%. Based on these results, it was determined that orally administered EC-18 was excreted primarily through exhaled air in the first 24 hrs and to a lesser extent through feces and urine in rats.

TABLE 28

Cumulative radioactive concentration relative to total administered dose measured in urine, feces, and exhaled air collected for 168 hrs after oral administration of [$^{14}$C] EC-18

| | Cumulative Radioactive Concentration Relative to the Administered Dose (%) | | | | | |
|---|---|---|---|---|---|---|
| Time (hr) | Urine | Feces | Exhaled Air | Cage-Cleaning Water | Cadaver | Total |
| 0-24 | 1.9 ± 0.3 | 3.0 ± 0.5 | 71.0 ± 3.2 | 0.0 ± 0.0 | — | 75.9 ± 3.2 |
| 0-48 | 2.1 ± 0.3 | 3.6 ± 0.7 | 75.0 ± 3.8 | 0.1 ± 0.1 | — | 80.7 ± 3.8 |
| 0-72 | 2.2 ± 0.3 | 3.8 ± 0.7 | 76.7 ± 3.9 | 0.1 ± 0.0 | — | 82.8 ± 3.9 |
| 0-96 | 2.3 ± 0.4 | 3.9 ± 0.7 | 77.7 ± 3.9 | 0.1 ± 0.0 | — | 84.0 ± 3.8 |
| 0-120 | 2.3 ± 0.4 | 4.0 ± 0.7 | 78.4 ± 3.9 | 0.1 ± 0.0 | — | 84.8 ± 3.8 |
| 0-144 | 2.3 ± 0.4 | 4.1 ± 0.7 | 78.9 ± 3.9 | 0.1 ± 0.0 | — | 85.4 ± 3.8 |
| 0-168 | 2.3 ± 0.4 | 4.2 ± 0.7 | 79.3 ± 3.9 | 0.1 ± 0.0 | 9.8 ± 1.0 | 95.7 ± 3.3 |

(7) Pharmacokinetic Drug Interactions

No studies on PK drug interactions of EC-18 have been conducted at this time.

(8) Toxicology Summary

Various toxicology studies have been performed. All studies were GLP-compliant unless otherwise noted. Table 29 summarizes the toxicology studies on EC-18.

TABLE 29

Summary of toxicology studies

| Test type | Animal/System | Route | Duration | Dose (mg/kg) | Results |
| --- | --- | --- | --- | --- | --- |
| Single-dose toxicity | SD rat | Oral | Single | 0, 2000 | No dead animals<br>Approximate lethal dose: >2000 mg/kg |
|  | Beagle dog | Oral | Days 1, 5, 9, 13 | 0, 500, 1000, 1500, 2000 | No dead animals<br>No specific findings<br>Approximate lethal dose: >2000 mg/kg |
| Repeated dose toxicity | SD rat | Oral | 4 weeks | 0, 500, 1000, 2000 (DRF) | No dead animals<br>No specific findings<br>NOAEL: >2000 mg/kg/day |
|  |  | Oral | 13 weeks | 0, 500, 1000, 2000 | No dead animals<br>No specific findings<br>NOAEL: >2000 mg/kg/day |
|  |  | Oral | 26 weeks (4-week recovery) | 0, 500, 1000, 2000 | A single case of death (male in the 500 mg/kg group) on 41st day: No relationship between the death and EC-18 dosing was determined<br>No specific findings<br>NOAEL: >2000 mg/kg/day |
|  | Beagle dog | Oral | 2 weeks | 0, 500, 1000, 2000 | No dead animals<br>Grayish stool observed in both males and females in the 1000 and 2000 mg/kg dose groups<br>NOAEL: >2000 mg/kg/day |
|  |  | Oral | 4 weeks (2-week recovery) | 0, 500, 1000, 2000 | No dead animals<br>Random signs of soft stool and diarrhea in all groups in both control and EC-18 dose groups<br>Grayish stool observed in the drug administration groups<br>No other specific findings<br>NOAEL: >2000 mg/kg/day |
|  |  | Oral | 13 weeks (4-week recovery) | 0, 500, 1000, 2000 | No dead animals<br>Random signs of soft stool and diarrhea in all groups in both control and EC-18 dose groups<br>Dose-dependent grayish stool observed<br>No other specific findings<br>NOAEL: >2000 mg/kg/day |
|  |  | Oral | 9 months (4-week recovery) | 0, 500, 1000, 2000 | No dead animals<br>Dose-dependent soft stool and grayish stool observed in the drug administration groups; diarrhea in males of the 500 mg/kg dose group and males and females of the 1000 and 2000 mg/kg dose groups appearing in the early stage, which then disappear. No changes in body weight, hematological and histopathological tests were determined, determined to be no toxicological significance. |

TABLE 29-continued

Summary of toxicology studies

| Test type | Animal/System | Route | Duration | Dose (mg/kg) | Results |
|---|---|---|---|---|---|
| | | | | | No other specific findings<br>NOAEL: 2000 mg/kg/day |
| Reverse mutation test | S. typhi-murium (TA98, TA100, TA1535, TA1537), E. coli (WP2uvrA(pKM101)) | in vitro | 48 hr | 312.5, 625, 1250, 2500, 5000 µg/plate | No potential of EC-18 for the induction of reserve mutation |
| Chromosomal aberration test | Chinese hamster lung cells (CHL/IU) | in vitro | 6 and 24 hrs | 550, 1100, 2200 µg/mL without metabolic activation, 62.5, 125, 250 µg/mL with metabolic activation. | EC-18 didn't have inducible effects on chromosomal aberration in cultured CHL/IU cells in a short time treatment test and continuous treatment test, regardless of whether a metabolic activation system was used or not. |
| Micronucleus assay | ICR mouse | Oral | Single | 0, 500, 1000, 2000, Positive control group (mitomycin C2) | EC-18 does not affect micronucleus induction in mouse bone marrow cells. |
| Embryo-fetal developmental toxicity study (DRF study) | SD rat | Oral | 11 days (day-7 to day-17 of pregnancy) | 0, 500, 1000, 2000 | No dead animals<br>There were no significant differences in implantation rate, the male-to-female ratio among the surviving fetuses, and fetal mortality rate compared to the control group.<br>A higher dose of 2000 mg/kg and a low dose of 500 mg/kg determined to be used |
| Embryo-fetal developmental toxicity study | SD rat | Oral | 11 days (day-7 to day-17 of pregnancy | 0, 500, 1000, 2000 | No dead animals<br>No specific findings caused by the administration of EC-18 in a dose-dependent manner<br>NOAEL: 2000 mg/kg/day |
| Embryo-fetal developmental toxicity study (DRF study) | NZW rabbit | Oral | 13 days (day-6 to day-18 of pregnancy) | 0, 125, 250, 500 | A single case of death (250 mg/kg dose group) on day 8 of pregnancy. The cause of death could not be determined by necropsy, but it was determined to have been caused by loss of appetite that was present even before drug administration.<br>No specific findings caused by the administration of EC-18 in a dose-dependent manner<br>The same or higher dose determined to be possibly used |
| Embryo-fetal developmental toxicity study | NZW rabbit | Oral | 13 days (day-6 to day-18 of pregnancy) | 0, 125, 250, 500 | No dead animals<br>The observed abnormalities having no direct sings that showed the effects of EC-18 administration<br>NOAEL: 500 mg/kg/day |

TABLE 29-continued

Summary of toxicology studies

| Test type | Animal/ System | Route | Duration | Dose (mg/kg) | Results |
|---|---|---|---|---|---|
| Fertility and early embryonic developmental toxicity study | SD rat | Oral | Males: 4 weeks before mating ~ necropsy Females: 2 weeks before mating ~ implantation | 0, 500, 1000, 2000 | No dead animals The observed abnormalities having no direct sings that showed the effects of EC-18 administration NOAEL: 2000 mg/kg/day (both males and females) |
| Immunotoxicity study | SD rat | Oral | 4 weeks | 0, 2000 | No immunotoxicity caused by EC-18 |
| Immunotoxicity study (splenic blastogenesis response test) | SD rat | Oral | 4 weeks | 0, 500, 1000, 2000 | No dead animals or changes in clinical signs No changes in T and B lymphocyte proliferation caused by EC-18 |
| Antigenicity test | Guinea pig | Oral | 2 weeks | EC-18: 500, 2000 mg/kg Mixed administration: EC-18 2000 mg/kg + FCA Positive control group: OVA 5 mg/kg + FCA | No anaphylaxis reaction caused by EC-18, indicating no antigenicity of EC-18 |

References in Example 12

Barcellos-Hoff M H, Park C, and Wright E G. Radiation and the microenvironment-tumorigenesis and therapy. Nat Rev Cancer. 2005, 5:867-875.

CDC. Acute Radiation Syndrome (ARS): A Fact Sheet for Physicians CDC: Radiation Emergencies: Department of Health and Human Services; 2005.

Coleman C N, Adams S, Adrianopoli C, Ansari A, Bader J L, Buddemeier B, et al. Medical planning and response for a nuclear detonation: A Practical Guide. Biosec Bioterror. 2012, 10:346-371.

Choi S, Shin S H, Lee H R, Sohn K Y, Yoon S Y, and Kim J W. 1-Palmitoyl-2-linoleoyl-3-acetyl-rac-glycerol ameliorates chemoradiation-induced oral mucositis. Oral Dis. 2020, 26:111-121. doi: 10.1111/odi.13224.

Davidovich P, Kearney C J, Martin S J. Inflammatory outcomes of apoptosis, necrosis, and necroptosis. Biol Chem. 2014, 395:1163-1171.

Farese A M, Cohen M V, Katz B P, Smith C P, Gibbs A, Cohen D M, et al. Filgrastim Improves Survival in Lethally Irradiated Nonhuman Primates. Radiat Res. 2013, 179:89-100.

Farese A M, Cohen M V, Katz B P, Smith C P, Jackson W III, Cohen D M, et al. A Nonhuman Primate Model of the Hematopoietic Acute Radiation Syndrome Plus Medical Management. Health Phys. 2012, 103:1-32.

FDA, Product Development Under the Animal Rule, Guidance for Industry, 2015. https://www.fda.gov/regulatory-information/search-fda-guidance-documents/product-development-under-animal-rule Goans R E and Flynn D F. Acute Radiation Syndrome in Humans. In: Textbook of Military Medicine. Series on Combat Casualty Care; Office of the Surgeon General; Department of the Army, U.S.A. 1989, 2:17-38.

Hankey K G, Farese A M, Blaauw E C, Gibbs A M, Smith C P, Katz B P, et al. Pegfilgrastim improves survival of lethally irradiated nonhuman primates. Radiat Res. 2015, 183:643-55.

He S and Wang X. RIP Kinases as modulators of inflammation and immunity. Nat Immun 2018, 19: 912-922.

Heslet L, Bay C, and Nepper-Christensen S. Acute radiation syndrome (ARS)—treatment of the reduced host defense. Int J Gen Med. 2012, 5:105-15.

Im K I, Nam Y S, Kim N, Song Y, Lee E S, Lim J Y, et al. Regulation of HMGB1 release protects chemoradiotherapy-associated mucositis. Mucosal Immunology. 2019, 12:1070-1081.

Kasper D L, Fauci A S, Hauser S L, Longo D L, Jameson J L, and Loscalzo J. Eds. Harrison's Principles of Internal Medicine, 19e. New York, NY: McGraw-Hill; 2012.

Kim K and McBride W H. Modifying radiation damage. Curr Drug Targets. 2010, 11:1352-1365.

Kim Y J, Jeong J, Shin S H, Lee D Y, Sohn K Y, Yoon S Y, et al. Mitigating Effects of 1-Palmitoyl-2-linoleoyl-3-acetyl-rac-glycerol (PLAG) on Hematopoietic Acute Radiation Syndrome after Total-Body Ionizing Irradiation in Mice. Radiat Res. 2019, 192:602-611. https://doi.org/10.1667/RR15440.1

Kim Y J, Shin J M, Shin S H, Kim J H, Sohn K Y, Kim H J, et al. 1-palmitoyl-2-linoleoyl-3-acetyl-rac-glycerol ameliorates arthritic joints through reducing neutrophil infiltration mediated by IL-6/STATS and MIP-2 activation. Oncotarget. 2017, 8:96636-96648.

Kim Y J, Jung J, Lee H R, Sohn K Y, Kim H J, Yoon S Y, et al. PLAG prevents the loss of circulating neutrophils in the chemotherapy induced neutropenia model. Proceedings: AACR Annual Meeting 2017; Apr. 1-5, 2017, Washington, D.C., Abstract 5664.

Lai H and Singh N P. Single- and double-strand DNA breaks in rat brain cells after acute exposure to radiofrequency electromagnetic radiation. Int J Radiat Biol. 1996, 69:513-21.

Lee H R, Yoo N, Kim J H, Sohn K Y, Kim H J, Kim M H, et al. The Therapeutic Effect of PLAG against Oral Mucositis in Hamster and Mouse Model. Front. Oncol. 2016, 6:209.

Lee H R, Shin S H, Kim J H, Sohn K Y, Yoon S Y, and Kim J W. 1-Palmitoyl-2-Linoleoyl-3-Acetyl-rac-Glycerol (PLAG) Rapidly Resolves LPS-Induced Acute Lung Injury Through the Effective Control of Neutrophil Recruitment. Front Immunol. 2019, 10:2177.

Lehninger A L, Nelson D L, and Cox M M. Lehninger principles of biochemistry. New York: Worth Publishers; 2000.

Xu C, Liu W, You X, Leimert K, Popowycz K, Fang X, et al. $PGF_{2\alpha}$ modulates the output of chemokines and pro-inflammatory cytokines in myometrial cells from term pregnant women through divergent signaling pathways. Mol Hum Reprod. 2015, 21:603-614.

Macià I Garau M, Lucas Calduch A, and López E C. Radiobiology of the acute radiation syndrome. Reports of Practical Oncology and Radiotherapy. 2011, 16:123-30.

Okayasu R, Suetomi K, Yu Y, Silver A, Bedford J S, Cox R, et al. A deficiency in DNA repair and DNA-PKcs expression in the radiosensitive BALB/c mouse. Cancer Res. 2000, 60:4342-5.

Pasparakis M and Vandenabeele P. Necroptosis and its role in inflammation. Nat. 2015, 517:311-20.

Petrie E J, Sandow J J, Lehmann W I L, Liang L Y, Coursier D, Young S N, et al. Viral MLKL Homologs Subvert Necroptotic Cell Death by Sequestering Cellular RIPK3. Cell reports. 2019, 28:3309-3319 e5.

Phillipson M and Kubes P. The neutrophil in vascular inflammation. Nat Med. 2011, 17:1381-90.

Plett P A, Sampson C H, Chua H L, Booth C, Gough A, Johnson C S, et al. Establishing a murine model of the hematopoietic syndrome of the acute radiation syndrome. Health Phys. 2012, 103:343-55.

Plett P A, Sampson C H, Chua H L, Jackson W, Vemula S, Sellamuthu R, et al. The ARS dose response relationship (DRR): Validation and variables. Health Phys. 2015, 109:391-398.

Schaue D and McBride W H. Links between innate immunity and normal tissue radiobiology. Radiat Res. 2010, 173:406-417.

Schaue D, Micewicz E D, Ratikan J A, Xie M W, Cheng G, McBride W H. Radiation and Inflammation. Semin Radiat Oncol. 2015, 25:4-10.

Schaue D, Kachikwu E L, and McBride W H. Cytokines in radiobiological responses: a review. Radiat Res. 2012, 178:505-523.

Schaue D, Micewicz E D, Ratikan J A, Xie M W, Cheng G, and McBride W H. Radiation and inflammation. Semin Radiat Oncol. 2015, 25:4-10.

Shin I S, Ahn K S, Shin N R, Lee H-J, Ryub H W, Kim J W, et al. Protective effect of EC-18, a synthetic monoacetyl-diglyceride on lung inflammation in a murine model induced by cigarette smoke and lipopolysaccharide. Int Immunopharmacol. 2016, 30:62-8.

Sonis S T. New thoughts on the initiation of mucositis. Oral Dis. 2010, 16:597-600.

Stone H B, Coleman C N, Anscher M S, McBride W H. Effects of radiation on normal tissue: consequences and mechanisms. The Lancet. 2003, 4:529-536.

Tang D, Kang R, Coyne C B, Zeh H J, and Lotze M T. PAMPs and DAMPs: Signal Os that Spur Autophagy and Immunity. Immunol Rev. 2012, 249:158-175.

Thrall K D, Love R, O'Donnell K C, Farese A M, Manning R G, and MacVittie T J. An Interlaboratory Validation of The Radiation Dose Response Relationship (DRR) for ARS in the Rhesus Macaque, Health Phys. 2015, 109: 502-510.

Thrall K D, Mahendra S, Jackson M K, William J, Farese A M, and MacVittie T J. A comparative dose response relationship (DRR) between genders for mortality and morbidity of radiation-induced lung injury in the rhesus macaque. Health Phys. 2019, 116:354-365.

Vasconcelos R M, Sanfilippo N, Paster B J, Kerr A R, Li Y, Ramalho L, et al. Host-Microbiome Cross-talk in Oral Mucositis. J Dent Res. 2016, 95:725-733.

Viet C, Corby P, Akinwande A, and Schmidt B. Review of Preclinical Studies on Treatment of Mucositis and Associated Pain. J Dent Res. 2014, 93:868-75.

Wardill H R, Gibson R J, Logan R M, and Bowen J M. TLR4/PKC-mediated tight junction modulation: a clinical marker of chemotherapy-induced gut toxicity? Int J Cancer. 2014, 135:2483-92.

Waselenko J K, MacVittie T J, Blakely W F, Pesik N, Wiley A L, Dickerson W E, et al. Medical management of the acute radiation syndrome: recommendations of the Strategic National Stockpile Radiation Working Group. Ann Intern Med. 2004, 140:1037-51.

Williams J P, Brown S L, Georges G E, Hauer-Jensen M, Hill R P, Huser A K, et al. Animal models for medical countermeasures to radiation exposure. Radiat Res. 2010, 173:557-78.

Yoo N, Lee H R, Shin S H, Sohn K Y, Kim H J, Han Y H, et al. PLAG (1-palmitoyl-2-linoleoyl-3-acetyl-rac-glycerol) augments the therapeutic effect of pegfilgrastim on gemcitabine-induced neutropenia. Cancer Letters. 2016, 377:25-31.

Yoon S Y, Kang H B, Ko Y E, Shin S H, Kim Y J, Sohn K Y, et al. 1-palmitoyl-2-linoleoyl-3-acetyl-rac-glycerol (EC-18) Modulates Th2 Immunity through Attenuation of IL-4 Expression. Immune Net. 2015, 15:100-9.

Example 13: Efficacy of EC-18 in ARS

Radiation exposure induces tissue damage (triggers DAMP release) and may also destroy epithelial barriers, increasing the vulnerability of bacterial and pathogenic invasions (PAMP release) into multiple host tissues (Stone, Coleman, Anscher, & McBride, 2003). There is an emerging need for radiation MCM that can protect and/or mitigate the consequences of acute and chronic low level radiation exposures. Necroptosis, a form of programmed necrosis, may play a significant role in radiation-induced cell death, contributing to radiation-associated diseases and mortality. Radiation can lead to direct induction of RIPK1/3-dependent necroptosis, plasma membrane permeabilization, and release of DAMPs.

Based on the proposed mechanism of action, we posit that EC-18 can facilitate the removal of radiation-induced DAMPs and PAMPs, yielding less damage to host tissue and restoring homeostasis early. In the following non-clinical studies, EC-18 demonstrated (1) improvement of the survival; (2) reduction in severity and duration of neutropenia; (3) prevention of PLT depletion; (4) reduction of pro-inflammatory cytokines/chemokines; and (5) prevention of excessive neutrophil infiltration in γ-radiation-induced ARS murine model. Hence, we propose that EC-18 may be a potent MCM for ARS to mitigate the severity of sub-syndromes of ARS, including skin, oral mucositis, lung, and pulmonary.

Determination of γ-Radiation Dose of LDXX/30 in γ-Radiation-Induced Acute Radiation Syndrome Mice Model The purpose of this study was to establish a reproducible murine ARS model for testing the efficacy of EC-18 against γ-radiation, indicated as percent survival described herein. Eleven-week-old male and female BALB/c mice (10 females and 10 males; 20 animals per study group) were exposed to 6.0, 6.2, 6.4, and 6.5 Gy dose of whole-body irradiation of γ-radiation ($^{60}$Co, 1553 R/min) and assessed for 30 day survival, mean survival time, and lethal dose (LD).

The mortality rate of irradiated mice was positively correlated with the dose of radiation. FIG. 28A shows the survival of BALB/c mice exposed to various doses of γ-radiation. The mean survival time (MST) of decedents for each radiation dose cohort ranged from 13.69 to 15.85 days, with the overall MST of decedents across all dose cohorts being 14.75 days (Table 30). During 30 days of observation, increased mortality and decreased the duration of survival time were found to be associated with an increase in strength of γ-radiation, as shown in Table 30.

TABLE 30

The 30-day mortality of BALB/c mice after γ-radiation

| Radiation dose (Gy) | Mortality | MST ± Standard deviation (SD) | Median |
|---|---|---|---|
| | | Survival time of decedents (days) | |
| 6.00 | 12/20 (60%) | 15.30 ± 4.98 | 15.50 |
| 6.20 | 16/20 (80%) | 13.69 ± 3.26 | 13.50 |
| 6.40 | 20/20 (100%) | 14.15 ± 3.48 | 14.00 |
| 6.50 | 20/20 (100%) | 15.85 ± 4.42 | 14.50 |

FIG. 28B shows the radiation dose-response relationship using a probit model. Thirty-day survival was calculated at each radiation dose and is shown as percent mortality on the y-axis. Based on the probit model in FIG. 28B, it was determined that the LDXX/30 with 95% confidence intervals (CIs) around each dose. The LD30/30, LD50/30, LD70/30, and LD95/30 were 5.45, 5.85, 6.11, and 6.35 Gy, respectively (Table 31). The established LD70/30 (6.11 Gy) in this experiment was applied in subsequent experiments for the efficacy test of EC-18.

TABLE 31

Estimated LD in BALB/c mice after γ-radiation

| LDxx/30 | LD estimate (Gy) | Lower 95% CI (Gy) | Upper 95% CI (Gy) |
|---|---|---|---|
| LD30/30 | 5.31 | 4.98 | 5.56 |
| LD50/30 | 5.79 | 5.59 | 5.96 |
| LD70/30 | 6.11 | 5.98 | 6.22 |
| LD95/30 | 6.39 | 6.30 | 6.48 |

Dose-Effect Relationship of EC-18 on the Survival Rate under γ-Radiation-Induced Acute Radiation Syndrome (ARS)

The purpose of this study was to investigate the dose-effect of EC-18 on increasing the survival in mice after exposure to γ-radiation to the entire body. Eleven-week-old male and female BALB/c mice (10 females and 10 males; 20 animals per study group) were tested for the LD70/30 study. This study is consisted of 4 experimental groups; γ-radiation only group, and γ-radiation with EC-18 treatment groups at 10, 50, or 250 mg/kg.

Compared to the control group, daily dosing of EC-18 at 250 mg/kg significantly improved survival by 4-fold, while EC-18 administered at 50 mg/kg significantly improved survival by 2-fold. EC-18 dose-dependently attenuated γ-radiation-induced mortality in mice (FIG. 30A). Moreover, the average life spans of the irradiated mice with EC-18 treatment at 10, 50, and 250 mg/kg were 19.3, 22.3, and 28.2 days, respectively (Table 32).

TABLE 32

Statistical comparisons of EC-18 dosages on the survival and average life duration of the irradiated mice

| Irradiated Animal group (6.11 Gy) | No. of mice that survived/total | Survival (%) | Average life span | Median survival, days | Log-rank test p* |
|---|---|---|---|---|---|
| EC-18 250 mg/kg | 16/20 | 80 | 28.2 | 30 | <0.0001 |
| EC-18 50 mg/kg | 8/20 | 40 | 22.3 | 20 | 0.0464 |
| EC-18 10 mg/kg | 4/20 | 20 | 19.3 | 17 | 0.4425 |
| EC-18 0 mg/kg | 4/20 | 20 | 17.9 | 15 | |

Radiation alone caused a substantial decrease in the bodyweight of the mice (FIG. 30B). The administration of the two higher doses (50 and 250 mg/kg) of EC-18 significantly prevented severe weight loss. The number of mice experiencing a 20% loss in body weight from baseline value decreased sharply as the EC-18 dose increased. For EC-18-treated at 250 mg/kg, statistically significant differences from the 18th day after irradiation to the end of the experiment were noted compared to the control group (p<0.05). Unpaired student t-test was used for the body weight data to evaluate the significance of the difference between the EC-18 administrated groups and the radiation control group. (FIG. 30B). This observation also supports that EC-18 is effective for mitigating body weight loss in γ-radiation-induced ARS.

Pharmacodynamics Study of EC-18 on the Hematopoietic Injury in γ-Radiation-Induced Acute Radiation Syndrome (ARS)

The dose optimization study was conducted to investigate the therapeutic effects of EC-18 on the kinetics of hematopoietic cells, including ANCs, RBC counts, and PLT counts, in mice after TBI with γ-radiation. Eleven-week-old mice (20:20=male:female; 40 mice per group) were monitored at least twice daily for survival for 30 days. For assessment of blood cell kinetics, the mice were divided into two cohorts of 20 mice/cohort based on blood collection time. Blood collection schedules were as follows. Cohort 1 collection was performed on days 1, 5, 10, 15, 20 and 27; cohort 2 collection was performed on days 3, 7, 12, 17, 22 and 30. The blood cells were counted and classified by CBC analysis. The values of the blood cells of the mice were recorded at the appointed dates for 30 days.

EC-18 was administered daily in-life at the dosages of 50, 100, 250, and 500 mg/kg 1 day after irradiation. Based on the 24-hr delayed dose-ranging study, there was a significant improvement (~4-fold) in survival for the EC-18-treated group with 250 and 500 mg/kg compared to the control group and the survival rate significantly improved in a dose-dependent manner. The percent survivals were equal for EC-18 treated at 250 and 500 mg/kg, not providing additional benefit above 250 mg/kg (FIG. 67 and Table 33).

TABLE 33

Statistical comparisons of different EC-18 dosages on the survival of the irradiated mice

| Treatment | No. of mice that survived/total | Survival (%) | Survival time of decedents (days) Mean ± SEM | Median | Log-rank test p* |
|---|---|---|---|---|---|
| Control | 13/40 | 32.5 | 21.2 ± 1.0 | 21.0 | |
| EC-18 50 mg/kg | 24/40 | 60 | 24.3 ± 1.2 | 25.5 | 0.0041 |
| EC-18 100 mg/kg | 27/40 | 67.5 | 22.8 ± 1.7 | 26.0 | 0.0008 |
| EC-18 250 mg/kg | 34/40 | 85 | 27.8 ± 0.4 | 27.5 | <0.0001 |
| EC-18 500 mg/kg | 34/40 | 85 | 20.3 ± 1.5 | 19.5 | <0.0001 |

Using CBC analysis, it was investigated whether enhanced survival by EC-18 results from the increase in nadir values. A single-dose of TBI rapidly diminished the WBC and ANC within 3 days after irradiation (FIG. 68 and FIG. 69). In particular, the administration of EC-18 (50 and 250 mg/kg) significantly attenuated radiation-induced depletion of WBC and ANC in mice in a dose-dependent manner (FIG. 69). The mean of the first day with SN (ANC<100 cells/μL) for control and EC-18 (50, 100, 250, and 500 mg/kg)-treated cohorts was 3.8±0.3, 5.7±0.6, 5.1±0.5, 8.5±1.0 and 7.0±0.9 days, respectively (Table 34).

TABLE 34

Mean of the first day and the mean duration of neutropenia (ANC <500 cells/μL) and SN (ANC <100 cells/pL) for control and EC-18-treated irradiated mice

| Treatment | Mean of the First Day of Neutropenia‡ (± SE, range) | Mean Duration of Neutropenia in Days (± SE, range) | Two-sided P-value | Mean of the First Day of SN‡ (± SE, range) | Mean Duration of SN in Days (± SE, range) | Two-sided P-value |
|---|---|---|---|---|---|---|
| Control | 3.0 ± 0.0 (3-3) | 23.8 ± 0.8$^a$ (19-27) | | 3.8 ± 0.3 (3-7) | 18.5 ± 1.0$^a$ (12-27) | |
| EC-18 50 mg/kg | 3.0 ± 0.0 (3-3) | 21.0 ± 0.7$^b$ (17-24) | 0.019 | 5.7 ± 0.6 (3-10) | 11.4 ± 0.9$^b$ (5-19) | <0.0001 |
| EC-18 100 mg/kg | 3.0 ± 0.0 (3-3) | 23.9 ± 0.5$^c$ (19-27) | 0.860 | 5.1 ± 0.5 (3-10) | 13.4 ± 1.3$^c$ (7-25) | 0.005 |
| EC-18 250 mg/kg | 3.2 ± 0.1 (3-5) | 21.2 ± 0.7$^d$ (17-27) | 0.027 | 8.5 ± 1.0 (3-17) | 7.2 ± 0.7$^d$ (2-12) | <0.0001 |
| EC-18 500 mg/kg | 3.4 ± 0.2 (3-5) | 21.9 ± 0.6$^e$ (17-27) | 0.089 | 7.0 ± 0.9 (3-20) | 9.6 ± 0.6$^e$ (2-14) | <0.0001 |

*Note that ANC durations do not include data from decedent animals unless recovery occurred to that level prior to death;
‡Includes all animals, $^a$n = 13, $^b$n = 19, $^c$n = 18, $^d$n = 20, $^e$n = 19

The mean PLT count in the EC-18 250 mg/kg-treated cohort significantly was higher than the control cohort from 15 days to the last day of the observation (FIG. 70 and Table 35). From these observations, the administration of EC-18 has a remarkable effect in recovering γ-radiation-induced depletion of PLT.

TABLE 35

Mean of the first day and the mean duration of thrombocytopenia (PLT <100 × 10$^3$ cells/μL) for control and EC-18-treated irradiated mice

| Treatment | Mean of the First Day of Thrombocytopenia‡ (±SE, range) | Mean Duration of Thrombocytopenia in Days (±SE, range) | Two-sided P-value |
|---|---|---|---|
| Control | 9.8 ± 0.1 (7-10) | 13.1 ± 1.1$^a$ (7-20) | |
| EC-18 50 mg/kg | 10.0 ± 0.0 (10-10) | 12.8 ± 0.8$^b$ (7-17) | 0.832 |
| EC-18 100 mg/kg | 10.0 ± 0.0 (10-10) | 14.7 ± 1.0$^c$ (5-20) | 0.288 |
| EC-18 250 mg/kg | 10.1 ± 0.1 (10-12) | 6.7 ± 0.5$^d$ (3-12) | <0.0001 |
| EC-18 500 mg/kg | 10.1 ± 0.1 (10-12) | 12.3 ± 0.7$^e$ (7-20) | 0.558 |

*Note that thrombocytopenia durations do not include data from decedent animals unless recovery occurred to that level prior to death;
‡Includes all animals,
$^a$n = 13,
$^b$n = 19,
$^c$n = 18,
$^d$n = 20,
$^e$n = 19

Besides the reduction of ANC and PLT, a γ-radiation induced the reduction of RBCs and hemoglobin. During 30 days of observation, the administration of EC-18 at 250 mg/kg significantly prevented the γ-radiation-induced reduction of RBC (FIG. 71A) and hemoglobin (FIG. 71B and Table 36). These results indicated that EC-18 has a remarkable effect in attenuating γ-radiation-induced anemia.

Moreover, the timing of nadirs for neutrophils, PLTs, red blood cells, and hemoglobin is unchanged (FIGS. 69, 70, 71A and 71B). However, the severity of the nadir is diminished, which is consistent with EC-18's hypothesized mechanism of action. That is, EC-18 modulates the inflammatory process, reducing the severity of the response to acute radiation exposure.

TABLE 36

Mean of the first day and the mean duration of anemia (HGB <12 g/dL) for control and EC-18-treated irradiated mice

| Treatment | Mean of the First Day Of Anemia‡ (±SE, range) | Mean Duration of Anemia in Days (±SE, range) | Two-sided P-value |
|---|---|---|---|
| Control | 9.5 ± 0.6 (3-12) | 15.5 ± 0.8$^a$ (10-18) | |
| EC-18 50 mg/kg | 10.4 ± 0.7 (5-15) | 15.0 ± 0.8$^b$ (7-19) | 0.684 |
| EC-18 100 mg/kg | 11.0 ± 0.5 (5-15) | 15.5 ± 0.5$^c$ (12-20) | 0.973 |
| EC-18 250 mg/kg | 12.1 ± 0.5 (10-15) | 9.7 ± 0.7$^d$ (5-17) | <0.0001 |
| EC-18 500 mg/kg | 12.2 ± 0.5 (7-15) | 14.0 ± 0.8$^e$ (7-20) | 0.277 |

*Note that anemia durations do not include data from decedent animals unless recovery occurred to that level prior to death;
‡Includes all animals,
$^a$n = 10,
$^b$n = 17,
$^c$n = 17,
$^d$n = 19,
$^e$n = 19

Delayed Effect of EC-18 on the Survival Rate under γ-Radiation-Induced Acute Radiation Syndrome (ARS)

The dosing schedule optimization study was conducted in a total of 120 BALB/c mice (60 females and 60 males; 20 animals per study group) at 11-week-old exposed to a 6.11Gy dose for TBI. EC-18 was administered daily in-life with its optimal dosage (250 mg/kg) at 0, 1, 2, and 3 days after irradiation on Day 0. The survival rate of the γ-radiation only group was 35%. The percentages of survival of the irradiated mice with EC-18 +0d, +1d, +2d, and +3d were 80, 70, 55, and 80%, respectively (FIG. 72). Moreover, the average life spans of the decedents with EC-18 +0d, +1d, +2d, and +3d were 25.0, 23.7, 18.1, and 22.3 days, respectively (Table 37). This observation indicates that upon EC-18 administration, the survival significantly improved for the EC-18-treated groups (even up to 3-day-delayed treatment regimen) compared to its negative control (NC) (FIG. 72). However, the optimal therapeutic outcome of the dosing schedule was achieved by the treatment of EC-18 at Day 0 In this set of experiments, the LD70/30 dose of γ-ray irradiation caused a mild decrease in the bodyweight of the mice. However, the administration of EC-18 effectively prevented and rapidly recovered weight loss induced by irradiation (FIG. 73).

TABLE 37

Statistical comparisons of the delayed treatment effect of EC-18 on the survival of the irradiated mice

| | No. of mice that survived/ total | Survival (%) | Survival time of decedents (days) Mean ± SEM | Median | Log-rank test p* |
|---|---|---|---|---|---|
| Negative control | 20/20 | 100 | | | |
| 6.11 Gy | 7/20 | 35 | 19.2 ± 0.9 | 20.0 | |
| 6.11 Gy + EC-18 (+0 d) | 16/20 | 80 | 25.0 ± 1.1 | 24.5 | <0.001 |
| 6.11 Gy + EC-18 (+1 d) | 14/20 | 70 | 23.7 ± 1.4 | 23.5 | <0.001 |
| 6.11 Gy + EC-18 (+2 d) | 11/20 | 55 | 18.1 ± 0.8 | 18.0 | 0.0080 |
| 6.11 Gy + EC-18 (+3 d) | 11/20 | 55 | 22.3 ± 1.6 | 23.0 | 0.0012 |

Calorie Effect of EC-18 on the Survival Rate under γ-Radiation-Induced Acute Radiation Syndrome (ARS)

The purpose of this study was to assess whether extra calories of EC-18 contribute to the enhanced survival in mice after exposure to a whole-body sublethal dose of γ-radiation. The study was performed with the structural analog in which the acetyl group in EC-18 is replaced with a hydroxyl group (yielding PLH) in a total of 100 BALB/c mice (60 females and 60 males; 20 animals per study group) aged at 11 weeks. Mice were irradiated with TBI of 6.11Gy at day 0 and the same dosage (250 mg/kg) of EC-18, PLH, or olive oil (vehicle control)_were given daily in-life.

The EC-18-treated group exhibited a significant increase in survival compared to both control and PLH-treated group (FIG. 74 and Table 38). Furthermore, there was no statistically significant difference in the survival of the PLH-treated group compared to that of the control group. The administration of EC-18 effectively prevented and rapidly recovered weight loss induced by irradiation, while olive oil and PLH aggravated body weight loss induced by γ-ray irradiation (FIG. 75B).

It is interesting to note that the deacetylation abolished the function of EC-18 and this indicates that the acetyl group is crucial to maintain the activity of EC-18. Besides having a distinctive mechanism of action for improving survival in γ-radiation-induced ARS condition, the therapeutic benefit of EC-18 was not affected by the administration of extra calories.

TABLE 38

Statistical comparisons of the effects of EC-18, olive oil, PLH on the survival of the irradiated mice

| | No. of mice that survived/ total | Survival (%) | Survival time of decedents (days) | | Log-rank test p* |
|---|---|---|---|---|---|
| | | | Mean ± SEM | Median | |
| Negative control | 20/20 | 100 | | | |
| 6.11 Gy | 7/20 | 35 | 19.2 ± 0.9 | 20.0 | |
| 6.11 Gy + EC-18 250 mg/kg | 14/20 | 70 | 23.7 ± 1.4 | 23.5 | <0.001 |
| 6.11 Gy + Olive oil 250 mg/kg | 5/20 | 25 | 17.9 ± 1.5 | 18 | 0.432 |
| 6.11 Gy + PLH 250 mg/kg | 8/20 | 40 | 18.8 ± 1.6 | 18 | 0.069 |

Effect of EC-18 on Skin Injury in γ-Radiation-Induced Acute Radiation Syndrome

The secondary measures of EC-18's efficacy on the supra-LD (8 Gy) of radiation-induced skin damage were assessed. Female BALB/c mice (9 weeks of age) were randomly divided into 2 cohorts and daily administered in-life with the vehicle control (PBS) and EC-18 at 250 mg/kg (n=5/each corhort).

The results indicated that two of five mice in the PBS control cohort experienced severe skin discoloration and edema formation on the front right feet and hemorrhagic telangiectasia on the tails at day 10 of post irradiation (FIG. 13B). On the other hand, the resulting skin damage (necrosis, ulceration, blistering, and hair loss) on tails and feet was extensively reduced by the EC-18 treatment as compared to the PBS control cohort. Only one individual in the EC-18-treated cohort showed slight hemorrhagic telangiectasia on the front right feet, while none of the five in EC-18-treated cohort showed any skin damage on the tails (FIG. 13B).

These results show that EC-18 treatment has significant efficacy in enhanced survival to include severe neutropenic conditions induced by high lethal TBI. These results also show that EC-18 is effective in treating cutaneous radiation syndrome.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating or preventing acute radiation syndrome in a human subject, comprising:
   identifying a human subject suffering from or susceptible to acute radiation syndrome; and
   administering to the identified human subject in need thereof a therapeutically effective amount of PLAG.

2. The method of claim 1, wherein the subject has been exposed to radiation from 0.7 Gy or more.

3. The method of claim 1 wherein the subject is identified as suffering from or susceptible to hematopoietic acute radiation syndrome and the identified subject is administered the therapeutically effective amount of PLAG.

4. The method of claim 1 wherein the subject is identified as suffering from or susceptible to radiation-induced coagulopathy and the identified subject is administered the therapeutically effective amount of PLAG.

5. The method of claim 1 wherein the subject is identified as suffering from or susceptible to gastrointestinal acute radiation syndrome and the identified subject is administered the therapeutically effective amount of PLAG.

6. The method of claim 1 wherein the subject is identified as suffering from or susceptible to cutaneous acute radiation syndrome and the identified subject is administered the therapeutically effective amount of PLAG.

7. The method of claim 1 wherein the subject is identified as suffering from or susceptible to central nervous system (CNS) acute radiation syndrome and the identified subject is administered the therapeutically effective amount of PLAG.

8. The method of claim 1, wherein the subject is identified as suffering from one or more hematopoietic, gastrointestinal, cutaneous or neurovascular subsyndrome of acute radiation syndrome and the identified subject is administered the therapeutically effective amount of PLAG.

9. The method of claim 1, wherein the PLAG is first administered to the subject within 72 hours after first acute radiation exposure.

10. The method of claim 1, wherein the PLAG is first administered to the subject within 48 hours after first acute radiation exposure.

11. The method of claim 1, wherein the PLAG is administered with G-CSF.

12. The method of claim 1, wherein the PLAG is administered with one or more selected from the group consisting of pain medicines, antiulcer drugs, antidiarrheal drugs, antibiotics, antifebriles, dietary supplements, and antioxidants.

13. A method of claim 1 wherein the subject has been exposed to radiation of 0.1 Gy or more.

14. The method of claim 1 wherein the subject is identified as suffering from or susceptible to cardiovascular (CV) acute radiation syndrome and the identified subject is administered the therapeutically effective amount of PLAG.

15. The method of claim 1 wherein the subject is identified as suffering from or susceptible to pulmonary dysfunction acute radiation syndrome and the identified subject is administered the therapeutically effective amount of PLAG.

* * * * *